(12) United States Patent
Kikuchi et al.

(10) Patent No.: US 9,890,142 B2
(45) Date of Patent: Feb. 13, 2018

(54) PDE4 INHIBITOR

(71) Applicant: Meiji Seika Pharma Co., Ltd., Tokyo (JP)

(72) Inventors: Chika Kikuchi, Yokohama (JP); Yuji Tabata, Yokohama (JP); Takeru Yamakawa, Yokohama (JP); Takashi Matsuhira, Yokohama (JP); Naoko Watanabe, Yokohama (JP); Natsuki Kubota, Yokohama (JP); Kaori Kaneda, Yokohama (JP)

(73) Assignee: Meiji Seika Pharma Co., Ltd., Tokyo (JP)

( * ) Notice: Subject to any disclaimer, the term of this patent is extended or adjusted under 35 U.S.C. 154(b) by 0 days.

(21) Appl. No.: 14/903,707

(22) PCT Filed: Jul. 10, 2014

(86) PCT No.: PCT/JP2014/068435
§ 371 (c)(1),
(2) Date: Jan. 8, 2016

(87) PCT Pub. No.: WO2015/005429
PCT Pub. Date: Jan. 15, 2015

(65) Prior Publication Data
US 2016/0159783 A1 Jun. 9, 2016

(30) Foreign Application Priority Data
Jul. 10, 2013 (WO) ............... PCT/JP2013/068902

(51) Int. Cl.
| C07D 413/04 | (2006.01) |
| C07D 413/14 | (2006.01) |
| C07D 417/04 | (2006.01) |
| C07D 417/14 | (2006.01) |
| A61K 31/496 | (2006.01) |

(52) U.S. Cl.
CPC ......... C07D 413/04 (2013.01); C07D 413/14 (2013.01); C07D 417/14 (2013.01)

(58) Field of Classification Search
None
See application file for complete search history.

(56) References Cited

U.S. PATENT DOCUMENTS

| 5,631,257 A | 5/1997 | Iwamatsu et al. |
| 6,037,342 A | 3/2000 | Sato et al. |
| 6,403,791 B1 | 6/2002 | Dyke et al. |
| 2007/0281945 A1 | 12/2007 | Liu et al. |
| 2007/0282145 A1 | 12/2007 | Iaccino et al. |
| 2008/0051415 A1 | 2/2008 | Clark et al. |
| 2008/0255114 A1 | 10/2008 | Yang et al. |

FOREIGN PATENT DOCUMENTS

| CN | 101490022 A | 7/2009 |
| CN | 101528225 A | 9/2009 |
| EP | 0621271 A1 | 10/1994 |
| EP | 0806419 A1 | 11/1997 |
| JP | H06-345744 A | 12/1994 |
| JP | H10-029987 A | 2/1998 |
| JP | 2003-522771 A | 7/2003 |
| JP | 2009-538908 A | 11/2009 |
| JP | 2009-538909 A | 11/2009 |
| JP | 2009-539848 A | 11/2009 |
| JP | 2010-500368 A | 1/2010 |
| WO | 01/58896 A1 | 8/2001 |
| WO | 2007/146066 A2 | 12/2007 |
| WO | 2008/019372 A2 | 2/2008 |
| WO | 2009/050242 A2 | 4/2009 |

OTHER PUBLICATIONS

CA Registry No. 1490016-27-7, entered into CA Registry File on Dec. 8, 2013, supplied by Aurora Fine Chemicals.*
Aurora Fine Chemicals Product Guide.1 page, retrieved from the Internet at http://www.aurorafinechemicals.com/abouthtml on Apr. 28, 2015.*
CA Registry No. 1329512-03-9, entered into the Registry File on Sep. 7, 2011, supplied by Ambinter.*
CA Registry No. 1330277-67-2, entered into the Registry File on Sep. 9, 2011, supplied by Ambinter.*
About Ambinter, 2 page retrieved from the Internet at http://www.ambinter.com/about-us on Mar. 17, 2015.*
International Preliminary Report on Patentability and Written Opinion issued in counterpart International Patent Application No. PCT/JP2014/068435 dated Jan. 21, 2016.
International Search Report issued in counterpart International Patent Application No. PCT/JP2014/068435 dated Aug. 26, 2014.

(Continued)

*Primary Examiner* — Emily A Bernhardt
(74) *Attorney, Agent, or Firm* — Morgan, Lewis & Bockius LLP

(57) ABSTRACT

Provided is a compound represented by formula (1a) or a pharmacologically acceptable salt thereof, which can be used as a phosphodiesterase (PDE) inhibitor. $R^1$ to $R^6$ in the formula each independently represent an alkyl group or the like.

[Formula 1a]

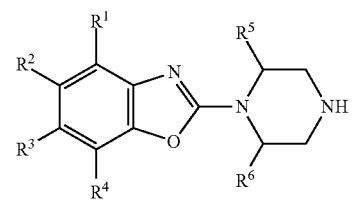

13 Claims, No Drawings

(56) References Cited

OTHER PUBLICATIONS

Sato et al., "Benzoxazole Derivatives as Novel 5-HT3 Receptor Partial Agonists in the Gut," Journal of Medicinal Chemistry, 41: 3015-3021 (1998).
Yoshida et al., "Orally Active Benzoxazole Derivative as 5-HT3 Receptor Partial Agonist for Treatment of Diarrhea-Predominant Irritable Bowel Syndrome," Journal of Medicinal Chemistry, 48: 7075-7079 (2005).
Spina, "PDE4 inhibitors: current status," British Journal of Pharmacology, 155: 308-315 (2008).
Kumar et al., "Phosphodiesterase 4-targeted treatments for autoimmune diseases," BMC Medicine, 11: 96 (2013).
Gavalda et al., "Phosphodiesterase-4 inhibitors: a review of current developments (2010-2012)," Expert Opinion on Therapeutic Patents, 23: 997-1016 (2013).
Cortijo et al., "Roflumilast, a phosphodiesterase 4 inhibitor, alleviates bleomycin-induced lung injury," British Journal of Pharmacology, 156: 534-544 (2009).
Rabe, "Update on roflumilast, a phosphodiesterase 4 inhibitor for the treatment of chronic obstructive pulmonary disease," British Journal of Pharmacology, 163: 53-67 (2011).
Dyke et al., "Update on the therapeutic potential of PDE4 inhibitors," Expert Opinion on Investigational Drugs, 11: 1-13 (2002).
Extended European Search Report issued in corresponding European Patent Application No. 14823220.0 dated Nov. 18, 2016.
Office Action issued in counterpart Japanese Patent Application No. 2015-526400 dated Dec. 12, 2017.

\* cited by examiner

PDE4 INHIBITOR

TECHNICAL FIELD

The present invention relates to a PDE4 inhibitor.

BACKGROUND ART

Phosphodiesterase (PDE) is an enzyme that play an important role in the process of degrading and inactivating cyclic nucleotides (cAMP or cGMP), which are important second messengers. PDE degrading cAMP is classified into some isozymes, among which type 4 PDE (PDE4) is a primary cAMP-degrading enzyme present in many inflammatory cells and immunocytes (see Non Patent Literature 1: Expert Opin. Investig. Drugs, 11, 1-13, 2002).

PDE4 inhibitors are known to be useful in the treatment of various inflammatory diseases in which TNF-α or the like is involved, because of suppressing the production or release of various cytokines, such as TNF-α, which play an important role in inflammation cascades (see Non Patent Literature 1: Expert Opin. Investig. Drugs, 11, 1-13, 2002). Also, it has been reported that PDE4 inhibitors exhibit effects on not only inflammation in the respiratory system but also inflammation in the skin, and additionally, it has been reported that they also exhibit effects on mental illness (see Non Patent Literature 1: Expert Opin. Investig. Drugs, 11, 1-13, 2002).

Theophylline known as a PDE inhibitor has heretofore been used in the treatment of asthma (see Non Patent Literature 2: British Journal of Pharmacology, 155, 308-315, 2008). In recent years, roflumilast, which is a potent PDE4 inhibitor, has been approved and used as a therapeutic drug for chronic obstructive pulmonary disease (COPD) in Europe and the United States (see Non Patent Literature 3: British Journal of Pharmacology, 163, 53-67, 2011), and additionally, the efficacy for interstitial pneumonia (idiopathic pulmonary fibrosis, etc.) in animal models has also been suggested (see Non Patent Literature 4: British Journal of Pharmacology, 156, 534-544, 2009). Moreover, it has been reported that apremilast, which is a PDE inhibitor, is effective for psoriatic arthritis and psoriasis vulgaris in clinical trials (see Non Patent Literature 5: Amadeu G and Richard S. R., Expert Opin. Ther. Patents, August 2013, Vol. 23, No. 8, 997-1016). In addition, clinical trials of PDE4 inhibitors for various inflammatory diseases (inflammatory bowel disease, Crohn's disease, multiple sclerosis, rheumatism, atopic dermatitis and sarcoidosis) have been carried out, and additionally, their possibilities for systemic lupus erythematosus have also been pointed out in nonclinical trials (see Non Patent Literature 1: Expert Opin. Investig. Drugs, 11, 1-13, 2002, and Non Patent Literature 6: BMC Medicine, 11, 96, 2013). Furthermore, among PDE4 inhibitors, there are many compounds having central effects, and there have also been reports on effects on depression, Parkinson's disease, learning and memory disorders and Alzheimer's disease (see Non Patent Literature 1: Expert Opin. Investig. Drugs, 11, 1-13, 2002, and Non Patent Literature 6: BMC Medicine, 11, 96, 2013). Examples of diseases on which PDE4 inhibitors are likely to exhibit effects as described above include asthma, COPD, interstitial pneumonia, inflammatory bowel disease, Crohn's disease, multiple sclerosis, rheumatism, atopic dermatitis, psoriatic arthritis, psoriasis vulgaris, sarcoidosis, systemic lupus erythematosus, depression, learning and memory disorders, Parkinson's disease and Alzheimer's disease.

Moreover, although the activity against serotonin 5-HT$_3$ of a compound having a structure similar to that of a benzoxazole derivative, which is the active ingredient of the present invention, is described in Patent Literature 1 (JP 6-345744 A), Patent Literature 2 (JP 10-29987 A), etc., there is no description about having PDE4 inhibitory activity.

CITATION LIST

Patent Literature

Patent Literature 1: JP 6-345744 A
Patent Literature 2: JP 10-29987 A

Non Patent Literature

Non Patent Literature 1: Dyke H. J. and Montana J. G, Expert Opin. Investig. Drugs, 11, 1-13, 2002
Non Patent Literature 2: Spina D, British Journal of Pharmacology, 155, 308-315, 2008
Non Patent Literature 3: Klaus F. R., British Journal of Pharmacology, 163, 53-67, 2011
Non Patent Literature 4: Cortijo J et al., British Journal of Pharmacology, 156, 534-544, 2009
Non Patent Literature 5: Amadeu G and Richard S. R., Expert Opin. Ther. Patents, August 2013, Vol. 23, No. 8, 997-1016.
Non Patent Literature 6: Kumar N. et al. BMC Medicine, 11, 96, 2013

SUMMARY OF INVENTION

Technical Problem

However, these PDE4 inhibitors also include many compounds having emetogenicity, and concentration-dependent side effects such as vomiting and nausea have also been reported. Thus, PDE4 inhibitors that can avoid these side effects have been demanded, and it is considered that such drugs may serve as excellent preventive or therapeutic agents for inflammatory diseases (respiratory diseases and skin diseases) and central nervous system diseases.

An object of the present invention is to provide a compound that has excellent PDE4 inhibitory activity and is useful as a pharmaceutical drug.

Solution to Problem

The present inventor has conducted diligent studies to attain the object and consequently completed the present invention by finding that a benzoxazole derivative having a piperazine ring, or a pharmacologically acceptable salt thereof has excellent PDE4 inhibitory activity.

Specifically, the present invention provides:

[1] A compound represented by formula (1a):

[Chemical Formula 1]

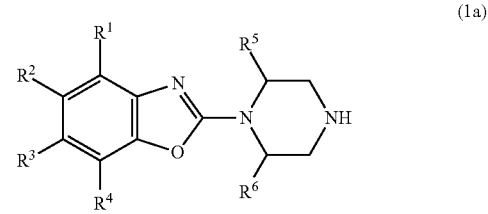

(1a)

wherein

R[1], R[2], R[3] and R[4] are each independently one group selected from the group consisting of a hydrogen atom, a halogen atom, a hydroxy group, a carboxy group, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted $C_{7-11}$ monocyclic or polycyclic aralkyl group, an optionally substituted 4- to 10-membered monocyclic or bicyclic heterocyclic group containing 1 to 4 heteroatoms selected from an oxygen atom, a nitrogen atom and a sulfur atom, a di-$C_{1-6}$ alkylamino group, an optionally substituted $C_{3-7}$cycloalkylamino group, an optionally substituted $C_{1-6}$ alkyloxy group, an optionally substituted $C_{3-7}$ cycloalkyloxy group, an optionally substituted $C_{6-10}$ monocyclic or polycyclic aryloxy group, an optionally substituted $C_{7-11}$ monocyclic or polycyclic aralkyloxy group, an optionally substituted 4- to 10-membered monocyclic or bicyclic heterocyclyloxy group containing 1 to 4 heteroatoms selected from an oxygen atom, a nitrogen atom and a sulfur atom, an optionally substituted $C_{1-6}$ alkylthio group, an optionally substituted $C_{1-6}$ alkylsulfonyl group, an optionally substituted $C_{1-6}$ (alkylcarbonyl group, a mono-$C_{1-6}$ alkylaminocarbonyl group, a di-$C_{1-6}$ alkylaminocarbonyl group, an optionally substituted $C_{1-6}$ alkyloxycarbonyl group and an optionally substituted hydroxyaminocarbonyl group, and R[5] and R[6] are each independently a hydrogen atom or a alkyl group, provided that the case where R[1] is a carboxy group, the case where R[1], R[2], R[3] and R[4] are hydrogen atoms at the same time and the case where R[5] and R[6] are hydrogen atoms at the same time are excluded;

or a pharmacologically acceptable salt thereof.

[2] The compound or a pharmacologically acceptable salt thereof according to [1], wherein R[2] is one group selected from the group consisting of a hydrogen atom, a halogen atom, a cyano group, an optionally substituted $C_{1-6}$ alkyl group and an optionally substituted 5- to 7-membered monocyclic heterocyclic group containing 1 to 4 heteroatoms selected from an oxygen atom, a nitrogen atom and a sulfur atom.

[3] The compound or a pharmacologically acceptable salt thereof according to [1], wherein R[1] is one group selected from the group consisting of a hydrogen atom, a halogen atom, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted 5- to 7-membered monocyclic heterocyclic group containing 1 to 4 heteroatoms selected from an oxygen atom, a nitrogen atom and a sulfur atom, an optionally substituted $C_{1-6}$ alkyloxy group, an optionally substituted $C_{1-6}$ alkylthio group and an optionally substituted $C_{1-6}$ alkylsulfonyl group, R[2] is one group selected from the group consisting of a hydrogen atom, a halogen atom, a cyano group, an optionally substituted $C_{1-6}$ alkyl group and an optionally substituted 5- to 7-membered monocyclic heterocyclic group containing 1 to 4 heteroatoms selected from an oxygen atom, a nitrogen atom and a sulfur atom, R[3] is one group selected from the group consisting of a hydrogen atom, a halogen atom, a hydroxy group, a cyano group, an optionally substituted $C_{1-6}$ alkyl group and an optionally substituted $C_{1-6}$ alkyloxy group, and R[4] is one group selected from the group consisting of a hydrogen atom, a halogen atom, a carboxy group, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted $C_{7-11}$ monocyclic or polycyclic aralkyl group, an optionally substituted 5- to 7-membered monocyclic heterocyclic group containing 1 to 4 heteroatoms selected from an oxygen atom, a nitrogen atom and a sulfur atom, a di-$C_{1-6}$ alkylamino group, an optionally substituted $C_{3-7}$ cycloalkylamino group, an optionally substituted $C_{1-6}$ alkyloxy group, an optionally substituted cycloalkyloxy group, an optionally substituted $C_{6-10}$ monocyclic or polycyclic aryloxy group, an optionally substituted 5- to 7-membered monocyclic heterocyclyloxy group containing 1 to 4 heteroatoms selected from an oxygen atom, a nitrogen atom and a sulfur atom, an optionally substituted $C_{1-6}$ alkylsulfonyl group, an optionally substituted $C_{1-6}$ alkylcarbonyl group, a mono-$C_{1-6}$ alkylaminocarbonyl group, a di-$C_{1-6}$ alkylaminocarbonyl group, an optionally substituted $C_{1-6}$ alkyloxycarbonyl group and an optionally substituted hydroxyaminocarbonyl group.

[4] A compound selected from (S)-5-chloro-7-isopropyl-2-(2-methylpiperazin-1-yl)benzoxazole, (S)-5-chloro-7-methoxy-2-(2-methylpiperazin-1-yl)benzoxazole, (S)-5-chloro-7-acetyl-2-(2-methylpiperazin-1-yl)benzoxazole, meso-5-chloro-2-(2,6-cis-dimethylpiperazin-1-yl)-7-methylbenzoxazole, (S)-5-fluoro-7-methyl-2-(2-methylpiperazin-1-yl)benzoxazole, (S)-5-bromo-7-methyl-2-(2-methylpiperazin-1-yl)benzoxazole, (S)-5-chloro-7-isopropoxy-2-(2-methylpiperazin-1-yl)benzoxazole, (S)-5-chloro-7-ethyl-2-(2-methylpiperazin-1-yl)benzoxazole, (S)-5-chloro-7-ethoxycarbonyl-2-(2-methylpiperazin-1-yl)benzoxazole, (S)-5-chloro-7-cyano-2-(2-methylpiperazin-1-yl)benzoxazole, (S)-5-chloro-7-ethyl-2-(2-isopropylpiperazin-1-yl)benzoxazole, (S)-5-chloro-7-ethyl-2-(2-isobutylpiperazin-1-yl)benzoxazole, (S)-2-(2-n-butylpiperazin-1-yl)-5-chloro-7-ethylbenzoxazole, (S)-5-chloro-7-ethyl-2-(2-ethylpiperazin-1-yl)benzoxazole, (S)-5-chloro-7-hydroxymethyl-2-(2-methylpiperazin-1-yl)benzoxazole, (S)-5-chloro-2-(2-methylpiperazin-1-yl)-7-(thiophen-3-yl)benzoxazole, (S)-5-chloro-7-(furan-3-yl)-2-(2-methylpiperazin-1-yl)benzoxazole, (S)-5-chloro-2-(2-methylpiperazin-1-yl)-7-(thiophen-2-yl)benzoxazole, (S)-5-chloro-2-(2-methylpiperazin-1-yl)-7-phenylbenzoxazole, (S)-5-chloro-2-(2-methylpiperazin-1-yl)-7-(pyrrolidin-1-yl)benzoxazole, (S)-5-chloro-2-(2-methylpiperazin-1-yl)-7-(morpholin-1-yl)benzoxazole, (S)-5-chloro-2-(2-methylpiperazin-1-yl)-7-(piperidin-1-yl)benzoxazole, (S)-5-chloro-7-(furan-2-yl)-2-(2-methylpiperazin-1-yl)benzoxazole, (S)-5-chloro-7-(cyclopentylamino)-2-(2-methylpiperazin-1-yl)benzoxazole,
(S)-5-chloro-7-diethylamino-2-(2-methylpiperazin-1-yl)benzoxazole,
(S)-5-chloro-7-dimethylamino-2-(2-methylpiperazin-1-yl)benzoxazole,
(S)-5-chloro-7-cyclopropyl-2-(2-methylpiperazin-1-yl)benzoxazole,
(S)-5-chloro-7-(cyclopentyloxy)-2-(2-methylpiperazin-1-yl)benzoxazole,
(S)-5-chloro-7-ethoxy-2-(2-methylpiperazin-1-yl)benzoxazole,
(S)-5-chloro-2-(2-methylpiperazin-1-yl)-7-n-propoxybenzoxazole,
(S)-5-chloro-7-cyclopentyl-2-(2-methylpiperazin-1-yl)benzoxazole,
(S)-7-n-butyl-5-chloro-2-(2-methylpiperazin-1-yl)benzoxazole,
(S)-5-chloro-2-(2-methylpiperazin-1-yl)-7-(1H-pyrazol-1-yl)benzoxazole,
(S)-5-chloro-2-(2-methylpiperazin-1-yl)-7-(oxazol-2-yl)benzoxazole,
(S)-5-chloro-2-(2-methylpiperazin-1-yl)-7-(thiazol-2-yl)benzoxazole,
(S)-5-chloro-7-(1H-imidazol-1-yl)-2-(2-methylpiperazin-1-yl)benzoxazole,
(S)-5-chloro-2-(2-methylpiperazin-1-yl)-7-(thiazol-4-yl)benzoxazole,
(S)-5-chloro-2-(2-methylpiperazin-1-yl)-7-(thiazol-5-yl)benzoxazole,
(S)-5-chloro-7-(5-methylfuran-2-yl)-2-(2-methylpiperazin-1-yl)benzoxazole,
(S)-5-chloro-7-(4-methyl-1H-pyrazol-1-yl)-2-(2-methylpiperazin-1-yl)benzoxazole,
(S)-5-chloro-2-(2-methylpiperazin-1-yl)-7-(pyridin-2-yl)benzoxazole,
(S)-5-chloro-2-(2-methylpiperazin-1-yl)-7-(pyridin-3-yl)benzoxazole,
(S)-5-chloro-2-(2-methylpiperazin-1-yl)-7-(pyridin-4-yl)benzoxazole,
(S)-5-chloro-7-cyclohexyl-2-(2-methylpiperazin-1-yl)benzoxazole,
(S)-5-chloro-2-(2-methylpiperazin-1-yl)-7-(2H-1,2,3-triazol-2-yl)benzoxazole,
(S)-5-chloro-2-(2-methylpiperazin-1-yl)-7-(1H-1,2,4-triazol-1-yl)benzoxazole,
(S)-5-chloro-7-isobutyl-2-(2-methylpiperazin-1-yl)benzoxazole,
(S)-5-chloro-2-(2-methylpiperazin-1-yl)-7-(2-hydroxymethylphenyl)benzoxazole,
(S)-5-chloro-7-(1-methyl-1H-imidazol-2-yl)-2-(2-methylpiperazin-1-yl)benzoxazole,
(S)-5-chloro-7-(1H-imidazol-2-yl)-2-(2-methylpiperazin-1-yl)benzoxazole,
(S)-5-chloro-7-(cyclohexylmethyl)-2-(2-methylpiperazin-1-yl)benzoxazole,
(S)-5-chloro-7-(cyclohexyloxy)-2-(2-methylpiperazin-1-yl)benzoxazole,
(S)-5-chloro-7-(cyclopropylmethoxy)-2-(2-methylpiperazin-1-yl)benzoxazole,
(S)-5-chloro-7-(isothiazol-3-yl)-2-(2-methylpiperazin-1-yl)benzoxazole,
(S)-5-chloro-7-(5-hydroxymethylthiazol-2-yl)-2-(2-methylpiperazin-1-yl)benzoxazole,
(S)-5-chloro-2-(2-methylpiperazin-1-yl)-7-(pyrimidin-2-yl)benzoxazole,
(S)-5-chloro-7-(5-chlorothiophen-2-yl)-2-(2-methylpiperazin-1-yl)benzoxazole,
(S)-5-chloro-7-(5-chloropyridin-2-yl)-2-(2-methylpiperazin-1-yl)benzoxazole,
(S)-5-chloro-7-(4-chloropyridin-2-yl)-2-(2-methylpiperazin-1-yl)benzoxazole,
(S)-5-chloro-7-(6-fluoropyridin-2-yl)-2-(2-methylpiperazin-1-yl)benzoxazole,
(S)-5-chloro-7-(3-fluoropyridin-2-yl)-2-(2-methylpiperazin-1-yl)benzoxazole,
(S)-5-chloro-7-(5-cyanothiazol-2-yl)-2-(2-methylpiperazin-1-yl)benzoxazole,
(S)-5-chloro-2-(2-methylpiperazin-1-yl)-7-(5-methylthiazol-2-yl)benzoxazole,
(S)-5-chloro-7-(2-chlorothiophen-3-yl)-2-(2-methylpiperazin-1-yl)benzoxazole,
(S)-5-chloro-7-(5-carbamoylthiazol-2-yl)-2-(2-methylpiperazin-1-yl)benzoxazole,
(S)-5-chloro-7-(3-cyanopyridin-2-yl)-2-(2-methylpiperazin-1-yl)benzoxazole,
(S)-5-chloro-7-(5-fluorothiophen-2-yl)-2-(2-methylpiperazin-1-yl)benzoxazole,
(S)-5-chloro-2-(2-methylpiperazin-1-yl)-7-(3-methylpyridin-2-yl)benzoxazole
(S)-5-chloro-2-(2-methylpiperazin-1-yl)-7-(2-methylthiazol-4-yl)benzoxazole,
(S)-5-chloro-2-(2-methylpiperazin-1-yl)-7-phenoxybenzoxazole,
(S)-5-chloro-2-(2-methylpiperazin-1-yl)-7-(2-oxo-pyrolidin-1-yl)benzoxazole,
(S)-5-chloro-2-(2-methylpiperazin-1-yl)-7-(2-oxo-oxazolidin-3-yl)benzoxazole,
(S)-5-chloro-7-(5-fluoropyridin-2-yl)-2-(2-methylpiperazin-1-yl)benzoxazole,
(S)-5-chloro-7-(5-chlorothiazol-2-yl)-2-(2-methylpiperazin-1-yl)benzoxazole,
(S)-7-benzyl-5-chloro-2-(2-methylpiperazin-1-yl)benzoxazole,
(S)-5-chloro-7-(5-(hydroxymethyl)thiazol-4-yl)-2-(2-methylpiperazin-1-yl)benzoxazole,
(S)-5-chloro-2-(2-methylpiperazin-1-yl)-7-(thiazol-2-yloxy)benzoxazole,
(S)-5-chloro-2-(2-methylpiperazin-1-yl)-7-(5-nitrothiazol-2-yl)benzoxazole,
(S)-5-chloro-7-(3-methoxypyridin-2-yl)-2-(2-methylpiperazin-1-yl)benzoxazole,
5-chloro-2-((S)-2-methylpiperazin-1-yl)-7-(tetrahydrofuran-2-yl)benzoxazole,
(S)-5-chloro-7-(4-fluorophenyl)-2-(2-methylpiperazin-1-yl)benzoxazole,
(S)-5-chloro-2-(2-methylpiperazin-1-yl)-7-(pyridin-2-yl)-4-(trifluoromethyl)benzoxazole,
(S)-5-chloro-2-(2-methylpiperazin-1-yl)-7-(1H-pyrazol-1-yl)-4-(trifluoromethyl)benzoxazole,
(S)-5-chloro-2-(2-methylpiperazin-1-yl)-7-(thiazol-2-yl)-4-(trifluoromethyl)benzoxazole,
(S)-5-chloro-2-(2-methylpiperazin-1-yl)-7-(pyridin-2-yl)-6-(trifluoromethyl)benzoxazole,
(S)-5-chloro-2-(2-methylpiperazin-1-yl)-7-(pyridin-2-yl)-4-(trifluoromethoxy)benzoxazole,
(S)-5-chloro-2-(2-methylpiperazin-1-yl)-7-(thiazol-2-yl)-4-(trifluoromethoxy)benzoxazole,
(S)-5-chloro-2-(2-methylpiperazin-1-yl)-7-(1H-pyrazol-1-yl)-4-(trifluoromethoxy)benzoxazole,
(S)-4,5-difluoro-2-(2-methylpiperazin-1-yl)-7-(pyridin-2-yl)benzoxazole, (S)-4,5-difluoro-2-(2-methylpiperazin-1-yl)-7-(thiazol-2-yl)benzoxazole,
(S)-4,5-difluoro-2-(2-methylpiperazin-1-yl)-7-(1H-pyrazol-1-yl)benzoxazole,
(S)-5-chloro-6-fluoro-2-(2-methylpiperazin-1-yl)-7-(pyridin-2-yl)benzoxazole
(S)-5-chloro-6-fluoro-2-(2-methylpiperazin-1-yl)-7-(thiazol-2-yl)benzoxazole,
(S)-5-chloro-6-fluoro-2-(2-methylpiperazin-1-yl)-7-(1H-pyrazol-1-yl)benzoxazole,
(S)-5-chloro-2-(2-methylpiperazin-1-yl)-7-n-propylbenzoxazole,
(S)-5-chloro-7-dimethylaminocarbonyl-2-(2-methylpiperazin-1-yl)benzoxazole,
(S)-5-chloro-7-diethylaminocarbonyl-2-(2-methylpiperazin-1-yl)benzoxazole,
(S)-5-chloro-7-hydroxyaminocarbonyl-2-(2-methylpiperazin-1-yl)benzoxazole,
(S)-5-chloro-7-carboxy-2-(2-methylpiperazin-1-yl)benzoxazole,
(S)-5-chloro-7-methylaminocarbonyl-2-(2-methylpiperazin-1-yl)benzoxazole,
(S)-5-chloro-7-ethylaminocarbonyl-2-(2-methylpiperazin-1-yl)benzoxazole,
(S)-5-fluoro-2-(2-methylpiperazin-1-yl)-7-(pyridin-2-yl)benzoxazole,
(S)-5-fluoro-2-(2-methylpiperazin-1-yl)-7-(thiazol-2-yl)benzoxazole,
(S)-5-fluoro-2-(2-methylpiperazin-1-yl)-7-(oxazol-2-yl)benzoxazole,
(S)-5-chloro-2-(2-methylpiperazin-1-yl)-7-(1,2,4-oxadiazol-3-yl)benzoxazole,
(S)-5-chloro-7-(4,5-dihydrooxazol-2-yl)-2-(2-methylpiperazin-1-yl)benzoxazole,
(S)-5-chloro-7-(methoxymethyl)-2-(2-methylpiperazin-1-yl)benzoxazole,
(S)-5-chloro-7-(isoxazol-3-yl)-2-(2-methylpiperazin-1-yl)benzoxazole,
(S)-5-chloro-7-(isoxazol-5-yl)-2-(2-methylpiperazin-1-yl)benzoxazole,
(S)-7-bromo-5-chloro-2-(2-methylpiperazin-1-yl)benzoxazole,
(S)-5-cyano-2-(2-methylpiperazin-1-yl)-7-(pyridin-2-yl)benzoxazole,
(S)-5-cyano-2-(2-methylpiperazin-1-yl)-7-(thiazol-2-yl)benzoxazole,
(S)-5-cyano-2-(2-methylpiperazin-1-yl)-7-(oxazol-2-yl)benzoxazole,
(S)-5-methyl-2-(2-methylpiperazin-1-yl)-7-(pyridin-2-yl)benzoxazole,
(S)-5-methyl-2-(2-methylpiperazin-1-yl)-7-(thiazol-2-yl)benzoxazole,
(S)-5-methyl-2-(2-methylpiperazin-1-yl)-7-(oxazol-2-yl)benzoxazole,
(S)-5-fluoro-2-(2-methylpiperazin-1-yl)-7-(pyridin-2-yl)-4-(trifluoromethyl)benzoxazole,
(S)-5-fluoro-2-(2-methylpiperazin-1-yl)-7-(thiazol-2-yl)-4-(trifluoromethyl)benzoxazole,
(S)-5-fluoro-2-(2-methylpiperazin-1-yl)=7-(1H-pyrazol-1-yl)-4-(trifluoromethyl)benzoxazole,
(S)-5-chloro-4,6-difluoro-2-(2-methylpiperazin-1-yl)-7-(pyridin-2-yl)benzoxazole,
(S)-5-chloro-4,6-difluoro-2-(2-methylpiperazin-1-yl)-7-(thiazol-2-yl)benzoxazole,
(S)-4,5,6-trifluoro-2-(2-methylpiperazin-1-yl)-7-(pyridin-2-yl)benzoxazole,
(S)-4,5,6-trifluoro-2-(2-methylpiperazin-1-yl)-7-(thiazol-2-yl)benzoxazole,
(S)-4,5,6-trifluoro-2-(2-methylpiperazin-1-yl)-7-(1H-pyrazol-1-yl)benzoxazole,
(S)-2-(2-methylpiperazin-1-yl)-7-(pyridin-2-yl)-5-(trifluoromethyl)benzoxazole,
(S)-2-(2-methylpiperazin-1-yl)-7-(thiazol-2-yl)-5-(trifluoromethyl)benzoxazole,
(S)-2-(2-methylpiperazin-1-yl)-7-(oxazol-2-yl)-5-(trifluoromethyl)benzoxazole,
(S)-5-chloro-4-fluoro-2-(2-methylpiperazin-1-yl)-7-(pyridin-2-yl)benzoxazole,
(S)-5-chloro-4-fluoro-2-(2-methylpiperazin-1-yl)-7-(thiazol-2-yl)benzoxazole,
(S)-5-chloro-4-fluoro-2-(2-methylpiperazin-1-yl)-7-(1H-pyrazol-1-yl)benzoxazole,
(S)-5-chloro-4-methyl-2-(2-methylpiperazin-1-yl)-7-(pyridin-2-yl)benzoxazole,
(S)-5-chloro-4-methyl-2-(2-methylpiperazin-1-yl)-7-(thiazol-2-yl)benzoxazole,
(S)-5-chloro-4-methyl-2-(2-methylpiperazin-1-yl)-7-(1H-pyrazol-1-yl)benzoxazole,
(S)-5-fluoro-2-(2-methylpiperazin-1-yl)-7-(pyridin-2-yl)-4-(trifluoromethoxy)benzoxazole,
(S)-5-fluoro-2-(2-methylpiperazin-1-yl)-7-(thiazol-2-yl)-4-(trifluoromethoxy)benzoxazole,
(S)-5-fluoro-2-(2-methylpiperazin-1-yl)-7-(1H-pyrazol-1-yl)-4-(trifluoromethoxy)benzoxazole,
(S)-5-chloro-6-methyl-2-(2-methylpiperazin-1-yl)-7-(pyridin-2-yl)benzoxazole,
(S)-5-chloro-6-methyl-2-(2-methylpiperazin-1-yl)-7-(thiazol-2-yl)benzoxazole,
(S)-5-chloro-6-methyl-2-(2-methylpiperazin-1-yl)-7-(1H-pyrazol-1-yl)benzoxazole,
(S)-5-chloro-6-methoxy-2-(2-methylpiperazin-1-yl)-7-(pyridin-2-yl)benzoxazole,
(S)-5-chloro-6-methoxy-2-(2-methylpiperazin-1-yl)-7-(thiazol-2-yl)benzoxazole,
(S)-5-chloro-6-cyano-2-(2-methylpiperazin-1-yl)-7-(thiazol-2-yl)benzoxazole,
(S)-5-chloro-4-cyano-2-(2-methylpiperazin-1-yl)-7-(thiazol-2-yl)benzoxazole,
(S)-5-fluoro-2-(2-methylpiperazin-1-yl)-7-(thiazol-2-yl)-6-(trifluoromethyl)benzoxazole,
(S)-5-chloro-2-(2-methylpiperazin-1-yl)-7-(methylsulfonyl)benzoxazole,
(S)-5-chloro-4-iodo-2-(2-methylpiperazin-1-yl)-7-(pyridin-2-yl)benzoxazole,
(S)-5-chloro-6-iodo-2-(2-methylpiperazin-1-yl)-7-(pyridin-2-yl)benzoxazole,
(S)-5-chloro-2-(2-methylpiperazin-1-yl)-4-phenyl-7-(pyridin-2-yl)benzoxazole,
(S)-5-chloro-4-cyclopropyl-2-(2-methylpiperazin-1-yl)-7-(pyridin-2-yl)benzoxazole,
(S)-5-chloro-2-(2-methylpiperazin-1-yl)-4-(methylthio)-7-(pyridin-2-yl)benzoxazole,
(S)-5-chloro-2-(2-methylpiperazin-1-yl)-4-(methylsulfonyl)-7-(pyridin-2-yl)benzoxazole,
(S)-6-bromo-5-chloro-2-(2-methylpiperazin-1-yl)-7-(pyridin-2-yl)benzoxazole,
(S)-5-chloro-4-methoxy-2-(2-methylpiperazin-1-yl)-7-(pyridin-2-yl)benzoxazole,
(S)-5-chloro-7-methyl-2-(2-methylpiperazin-1-yl)benzoxazole,
(S)-5-chloro-4-methoxy-2-(2-methylpiperazin-1-yl)-7-(thiazol-2-yl)benzoxazole, (S)-5-chloro-4-methoxy-2-(2-methylpiperazin-1-yl)-7-(1H-pyrazol-1-yl)benzoxazole,
(R)-5-chloro-2-(2-methylpiperazin-1-yl)-7-(pyridin-2-yl)-4-(trifluoromethoxy)benzoxazole,
(R)-5-chloro-2-(2-methylpiperazin-1-yl)-7-(thiazol-2-yl)-4-(trifluoromethoxy)benzoxazole,
(R)-5-chloro-2-(2-methylpiperazin-1-yl)-7-(1H-pyrazol-1-yl)-4-(trifluoromethoxy)benzoxazole,
(S)-5-chloro-2-(2-methylpiperazin-1-yl)-7-(thiazol-2-yl)-6-(trifluoromethoxy)benzoxazole,
(S)-5-chloro-6-methoxy-7-methyl-2-(2-methylpiperazin-1-yl)benzoxazole,
(S)-5-chloro-6-hydroxy-7-methyl-2-(2-methylpiperazin-1-yl)benzoxazole,
(S)-4-bromo-6-chloro-2-(2-methylpiperazin-1-yl)benzoxazole,
(S)-6-chloro-4-(furan-2-yl)-2-(2-methylpiperazin-1-yl)benzoxazole,
(R)-6-chloro-4-(furan-2-yl)-2-(2-methylpiperazin-1-yl)benzoxazole,
(S)-6-chloro-2-(2-methylpiperazin-1-yl)-4-(1H-pyrazol-1-yl)benzoxazole,
(S)-5-bromo-2-(2-methylpiperazin-1-yl)benzoxazole,
(S)-5-cyano-7-methoxy-2-(2-methylpiperazin-1-yl)benzoxazole,
(S)-5-chloro-6,7-dimethoxy-2-(2-methylpiperazin-1-yl)benzoxazole,
(S)-5-chloro-6-methyl-2-(2-methylpiperazin-1-yl)benzoxazole,
(S)-5-chloro-6-methoxy-2-(2-methylpiperazin-1-yl)benzoxazole,
(S)-7-methyl-5-(pyrrolidin-1-yl)-2-(2-methylpiperazin-1-yl)benzoxazole,
(S)-7-methyl-5-(thiophen-3-yl)-2-(2-methylpiperazin-1-yl)benzoxazole,
(R)-5-chloro-7-ethyl-2-(2-methylpiperazin-1-yl)benzoxazole,
5-chloro-2-(piperazin-1-yl)-7-(thiazol-2-yl)-4-(trifluoromethoxy)benzoxazole,
(R)-5-chloro-2-(3-methylpiperazin-1-yl)-7-(thiazol-2-yl)-4-(trifluoromethoxy)benzoxazole,
(S)-5-chloro-2-(3-methylpiperazin-1-yl)-7-(thiazol-2-yl)-4-(trifluoromethoxy)benzoxazole,
(R)-5-chloro-2-(2-methylpiperazin-1-yl)-7-(pyridin-2-yl)-4-(trifluoromethyl)benzoxazole,
(R)-5-chloro-2-(2-methylpiperazin-1-yl)-7-(thiazol-2-yl)-4-(trifluoromethyl)benzoxazole, and
(R)-5-chloro-2-(2-methylpiperazin-1-yl)-7-(1H-pyrazol-1-yl)-4-(trifluoromethyl)benzoxazole,
or a pharmacologically acceptable salt thereof.

[5] A PDE4 inhibitor comprising a compound represented by formula (1a):

[Chemical Formula 2]

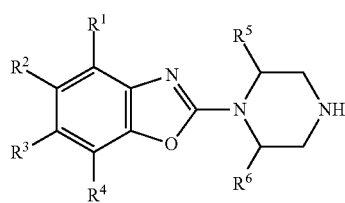

(1a)

wherein
$R^1$, $R^2$, $R^3$ and $R^4$ are each independently one group selected from the group consisting of a hydrogen atom, a halogen atom, a hydroxy group, a carboxy group, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted $C_{7-11}$ monocycle or polycyclic aralkyl group, an optionally substituted 4- to 10-membered monocycle or bicyclic heterocyclic group containing 1 to 4 heteroatoms selected from an oxygen atom, a nitrogen atom and a sulfur atom, a di-$C_{1-6}$ alkylamino group, an optionally substituted $C_{3-7}$ cycloalkylamino group, an optionally substituted $C_{1-6}$ alkyloxy group, an optionally substituted $C_{3-7}$ cycloalkyloxy group, an optionally substituted $C_{6-10}$ monocyclic or polycyclic aryloxy group, an optionally substituted $C_{7-11}$ monocyclic or polycyclic aralkyloxy group, an optionally substituted 4- to 10-membered monocycle or bicyclic heterocyclyloxy group containing 1 to 4 heteroatoms selected from an oxygen atom, a nitrogen atom and a sulfur atom, an optionally substituted $C_{1-6}$ alkylthio group, an optionally substituted $C_{1-6}$ alkylsulfonyl group, an optionally substituted $C_{1-6}$ alkylcarbonyl group, a mono-$C_{1-6}$ alkylaminocarbonyl group, a di-$C_{1-6}$ alkylaminocarbonyl group, an optionally substituted $C_{1-6}$ alkyloxycarbonyl group and an optionally substituted hydroxyaminocarbonyl group, and
$R^5$ and $R^6$ are each independently a hydrogen atom or a $C_{1-6}$ alkyl group;
or a pharmacologically acceptable salt thereof as an active ingredient.

[6] The PDE4 inhibitor according to [5], wherein $R^2$ is one group selected from the group consisting of a hydrogen atom, a halogen atom, a cyano group, an optionally substituted $C_{1-6}$ alkyl group and an optionally substituted 5- to 7-membered monocycle heterocyclic group containing 1 to 4 heteroatoms selected from an oxygen atom, a nitrogen atom and a sulfur atom.

[7] The PDE4 inhibitor according to [5], wherein
$R^1$ is one group selected from the group consisting of a hydrogen atom, a halogen atom, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted 5- to 7-membered monocyclic heterocyclic group containing 1 to 4 heteroatoms selected from an oxygen atom, a nitrogen atom and a sulfur atom, an optionally substituted $C_{1-6}$ alkyloxy group, an optionally substituted $C_{1-6}$ alkylthio group and an optionally substituted $C_{1-6}$ alkylsulfonyl group,
$R^2$ is one group selected from the group consisting of a hydrogen atom, a halogen atom, a cyano group, an optionally substituted $C_{1-6}$ alkyl group and an optionally substituted 5- to 7-membered monocyclic heterocyclic group containing 1 to 4 heteroatoms selected from an oxygen atom, a nitrogen atom and a sulfur atom,
$R^3$ is one group selected from the group consisting of a hydrogen atom, a halogen atom, a hydroxy group, a cyano group, an optionally substituted $C_{1-6}$ alkyl group and an optionally substituted $C_{1-6}$ alkyloxy group, and
$R^4$ is one group selected from the group consisting of a hydrogen atom, a halogen atom, a carboxy group, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted $C_{7-11}$ monocycle or polycyclic aralkyl group, an optionally substituted 5- to 7-membered monocyclic heterocyclic group containing 1 to 4 heteroatoms selected from an oxygen atom, a nitrogen atom and a sulfur atom, a di-$C_{1-6}$ alkylamino group, an optionally substituted $C_{3-7}$ cycloalkylamino group, an optionally substituted $C_{1-6}$ alkyloxy group, an optionally substituted $C_{3-7}$ cycloalkyloxy group, an optionally substituted $C_{6-10}$ monocyclic or polycyclic aryloxy group, an optionally substituted 5- to 7-membered monocycle heterocyclyloxy group containing 1 to 4 heteroatoms selected from an oxygen atom, a nitrogen atom and a sulfur atom, an optionally substituted $C_{1-6}$ alkylsulfonyl group, an optionally substituted $C_{1-6}$ alkylcarbonyl group, a mono-$C_{1-6}$ alkylaminocarbonyl group, a di-$C_{1-6}$ alkylaminocarbonyl group, an optionally substituted $C_{1-6}$ alkyloxycarbonyl group and an optionally substituted hydroxyaminocarbonyl group.

[8] A PDE4 inhibitor comprising a compound represented by formula (1) or a pharmacologically acceptable salt thereof as an active ingredient:

[Chemical Formula 3]

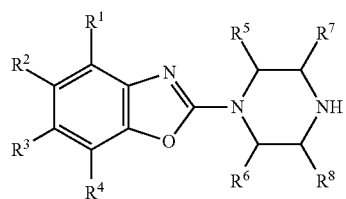

(1)

wherein $R^1$ is one group selected from the group consisting of a hydrogen atom, a halogen atom, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted 5- to 7-membered monocyclic heterocyclic group containing 1 to 4 heteroatoms selected from an oxygen atom, a nitrogen atom and a sulfur atom, an optionally substituted $C_{1-6}$ alkyloxy group, an optionally substituted $C_{1-6}$ alkylthio group and an optionally substituted $C_{1-6}$ alkylsulfonyl group, $R^2$ is one group selected from the group consisting of a hydrogen atom, a halogen atom, a cyano group, an optionally substituted $C_{1-6}$ alkyl group and an optionally substituted 5- to 7-membered monocyclic heterocyclic group containing 1 to 4 heteroatoms selected from an oxygen atom, a nitrogen atom and a sulfur atom, $R^3$ is one group selected from the group consisting of a hydrogen atom, a halogen atom, a hydroxy group, a cyano group, an optionally substituted $C_{1-6}$ alkyl group and an optionally substituted $C_{1-6}$ alkyloxy group, and $R^4$ is one group selected from the group consisting of a hydrogen atom, a halogen atom, a carboxy group, a cyano group, an optionally substituted $C_{1-6}$ alkyl group, an optionally substituted $C_{3-7}$cycloalkyl group, an optionally substituted $C_{6-10}$ monocyclic or polycyclic aryl group, an optionally substituted $C_{7-11}$ monocycle or polycyclic aralkyl group, an optionally substituted 5- to 7-membered monocyclic heterocyclic group containing 1 to 4 heteroatoms selected from an oxygen atom, a nitrogen atom and a sulfur atom, a di-$C_{1-6}$alkylamino group, an optionally substituted $C_{3-7}$cycloalkylamino group, an optionally substituted $C_{1-6}$ alkyloxy group, an optionally substituted $C_{3-7}$ cycloalkyloxy group, an optionally substituted $C_{6-10}$ monocyclic or polycyclic aryloxy group, an optionally substituted 5- to 7-membered monocycle heterocyclyloxy group containing 1 to 4 heteroatoms selected from an oxygen atom, a nitrogen atom and a sulfur atom, an optionally substituted $C_{1-6}$ alkylsulfonyl group, an optionally substituted $C_{1-6}$ alkylcarbonyl group, a mono-$C_{1-6}$ alkylaminocarbonyl group, a di-$C_{1-6}$alkylaminocarbonyl group, an optionally substituted $C_{1-6}$ alkyloxycarbonyl group and an optionally substituted hydroxyaminocarbonyl group, and $R^5$ to $R^8$ are each independently a hydrogen atom or a $C_{1-6}$ alkyl group.

[9] A PDE4 inhibitor comprising the compound or the pharmacologically acceptable salt thereof according to [4] as an active ingredient.

[10] A pharmaceutical composition comprising the compound or the pharmacologically acceptable salt thereof according to any one of [1] to [4] as an active ingredient.

[11] A pharmaceutical composition comprising the PDE4 inhibitor according to any one of [5] to [9] as an active ingredient.

[12] A therapeutic agent for diseases caused by PDE4, comprising the compound or the pharmacologically acceptable salt thereof according to any one of [1] to [4] as an active ingredient.

[13] A method for inhibiting PDE4, comprising administering the compound or the pharmacologically acceptable salt thereof according to any one of [1] to [4] to a patient.

[14] A method for treating diseases caused by PDE4, comprising administering the compound or the pharmacologically acceptable salt thereof according to any one of [1] to [4] to a patient.

[15] The compound or the pharmaceutically acceptable salt thereof according to any one of [1] to [4], wherein the compound or the pharmacologically acceptable salt thereof is for use in the inhibition of PDE4.

[16] The compound or the pharmaceutically acceptable salt thereof according to any one of [1] to [4], wherein the compound or pharmacologically acceptable salt thereof is for use in the treatment of diseases caused by PDE4.

[17] Use of the compound or the pharmacologically acceptable salt thereof according to any one of [1] to [4] for producing a PDE4 inhibitor.

[18] Use of the compound or the pharmacologically acceptable salt thereof according to any one of [1] to [4] for manufacturing a therapeutic agent for diseases caused by PDE4.

Advantageous Effects of Invention

The compound represented by formula (1) or the pharmacologically acceptable salt of the present invention has an excellent PDE4 inhibitory effect and is useful in the treatment or prevention of various diseases caused by PDE4. Examples of the diseases caused by PDE4 include asthma, chronic obstructive pulmonary disease (COPD), interstitial pneumonia, inflammatory bowel disease, Crohn's disease, multiple sclerosis, rheumatism, atopic dermatitis, psoriatic arthritis, psoriasis vulgaris, sarcoidosis, systemic lupus erythematosus, depression, learning and memory disorders, Parkinson's disease and Alzheimer's disease.

DESCRIPTION OF EMBODIMENTS

Hereinafter, the terms used in the present specification will be described specifically.

In the present specification, the halogen atom refers to a fluorine atom, a chlorine atom, a bromine atom or an iodine atom and is preferably a fluorine atom, a chlorine atom, a bromine atom or an iodine atom.

In the present specification, the $C_{1-6}$ alkyl group refers to a linear or branched alkyl group having 1 to 6 carbon atoms. Examples of the $C_{1-6}$ alkyl group include a methyl group, an ethyl group, a n-propyl group, an isopropyl group, a n-butyl group, an isobutyl group, a tert-butyl group, a n-pentyl group, an isoamyl group and a n-hexyl group, and preferred is a methyl group, an ethyl group, a n-propyl group, an isopropyl group, a n-butyl group or an isobutyl group.

In the present specification, the $C_{3-7}$ cycloalkyl group refers to a cyclic alkyl group having 3 to 7 carbon atoms. Examples of the $C_{3-7}$ cycloalkyl group include a cyclopropyl group, a cyclobutyl group, a cyclopentyl group, a cyclohexyl group and a cycloheptyl group, and preferred is a cyclopropyl group, a cyclopentyl group or a cyclohexyl group.

In the present specification, the $C_{6-10}$ monocyclic or polycyclic aryl group refers to a monocyclic or polycyclic aromatic hydrocarbon group having 6 to 10 carbon atoms. Examples of the $C_{6-10}$ monocyclic or polycyclic aryl group include a phenyl group and a naphthyl group, and preferred is a phenyl group.

In the present specification, the $C_{7-11}$ monocyclic or polycyclic aralkyl group refers to an alkyl group having a monocyclic or polycyclic aromatic hydrocarbon group having 7 to 11 carbon atoms. Examples of the $C_{7-11}$ monocyclic or polycyclic aralkyl group include a benzyl group and a naphthylmethyl group, and preferred is a benzyl group.

In the present specification, the 4- to 10-membered monocyclic or bicyclic heterocyclic group refers to a 4- to 10-membered monocyclic or bicyclic heterocyclic ring containing 1 to 4 heteroatoms selected from an oxygen atom, a nitrogen atom and a sulfur atom. Examples of the 4- to 10-membered monocyclic or bicyclic heterocyclic group include a tetrahydrofuranyl group, a pyrrolidyl group, a piperidyl group, an oxazolidinyl group, a morpholinyl group, a thienyl group, a furanyl group, a pyrazolyl group, an oxazolyl group, an isoxazolyl group, an oxadiazolyl group, a thiazolyl group, an isothiazolyl group, an imidazolyl group, a 1,2,3-triazolyl group, a 1,2,4-triazolyl group, a pyridyl group, a pyrimidyl group, an aziridinyl group, a tetrazolyl group, a quinolyl group and an isoquinolyl group, and preferred is a pyrrolidyl group, a morpholinyl group, a thienyl group, a furanyl group, a pyrazolyl group, an oxazolyl group, an isoxazolyl group, an oxadiazolyl group, a thiazolyl group, an isothiazolyl group, an imidazolyl group, a triazolyl group, a pyridyl group or a pyrimidyl group.

In the present specification, the di-$C_{1-6}$ alkylamino group refers to an amino group substituted by two $C_{1-6}$ alkyl groups mentioned above. Examples of the di-$C_{1-6}$ alkylamino group include a dimethylamino group, a diethylamino group and a methylethylamino group, and preferred is a dimethylamino group or a diethylamino group.

In the present specification, the $C_{3-7}$ cycloalkylamino group refers to an amino group substituted by the $C_{3-7}$ cycloalkyl group mentioned above. Examples of the $C_{3-7}$ cycloalkylamino group include a cyclobutylamino group, a cyclopentylamino group and a cyclohexylamino group, and preferred is a cyclopentylamino group.

In the present specification, the $C_{1-6}$ alkyloxy group refers to a group composed of an oxygen atom substituted by the $C_{1-6}$ alkyl group mentioned above. Examples of the $C_{1-6}$ alkyloxy group include a methoxy group, an ethoxy group, a n-propoxy group, an isopropoxy group, a n-butoxy group and an isobutoxy group, and preferred is a methoxy group, an ethoxy group, a n-propoxy group or an isopropoxy group.

In the present specification, the $C_{3-7}$ cycloalkyloxy group refers to a group composed of an oxygen atom substituted by the $C_{3-7}$ cycloalkyl group mentioned above. Examples of the $C_{3-7}$ cycloalkyloxy group include a cyclopropyloxy group, a cyclobutyloxy group, a cyclopentyloxy group and a cyclohexyloxy group, and preferred is a cyclopentyloxy group or a cyclohexyloxy group.

In the present specification, the $C_{6-10}$ monocyclic or polycyclic aryloxy group refers to a group composed of an oxygen atom substituted by the $C_{6-10}$ monocycle or polycyclic aryl group mentioned above. Examples of the $C_{6-10}$ monocycle or polycyclic aryloxy group include a phenyloxy group and a naphthyloxy group, and preferred is a phenyloxy group.

In the present specification, the $C_{7-11}$ monocyclic or polycyclic aralkyloxy group refers to a group composed of an oxygen atom substituted by the $C_{7-11}$ monocycle or polycyclic aralkyl group mentioned above. Examples of the $C_{7-11}$ monocyclic or polycyclic aralkyloxy group include a benzyloxy group and a naphthylmethyloxy group, and preferred is a benzyloxy group.

In the present specification, the 4- to 10-membered monocycle or bicyclic heterocyclyloxy group refers to a group composed of an oxygen atom substituted by the 4 to 10-membered monocyclic or bicyclic heterocyclic group mentioned above. Examples of the 4- to 10-membered monocyclic or bicyclic heterocyclyloxy group include a thiazolyloxy group and an oxazolyloxy group, and preferred is a thiazolyloxy group.

In the present specification, the $C_{1-6}$ alkylthio group refers to a group composed of a sulfur atom substituted by the $C_{1-6}$ alkyl group mentioned above. Examples of the $C_{1-6}$ alkylthio group include a methylthio group, an ethylthio group, a propylthio group and an isopropylthio group, and preferred is a methylthio group.

In the present specification, the $C_{1-6}$ alkylsulfonyl group refers to a sulfonyl group substituted by the $C_{1-6}$ alkyl group mentioned above. Examples of the $C_{1-6}$ alkylsulfonyl group include a methylsulfonyl group, an ethylsulfonyl group and a propylsulfonyl group, and preferred is a methylsulfonyl group.

In the present specification, the $C_{1-6}$ alkylcarbonyl group refers to a carbonyl group substituted by the $C_{1-6}$ alkyl group mentioned above. Examples of the $C_{1-6}$ alkylcarbonyl group include an acetyl group, an ethylcarbonyl group, a propylcarbonyl group and a butylcarbonyl group, and preferred is an acetyl group.

In the present specification, the mono-$C_{1-6}$ alkylaminocarbonyl group refers to an aminocarbonyl group substituted by one $C_{1-6}$ alkyl group mentioned above. Examples of the mono-$C_{1-6}$ alkylaminocarbonyl group include a methylaminocarbonyl group, an ethylaminocarbonyl group and a propylaminocarbonyl group, and preferred is a methylaminocarbonyl group or an ethylaminocarbonyl group.

In the present specification, the di-$C_{1-6}$ alkylaminocarbonyl group refers to an aminocarbonyl group substituted by two $C_{1-6}$ alkyl groups mentioned above. Examples of the di-$C_{1-6}$ alkylaminocarbonyl group include a dimethylaminocarbonyl group, a diethylaminocarbonyl group and a dipropylaminocarbonyl group, and preferred is a dimethylaminocarbonyl group or a diethylaminocarbonyl group.

In the present specification, the $C_{1-6}$ alkyloxycarbonyl group refers to a carbonyl group substituted by the $C_{1-6}$ alkyloxy group mentioned above. Examples of the $C_{1-6}$ alkyloxycarbonyl group include a methoxycarbonyl group, an ethoxycarbonyl group, a n-propoxycarbonyl group and an isopropoxycarbonyl group, and preferred is an ethoxycarbonyl group.

In the present specification, the hydroxyaminocarbonyl group refers to a carbonyl group substituted by an amino group substituted by a hydroxy group.

In the present specification, a substituent for the term "optionally substituted" can be any substituent as long as it is a group that can substitute each group, and each group may have one or more substituents. Examples of the group that can substitute each group include a halogen atom, a cyano group, a hydroxy group, a $C_{1-6}$ alkyl group, a $C_{3-6}$ cycloalkyl group, a hydroxy-$C_{1-6}$ alkyl group, a $C_{1-6}$ alkyloxy group, an aminocarbonyl group, an oxo group, a nitro group, a $C_{1-6}$ alkylthio group, a $C_{1-6}$ alkylsulfonyl group and a $C_{6-10}$ aryl group. The hydroxy-$C_{1-6}$ alkyl group refers to, for example, a $C_{1-6}$ alkyl group substituted by a hydroxy group and is, for example, a hydroxymethyl group. Also, examples of the $C_{1-6}$ alkyl group substituted by a fluorine atom include a trifluoromethyl group and a trifluoroethyl group, and examples of the $C_{1-6}$ alkyloxy group substituted by a fluorine atom include a trifluoromethoxy group.

One embodiment of the present invention is a compound represented by formula (1) or a pharmacologically acceptable salt thereof:

[Chemical Formula 4]

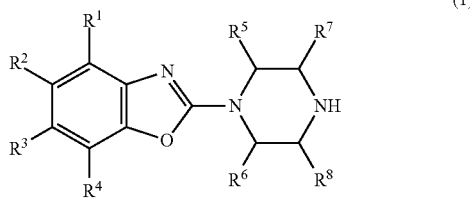

(1)

In formula (1), the group represented by $R^1$ is a hydrogen atom, a halogen atom, a cyano group, an optionally substituted $C_{1-6}$ alkyl group, an optionally substituted $C_{3-7}$cycloalkyl group, an optionally substituted $C_{6-10}$ monocyclic or polycyclic aryl group, an optionally substituted 5- to 7-membered monocyclic heterocyclic group containing 1 to 4 heteroatoms selected from an oxygen atom, a nitrogen atom and a sulfur atom, an optionally substituted $C_{1-6}$ alkyloxy group, an optionally substituted $C_{1-6}$ alkylthio group or an optionally substituted $C_{1-6}$ alkylsulfonyl group and is preferably a hydrogen atom, a fluorine atom, an iodine atom, a cyano group, a methyl group, a trifluoromethyl group, a cyclopropyl group, a phenyl group, a furanyl group, a pyrazolyl group, a methoxy group, a trifluoromethoxy group, a methylthio group or a methylsulfonyl group, more preferably a hydrogen atom, a fluorine atom, an iodine atom, a cyano group, a methyl group, a trifluoromethyl group, a cyclopropyl group, a phenyl group, a furanyl group, a pyrazolyl group, a methoxy group, a trifluoromethoxy group, a methylthio group or a methylsulfonyl group.

In formula (1), the group represented by $R^2$ is a hydrogen atom, a halogen atom, a cyano group, an optionally substituted $C_{1-6}$ alkyl group or an optionally substituted 5- to 7-membered monocycle heterocyclic group containing 1 to 4 heteroatoms selected from an oxygen atom, a nitrogen atom and a sulfur atom and is preferably a hydrogen atom, a fluorine atom, a chlorine atom, a bromine atom, a cyano group, a methyl group, a trifluoromethyl group, a pyrrolidyl group or a thienyl group, more preferably a hydrogen atom, a fluorine atom, a chlorine atom, a cyano group, a methyl group, a trifluoromethyl group or a thienyl group.

In formula (1), the group represented by $R^3$ is a hydrogen atom, a halogen atom, a hydroxy group, a cyano group, an optionally substituted $C_{1-6}$ alkyl group or an optionally substituted $C_{1-6}$ alkyloxy group and is preferably a hydrogen atom, a fluorine atom, an iodine atom, a hydroxy group, a cyano group, a methyl group, a trifluoromethyl group or a methoxy group, more preferably a hydrogen atom, a fluorine atom, a cyano group or a methyl group.

In formula (1), the group represented by $R^4$ is a hydrogen atom, a halogen atom, a carboxy group, a cyano group, an optionally substituted $C_{1-6}$ alkyl group, an optionally substituted $C_{3-7}$cycloalkyl group, an optionally substituted $C_{6-10}$ monocyclic or polycyclic aryl group, an optionally substituted $C_{7-11}$ monocyclic or polycyclic aralkyl group, an optionally substituted 5- to 7-membered monocyclic heterocyclic group containing 1 to 4 heteroatoms selected from an oxygen atom, a nitrogen atom and a sulfur atom, a di-$C_{1-6}$ alkylamino group, an optionally substituted $C_{3-7}$cycloalkylamino group, an optionally substituted $C_{1-6}$ alkyloxy group, an optionally substituted $C_{3-7}$ cycloalkyloxy group, an optionally substituted $C_{6-10}$ monocyclic or polycyclic aryloxy group, an optionally substituted 5- to 7-membered monocyclic heterocyclyloxy group containing 1 to 4 heteroatoms selected from an oxygen atom, a nitrogen atom and a sulfur atom, an optionally substituted $C_{1-6}$ alkylsulfonyl group, an optionally substituted $C_{1-6}$ alkylcarbonyl group, a mono-$C_{1-6}$ alkylaminocarbonyl group, a di-$C_{1-6}$ alkylaminocarbonyl group, an optionally substituted $C_{1-6}$alkyloxycarbonyl group or an optionally substituted hydroxyaminocarbonyl group and is preferably a hydrogen atom, a bromine atom, a carboxy group, a cyano group, a methyl group, an ethyl group, a n-propyl group, an isopropyl group, a n-butyl group, an isobutyl group, a tert-butyl group, a hydroxymethyl group, a cyclohexylmethyl group, a methoxymethyl group, a cyclopropyl group, a cyclobutyl group, a cyclopentyl group, a cyclohexyl group, a cycloheptyl group, a phenyl group, a hydroxymethylphenyl group, a fluorophenyl group, a benzyl group, a naphthyl group, a tetrahydrofuranyl group, a pyrrolidyl group, an oxopyrrolidyl group, a piperidyl group, an oxazolidinyl group, an oxooxazolidinyl group, a morpholinyl group, a thienyl group, a fluorothienyl group, a chlorothienyl group, a furanyl group, a methylfuranyl group, a pyrazolyl group, a methylpyrazolyl group, an oxazolyl group, an isoxazolyl group, an oxadiazolyl group, a thiazolyl group, a chlorothiazolyl group, a cyanothiazolyl group, a methylthiazolyl group, a hydroxymethylthiazolyl group, a carbamoylthiazolyl group, a nitrothiazolyl group, an isothiazolyl group, an imidazolyl group, a methylimidazolyl group, a triazolyl group, a pyridyl group, a chloropyridyl group, a fluoropyridyl group, a cyanopyridyl group, a methylpyridyl group, a pyrimidyl group, an aziridinyl group, a tetrazolyl group, a quinolyl group, an isoquinolyl group, a dimethylamino group, a diethylamino group, a cyclopentylamino group, a methoxy group, an ethoxy group, a propoxy group, an isopropoxy group, a trifluoromethoxy group, a cyclopropylmethoxy group, a cyclopropyloxy group, a cyclopentyloxy group, a cyclohexyloxy group, a phenyloxy group, a thiazolyloxy group, a methylsulfonyl group, an acetyl group, a methylaminocarbonyl group, an ethylaminocarbonyl group, a dimethylaminocarbonyl group, a diethylaminocarbonyl group, an ethoxycarbonyl group or a hydroxyaminocarbonyl group, more preferably a hydrogen atom, a bromine atom, a methyl group, an ethyl group, a n-propyl group, an isopropyl group, a n-butyl group, a methoxymethyl group, a cyclopropyl group, a cyclohexyl group, a phenyl group, a hydroxymethylphenyl group, a fluorophenyl group, a pyrrolidyl group, a morpholinyl group, a thienyl group, a fluorothienyl group, a chlorothienyl group, a furanyl group, a pyrazolyl group, a methylpyrazolyl group, an oxazolyl group, an isoxazolyl group, an oxadiazolyl group, a thiazolyl group, a chlorothiazolyl group, a cyanothiazolyl group, a methylthiazolyl group, a hydroxymethylthiazolyl group, a carbamoylthiazolyl group, a nitrothiazolyl group, an isothiazolyl group, an imidazolyl group, a triazolyl group, a pyridyl group, a chloropyridyl group, a fluoropyridyl group, a cyanopyridyl group, a methylpyridyl group, a pyrimidyl group, a dimethylamino group, a diethylamino group, an ethoxy group, a propoxy group, an isopropoxy group, a cyclopropylmethoxy group, a cyclopentyloxy group, a cyclohexyloxy group, a methylsulfonyl group or an ethoxycarbonyl group.

In formula (1), the groups represented by $R^5$ and $R^6$ are each independently a hydrogen atom or a $C_{1-6}$ alkyl group and are preferably a hydrogen atom, a methyl group, an ethyl group, an isopropyl group, a n-butyl group or an isobutyl group, more preferably a hydrogen atom or a methyl group.

In formula (1), the groups represented by $R^7$ and $R^8$ are each independently a hydrogen atom or a $C_{1-6}$ alkyl group and are preferably a hydrogen atom or a methyl group.

According to a preferred embodiment of the present invention, the compound represented by formula (1) or the pharmacologically acceptable salt thereof may be a compound represented by formula (1a) or a pharmacologically acceptable salt thereof

[Chemical Formula 5]

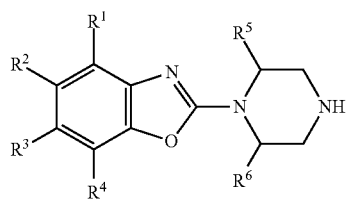

(1a)

Here, in formula (1a), $R^1$, $R^2$, $R^3$ and $R^4$ are each independently one group selected from the group consisting of a hydrogen atom, a halogen atom, a hydroxy group, a carboxy group, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted $C_{7-11}$ monocyclic or polycyclic aralkyl group, an optionally substituted 4- to 10-membered monocyclic or bicyclic heterocyclic group containing 1 to 4 heteroatoms selected from an oxygen atom, a nitrogen atom and a sulfur atom, a di-$C_{1-6}$ alkylamino group, an optionally substituted $C_{3-7}$ cycloalkylamino group, an optionally substituted $C_{1-6}$ alkyloxy group, an optionally substituted $C_{3-7}$ cycloalkyloxy group, an optionally substituted $C_{6-10}$ monocyclic or polycyclic aryloxy group, an optionally substituted $C_{7-11}$ monocyclic or polycyclic aralkyloxy group, an optionally substituted 4- to 10-membered monocyclic or bicyclic heterocyclyloxy group containing 1 to 4 heteroatoms selected from an oxygen atom, a nitrogen atom and a sulfur atom, an optionally substituted $C_{1-6}$ alkylthio group, an optionally substituted $C_{1-6}$ alkylsulfonyl group, an optionally substituted $C_{1-6}$ alkylcarbonyl group, a mono-$C_{1-6}$ alkylaminocarbonyl group, a di-$C_{1-6}$ alkylaminocarbonyl group, an optionally substituted $C_{1-6}$ alkyloxycarbonyl group and an optionally substituted hydroxyaminocarbonyl group, and $R^5$ and $R^6$ are each independently a hydrogen atom or a $C_{1-6}$ alkyl group. However, the case where $R^1$ is a carboxy group, the case where $R^1$, $R^2$, $R^3$ and $R^4$ are hydrogen atoms at the same time and the case where $R^5$ and $R^6$ are hydrogen atoms at the same time are excluded.

Also, the compound represented by formula (1) or the pharmacologically acceptable salt thereof may be a compound represented by formula (1b) or a pharmacologically acceptable salt thereof.

[Chemical Formula 6]

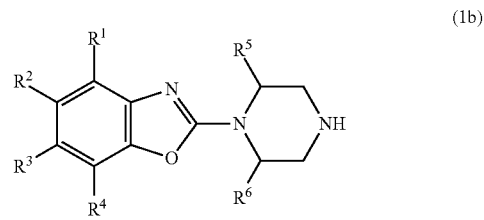

(1b)

Here, in formula (1b), $R^1$, $R^2$, $R^3$ and $R^4$ are each independently one group selected from the group consisting of a hydrogen atom, a fluorine atom, a chlorine atom, a bromine atom, an iodine atom, a hydroxy group, a carboxy group, a cyano group, a methyl group, an ethyl group, a n-propyl group, an isopropyl group, a n-butyl group, an isobutyl group, a tert-butyl group, a trifluoromethyl group, a hydroxymethyl group, a cyclohexylmethyl group, a methoxymethyl group, a cyclopropyl group, a cyclobutyl group, a cyclopentyl group, a cyclohexyl group, a cycloheptyl group, a phenyl group, a hydroxymethylphenyl group, a fluorophenyl group, a benzyl group, a naphthyl group, a tetrahydrofuranyl group, a pyrrolidyl group, an oxopyrrolidyl group, a piperidyl group, an oxazolidinyl group, an oxooxazolidinyl group, a morpholinyl group, a thienyl group, a fluorothienyl group, a chlorothienyl group, a furanyl group, a methylfuranyl group, a pyrazolyl group, a methylpyrazolyl group, an oxazolyl group, an isoxazolyl group, an oxadiazolyl group, a thiazolyl group, a chlorothiazolyl group, a cyanothiazolyl group, a methylthiazolyl group, a hydroxymethylthiazolyl group, a carbamoylthiazolyl group, a nitrothiazolyl group, an isothiazolyl group, an imidazolyl group, a methylimidazolyl group, a triazolyl group, a pyridyl group, a chloropyridyl group, a fluoropyridyl group, a cyanopyridyl group, a methylpyridyl group, a pyrimidyl group, an aziridinyl group, a tetrazolyl group, a quinolyl group, an isoquinolyl group, a dimethylamino group, a diethylamino group, a cyclopentylamino group, a methoxy group, an ethoxy group, a propoxy group, an isopropoxy group, a trifluoromethoxy group, a cyclopropylmethoxy group, a cyclopropyloxy group, a cyclopentyloxy group, a cyclohexyloxy group, a phenyloxy group, a thiazolyloxy group, a methylthio group, a methylsulfonyl group, an acetyl group, a methylaminocarbonyl group, an ethylaminocarbonyl group, a dimethylaminocarbonyl group, a diethylaminocarbonyl group, an ethoxycarbonyl group and a hydroxyaminocarbonyl group, $R^5$ and $R^6$ are each independently a hydrogen atom, a methyl group, an ethyl group, an isopropyl group, a n-butyl group or an isobutyl group, and $R^7$ and $R^8$ are hydrogen atoms at the same time. However, the case where $R^1$ is a carboxy group, the case where $R^1$, $R^2$, $R^3$ and $R^4$ are hydrogen atoms at the same time and the case where $R^5$ and $R^6$ are hydrogen atoms at the same time are excluded.

Further, the compound represented by formula (1) or the pharmacologically acceptable salt thereof may be a compound represented by formula (1c) or a pharmacologically acceptable salt thereof:

[Chemical Formula 7]

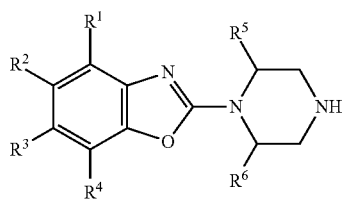

(1c)

Here, in formula (1c), $R^1$, $R^2$, $R^3$ and $R^4$ are each independently one group selected from the group consisting of a hydrogen atom, a fluorine atom, a chlorine atom, a bromine atom, an iodine atom, a cyano group, a methyl group, an ethyl group, a n-propyl group, an isopropyl group, a n-butyl group, a methoxymethyl group, a trifluoromethyl group, a cyclopropyl group, a cyclohexyl group, a phenyl group, a hydroxymethylphenyl group, a fluorophenyl group, a pyrrolidyl group, a morpholinyl group, a thienyl group, a fluorothienyl group, a chlorothienyl group, a furanyl group, a pyrazolyl group, a methylpyrazolyl group, an oxazolyl group, an isoxazolyl group, an oxadiazolyl group, a thiazolyl group, a chlorothiazolyl group, a cyanothiazolyl group, a methylthiazolyl group, a hydroxymethylthiazolyl group, a carbamoylthiazolyl group, a nitrothiazolyl group, an isothiazolyl group, an imidazolyl group, a triazolyl group, a pyridyl group, a chloropyridyl group, a fluoropyridyl group, a cyanopyridyl group, a methylpyridyl group, a pyrimidyl group, a dimethylamino group, a diethylamino group, a methoxy group, an ethoxy group, a propoxy group, an isopropoxy group, a trifluoromethoxy group, a cyclopropylmethoxy group, a cyclopentyloxy group, a cyclohexyloxy group, a methylthio group, a methylsulfonyl group and an ethoxycarbonyl group, and $R^5$ and $R^6$ are each independently a hydrogen atom or a methyl group. However, the case where $R^1$ is a carboxy group, the case where $R^1$, $R^2$, $R^3$ and $R^4$ are hydrogen atoms at the same time and the case where $R^5$ and $R^6$ are hydrogen atoms at the same time are excluded.

Moreover, in formula (1c), it is preferable that $R^2$ should be one group selected from the group consisting of a hydrogen atom, a halogen atom, a cyano group, an optionally substituted $C_{1-6}$ alkyl group and an optionally substituted 5- to 7-membered monocyclic heterocyclic group containing 1 to 4 heteroatoms selected from an oxygen atom, a nitrogen atom and a sulfur atom, and $R^5$ and $R^6$ should be each independently a hydrogen atom or a $C_{1-6}$ alkyl group.

Furthermore, in formula (1c), it is more preferable that $R^2$ should be one group selected from the group consisting of a hydrogen atom, a fluorine atom, a chlorine atom, a bromine atom, a cyano group, a methyl group, a trifluoromethyl group, a pyrrolidyl group and a thienyl group, and $R^5$ and $R^6$ should be each independently one group selected from the group consisting of a hydrogen atom, a methyl group, an ethyl group, an isopropyl group, a n-butyl group and an isobutyl group.

Furthermore, in formula (1c) it is further preferable that $R^2$ should be one group selected from the group consisting of a fluorine atom, a chlorine atom, a cyano group, a methyl group, a trifluoromethyl, group and a thienyl group, and $R^5$ and $R^6$ should be each independently a hydrogen atom or a methyl group.

Particularly, the compound represented by formula (1) or the pharmacologically acceptable salt thereof may be a compound represented by formula (1d) or a pharmacologically acceptable salt thereof:

[Chemical Formula 8]

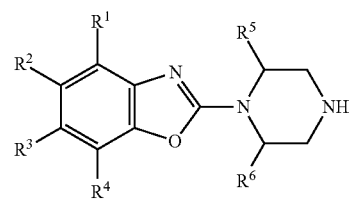

(1d)

Here, in formula (1d), $R^1$ is one group selected from the group consisting of a hydrogen atom, a halogen atom, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted 5- to 7-membered monocyclic heterocyclic group containing 1 to 4 heteroatoms selected from an oxygen atom, a nitrogen atom and a sulfur atom, an optionally substituted $C_{1-6}$ alkyloxy group, an optionally substituted $C_{1-6}$ alkylthio group and an optionally substituted $C_{1-6}$ alkylsulfonyl group, $R^2$ is one group selected from the group consisting of a hydrogen atom, a halogen atom, a cyano group, an optionally substituted $C_{1-6}$ alkyl group and an optionally substituted 5- to 7-membered monocycle heterocyclic group containing 1 to 4 heteroatoms selected from an oxygen atom, a nitrogen atom and a sulfur atom, $R^3$ is one group selected from the group consisting of a hydrogen atom, a halogen atom, a hydroxy group, a cyano group, an optionally substituted $C_{1-6}$ alkyl group and an optionally substituted $C_{1-6}$ alkyloxy group, $R^4$ is one group selected from the group consisting of a hydrogen atom, a halogen atom, a carboxy group, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted $C_{7-11}$ monocyclic or polycyclic aralkyl group, an optionally substituted 5- to 7-membered monocyclic heterocyclic group containing 1 to 4 heteroatoms selected from an oxygen atom, a nitrogen atom and a sulfur atom, a di-$C_{1-6}$ alkylamino group, an optionally substituted $C_{3-7}$ cycloalkylamino group, an optionally substituted $C_{1-6}$ alkyloxy group, an optionally substituted $C_{3-7}$ cycloalkyloxy group, an optionally substituted $C_{6-10}$ monocycle or polycyclic aryloxy group, an optionally substituted 5- to 7-membered monocycle heterocyclyloxy group containing 1 to 4 heteroatoms selected from an oxygen atom, a nitrogen atom and a sulfur atom, an optionally substituted $C_{1-6}$ alkylsulfonyl group, an optionally substituted $C_{1-6}$ alkylcarbonyl group, a mono-$C_{1-6}$ alkylaminocarbonyl group, a di-$C_{1-6}$ alkylaminocarbonyl group, an optionally substituted $C_{1-6}$ alkyloxycarbonyl group and an optionally substituted hydroxyaminocarbonyl group, and $R^5$ and $R^6$ are each independently a hydrogen atom or a $C_{1-6}$ alkyl group, provided that the case where $R^5$ and $R^6$ are hydrogen atoms at the same time is excluded.

In formula (1d), it is preferable that $R^1$ should be one group selected from the group consisting of a hydrogen atom, a fluorine atom, an iodine atom, a cyano group, a methyl group, a trifluoromethyl group, a cyclopropyl group, a phenyl group, a furanyl group, a pyrazolyl group, a methoxy group, a trifluoromethoxy group, a methylthio group and a methylsulfonyl group, $R^2$ should be one group selected from the group consisting of a hydrogen atom, a fluorine atom, a chlorine atom, a bromine atom, a cyano group, a methyl group, a trifluoromethyl group, a pyrrolidyl group and a thienyl group, $R^3$ should be one group selected from the group consisting of a hydrogen atom, a fluorine atom, an iodine atom, a hydroxy group, a cyano group, a methyl group, a trifluoromethyl group and a methoxy group, $R^4$ should be one group selected from the group consisting of a hydrogen atom, a bromine atom, a carboxy group, a cyano group, a methyl group, an ethyl group, a n-propyl group, an isopropyl group, a n-butyl group, an isobutyl group, a tert-butyl group, a hydroxymethyl group, a cyclohexylmethyl group, a methoxymethyl group, a cyclopropyl group, a cyclobutyl group, a cyclopentyl group, a cyclohexyl group, a cycloheptyl group, a phenyl group, a hydroxymethylphenyl group, a fluorophenyl group, a benzyl group, a naphthyl group, a tetrahydrofuranyl group, a pyrrolidyl group, an oxopyrrolidyl group, a piperidyl group, an oxazolidinyl group, an oxoxazolidinyl group, a morpholinyl group, a thienyl group, a fluorothienyl group, a chlorothienyl group, a furanyl group, a methylfuranyl group, a pyrazolyl group, a methylpyrazolyl group, an oxazolyl group, an isoxazolyl group, an oxadiazolyl group, a thiazolyl group, a chlorothiazolyl group, a cyanothiazolyl group, a methylthiazolyl group, a hydroxymethylthiazolyl group, a carbamoylthiazolyl group, a nitrothiazolyl group, an isothiazolyl group, an imidazolyl group, a methylimidazolyl group, a triazolyl group, a pyridyl group, a chloropyridyl group, a fluoropyridyl group, a cyanopyridyl group, a methylpyridyl group, a pyrimidyl group, an aziridinyl group, a tetrazolyl group, a quinolyl group, an isoquinolyl group, a dimethylamino group, a diethylamino group, a cyclopentylamino group, a methoxy group, an ethoxy group, a propoxy group, an isopropoxy group, a trifluoromethoxy group, a cyclopropylmethoxy group, a cyclopropyloxy group, a cyclopentyloxy group, a cyclohexyloxy group, a phenyloxy group, a thiazolyloxy group, a methylsulfonyl group, an acetyl group, a methylaminocarbonyl group, an ethylaminocarbonyl group, a dimethylaminocarbonyl group, a diethylaminocarbonyl group, an ethoxycarbonyl group and a hydroxyaminocarbonyl group, and $R^5$ and $R^6$ should be each independently one group selected from the group consisting of a hydrogen atom, a methyl group, an ethyl group, an isopropyl group, a n-butyl group and an isobutyl group.

Moreover, in formula (1d), it is more preferable that $R^1$ should be one group selected from the group consisting of a hydrogen atom, a fluorine atom, an iodine atom, a cyano group, a methyl group, a trifluoromethyl group, a cyclopropyl group, a phenyl group, a furanyl group, a pyrazolyl group, a methoxy group, a trifluoromethoxy group, a methylthio group and a methylsulfonyl group, $R^2$ should be one group selected from the group consisting of a hydrogen atom, a fluorine atom, a chlorine atom, a cyano group, a methyl group, a trifluoromethyl group and a thienyl group, $R^3$ should be one group selected from the group consisting of a hydrogen atom, a fluorine atom, a cyano group and a methyl group, $R^4$ should be one group selected from the group consisting of a hydrogen atom, a bromine atom, a methyl group, an ethyl group, a n-propyl group, an isopropyl group, a n-butyl group, a methoxymethyl group, a cyclopropyl group, a cyclohexyl group, a phenyl group, a hydroxymethylphenyl group, a fluorophenyl group, a pyrrolidyl group, a morpholinyl group, a thienyl group, a fluorothienyl group, a chlorothienyl group, a furanyl group, a pyrazolyl group, a methylpyrazolyl group, an oxazolyl group, an isoxazolyl group, an oxadiazolyl group, a thiazolyl group, a chlorothiazolyl group, a cyanothiazolyl group, a methylthiazolyl group, a hydroxymethylthiazolyl group, a carbamoylthiazolyl group, a nitrothiazolyl group, an isothiazolyl group, an imidazolyl group, a triazolyl group, a pyridyl group, a chloropyridyl group, a fluoropyridyl group, a cyanopyridyl group, a methylpyridyl group, a pyrimidyl group, a dimethylamino group, a diethylamino group, an ethoxy group, a propoxy group, an isopropoxy group, a cyclopropylmethoxy group, a cyclopentyloxy group, a cyclohexyloxy group, a methylsulfonyl group and an ethoxycarbonyl group, and $R^5$ and $R^6$ should be each independently a hydrogen atom or a methyl group.

Examples of the compound represented by formula (1) include the following compounds or salts thereof, though the present invention is not intended to be limited by these specific examples:

(S)-5-chloro-7-isopropyl-2-(2-methylpiperazin-1-yl)benzoxazole, (S)-5-chloro-7-methoxy-2-(2-methylpiperazin-1-yl)benzoxazole, (S)-5-chloro-7-acetyl-2-(2-methylpiperazin-1-yl)benzoxazole, meso-5-chloro-2-(2,6-cis-dimethylpiperazin-1-yl)-7-methylbenzoxazole, (S)-5-fluoro-7-methyl-2-(2-methylpiperazin-1-yl)benzoxazole, (S)-5-bromo-7-methyl-2-(2-methylpiperazin-1-yl)benzoxazole, (S)-5-chloro-7-isopropoxy-2-(2-methylpiperazin-1-yl)benzoxazole, (S)-5-chloro-7-ethyl-2-(2-methylpiperazin-1-yl)benzoxazole, (S)-5-chloro-7-ethoxycarbonyl-2-(2-methylpiperazin-1-yl)benzoxazole, (S)-5-chloro-7-cyano-2-(2-methylpiperazin-1-yl)benzoxazole, (S)-5-chloro-7-ethyl-2-(2-isopropylpiperazin-1-yl)benzoxazole, (S)-5-chloro-7-ethyl-2-(2-isobutylpiperazin-1-yl)benzoxazole, (S)-2-(2-n-butylpiperazin-1-yl)-5-chloro-7-ethylbenzoxazole, (S)-5-chloro-7-ethyl-2-(2-ethylpiperazin-1-yl)benzoxazole, (S)-5-chloro-7-hydroxymethyl-2-(2-methylpiperazin-1-yl)benzoxazole, (S)-5-chloro-2-(2-methylpiperazin-1-yl)-7-(thiophen-3-yl)benzoxazole, (S)-5-chloro-7-(furan-3-yl)-2-(2-methylpiperazin-1-yl)benzoxazole, (S)-5-chloro-2-(2-methylpiperazin-1-yl)-7-(thiophen-2-yl)benzoxazole, (S)-5-chloro-2-(2-methylpiperazin-1-yl)-7-phenylbenzoxazole, (S)-5-chloro-2-(2-methylpiperazin-1-yl)-7-(pyrrolidin-1-yl)benzoxazole, (S)-5-chloro-2-(2-methylpiperazin-1-yl)-7-(morpholin-1-yl)benzoxazole, (S)-5-chloro-2-(2-methylpiperazin-1-yl)-7-(piperidin-1-yl)benzoxazole, (S)-5-chloro-7-(furan-2-yl)-2-(2-methylpiperazin-1-yl)benzoxazole, (S)-5-chloro-7-(cyclopentylamino)-2-(2-methylpiperazin-1-yl)benzoxazole, (S)-5-chloro-7-diethylamino-2-(2-methylpiperazin-1-yl)benzoxazole, (S)-5-chloro-7-dimethylamino-2-(2-methylpiperazin-1-yl)benzoxazole,
(S)-5-chloro-7-cyclopropyl-2-(2-methylpiperazin-1-yl)benzoxazole,
(S)-5-chloro-7-(cyclopentyloxy)-2-(2-methylpiperazin-1-yl)benzoxazole,
(S)-5-chloro-7-ethoxy-2-(2-methylpiperazin-1-yl)benzoxazole,
(S)-5-chloro-2-(2-methylpiperazin-1-yl)-7-n-propoxybenzoxazole,
(S)-5-chloro-7-cyclopentyl-2-(2-methylpiperazin-1-yl)benzoxazole,
(S)-7-n-butyl-5-chloro-2-(2-methylpiperazin-1-yl)benzoxazole,
(S)-5-chloro-2-(2-methylpiperazin-1-yl)-7-(1H-pyrazol-1-yl)benzoxazole,
(S)-5-chloro-2-(2-methylpiperazin-1-yl)-7-(oxazol-2-yl)benzoxazole,
(S)-5-chloro-2-(2-methylpiperazin-1-yl)-7-(thiazol-2-yl)benzoxazole,
(S)-5-chloro-7-(1H-imidazol-1-yl)-2-(2-methylpiperazin-1-yl)benzoxazole,
(S)-5-chloro-2-(2-methylpiperazin-1-yl)-7-(thiazol-4-yl)benzoxazole,
(S)-5-chloro-2-(2-methylpiperazin-1-yl)-7-(thiazol-5-yl)benzoxazole,
(S)-5-chloro-7-(5-methylfuran-2-yl)-2-(2-methylpiperazin-1-yl)benzoxazole,
(S)-5-chloro-7-(4-methyl-1H-pyrazol-1-yl)-2-(2-methylpiperazin-1-yl)benzoxazole,
(S)-5-chloro-2-(2-methylpiperazin-1-yl)-7-(pyridin-2-yl)benzoxazole,
(S)-5-chloro-2-(2-methylpiperazin-1-yl)-7-(pyridin-3-yl)benzoxazole,
(S)-5-chloro-2-(2-methylpiperazin-1-yl)-7-(pyridin-4-yl)benzoxazole,
(S)-5-chloro-7-cyclohexyl-2-(2-methylpiperazin-1-yl)benzoxazole,
(S)-5-chloro-2-(2-methylpiperazin-1-yl)-7-(2H-1,2,3-triazol-2-yl)benzoxazole,
(S)-5-chloro-2-(2-methylpiperazin-1-yl)-7-(1H-1,2,4-triazol-1-yl)benzoxazole,
(S)-5-chloro-7-isobutyl-2-(2-methylpiperazin-1-yl)benzoxazole,
(S)-5-chloro-2-(2-methylpiperazin-1-yl)-7-(2-hydroxymethylphenyl)benzoxazole,
(S)-5-chloro-7-(1-methyl-1H-imidazol-2-yl)-2-(2-methylpiperazin-1-yl)benzoxazole,
(S)-5-chloro-7-(1H-imidazol-2-yl)-2-(2-methylpiperazin-1-yl)benzoxazole,
(S)-5-chloro-7-(cyclohexylmethyl)-2-(2-methylpiperazin-1-yl)benzoxazole,
(S)-5-chloro-7-(cyclohexyloxy)-2-(2-methylpiperazin-1-yl)benzoxazole,
(S)-5-chloro-7-(cyclopropylmethoxy)-2-(2-methylpiperazin-1-yl)benzoxazole,
(S)-5-chloro-7-(isothiazol-3-yl)-2-(2-methylpiperazin-1-yl)benzoxazole,
(S)-5-chloro-7-(5-hydroxymethylthiazol-2-yl)-2-(2-methylpiperazin-1-yl)benzoxazole,
(S)-5-chloro-2-(2-methylpiperazin-1-yl)-7-(pyrimidin-2-yl)benzoxazole,
(S)-5-chloro-7-(5-chlorothiophen-2-yl)-2-(2-methylpiperazin-1-yl)benzoxazole,
(S)-5-chloro-7-(5-chloropyridin-2-yl)-2-(2-methylpiperazin-1-yl)benzoxazole,
(S)-5-chloro-7-(4-chloropyridin-2-yl)-2-(2-methylpiperazin-1-yl)benzoxazole,
(S)-5-chloro-7-(6-fluoropyridin-2-yl)-2-(2-methylpiperazin-1-yl)benzoxazole,
(S)-5-chloro-7-(3-fluoropyridin-2-yl)-2-(2-methylpiperazin-1-yl)benzoxazole,
(S)-5-chloro-7-(5-cyanothiazol-2-yl)-2-(2-methylpiperazin-1-yl)benzoxazole,
(S)-5-chloro-2-(2-methylpiperazin-1-yl)-7-(5-methylthiazol-2-yl)benzoxazole,
(S)-5-chloro-7-(2-chlorothiophen-3-yl)-2-(2-methylpiperazin-1-yl)benzoxazole,
(S)-5-chloro-7-(5-carbamoylthiazol-2-yl)-2-(2-methylpiperazin-1-yl)benzoxazole,
(S)-5-chloro-7-(3-cyanopyridin-2-yl)-2-(2-methylpiperazin-1-yl)benzoxazole,
(S)-5-chloro-7-(5-fluorothiophen-2-yl)-2-(2-methylpiperazin-1-yl)benzoxazole,
(S)-5-chloro-2-(2-methylpiperazin-1-yl)-7-(3-methylpyridin-2-yl)benzoxazole
(S)-5-chloro-2-(2-methylpiperazin-1-yl)-7-(2-methylthiazol-4-yl)benzoxazole,
(S)-5-chloro-2-(2-methylpiperazin-1-yl)-7-phenoxybenzoxazole,
(S)-5-chloro-2-(2-methylpiperazin-1-yl)-7-(2-oxo-pyrrolidin-1-yl)benzoxazole
(S)-5-chloro-2-(2-methylpiperazin-1-yl)-7-(2-oxo-oxazolidin-3-yl)benzoxazole,
(S)-5-chloro-7-(5-fluoropyridin-2-yl)-2-(2-methylpiperazin-1-yl)benzoxazole,
(S)-5-chloro-7-(5-chlorothiazol-2-yl)-2-(2-methylpiperazin-1-yl)benzoxazole,
(S)-7-benzyl-5-chloro-2-(2-methylpiperazin-1-yl)benzoxazole,
(S)-5-chloro-7-(5-(hydroxymethyl)thiazol-4-yl)-2-(2-methylpiperazin-1-yl)benzoxazole,
(S)-5-chloro-2-(2-methylpiperazin-1-yl)-7-(thiazol-2-yloxy)benzoxazole,
(S)-5-chloro-2-(2-methylpiperazin-1-yl)-7-(5-nitrothiazol-2-yl)benzoxazole,
(S)-5-chloro-7-(3-methoxypyridin-2-yl)-2-(2-methylpiperazin-1-yl)benzoxazole,
5-chloro-2-((S)-2-methylpiperazin-1-yl)-7-(tetrahydrofuran-2-yl)benzoxazole,
(S)-5-chloro-7-(4-fluorophenyl)-2-(2-methylpiperazin-1-yl)benzoxazole,
(S)-5-chloro-2-(2-methylpiperazin-1-yl)-7-(pyridin-2-yl)-4-(trifluoromethyl)benzoxazole,
(S)-5-chloro-2-(2-methylpiperazin-1-yl)-7-(1H-pyrazol-1-yl)-4-(trifluoromethyl)benzoxazole,
(S)-5-chloro-2-(2-methylpiperazin-1-yl)-7-(thiazol-2-yl)-4-(trifluoromethyl)benzoxazole,
(S)-5-chloro-2-(2-methylpiperazin-1-yl)-7-(pyridin-2-yl)-6-(trifluoromethyl)benzoxazole,
(S)-5-chloro-2-(2-methylpiperazin-1-yl)-7-(pyridin-2-yl)-4-(trifluoromethoxy)benzoxazole,
(S)-5-chloro-2-(2-methylpiperazin-1-yl)-7-(thiazol-2-yl)-4-(trifluoromethoxy)benzoxazole,
(S)-5-chloro-2-(2-methylpiperazin-1-yl)-7-(1H-pyrazol-1-yl)-4-(trifluoromethoxy)benzoxazole,
(S)-4,5-difluoro-2-(2-methylpiperazin-1-yl)-7-(pyridin-2-yl)benzoxazole,
(S)-4,5-difluoro-2-(2-methylpiperazin-1-yl)-7-(thiazol-2-yl)benzoxazole,
(S)-4,5-difluoro-2-(2-methylpiperazin-1-yl)-7-(1H-pyrazol-1-yl)benzoxazole, (S)-5-chloro-6-fluoro-2-(2-methylpiperazin-1-yl)-7-(pyridin-2-yl)benzoxazole,
(S)-5-chloro-6-fluoro-2-(2-methylpiperazin-1-yl)-7-(thiazol-2-yl)benzoxazole,
(S)-5-chloro-6-fluoro-2-(2-methylpiperazin-1-yl)-7-(1H-pyrazol-1-yl)benzoxazole,
(S)-5-chloro-2-(2-methylpiperazin-1-yl)-7-n-propylbenzoxazole,
(S)-5-chloro-7-dimethylaminocarbonyl-2-(2-methylpiperazin-1-yl)benzoxazole,
(S)-5-chloro-7-diethylaminocarbonyl-2-(2-methylpiperazin-1-yl)benzoxazole,
(S)-5-chloro-7-hydroxyaminocarbonyl-2-(2-methylpiperazin-1-yl)benzoxazole,
(S)-5-chloro-7-carboxy-2-(2-methylpiperazin-1-yl)benzoxazole,
(S)-5-chloro-7-methylaminocarbonyl-2-(2-methylpiperazin-1-yl)benzoxazole,
(S)-5-chloro-7-ethylaminocarbonyl-2-(2-methylpiperazin-1-yl)benzoxazole,
(S)-5-fluoro-2-(2-methylpiperazin-1-yl)-7-(pyridin-2-yl)benzoxazole,
(S)-5-fluoro-2-(2-methylpiperazin-1-yl)-7-(thiazol-2-yl)benzoxazole,
(S)-5-fluoro-2-(2-methylpiperazin-1-yl)-7-(oxazol-2-yl)benzoxazole,
(S)-5-chloro-2-(2-methylpiperazin-1-yl)-7-(1,2,4-oxadiazol-3-yl)benzoxazole,
(S)-5-chloro-7-(4,5-dihydrooxazol-2-yl)-2-(2-methylpiperazin-1-yl)benzoxazole,
(S)-5-chloro-7-(methoxymethyl)-2-(2-methylpiperazin-1-yl)benzoxazole,
(S)-5-chloro-7-(isoxazol-3-yl)-2-(2-methylpiperazin-1-yl)benzoxazole,
(S)-5-chloro-7-(isoxazol-5-yl)-2-(2-methylpiperazin-1-yl)benzoxazole,
(S)-7-bromo-5-chloro-2-(2-methylpiperazin-1-yl)benzoxazole,
(S)-5-cyano-2-(2-methylpiperazin-1-yl)-7-(pyridin-2-yl)benzoxazole,
(S)-5-cyano-2-(2-methylpiperazin-1-yl)-7-(thiazol-2-yl)benzoxazole,
(S)-5-cyano-2-(2-methylpiperazin-1-yl)-7-(oxazol-2-yl)benzoxazole,
(S)-5-methyl-2-(2-methylpiperazin-1-yl)-7-(pyridin-2-yl)benzoxazole,
(S)-5-methyl-2-(2-methylpiperazin-1-yl)-7-(thiazol-2-yl)benzoxazole,
(S)-5-methyl-2-(2-methylpiperazin-1-yl)-7-(oxazol-2-yl)benzoxazole,
(S)-5-fluoro-2-(2-methylpiperazin-1-yl)-7-(pyridin-2-yl)-4-(trifluoromethyl)benzoxazole,
(S)-5-fluoro-2-(2-methylpiperazin-1-yl)-7-(thiazol-2-yl)-4-(trifluoromethyl)benzoxazole,
(S)-5-fluoro-2-(2-methylpiperazin-1-yl)-7-(1H-pyrazol-1-yl)-4-(trifluoromethyl)benzoxazole,
(S)-5-chloro-4,6-difluoro-2-(2-methylpiperazin-1-yl)-7-(pyridin-2-yl)benzoxazole,
(S)-5-chloro-4,6-difluoro-2-(2-methylpiperazin-1-yl)-7-(thiazol-2-yl)benzoxazole,
(S)-4,5,6-trifluoro-2-(2-methylpiperazin-1-yl)-7-(pyridin-2-yl)benzoxazole,
(S)-4,5,6-trifluoro-2-(2-methylpiperazin-1-yl)-7-(thiazol-2-yl)benzoxazole,
(S)-4,5,6-trifluoro-2-(2-methylpiperazin-1-yl)-7-(1H-pyrazol-1-yl)benzoxazole,
(S)-2-(2-methylpiperazin-1-yl)-7-(pyridin-2-yl)-5-(trifluoromethyl)benzoxazole,
(S)-2-(2-methylpiperazin-1-yl)-7-(thiazol-2-yl)-5-(trifluoromethyl)benzoxazole,
(S)-2-(2-methylpiperazin-1-yl)-7-(oxazol-2-yl)-5-(trifluoromethyl)benzoxazole,
(S)-5-chloro-4-fluoro-2-(2-methylpiperazin-1-yl)-7-(pyridin-2-yl)benzoxazole,
(S)-5-chloro-4-fluoro-2-(2-methylpiperazin-1-yl)-7-(thiazol-2-yl)benzoxazole,
(S)-5-chloro-4-fluoro-2-(2-methylpiperazin-1-yl)-7-(1H-pyrazol-1-yl)benzoxazole,
(S)-5-chloro-4-methyl-2-(2-methylpiperazin-1-yl)-7-(pyridin-2-yl)benzoxazole,
(S)-5-chloro-4-methyl-2-(2-methylpiperazin-1-yl)-7-(thiazol-2-yl)benzoxazole,
(S)-5-chloro-4-methyl-2-(2-methylpiperazin-1-yl)-7-(1H-pyrazol-1-yl)benzoxazole,
(S)-5-fluoro-2-(2-methylpiperazin-1-yl)-7-(pyridin-2-yl)-4-(trifluoromethoxy)benzoxazole,
(S)-5-fluoro-2-(2-methylpiperazin-1-yl)-7-(thiazol-2-yl)-4-(trifluoromethoxy)benzoxazole,
(S)-5-fluoro-2-(2-methylpiperazin-1-yl)-7-(1H-pyrazol-1-yl)-4-(trifluoromethoxy)benzoxazole,
(S)-5-chloro-6-methyl-2-(2-methylpiperazin-1-yl)-7-(pyridin-2-yl)benzoxazole,
(S)-5-chloro-6-methyl-2-(2-methylpiperazin-1-yl)-7-(thiazol-2-yl)benzoxazole,
(S)-5-chloro-6-methyl-2-(2-methylpiperazin-1-yl)-7-(1H-pyrazol-1-yl)benzoxazole,
(S)-5-chloro-6-methoxy-2-(2-methylpiperazin-1-yl)-7-(pyridin-2-yl)benzoxazole,
(S)-5-chloro-6-methoxy-2-(2-methylpiperazin-1-yl)-7-(thiazol-2-yl)benzoxazole,
(S)-5-chloro-6-cyano-2-(2-methylpiperazin-1-yl)-7-(thiazol-2-yl)benzoxazole,
(S)-5-chloro-4-cyano-2-(2-methylpiperazin-1-yl)-7-(thiazol-2-yl)benzoxazole,
(S)-5-fluoro-2-(2-methylpiperazin-1-yl)-7-(thiazol-2-yl)-6-(trifluoromethyl)benzoxazole,
(S)-5-chloro-2-(2-methylpiperazin-1-yl)-7-(methylsulfonyl)benzoxazole,
(S)-5-chloro-4-iodo-2-(2-methylpiperazin-1-yl)-7-(pyridin-2-yl)benzoxazole,
(S)-5-chloro-6-iodo-2-(2-methylpiperazin-1-yl)-7-(pyridin-2-yl)benzoxazole,
(S)-5-chloro-2-(2-methylpiperazin-1-yl)-4-phenyl-7-(pyridin-2-yl)benzoxazole,
(S)-5-chloro-4-cyclopropyl-2-(2-methylpiperazin-1-yl)-7-(pyridin-2-yl)benzoxazole,
(S)-5-chloro-2-(2-methylpiperazin-1-yl)-4-(methylthio)-7-(pyridin-2-yl)benzoxazole,
(S)-5-chloro-2-(2-methylpiperazin-1-yl)-4-(methylsulfonyl)-7-(pyridin-2-yl)benzoxazole,
(S)-6-bromo-5-chloro-2-(2-methylpiperazin-1-yl)-7-(pyridin-2-yl)benzoxazole,
(S)-5-chloro-4-methoxy-2-(2-methylpiperazin-1-yl)-7-(pyridin-2-yl)benzoxazole,
(S)-5-chloro-7-methyl-2-(2-methylpiperazin-1-yl)benzoxazole, (S)-5-chloro-4-methoxy-2-(2-methylpiperazin-1-yl)-7-(thiazol-2-yl)benzoxazole,
(S)-5-chloro-4-methoxy-2-(2-methylpiperazin-1-yl)-7-(1H-pyrazol-1-yl)benzoxazole,
(R)-5-chloro-2-(2-methylpiperazin-1-yl)-7-(pyridin-2-yl)-4-(trifluoromethoxy)benzoxazole,
(R)-5-chloro-2-(2-methylpiperazin-1-yl)-7-(thiazol-2-yl)-4-(trifluoromethoxy)benzoxazole, (R)-5-chloro-2-(2-methylpiperazin-1-yl)-7-(1H-pyrazol-1-yl)-4-(trifluoromethoxy)benzoxazole,
(S)-5-chloro-2-(2-methylpiperazin-1-yl)-7-(thiazol-2-yl)-6-(trifluoromethoxy)benzoxazole,
(S)-5-chloro-6-methoxy-7-methyl-2-(2-methylpiperazin-1-yl)benzoxazole,
(S)-5-chloro-6-hydroxy-7-methyl-2-(2-methylpiperazin-1-yl)benzoxazole,
(S)-4-bromo-6-chloro-2-(2-methylpiperazin-1-yl)benzoxazole,
(S)-6-chloro-4-(furan-2-yl)-2-(2-methylpiperazin-1-yl)benzoxazole,
(R)-6-chloro-4-(furan-2-yl)-2-(2-methylpiperazin-1-yl)benzoxazole,
(S)-6-chloro-2-(2-methylpiperazin-1-yl)-4-(1H-pyrazol-1-yl)benzoxazole,
(S)-5-bromo-2-(2-methylpiperazin-1-yl)benzoxazole,
(S)-5-cyano-7-methoxy-2-(2-methylpiperazin-1-yl)benzoxazole,
(S)-5-chloro-6,7-dimethoxy-2-(2-methylpiperazin-1-yl)benzoxazole,
(S)-5-chloro-6-methyl-2-(2-methylpiperazin-1-yl)benzoxazole,
(S)-5-chloro-6-methoxy-2-(2-methylpiperazin-1-yl)benzoxazole,
(S)-7-methyl-5-(pyrrolidin-1-yl)-2-(2-methylpiperazin-1-yl)benzoxazole,
(S)-7-methyl-5-(thiophen-3-yl)-2-(2-methylpiperazin-1-yl)benzoxazole,
(R)-5-chloro-7-ethyl-2-(2-methylpiperazin-1-yl)benzoxazole,
5-chloro-2-(piperazin-1-yl)-7-(thiazol-2-yl)-4-(trifluoromethoxy)benzoxazole,
(R)-5-chloro-2-(3-methylpiperazin-1-yl)-7-(thiazol-2-yl)-4-(trifluoromethoxy)benzoxazole,
(S)-5-chloro-2-(3-methylpiperazin-1-yl)-7-(thiazol-2-yl)-4-(trifluoromethoxy)benzoxazole,
(R)-5-chloro-2-(2-methylpiperazin-1-yl)-7-(pyridin-2-yl)-4-(trifluoromethyl)benzoxazole,
(R)-5-chloro-2-(2-methylpiperazin-1-yl)-7-(thiazol-2-yl)-4-(trifluoromethyl)benzoxazole, and
(R)-5-chloro-2-(2-methylpiperazin-1-yl)-7-(1H-pyrazol-1-yl)-4-(trifluoromethyl)benzoxazole.

The compound represented by formula (1) of the present embodiment can be produced by various method, but can be produced by a typical method shown below.

[Chemical Formula 9]

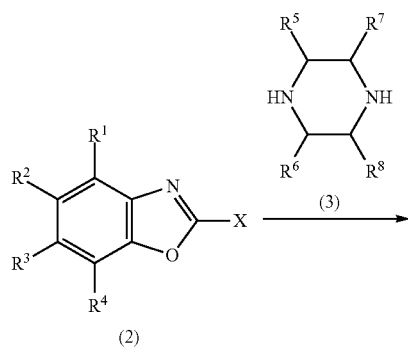

(2)

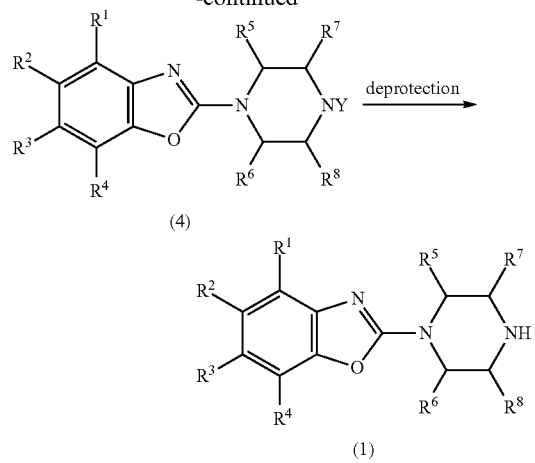

A compound represented by formula (2) [wherein $R^1$, $R^2$, $R^3$ and $R^4$ have the same meanings as those in formula (1), also including preferable forms, and X is a leaving group such as a halogen atom, a thiol group, a p-toluenesulfonyloxy group, a trifluoromethanesulfonyloxy group or a phenoxy group] is reacted with a cyclic diamine represented by formula (3) [wherein $R^5$, $R^6$, $R^7$ and $R^8$ have the same meanings as those in formula (1), also including preferable forms, and Y is a protective group for the amino group] at 1 equivalent to 50 equivalents with respect to the molar number of the compound represented by formula (2) to obtain a compound represented by formula (4) [wherein $R^1$, $R^2$, $R^3$, $R^4$, $R^5$, $R^6$, $R^7$ and $R^8$ have the same meanings as those in formula (1), also including preferable forms, and Y has the same meaning as that in formula (3)], and subsequently, Y, which is a protective group, can be removed by a suitable method to thereby obtain the compound represented by formula (1). For example, a tert-butoxycarbonyl group or a benzyloxycarbonyl group described in "Protective Groups in Organic Synthesis" authored by T. W. Greene ((John Wiley and Sons, Inc.), 1991) can be used as the protective group for the amino group.

Dichloromethane, chloroform, benzene, toluene, xylene, tetrahydrofuran, diethyl ether, dimethoxyethane, N,N-dimethylformamide, dimethyl sulfoxide or the like can be used as a solvent used in the production method. The reaction temperature is selected from the range of −50 to 200° C., preferably 0 to 150° C., and the reaction time is in the range of 5 minutes to 48 hours, preferably 30 minutes to 20 hours. For the purpose of promoting the reaction or for the purpose of carrying out the reaction under mild conditions, an additive (for example, triethylamine or N,N-diisopropylethylamine) may be added to the production method.

The compound represented by formula (4) produced by this method may be derivatized into another compound that falls within the scope of the present invention by subjecting each substituent ($R^1$, $R^2$, $R^3$, $R^4$, $R^5$, $R^6$, $R^7$ and $R^8$) to functional group conversion. Examples include the introduction of a functional group by various coupling reactions or the like using a metal catalyst. Typical examples of the coupling reactions include Kumada-Tamao-Corriu coupling, Migita-Kosugi-Stille coupling, Suzuki-Miyaura coupling, Negishi coupling and Buchwald-Hartwig coupling.

The compound represented by formula (1) of the present embodiment can exist in the form of an acid-addition salt in addition to the form of a free base. Examples of the acid-addition salt include: salts of hydrohalic acids such as hydrofluoric acid, hydrochloric acid, hydrobromic acid and hydroiodic acid; salts of inorganic acids such as sulfuric acid, nitric acid, phosphoric acid, perchloric acid and carbonic acid; salts of organic carboxylic acids such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid and malic acid; salts of acidic amino acids such as aspartic acid and glutamic acid; salts of alkylsulfonic acids such as methanesulfonic acid; and salts of arylsulfonic acids such as p-toluenesulfonic acid.

As the compound represented by formula (1) of the present embodiment may have one or two or more asymmetric carbon atoms according to the type of a substituent, optically active forms and diastereomers based on the one or two or more asymmetric carbon atoms, arbitrary mixtures thereof, racemates and the like are all included in the scope of the present invention. Moreover, corresponding hydrates or solvents are also included in the compound represented by formula (1) of the present invention or the pharmacologically acceptable salt thereof. Examples of the solvates include isopropanol solvates.

The compound represented by formula (1) of the present embodiment can be used as a PDE4 inhibitor.

An alternative embodiment of the present invention is a pharmaceutical composition comprising the compound represented by formula (1) or the pharmacologically acceptable salt thereof as an active ingredient. The pharmaceutical composition of the present embodiment permits any of oral and parenteral administration routes and can be administered to a human or a non-human animal. Thus, the pharmaceutical composition comprising the compound represented by formula (1) of the present embodiment or the pharmacologically acceptable salt thereof as an active ingredient is prepared into an appropriate dosage form according to an administration route.

Examples of the pharmaceutical composition specifically include: oral formulations such as tablets, pills, capsules, granules, powders, elixirs, suspensions, emulsions and syrups; and parenteral formulations such as injections, inhalants, formulations for rectal administrations, suppositories, lotions, sprays, ointments, creams and patches.

These various formulations can be manufactured by conventional methods using an excipient, a disintegrant, a binder, a lubricant, a colorant and the like usually used in the pharmaceutical field.

The content of the compound represented by formula (1) or the pharmacologically acceptable salt thereof in the pharmaceutical composition of the present embodiment differs depending on its dosage form and is usually 0.01 to 50% by mass, preferably 0.05 to 20% by mass, with respect to the total mass of the pharmaceutical composition in terms of a free form. The dosage form is appropriately determined according to each individual case in consideration of the age, body weight, and sex of a patient, difference in disease, the degree of symptoms, etc., and is usually 0.1 to 1000 mg, preferably 1 to 300 mg, per day in an adult, which is administered once a day or in several divided portions per day.

EXAMPLES

The present invention will be described below in more detail with reference to examples, however, the present invention is not limited to these examples. Methods of producing starting material compounds used in the examples will be described as reference examples.

Hereinbelow, the abbreviations used in the examples and reference examples have the following meaning.
APCI: Atmospheric Pressure Chemical Ionization
9-BBN: 9-borabicyclo[3.3.1]nonane
DMF: N,N-dimethylformamide
DMSO: Dimethylsulfoxide
ESI: Electronic spray ionization
HOBT: 1-hydroxybenzotriazole
Me4t-butylXphos:
2-di-tert-butylphosphino-3,4,5,6-tetramethyl-2',4',6'-triisopropylbiphenyl
MIDA: N-methyliminodiacetic acid
MS: Mass spectrum
n: Normal
RockPhos: 2-(di-tert-butylphosphino)-3-methoxy-6-methyl-2'-4'-6'-triisopropyl-1,1'-biphenyl
tert: tertiary
RuPhos: 2-Dicyclohexylphosphino-2',6'-diisopropoxybiphenyl
(S)-Tol BINAP: (S)-(−)-2,2'-bis(di-para-tolylphosphino)-1,1'-binaphthyl
THF: tetrahydrofuran
XantPhos: 4,5-bis(Diphenylphosphino)-9,9-dimethyxanthene
WSCI: 1-Ethyl-3-(3-dimethylaminopropyl)carbodiimide hydrochloride Reference Example 1

5-Chloro-7-isopropyl-2-mercaptobenzoxazole (a) 4-Chloro-2-isopropylphenol

2-Isopropylphenol (1.36 g), 2-aminopyridine (75 mg, 0.08 equivalents), and sulfuryl chloride (803 μL, 1.0 equivalent) were dissolved in toluene (20 mL), and the resulting mixture was stirred in an oil bath at 65° C. for 23 hours. Water was added to the reaction mixture, the product was extracted with ethyl acetate, the organic layer was dried over anhydrous magnesium sulfate, and then the solvent was distilled off under reduced pressure to obtain a crude product. The obtained crude product was purified by silica gel column chromatography (developing solvent, ethyl acetate:hexane=1:15) to obtain 1.29 g of the title compound.

$^1$H-NMR (400 MHz, CDCl$_3$) δ: 1.27 (6H, d, J=6.8 Hz), 3.14-3.21 (1H, m), 6.67 (1H, d, J=8.4 Hz), 7.01 (1H, dd, J=2.4, 8.4 Hz), 7.14 (1H, d, J=2.4 Hz)

(b) 4-Chloro-2-isopropyl-6-nitrophenol

4-Chloro-2-isopropylphenol obtained in Reference Example 1(a) (1.29 g) was dissolved in acetic acid (4.8 mL), and a separately prepared solution of nitric acid (a mixed solution of 70% nitric acid (477 μL) and acetic acid (1.2 mL)) was added dropwise thereto under ice cooling. After the dropping is completed, the resulting mixture was stirred at room temperature for 1.5 hours, then water was added thereto, and the product was extracted with ethyl acetate. The organic layer was washed with an aqueous solution of sodium hydrogencarbonate and then dried over anhydrous magnesium sulfate, and then the solvent was distilled off under reduced pressure to obtain a crude product. The obtained crude product was purified by silica gel column chromatography (developing solvent, ethyl acetate:hexane=1:15) to obtain 882 mg of the title compound.

¹H-NMR (400 MHz, CDCl₃) δ: 1.26 (6H, d, J=6.8 Hz), 3.38-3.45 (1H, m), 7.45 (1H, d, J=2.4 Hz), 7.96 (1H, d, J=2.4 Hz), 10.97 (1H, s)

(c) 2-Amino-4-chloro-6-isopropylphenol

4-Chloro-2-isopropyl-6-nitrophenol obtained in Reference Example 1(b) (881 mg) was dissolved in acetic acid (8.8 mL) and ethanol (8.8 mL), 5% platinum on sulfide carbon (264 mg) was added thereto, and the resulting mixture was stirred at room temperature in a hydrogen atmosphere for 30 minutes. The insoluble matter was filtered off, and then the solvent was distilled off under reduced pressure to obtain 745 mg of the title compound.
¹H-NMR (400 MHz, CDCl₃) δ: 1.23 (6H, d, J=6.8 Hz), 3.03-3.10 (1H, m), 6.63-6.65 (2H, m)

(d) 5-Chloro-7-isopropyl-2-mercaptobenzoxazole

2-Amino-4-chloro-6-isopropylphenol obtained in Reference Example 1(c) (745 mg) was dissolved in ethanol (13.4 mL), carbon disulfide (6.7 mL) and potassium hydroxide (120 mg) were added thereto, and the resulting mixture was stirred in an oil bath at 60° C. for 2 hours. The solvent was distilled off from the reaction mixture under reduced pressure, and then water was added to the residue and further acidified with 5 N hydrochloric acid. The precipitate was filtered off and dried to obtain 937 mg of the title compound.
¹H-NMR (400 MHz, CDCl₃) δ: 1.33 (6H, d, J=6.8 Hz), 3.28-3.35 (1H, 7.04 (1H, d, J=2 Hz), 7.09 (1H, d, J=2 Hz) MS(ESI) m/z: 228 (M+H)⁺

Reference Example 2

5-Chloro-7-methoxy-2-mercaptobenzoxazole (a) 4-Chloro-2-methoxy-6-nitrophenol

The title compound was obtained in a similar manner as in Reference Example 1(b) except that 4-chloro-2-methoxyphenol was used instead of 4-chloro-2-isopropylphenol.

(b) 2-Amino-4-chloro-6-methoxyphenol

The title compound was obtained in a similar manner as in Reference Example 1(c) except that 4-chloro-2-methoxy-6-nitrophenol obtained in Reference Example 2(a) was used instead of 4-chloro-2-isopropyl-6-nitrophenol.
¹H-NMR (400 MHz, CDCl₃) δ: 3.84 (3H, s), 6.34 (1H, d, J=2.4 Hz), 6.39 (1H, d, J=2.4 Hz)

(c) 5-Chloro-7-methoxy-2-mercaptobenzoxazole

The title compound was obtained in a similar manner as in Reference Example 1(d) except that 2-amino-4-chloro-6-methoxyphenol obtained in Reference Example 2(b) was used instead of 2-amino-4-chloro-6-isopropylphenol.
MS(ESI) m/z: 216 (M+H)⁺

Reference Example 3

7-Acetyl-5-chloro-2-mercaptobenzoxazole (a) 3'-Amino-5'-chloro-2'-hydroxyacetophenone The title compound was obtained in a similar manner as in Reference Example 1(c) except that 5'-chloro-2'-hydroxy-3'-nitroacetophenone was used instead of 4-chloro-2-isopropyl-6-nitrophenol.
¹H-NMR (400 MHz, CDCl₃) δ: 2.59 (3H, s), 4.02-4.04 (2H, br s), 6.83 (1H, s), 7.08 (1H, s), 12.41 (1H, s)

(b) 7-Acetyl-5-chloro-2-mercaptobenzoxazole

The title compound was obtained in a similar manner as in Reference Example 1(d) except that 3'-amino-5'-chloro-2'-hydroxyacetophenone obtained in Reference Example 3(a) was used instead of 2-amino-4-chloro-6-isopropylphenol.
¹H-NMR (400 MHz, CD₃OD) δ: 2.75 (3H, s), 7.39 (1H, d, J=2.4 Hz), 7.65 (1H, d, J=2.4 Hz)
MS(ESI) m/z: 228 (M+H)⁺

Reference Example 4

5-Fluoro-7-methyl-2-mercaptobenzoxazole (a) 4-Fluoro-2-methyl-6-nitrophenol

The title compound was obtained in a similar manner as in Reference Example 1(b) except that 4-fluoro-2-methylphenol was used instead of 4-chloro-2-isopropylphenol.

(b) 2-Amino-4-fluoro-6-methylphenol

The title compound was obtained in a similar manner as in Reference Example 1(c) except that 4-fluoro-2-methyl-6-nitrophenol obtained in Reference Example 4(a) was used instead of 4-chloro-2-isopropyl-6-nitrophenol.
¹H-NMR (400 MHz, CD₃OD) δ: 2.16 (3H, s), 6.16-6.20 (1H, m), 6.31 (1H, dd, J=2.4, 10.0 Hz)
MS(ESI) m/z: 142 (M+H)⁺

(c) 5-Fluoro-7-methyl-2-mercaptobenzoxazole

The title compound was obtained in a similar manner as in Reference Example 1(d) except that 2-amino-4-fluoro-6-methylphenol obtained in Reference Example 4(b) was used instead of 2-amino-4-chloro-6-isopropylphenol.
¹H-NMR (400 MHz, CD₃OD) δ: 2.42 (3H, s), 6.78-6.86 (2H, m)
MS(ESI) m/z: 184 (M+H)⁺

Reference Example 5

5-Bromo-7-methyl-2-mercaptobenzoxazole (a) 4-Bromo-2-methyl-6-nitrophenol

The title compound was obtained in a similar manner as in Reference Example 1(b) except that 4-bromo-2-methylphenol was used instead of 4-chloro-2-isopropylphenol.

(b) 2-Amino-4-bromo-6-methylphenol

The title compound was obtained in a similar manner as in Reference Example 1(c) except that 4-bromo-2-methyl-6-nitrophenol obtained in Reference Example 5(a) was used instead of 4-chloro-2-isopropyl-6-nitrophenol.
¹H-NMR (400 MHz, CD₃OD) δ: 2.15 (3H, s), 6.57 (1H, s), 6.71 (1H, s)

(c) 5-Bromo-7-methyl-2-mercaptobenzoxazole

The title compound was obtained in a similar manner as in Reference Example 1(d) except that 2-amino-4-bromo- 6-methylphenol obtained in Reference Example 5(b) was used instead of 2-amino-4-chloro-6-isopropylphenol.
$^1$H-NMR (400 MHz, DMSO-d$_6$) δ: 2.36 (3H, s), 7.21 (1H, s), 7.31 (1H, s)
MS(ESI) m/z: 243 (M+H)$^+$ Reference Example 6

5-Chloro-7-isopropoxy-2-mercaptobenzoxazole (a) 4-Chloro-2-isopropoxyphenol

The title compound was obtained in a similar manner as in Reference Example 1(a) except that 2-isopropoxyphenol was used instead of 2-isopropylphenol.

(b) 4-Chloro-2-isopropoxy-6-nitrophenol

The title compound was obtained in a similar manner as in Reference Example 1(b) except that 4-chloro-2-isopropoxyphenol obtained in Reference Example 6(a) was used instead of 4-chloro-2-isopropylphenol.

(c) 2-Amino-4-chloro-6-isopropoxyphenol

The title compound was obtained in a similar manner as in Reference Example 1(c) except that 4-chloro-2-isopropoxy-6-nitrophenol obtained in Reference Example 6(b) was used instead of 4-chloro-2-isopropyl-6-nitrophenol.

(d) 5-Chloro-7-isopropoxy-2-mercaptobenzoxazole

The title compound was obtained in a similar manner as in Reference Example 1(d) except that 2-amino-4-chloro-6-isopropoxyphenol obtained in Reference Example 6(c) was used instead of 2-amino-4-chloro-6-isopropylphenol.
$^1$H-NMR (400 MHz, DMSO-d$_6$) δ: 1.31 (6H, d, J=2 Hz), 4.85 (1H, m), 6.84 (1H, s), 7.03 (1H, s)
MS(ESI) m/z: 242 (M−H)$^-$ Reference Example 7

5-Chloro-7-ethyl-2-mercaptobenzoxazole (a) 4-Chloro-2-ethylphenol

The title compound was obtained in a similar manner as in Reference Example 1(a) except that 2-ethylphenol was used instead of 2-isopropylphenol.

(b) 4-Chloro-2-ethyl-6-nitrophenol

The title compound was obtained in a similar manner as in Reference Example 1(b) except that 4-chloro-2-ethylphenol obtained in Reference Example 7(a) was used instead of 4-chloro-2-isopropylphenol.

(c) 2-Amino-4-chloro-6-ethylphenol

The title compound was obtained in a similar manner as in Reference Example 1(c) except that 4-chloro-2-ethyl-6-nitrophenol obtained in Reference Example 7(b) was used instead of 4-chloro-2-isopropyl-6-nitrophenol.

(d) 5-Chloro-7-ethyl-2-mercaptobenzoxazole

The title compound was obtained in a similar manner as in Reference Example 1(d) except that 2-amino-4-chloro-6-ethylphenol obtained in Reference Example 7(c) was used instead of 2-amino-4-chloro-6-ethylphenol.

Reference Example 8

5-Chloro-7-cyano-2-mercaptobenzoxazole (a) 4-Chloro-2-cyano-6-nitrophenol

The title compound was obtained in a similar manner as in Reference Example 1(b) except that 5-chloro-2-hydroxybenzonitrile was used instead of 4-chloro-2-isopropylphenol.

(b) 2-Amino-4-chloro-6-cyanophenol

The title compound was obtained in a similar manner as in Reference Example 1(c) except that 4-chloro-2-cyano-6-nitrophenol obtained in Reference Example 8(a) was used instead of 4-chloro-2-isopropyl-6-nitrophenol.

(c) 5-Chloro-7-cyano-2-mercaptobenzoxazole

The title compound was obtained in a similar manner as in Reference Example 1(d) except that 2-amino-4-chloro-6-cyanophenol obtained in Reference Example 8(b) was used instead of 2-amino-4-chloro-6-isopropylphenol.
MS(ESI) m/z: 209 (M−H)$^-$ Reference Example 9

7-Bromo-5-chloro-2-mercaptobenzoxazole (a) 2-Bromo-4-chloro-6-nitrophenol

The title compound was obtained in a similar manner as in Reference Example 1(b) except that 2-bromo-4-chlorophenol was used instead of 4-chloro-2-isopropylphenol.

(b) 2-Amino-6-bromo-4-chlorophenol

The title compound was obtained in a similar manner as in Reference Example 1(c) except that 2-bromo-4-chloro-6-nitrophenol obtained in Reference Example 8(a) was used instead of 4-chloro-2-isopropyl-6-nitrophenol.

(c) 7-Bromo-5-chloro-2-mercaptobenzoxazole

The title compound was obtained in a similar manner as in Reference Example 1(d) except that 2-amino-6-bromo-4-chlorophenol obtained in Reference Example 8(b) was used instead of 2-amino-4-chloro-6-isopropylphenol.
MS(ESI) m/z: 262 (M−H)$^-$ Reference Example 10

7-Bromo-5-chloro-2-mercapto-4-(trifluoromethyl)benzoxazole (a) 6-Bromo-4-chloro-2-nitro-3-(trifluoromethyl)phenol (b) 2-Bromo-4-chloro-6-nitro-3-(trifluoromethyl)phenol 4-Chloro-3-(trifluoromethyl)phenol (5.0 g) was dissolved in acetic acid (50 mL), then bromine (1.54 mL, 1.2 equivalents) was added thereto, and the resulting mixture was stirred at room temperature for 7 hours. Water was added to the reaction mixture, and the product was extracted with ethyl acetate and chloroform. The organic layer was dried over anhydrous sodium sulfate, and then the solvent was distilled off under reduced pressure to obtain a crude product. The obtained crude product was purified by silica gel column chromatography (developing solvent, chloroform) to obtain 1.88 g of a mixture of 2-bromo-4-chloro-5-(trifluoromethyl)phenol and 2-bromo-4-chloro-3-(trifluoromethyl)phenol. The obtained mixture (826 mg) was dissolved in acetic acid (3.0 mL), then 70% nitric acid (380 μL) was added thereto under ice cooling, and the resulting mixture was stirred for 1 hour in this state. After that, the resulting mixture was stirred at room temperature for 1 hour, then water was added thereto, and the product was extracted with ethyl acetate. The organic layer was washed with water and a saturated saline solution sequentially and dried over anhydrous sodium sulfate, then the solvent was distilled off under reduced pressure, and the obtained residue was purified by silica gel column chromatography (developing solvent, chloroform) to obtain 323 mg of the compound of Title (a) and 142 mg of the compound of Title (b).

(c) 2-Amino-6-bromo-4-chloro-3-(trifluoromethyl) phenol

The title compound was obtained in a similar manner as in Reference Example 1(c) except that 6-bromo-4-chloro-2-nitro-3-(trifluoromethyl)phenol obtained in Reference Example 10(a) was used instead of 4-chloro-2-isopropyl-6-nitrophenol.

(d) 7-Bromo-5-chloro-2-mercapto-4-(trifluoromethyl)benzoxazole

The title compound was obtained in a similar manner as in Reference Example 1(d) except that 2-amino-6-bromo-4-chloro-6-(trifluoromethyl)phenol obtained in Reference Example 10(c) was used instead of 2-amino-4-chloro-6-isopropylphenol.
MS(ESI) m/z: 330 (M−H)⁻

Reference Example 11

7-Bromo-5-chloro-2-mercapto-6-(trifluoromethyl) benzoxazole (a) 6-Amino-2-bromo-4-chloro-3-(trifluoromethyl) phenol The title compound was obtained in a similar manner as in Reference Example 1(c) except that 2-bromo-4-chloro-6-nitro-3-(trifluoromethyl)phenol obtained in Reference Example 10(b) was used instead of 4-chloro-2-isopropyl-6-nitrophenol.

(d) 7-Bromo-5-chloro-2-mercapto-6-(trifluoromethyl)benzoxazole

The title compound was obtained in a similar manner as in Reference Example 1(d) except that 6-amino-2-bromo-4-chloro-3-(trifluoromethyl)phenol obtained in Reference Example 11(a) was used instead of 2-amino-4-chloro-6-isopropylphenol.
MS(ESI) m/z: 330 (M−H)⁻

Reference Example 12

7-Bromo-5-chloro-2-mercapto-4-(trifluoromethoxy) benzoxazole (a) 2-Bromo-4-chloro-5-(trifluoromethoxy)phenol The title compound was obtained in a similar manner as in Reference Example 1(a) except that 2-bromo-5-(trifluoromethoxy)phenol was used instead of 2-isopropylphenol.

(b) 6-Bromo-4-chloro-2-nitro-3-(trifluoromethoxy) phenol

The title compound was obtained in a similar manner as in Reference Example 1(b) except that 2-bromo-4-chloro-5-(trifluoromethoxy)phenol obtained in Reference Example 12(a) was used instead of 4-chloro-2-isopropylphenol.

(c) 2-Amino-6-bromo-4-chloro-3-(trifluoromethoxy) phenol

The title compound was obtained in a similar manner as in Reference Example 1(c) except that 6-bromo-4-chloro-2-nitro-3-(trifluoromethoxy)phenol obtained in Reference Example 12(b) was used instead of 4-chloro-2-isopropyl-6-nitrophenol.

(d) 7-Bromo-5-chloro-2-mercapto-4-(trifluoromethoxy)benzoxazole

The title compound was obtained in a similar manner as in Reference Example 1(d) except that 2-amino-6-bromo-4-chloro-3-(trifluoromethoxy)phenol obtained in Reference Example 12(c) was used instead of 2-amino-4-chloro-6-ethylphenol.
$^1$H-NMR (400 MHz, DMSO-$d_6$) δ: 7.84 (1H, s)
MS(ESI) m/z: 346 (M−H)⁻

Reference Example 13

7-Bromo-4,5-difluoro-2-mercaptobenzoxazole (a) 6-Bromo-3,4-difluoro-2-nitrophenol The title compound was obtained in a similar manner as in Reference Example 1(b) except that 2-bromo-4,5-difluorophenol was used instead of 4-chloro-2-isopropylphenol.

(b) 2-Amino-6-bromo-3,4-di fluorophenol

The title compound was obtained in a similar manner as in Reference Example 1(c) except that the whole quantity of 6-bromo-3,4-difluoro-2-nitrophenol obtained in Reference Example 13(a) was used instead of 4-chloro-2-isopropyl-6-nitrophenol.

(c) 7-Bromo-4,5-difluoro-2-mercaptobenzoxazole

The title compound was obtained in a similar manner as in Reference Example 1(d) except that 2-amino-6-bromo-3,4-difluorophenol obtained in Reference Example 13(b) was used instead of 2-amino-4-chloro-6-ethylphenol.
MS(ESI) m/z: 264 (M−H)⁻

Reference Example 14

7-Bromo-5-chloro-6-fluoro-2-mercaptobenzoxazole (a) 2-Bromo-4-chloro-3-fluorophenol The title compound was obtained in a similar manner as in Reference Example 1(a) except that 2-bromo-3-fluorophenol was used instead of 2-isopropylphenol.

(b) 2-Bromo-4-chloro-3-fluoro-6-nitrophenol

The title compound was obtained in a similar manner as in Reference Example 1(b) except that 2-bromo-4-chloro-3-fluorophenol obtained in Reference Example 14(a) was used instead of 4-chloro-2-isopropylphenol.

(c) 6-Amino-2-bromo-4-chloro-3-fluorophenol

The title compound was obtained in a similar manner as in Reference Example 1(c) except that 2-bromo-4-chloro-3-fluoro-6-nitrophenol obtained in Reference Example 14(b) was used instead of 4-chloro-2-isopropyl-6-nitrophenol.

(d) 7-Bromo-5-chloro-6-fluoro-2-mercaptobenzoxazole

The title compound was obtained in a similar manner as in Reference Example 14(d) except that 6-amino-2-bromo-4-chloro-3-fluorophenol obtained in Reference Example 14(c) was used instead of 2-amino-4-chloro-6-ethylphenol.
MS(ESI) m/z: 280 (M–H)$^-$

Reference Example 15

5-Chloro-2-mercapto-7-n-propylbenzoxazole (a) 4-Chloro-2-nitro-6-n-propylphenol The title compound was obtained in a similar manner as in Reference Example 1(b) except that 4-chloro-2-n-propylphenol was used instead of 4-chloro-2-isopropylphenol.

(b) 2-Amino-4-chloro-6-n-propylphenol

The title compound was obtained in a similar manner as in Reference Example 1(c) except that 4-chloro-2-nitro-6-n-propylphenol obtained in Reference Example 15(a) was used instead of 4-chloro-2-isopropyl-6-nitrophenol.

(c) 5-Chloro-2-mercapto-7-n-propylbenzoxazole

The title compound was obtained in a similar manner as in Reference Example 1(d) except that 2-amino-4-chloro-6-n-propylphenol obtained in Reference Example 15(b) was used instead of 2-amino-4-chloro-6-isopropylphenol.
MS(ESI) 228 (M+H)$^+$

Reference Example 16

7-Bromo-5-fluoro-2-mercaptobenzoxazole (a) 2-Bromo-4-fluoro-6-nitrophenol

The title compound was obtained in a similar manner as in Reference Example 1(b) except that 2-bromo-4-fluorophenol was used instead of 4-chloro-2-isopropylphenol.

(b) 2-Amino-6-bromo-4-fluorophenol

The title compound was obtained in a similar manner as in Reference Example 1(c) except that 2-bromo-4-fluoro-6-nitrophenol obtained in Reference Example 16(a) was used instead of 4-chloro-2-isopropyl-6-nitrophenol.

(c) 7-Bromo-5-fluoro-2-mercaptobenzoxazole

The title compound was obtained in a similar manner as in Reference Example 1(d) except that 2-amino-6-bromo-4-fluorophenol obtained in Reference Example 16(b) was used instead of 2-amino-4-chloro-6-isopropylphenol.
MS(ESI) m/z: 246 (M–H)$^-$

Reference Example 17

7-Bromo-5-cyano-2-mercaptobenzoxazole (a) 3-Bromo-4-hydroxy-5-nitrobenzonitrile The title compound was obtained in a similar manner as in Reference Example 1(b) except that 3-bromo-4-hydroxybenzonitrile was used instead of 4-chloro-2-isopropylphenol.

(b) 3-Amino-5-bromo-4-hydroxybenzonitrile

The title compound was obtained in a similar manner as in Reference Example 1(c) except that 3-bromo-4-hydroxy-5-nitrobenzonitrile obtained in Reference Example 17(a) was used instead of 4-chloro-2-isopropyl-6-nitrophenol.

(c) 7-Bromo-5-cyano-2-mercaptobenzoxazole

The title compound was obtained in a similar manner as in Reference Example 1(d) except that 3-amino-5-bromo-4-hydroxybenzonitrile obtained in Reference Example 17(b) was used instead of 2-amino-4-chloro-6-isopropylphenol.
MS(ESI) m/z: 253 (M–H)$^-$

Reference Example 18

7-Bromo-2-mercapto-5-methylbenzoxazole (a) 2-Bromo-4-methyl-6-nitrophenol

The title compound was obtained in a similar manner as in Reference Example 1(b) except that 2-bromo-4-methylphenol was used instead of 4-chloro-2-isopropylphenol.

(b) 2-Amino-6-bromo-4-methylphenol

The title compound was obtained in a similar manner as in Reference Example 1(c) except that 2-bromo-4-methyl- 6-nitrophenol obtained in Reference Example 18(a) was used instead of 4-chloro-2-isopropyl-6-nitrophenol.

(c) 7-Bromo-2-mercapto-5-methylbenzoxazole

The title compound was obtained in a similar manner as in Reference Example 1(d) except that 2-amino-6-bromo-4-methylphenol obtained in Reference Example 18(b) was used instead of 2-amino-4-chloro-6-isopropylphenol.
MS(ESI) m/z: 242 (M–H)⁻

Reference Example 19

7-Bromo-5-fluoro-2-mercapto-4-(trifluoromethyl) benzoxazole and 7-bromo-5-fluoro-2-mercapto-6-(trifluoromethyl)benzoxazole (mixture)

(a) 6-Bromo-4-fluoro-2-nitro-3-(trifluoromethyl) phenol, and 2-bromo-4-fluoro-6-nitro-3-(trifluoromethyl)phenol (mixture)

The title compound was obtained in a similar manner as in Reference Examples 10(a) and 10(b) as a mixture except that 4-fluoro-3-(trifluoromethyl)phenol was used instead of 4-chloro-3-(trifluoromethyl)phenol.

(b) 2-Amino-6-bromo-4-fluoro-3-(trifluoromethyl) phenol and 6-amino-2-bromo-4-fluoro-3-(trifluoromethyl)phenol (mixture)

The title compound was obtained in a similar manner as in Reference Example 1(c) as a mixture except that a mixture of 6-bromo-4-fluoro-2-nitro-3-(trifluoromethyl) phenol and 2-bromo-4-fluoro-6-nitro-3-(trifluoromethyl) phenol obtained in Reference Example 19(a) was used instead of 4-chloro-2-isopropyl-6-nitrophenol.

(c) 7-Bromo-5-fluoro-2-mercapto-4-(trifluoromethyl)benzoxazole and 7-bromo-5-fluoro-2-mercapto-6-(trifluoromethyl)benzoxazole (mixture)

The title compound was obtained in a similar manner as in Reference Example 1(d) except that a mixture of 2-amino-6-bromo-4-fluoro-3-(trifluoromethyl)phenol and 6-amino-2-bromo-4-fluoro-3-(trifluoromethyl)phenol obtained in Reference Example 19(b) was used instead of 2-amino-4-chloro-6-isopropylphenol.
MS(ESI) m/z: 314 (M–H)⁻

Reference Example 20

7-Bromo-5-chloro-4,6-difluoro-2-mercaptobenzoxazole (a) 2-Bromo-4-chloro-3,5-difluoro-6-nitrophenol The title compound was obtained in a similar manner as in Reference Examples 10(a) and 10(b) except that 4-chloro-3,5-difluorophenol was used instead of 4-chloro-3-(trifluoromethyl)phenol.

(b) 2-Amino-6-bromo-4-chloro-3,5-difluorophenol

The title compound was obtained in a similar manner as in Reference Example 1(c) except that 2-bromo-4-chloro-3,5-difluoro-6-phenol obtained in Reference Example 20(a) was used instead of 4-chloro-2-isopropyl-6-nitrophenol.

(c) 7-Bromo-5-chloro-4,6-difluoro-2-mercaptobenzoxazole

The title compound was obtained in a similar manner as in Reference Example 1(d) except that 2-amino-6-bromo-4-chloro-3,5-difluorophenol obtained in Reference Example 20(b) was used instead of 2-amino-4-chloro-6-isopropylphenol.
MS(ESI) m/z: 298 (M–H)⁻

Reference Example 21

7-Bromo-4,5,6-trifluoro-2-mercaptobenzoxazole (a) 2-Bromo-3,4,5-trifluoro-6-nitrophenol The title compound was obtained in a similar manner as in Reference Examples 10(a) and 10(b) except that 3,4,5-trifluorophenol was used instead of 4-chloro-3-(trifluoromethyl)phenol.

(b) 2-Amino-6-bromo-3,4,5-trifluorophenol

The title compound was obtained in a similar manner as in Reference Example 1(c) except that 2-bromo-3,4,5-trifluoro-6-nitrophenol obtained in Reference Example 21(a) was used instead of 4-chloro-2-isopropyl-6-nitrophenol.

(c) 7-Bromo-4,5,6-trifluoro-2-mercaptobenzoxazole

The title compound was obtained in a similar manner as in Reference Example 1(d) except that 2-amino-6-bromo-3,4,5-trifluorophenol obtained in Reference Example 21(b) was used instead of 2-amino-4-chloro-6-isopropylphenol.
MS(ESI) m/z: 282 (M–H)⁻

Reference Example 22

7-Bromo-2-mercapto-5-(trifluoromethyl)benzoxazole (a) 2-Bromo-6-nitro-4-(trifluoromethyl)phenol The title compound was obtained in a similar manner as in Reference Example 1(b) except that 2-bromo-4-methylphenol was used instead of 4-chloro-2-isopropylphenol.

(b) 2-Amino-6-bromo-4-(trifluoromethyl)phenol

The title compound was obtained in a similar manner as in Reference Example 1(c) except that 2-bromo-6-nitro-4-(trifluoromethyl)phenol obtained in Reference Example 22(a) was used instead of 4-chloro-2-isopropyl-6-nitrophenol.

(c) 7-Bromo-2-mercapto-5-(trifluoromethyl)benzoxazole

The title compound was obtained in a similar manner as in Reference Example 1(d) except that 2-amino-6-bromo-4-(trifluoromethyl)phenol obtained in Reference Example 22(b) was used instead of 2-amino-4-chloro-6-isopropylphenol.
MS(ESI) m/z: 296 (M–H)⁻

Reference Example 23

7-Bromo-5-chloro-4-fluoro-2-mercaptobenzoxazole (a) 2-Bromo-4-chloro-5-fluorophenol The title compound was obtained in a similar manner as in Reference Example 1(a) except that 2-bromo-5-fluorophenol was used instead of 2-isopropylphenol.

(b) 2-Bromo-4-chloro-5-fluoro-6-nitrophenol

The title compound was obtained in a similar manner as in Reference Example 1(b) except that 2-bromo-4-chloro-5-fluorophenol obtained in Reference Example 23(a) was used instead of 4-chloro-2-isopropylphenol.

(c) 6-Amino-2-bromo-4-chloro-5-fluorophenol

The title compound was obtained in a similar manner as in Reference Example 1(c) except that 2-bromo-4-chloro-5-fluoro-6-nitrophenol obtained in Reference Example 23(b) was used instead of 4-chloro-2-isopropyl-6-nitrophenol.

(d)
7-Bromo-5-chloro-4-fluoro-2-mercaptobenzoxazole

The title compound was obtained in a similar manner as in Reference Example 1(d) except that 6-amino-2-bromo-4-chloro-3-fluorophenol obtained in Reference Example 23(c) was used instead of 2-amino-4-chloro-6-ethylphenol.
MS(ESI) 280 (M−H)⁻

Reference Example 24

7-Bromo-5-chloro-2-mercapto-4-methylbenzoxazole (a) 2-Bromo-4-chloro-5-methylphenol The title compound was obtained in a similar manner as in Reference Example 1(a) except that 2-bromo-5-methylphenol was used instead of 2-isopropylphenol.

(b) 2-Bromo-4-chloro-5-methyl-6-nitrophenol

The title compound was obtained in a similar manner as in Reference Example 1(b) except that 2-bromo-4-chloro-5-methylphenol obtained in Reference Example 24(a) was used instead of 4-chloro-2-isopropylphenol and that chloroform was used instead of acetic acid.

(c) 6-Amino-2-bromo-4-chloro-5-methylphenol

The title compound was obtained in a similar manner as in Reference Example 1(c) except that 2-bromo-4-chloro-5-methyl-6-nitrophenol obtained in Reference Example 24(b) was used instead of 4-chloro-2-isopropyl-6-nitrophenol.

(d)
7-Bromo-5-chloro-2-mercapto-4-methylbenzoxazole

The title compound was obtained in a similar manner as in Reference Example 1(d) except that 6-amino-2-bromo-4-chloro-5-methylphenol obtained in Reference Example 24(c) was used instead of 2-amino-4-chloro-6-ethylphenol.
¹H-NMR (400 MHz, CDCl₃) δ:2.36 (3H, s), 7.42 (1H,$), 10.06 (1H, br s)
MS(ESI) m/z: 276 (M−H)⁻

Reference Example 25

7-Bromo-5-fluoro-2-mercapto-4-(trifluoromethoxy)benzoxazole (a) 6-Bromo-4-fluoro-2-nitro-3-(trifluoromethoxy)phenol The title compound was obtained in a similar manner as in Reference Examples 10(a) and 10(b) except that 4-fluoro-3-(trifluoromethoxy)phenol was used instead of 4-chloro-3-(trifluoromethyl)phenol.

(b) 2-Amino-6-bromo-4-fluoro-3-(trifluoromethoxy)phenol

The title compound was obtained in a similar manner as in Reference Example 1(c) except that 6-bromo-4-fluoro-2-nitro-3-(trifluoromethoxy)phenol obtained in Reference Example 25(a) was used instead of 4-chloro-2-isopropyl-6-nitrophenol.

(c) 7-Bromo-5-fluoro-2-mercapto-4-(trifluoromethoxy)benzoxazole

The title compound was obtained in a similar manner as in Reference Example 1(d) except that 2-amino-6-bromo-4-fluoro-3-(trifluoromethoxy)phenol obtained in Reference Example 25(b) was used instead of 2-amino-4-chloro-6-isopropylphenol.
MS(ESI) m/z: 330 (M−H)⁻

Reference Example 26

7-Bromo-5-chloro-2-mercapto-6-methylbenzoxazole (a) 2-Bromo-4-chloro-3-methylphenol The title compound was obtained in a similar manner as in Reference Example 1(a) except that 2-bromo-3-methylphenol was used instead of 2-isopropylphenol.

(b) 2-Bromo-4-chloro-3-methyl-6-nitrophenol

The title compound was obtained in a similar manner as in Reference Example 1(b) except that 2-bromo-4-chloro-5-methylphenol obtained in Reference Example 26(a) was used instead of 4-chloro-2-isopropylphenol and that chloroform was used instead of acetic acid.

(c) 6-Amino-2-bromo-4-chloro-3-methylphenol

The title compound was obtained in a similar manner as in Reference Example 1(c) except that 2-bromo-4-chloro-3-methyl-6-nitrophenol obtained in Reference Example 26(b) was used instead of 4-chloro-2-isopropyl-6-nitrophenol.

(d)
7-Bromo-5-chloro-2-mercapto-6-methylbenzoxazole

The title compound was obtained in a similar manner as in Reference Example 1(d) except that 6-amino-2-bromo- 4-chloro-5-methylphenol obtained in Reference Example 26(c) was used instead of 2-amino-4-chloro-6-ethylphenol.

$^1$H-NMR (400 MHz, CDCl$_3$) δ: 2.55 (3H, s), 7.17 (1H, s), 10.24 (1H, br s)

MS(ESI) m/z: 276 (M−H)$^−$

Reference Example 27

7-Bromo-5-chloro-2-mercapto-6-methoxybenzoxazole (a) 2-Bromo-4-chloro-5-methoxyphenol The title compound was obtained in a similar manner as in Reference Example 1(a) except that 2-bromo-5-methoxyphenol was used instead of 2-isopropylphenol.

$^1$H-NMR (400 MHz, CDCl$_3$) δ: 3.83 (3H, s), 6.65 (1H, s), 7.43 (1H, s)

(b) 2-Bromo-4-chloro-3-methoxy-6-nitrophenol

2-Bromo-4-chloro-5-methoxyphenol (2:15 g) obtained in Reference Example 27(a) was dissolved in ethyl acetate (21.5 mL), and 70% nitric acid (1.15 mL) was added dropwise thereto under ice cooling After the dropping was completed, concentrated sulfuric acid (0.3 mL) was added while stirring the resulting mixture at room temperature, and the reaction mixture was further stifled for 22 hours. Ethyl acetate was added to the reaction mixture, the organic layer was sequentially washed with an aqueous solution of sodium hydrogencarbonate and a saturated saline solution and then dried over anhydrous magnesium sulfate, and the solvent was distilled off under reduced pressure to obtain a crude product. This crude product was purified by silica gel column chromatography (developing solvent, ethyl acetate:hexane=1:8) to obtain 1.21 g of the title compound.

$^1$H-NMR (400 MHz, CDCl$_3$) δ: 4.01 (3H, s), 8.22 (1H, s), 11.25 (1H, s)

(c) 6-Amino-2-bromo-4-chloro-3-methoxyphenol

The title compound was obtained in a similar manner as in Reference Example 1(c) except that 2-bromo-4-chloro-3-methoxy-6-nitrophenol obtained in Reference Example 27(b) was used instead of 4-chloro-2-isopropyl-6-nitrophenol.

(d) 7-Bromo-5-chloro-2-mercapto-6-methoxybenzoxazole

The title compound was obtained in a similar manner as in Reference Example 1(d) except that 6-amino-2-bromo-4-chloro-3-methoxyphenol obtained in Reference Example 27(c) was used instead of 2-amino-4-chloro-6-ethylphenol.

$^1$H-NMR (500 MHz, CDCl$_3$) δ: 3.92 (3H, s), 7.16 (1H, s)

MS(EI) m/z: 293(M$^+$)

Reference Example 28

7-Bromo-5-chloro-4-cyano-2-mercaptobenzoxazole and 7-bromo-5-chloro-6-cyano-2-mercaptobenzoxazole (mixture)

(a) 4-Bromo-6-chloro-3-hydroxy-2-nitrobenzonitrile and 2-bromo-6-chloro-3-hydroxy-4-nitrobenzonitrile (mixture)

The title compound was obtained in a similar manner as in Reference Examples 10(a) and 10(b) as a mixture except that 2-chloro-5-hydroxybenzonitrile was used instead of 4-chloro-3-(trifluoromethyl)phenol.

(b) 2-Amino-4-bromo-6-chloro-3-hydroxybenzonitrile and 4-amino-2-bromo-6-chloro-3-hydroxybenzonitrile (mixture)

The title compound was obtained in a similar manner as in Reference Example 1(c) as a mixture except that a mixture of 4-bromo-6-chloro-3-hydroxy-2-nitrobenzonitrile and 2-bromo-6-chloro-3-hydroxy-4-nitrobenzonitrile obtained in Reference Example 28(a) was used instead of 4-chloro-2-isopropyl-6-nitrophenol.

(c) 7-Bromo-5-chloro-4-cyano-2-mercaptobenzoxazole and 7-bromo-5-chloro-6-cyano-2-mercaptobenzoxazole (mixture)

The title compound was obtained in a similar manner as in Reference Example 1(d) except that a mixture of 2-amino-4-bromo-6-chloro-3-hydroxybenzonitrile and 4-amino-2-bromo-6-chloro-3-hydroxybenzonitrile obtained in Reference Example 28(b) was used instead of 2-amino-4-chloro-6-isopropylphenol.

MS(ESI) m/z: 287 (M−H)$^−$

Reference Example 29

7-Bromo-5-chloro-2-mercapto-6-(trifluoromethoxy)benzoxazole (a) 6-Bromo-4-chloro-2-nitro-5-(trifluoromethoxy)phenol In Reference Example 12(b), the title compound was obtained as a byproduct at the same time in which 6-bromo-4-chloro-2-nitro-3-(trifluoromethoxy)phenol was obtained.

(b) 2-Amino-6-bromo-4-chloro-5-(trifluoromethoxy)phenol

The title compound was obtained in a similar manner as in Reference Example 1(c) except that 6-bromo-4-chloro-2-nitro-5-(trifluoromethoxy)phenol obtained in Reference Example 29(a) was used instead of 4-chloro-2-isopropyl-6-nitrophenol.

(c) 7-Bromo-5-chloro-2-mercapto-6-(trifluoromethoxy)benzoxazole

The title compound was obtained in a similar manner as in Reference Example 1(d) except that 2-amino-6-bromo-4-chloro-5-(trifluoromethoxy)phenol obtained in Reference Example 29(b) was used instead of 2-amino-4-chloro-6-ethylphenol.

$^1$H-NMR (400 MHz, DMSO-d$_6$) δ: 7.54 (1H, s)

Reference Example 30

5-Chloro-6-methoxy-7-methyl-2-mercaptobenzoxazole (a) 1-Chloro-2,4-dimethoxy-3-methylbenzene The title compound was obtained in a similar manner as in Reference Example 1(a) except that 1,3-dimethoxy-2-methylbenzene was used instead of 2-isopropylphenol.

(b) 1-Chloro-2,4-dimethoxy-3-methyl-5-nitrobenzene

The title compound was obtained in a similar manner as in Reference Example 1(b) except that 1-chloro-2,4-dimethoxy-3-methylbenzene obtained in Reference Example 30(a) was used instead of 4-chloro-2-isopropylphenol.

(c) 4-Chloro-3-methoxy-2-methyl-6-nitrophenol

1-Chloro-2,4-dimethoxy-3-methyl-5-nitrobenzene obtained in Reference Example 30(b) (1.77 g) was dissolved in dichloromethane (20 mL), boron tribromide (a 1 M solution in dichloromethane, 9.5 mL) was added thereto at −78° C., and then the resulting mixture was stirred for 70 minutes in this state. Water was added to the reaction mixture, and the product was extracted with dichloromethane. The organic layer was dried over magnesium sulfate, the solvent was distilled off under reduced pressure, and the residue was purified by silica gel chromatography (developing solvent, n-hexane:ethyl acetate=10:1) to obtain 1.25 g of the title compound.
$^1$H-NMR (400 MHz, CDCl$_3$) δ: 2.28 (3H, s), 3.90 (3H, s), 8.06 (1H, s), 10.97 (1H, s)

(d) 6-Amino-4-chloro-3-methoxy-2-methylphenol

The title compound was obtained in a similar manner as in Reference Example 1(c) except that 4-chloro-3-methoxy-2-methyl-6-nitrophenol obtained in Reference Example 30(c) was used instead of 4-chloro-2-isopropyl-6-nitrophenol.

(e) 5-Chloro-6-methoxy-7-methyl-2-mercaptobenzoxazole

The title compound was obtained in a similar manner as in Reference Example 1(d) except that 6-amino-4-chloro-3-methoxy-2-methylphenol obtained in Reference Example 30(d) was used instead of 2-amino-4-chloro-6-isopropylphenol.
$^1$H-NMR (400 MHz, DMSO-d$_6$) δ: 2.34 (3H, s), 3.76 (3H, s), 7.19 (1H, s)

Reference Example 31

4-Bromo-6-chloro-2-mercaptobenzoxazole (a) 2-Amino-3-bromo-5-chlorophenol

The title compound was obtained in a similar manner as in Reference Example 30(c) except that 2-bromo-4-chloro-6-methoxyaniline was used instead of 1-chloro-2,4-dimethoxy-3-methyl-5-nitrobenzene and that the reaction was performed at room temperature.

(b) 4-Bromo-6-chloro-2-mercaptobenzoxazole

The title compound was obtained in a similar manner as in Reference Example 1(d) except that 2-amino-3-bromo-5-chlorophenol obtained in Reference Example 31(a) was used instead of 2-amino-4-chloro-6-isopropylphenol.
MS(ESI) m/z: 262 (M−H)$^-$ Reference Example 32

5-Bromo-2-mercaptobenzoxazole

The title compound was obtained in a similar manner as in Reference Example 1(d) except that 2-amino-4-bromophenol was used instead of 2-amino-4-chloro-6-isopropylphenol.
$^1$H-NMR (400 MHz, DMSO-d$_6$) δ: 7.39-7.48 (3H, m)
MS(ESI) m/z: 230 (M+H)$^+$ Reference Example 33

5-Cyano-7-methoxy-2-mercaptobenzoxazole (a) 4-Hydroxy-3-methoxy-5-nitrobenzonitrile The title compound was obtained in a similar manner as in Reference Example 1(b) except that 4-hydroxy-3-methoxybenzonitrile was used instead of 4-chloro-2-isopropylphenol.

(b) 3-Amino-4-hydroxy-5-methoxybenzonitrile

The title compound was obtained in a similar manner as in Reference Example 1(c) except that 4-hydroxy-3-methoxy-5-nitrobenzonitrile obtained in Reference Example 33(a) was used instead of 4-chloro-2-isopropyl-6-nitrophenol.

(c) 5-Cyano-7-methoxy-2-mercaptobenzoxazole

The title compound was obtained in a similar manner as in Reference Example 1(d) except that 3-amino-4-hydroxy-5-methoxybenzonitrile obtained in Reference Example 33(b) was used instead of 2-amino-4-chloro-6-isopropylphenol.
$^1$H-NMR (400 MHz, DMSO-d$_6$) δ: 3.97 (3H, s), 7.34 (1H, s), 7.48 (1H, s)
MS(ESI) m/z: 207 (M+H)$^+$ Reference Example 34

5-Chloro-6,7-dimethoxy-2-mercaptobenzoxazole (a) 4-Chloro-2,3-dimethoxy-6-nitrophenol The title compound was obtained in a similar manner as in Reference Example 1(b) except that 4-chloro-2,3-dimethoxyphenol was used instead of 4-chloro-2-isopropylphenol.

(b) 6-Amino-4-chloro-2,3-dimethoxyphenol

The title compound was obtained in a similar manner as in Reference Example 1(c) except that 4-chloro-2,3-dimethoxy-6-nitrophenol obtained in Reference Example 34(a) was used instead of 4-chloro-2-isopropyl-6-nitrophenol.

(c) 5-Chloro-6,7-dimethoxy-2-mercaptobenzoxazole

The title compound was obtained in a similar manner as in Reference Example 1(d) except that 6-amino-4-chloro-2,3-dimethoxyphenol obtained in Reference Example 34(b) was used instead of 2-amino-4-chloro-6-isopropylphenol.
MS(ESI) m/z: 246 (M+H)$^+$

Reference Example 35

5-Chloro-6-methyl-2-mercaptobenzoxazole (a) 2-Amino-4-chloro-5-methylphenol

The title compound was obtained in a similar manner as in Reference Example 1(c) except that 4-chloro-5-methyl-2-nitrophenol was used instead of 4-chloro-2-isopropyl-6-nitrophenol.

(b) 5-Chloro-6-methyl-2-mercaptobenzoxazole

The title compound was obtained in a similar manner as in Reference Example 1(d) except that 2-amino-4-chloro-5-methylphenol obtained in Reference Example 35(a) was used instead of 2-amino-4-chloro-6-isopropylphenol.
MS(ESI) m/z: 198 (M−H)−

Reference Example 36

5-Chloro-6-methoxy-2-mercaptobenzoxazole

The title compound was obtained in a similar manner as in Reference Example 1(d) except that 2-amino-4-chloro-5-methoxyphenol was used instead of 2-amino-4-chloro-6-isopropylphenol.
MS(ESI) m/z: 214 (M−H)−

Example 1

(S)-5-Chloro-7-isopropyl-2-(2-methylpiperazin-1-yl)benzoxazole

5-Chloro-7-isopropyl-2-mercaptobenzoxazole obtained in Reference Example 1 (203 mg) and (S)-1-tert-butoxycarbonyl-3-methylpiperazine (357 mg, 2.0 equivalents) were dissolved in xylene (2.0 mL), and the resulting mixture was stirred in an oil bath at 140° C. overnight. TLC (developing solvent, hexane:ethyl acetate=3:1) was carried out to verify that the starting material had vanished, then 1 N hydrochloric acid was added to weakly acidify the reaction mixture, and the product was extracted with ethyl acetate. A 4 N solution of hydrogen chloride/dioxane was added to the extract, and the resulting mixture was stirred at room temperature, TLC (developing solvent, ethyl acetate:methanol=10:1) was carried out to verify that the target product had been produced, then water was added thereto, and the product was extracted from the organic layer. A 5 N aqueous solution of sodium hydroxide was added to the water layer for neutralization, then the resulting mixture was extracted with ethyl acetate and dried over anhydrous magnesium sulfate, and then the solvent was distilled off under reduced pressure to obtain 181 mg of the title compound.
$^1$H-NMR (400 MHz, CDCl$_3$) δ: 1.32 (6H, d, J=6.8 Hz), 1.39 (3H, d, J=6.8 Hz), 2.85-2.93 (2H, m), 3.01-3.11 (2H, m), 3.14-3.21 (1H, m), 3.37 (1H, dt, J=3.6, 12.8 Hz), 3.95-3.98 (1H, m), 4.35-4.40 (1H, m), 6.84 (1H, d, J=2.4 Hz), 7.15 (1H, d, J=2.4 Hz)
MS(ESI) m/z: 294 (M+H)+

Example 2

(S)-5-Chloro-7-methoxy-2-(2-methylpiperazin-1-yl)benzoxazole

5-Chloro-7-methoxy-2-mercaptobenzoxazole obtained in Reference Example 2 (80 mg) and (S)-1-tert-butoxycarbonyl-3-methylpiperazine (149 mg, 2.0 equivalents) were dissolved in xylene (1.6 mL), and the resulting mixture was stirred in an oil bath at 140° C. overnight. TLC (developing solvent, dichloromethane) was carried out to verify that the starting material had vanished, then 1 N hydrochloric acid was added to weakly acidify the reaction mixture, and the product was extracted with ethyl acetate. A 4 N solution of hydrogen chloride/dioxane was added to the extract, the resulting mixture was stirred at room temperature, and TLC (developing solvent, dichloromethane:methanol=5:1) was carried out to verify that the target product had been produced, then water was added thereto, and the product was extracted from the organic layer. A 5 N aqueous solution of sodium hydroxide was added to the water layer for neutralization, then the reaction mixture was extracted with ethyl acetate and dried over anhydrous magnesium sulfate, then the solvent was distilled off under reduced pressure, and the residue was purified by preparative TLC (developing solvent, ethyl acetate:methanol=5:1) to obtain 23 mg of the title compound.
$^1$H-NMR (400 MHz, CDCl$_3$) δ: 1.38 (3H, d, J=6.8 Hz), 2.83-2.92 (2H, m), 3.05-3.11 (2H, m), 3.38 (1H, dt, J=3.2, 12.4 Hz), 3.95 (3H, s), 3.96-4.00 (1H, m), 4.39-4.43 (1H, m), 6.60 (1H, d, J=1.6 Hz), 6.97 (1H, d, J=1.6 Hz) MS(ESI) m/z: 282 (M+H)+

Example 3

(S)-7-Acetyl-5-chloro-2-(2-methylpiperazin-1-yl)benzoxazole

The title compound was obtained in a similar manner as in Example 2 from 7-acetyl-5-chloro-2-mercaptobenzoxazole obtained in Reference Example 3 and (S)-1-tert-butoxycarbonyl-3-methylpiperazine
$^1$H-NMR (400 MHz, CDCl$_3$) δ: 1.43 (3H, d, J=6.8 Hz), 2.72 (3H, s), 2.86-2.95 (2H, m), 3.08-3.14 (2H, m), 3.43 (1H, dt, J=3.6, 12.4 Hz), 3.98-4.01 (1H, m), 4.39-4.43 (1H, m), 7.45 (1H, d, J=2.0 Hz), 7.51 (1H, d, J=2.0 Hz) MS(ESI) m/z: 294 (M+H)+

Example 4 meso-5-Chloro-2-(2,6-cis-dimethylpiperazin-1-yl)-7-methylbenzoxazole

The title compound was obtained in a similar manner as in Example 2 from 5-chloro-7-methyl-2-mercaptobenzoxazole and (3S,5R)-1-tert-butoxycarbonyl-3,5-dimethylpiperazine.
$^1$H-NMR (400 MHz, CDCl$_3$) δ:1.44 (6H, d, J=6.8 Hz), 2.38 (3H, s), 2.91-3.06 (4H, m), 4.24-4.32 (2H, m), 6.79 (1H, d, J=2 Hz), 7.15 (1H, d, J=2 Hz)

Example 5

(S)-5-Fluoro-7-methyl-2-(2-methylpiperazin-1-yl)benzoxazole

The title compound was obtained in a similar manner as in Example 2 from 5-fluoro-7-methyl-2-mercaptobenzoxazole obtained in Reference Example 4 and (S)-1-tert-butoxycarbonyl-3-methylpiperazine.
$^1$H-NMR (400 MHz, CDCl$_3$) δ: 1.39 (3H, d, J=6.8 Hz), 2.38 (3H, s), 2.83-2.92 (2H, m), 3.06-3.10 (2H, m), 3.36

(1H, dt, J=3.6, 12.4 Hz), 3.95-3.99 (1H, m), 4.38-4.41 (1H, m), 6.53 (1H, dd, J=2.4, 10.4 Hz), 6.87 (1H, dd, J=2.4, 8.8 Hz)

MS(ESI) m/z: 250 (M+H)$^+$

Example 6

(S)-5-Bromo-7-methyl-2-(2-methylpiperazin-1-yl)benzoxazole

The title compound was obtained in a similar manner as in Example 2 from 5-bromo-7-methyl-2-mercaptobenzoxazole obtained in Reference Example 5 and (S)-1-tert-butoxycarbonyl-3-methylpiperazine.

$^1$H-NMR (400 MHz, CDCl$_3$) δ: 1.39 (3H, d, J=6.8 Hz), 2.37 (3H, s), 2.89-2.92 (2H, m), 3.06-3.10 (2H, m), 3.32-3.40 (1H, m), 3.95-3.99 (1H, m), 4.39-4.42 (1H, m), 6.95 (1H, d, J=1.2 Hz), 7.28 (1H, d, J=1.2 Hz)

MS(ESI) m/z: 310 (M+H)$^+$

Example 7

(S)-5-Chloro-7-isopropoxy-2-(2-methylpiperazin-1-yl)benzoxazole

The title compound was obtained in a similar manner as in Example 2 from 5-chloro-7-isopropoxy-2-mercaptobenzoxazole obtained in Reference Example 6 and (S)-1-tert-butoxycarbonyl-3-methylpiperazine.

$^1$H-NMR (400 MHz, CDCl$_3$) δ: 1.38-1.40 (9H, m), 2.84-2.92 (2H, m), 3.07-3.10 (2H, m), 3.33-3.39 (1H, m), 3.96-3.99 (1H, m), 4.38-4.41 (1H, m), 4.65-4.70 (1H, m), 6.61 (1H, d, J=2.0 Hz), 6.95 (1H, d, J=2.0 Hz)

MS(ESI) m/z: 310 (M+H)$^+$

Example 8

(S)-5-Chloro-7-ethyl-2-(2-methylpiperazin-1-yl)benzoxazole

The title compound was obtained in a similar manner as in Example 2 from 5-chloro-7-ethyl-2-mercaptobenzoxazole obtained in Reference Example 7 and (S)-1-tert-butoxycarbonyl-3-methylpiperazine.

$^1$H-NMR (400 MHz, CDCl$_3$) δ: 1.30 (3H, t, J=7.6 Hz), 1.40 (3H, d, J=6.8 Hz), 2.76 (2H, q, J=7.6 Hz), 2.91 (2H, m), 3.09 (2H, m), 3.37 (1H, m), 3.97 (1H, m), 4.39 (1H, m), 6.83 (1H, d, J=2.0 Hz), 7.15 (1H, d, J=2.0 Hz)

MS(ESI) m/z: 280 (M+H)$^+$

Example 9

(S)-5-Chloro-7-ethoxycarbonyl-2-(2-methylpiperazin-1-yl)benzoxazole

The title compound was obtained in a similar manner as in Example 2 from 5-chloro-7-ethoxycarbonyl-2-mercaptobenzoxazole and (S)-1-tert-butoxycarbonyl-3-methylpiperazine.

$^1$H-NMR (400 MHz, CDCl$_3$) δ:1.42 (3H, d, J=7.1 Hz), 1.43 (3H, t, J=7.3 Hz), 2.84-2.93 (2H, m), 3.07-3.11 (2H, m), 3.37-3.45 (1H, m), 4.00-4.04 (1H, m), 4.39-4.45 (3H, m), 7.44 (1H, d, J=2.2 Hz), 7.56 (1H, d, J=2.2 Hz)

MS(ESI) m/z: 324 (M+H)$^+$

Example 10

(S)-5-Chloro-7-cyano-2-(2-methylpiperazin-1-yl)benzoxazole

The title compound was obtained in a similar manner as in Example 2 from 5-chloro-7-cyano-2-mercaptobenzoxazole obtained in Reference Example 8 and (S)-1-tert-butoxycarbonyl-3-methylpiperazine.

$^1$H-NMR (400 MHz, CDCl$_3$) δ:1.43 (3H, d, J=6.8 Hz), 2.83-2.96 (2H, m), 3.04-3.15 (2H, m), 3.38-3.46 (1H, m), 3.99-4.06 (1H, m), 4.38-4.46 (1H, m), 7.20 (1H, d, J=2 Hz), 7.45 (1H, d, J=2 Hz)

MS(ESI) m/z: 277 (M+H)$^+$

Example 11

(S)-5-Chloro-7-ethyl-2-(2-isopropylpiperazin-1-yl)benzoxazole

The title compound was obtained in a similar manner as in Example 2 from 5-chloro-7-ethyl-2-mercaptobenzoxazole obtained in Reference Example 7 and (S)-1-tert-butoxycarbonyl-3-isopropylpiperazine.

$^1$H-NMR (400 MHz, CDCl$_3$) δ: 0.90 (3H, d, J=6.8 Hz), 1.05 (3H, d, J=6.6 Hz), 1.30 (3H, t, J=7.6 Hz), 2.44-2.54 (1H, m), 2.70-2.95 (4H, m), 3.00-3.07 (1H, m), 3.18-3.34 (2H, m), 3.77-3.83 (1H, m), 4.06-4.14 (1H, m), 6.80 (1H, d, J=2 Hz), 7.12 (1H, d, J=2 Hz)

MS(ESI) m/z: 308 (M+H)$^+$

Example 12

(S)-5-Chloro-7-ethyl-2-(2-isobutylpiperazin-1-yl)benzoxazole

The title compound was obtained in a similar manner as in Example 2 from 5-chloro-7-ethyl-2-mercaptobenzoxazole obtained in Reference Example 7 and (S)-1-tert-butoxycarbonyl-3-isobutylpiperazine.

$^1$H-NMR (400 MHz, CDCl$_3$) δ: 0.89 (3H, t, J=7 Hz), 1.25-1.50 (6H, m), 1.57 (2H, m), 1.67-1.76 (2H, m), 2.72-2.84 (2H, m), 2.85-3.15 (2H, m), 3.29-3.38 (1H, m), 4.02-4.28 (3H, m), 6.84 (1H, d, J=2 Hz), 7.14 (1H, d, J=2 Hz)

MS(ESI) m/z: 322 (M+H)$^+$

Example 13

(S)-2-(2-n-Butylpiperazin-1-yl)-5-chloro-7-ethylbenzoxazole

The title compound was obtained in a similar manner as in Example 2 from 5-chloro-7-ethyl-2-mercaptobenzoxazole obtained in Reference Example 7 and (S)-1-tert-butoxycarbonyl-3-n-butylpiperazine.

$^1$H-NMR (400 MHz, CDCl$_3$) δ: 0.89 (3H, t, J=7 Hz), 1.25-1.40 (7H, m), 1.74-1.94 (2H, m), 2.71-2.79 (2H, m), 2.82-2.91 (1H, m), 2.96-3.08 (3H, m), 3.30-3.38 (1H, m), 4.00-4.06 (1H, m), 4.17-4.24 (1H, m), 6.81 (1H, d, J=2 Hz), 7.13 (1H, d, J=2 Hz)

MS(ESI) m/z: 322 (M+H)$^+$

Example 14

(S)-5-Chloro-7-ethyl-2-(2-ethylpiperazin-1-yl)benzoxazole

The title compound was obtained in a similar manner as in Example 2 from 5-chloro-7-ethyl-2-mercaptobenzoxazole obtained in Reference Example 7 and (S)-1-tert-butoxycarbonyl-3-ethylpiperazine.

$^1$H-NMR (400 MHz, CDCl$_3$) δ: 0.95 (3H, t, J=7.6 Hz), 1.30 (3H, t, J=7.6 Hz), 1.78-1.97 (2H, m), 2.72-2.80 (2H, m), 2.83-2.91 (1H, m), 3.00-3.09 (3H, m), 3.28-3.36 (1H, m), 4.00-4.06 (1H, m), 4.10-4.16 (1H, m), 6.81 (1H, d, J=2 Hz), 7.13 (1H, d, J=2 Hz)

MS(ESI) m/z: 294 (M+1-1)$^+$

Example 15

(S)-5-Chloro-7-hydroxymethyl-2-(2-methylpiperazin-1-yl)benzoxazole

(a) (S)-1-tert-Butoxycarbonyl-4-(5-chloro-7-ethoxycarbonylbenzoxazol-2-yl)-3-methylpiperazine 5-Chloro-7-ethoxycarbonyl-2-mercaptobenzoxazole (1.03 g) and (S)-1-tert-butoxycarbonyl-3-methylpiperazine (1.60 g, 2.0 equivalents) were dissolved in xylene (10 mL), and the resulting mixture was stirred in an oil bath at 140° C. overnight. TLC (developing solvent, hexane:ethyl acetate=4:1) was carried out to verify the product, then 1 N hydrochloric acid was added thereto to weakly acidify the reaction mixture, and the resulting mixture was extracted with ethyl acetate. The organic layer was washed with a saturated saline solution and dried over anhydrous magnesium sulfate, then the solvent was distilled off under reduced pressure, and the residue was purified by silica gel column chromatography (developing solvent, hexane:ethyl acetate=7:3) to obtain 1.16 g of the title compound.

(b) (S)-1-tert-Butoxycarbonyl-4-(5-chloro-7-carboxybenzoxazol-2-yl)-3-methylpiperazine (S)-1-tert-Butoxycarbonyl-4-(5-chloro-7-ethoxycarbonylbenzoxazol-2-yl)-3-methylpiperazine obtained in Example 15(a) (370 mg) was dissolved in 1,4-dioxane (9 mL), a 1 N aqueous solution of sodium hydroxide (1.74 mL) was added under ice cooling, and then the resulting mixture was stirred at room temperature for 18 hours. Water was added to the reaction mixture, the resulting mixture was washed with diethyl ether, then a 1% aqueous solution of citric acid was added to the water layer for neutralization. The product was extracted from the water layer with ethyl acetate and dried over anhydrous sodium sulfate, and then the solvent was distilled off under reduced pressure to obtain 342 mg of the title compound.

(c) (S)-1-tert-Butoxycarbonyl-4-(5-chloro-7-(hydroxymethyl)benzoxazol-2-yl)-3-methylpiperazine (S)-1-tert-Butoxycarbonyl-4-(5-chloro-7-carboxybenzoxazol-2-yl)-3-methylpiperazine obtained in Example 15(b) (40 mg) was dissolved in THF (1 mL), borane (a 1 M solution in THF, 0.2 mL) was added thereto under ice cooling, and the resulting mixture was stirred for 2 hours in this state. The reaction mixture was heated up to room temperature and then was further stirred for 4 hours, then ammonium chloride (53 mg) and water were added thereto, and the product was extracted with ethyl acetate. The organic layer was washed with a saturated saline solution and then dried over anhydrous sodium sulfate, the solvent was distilled off under reduced pressure, and the residue was purified by preparative TLC (developing solvent, chloroform:methanol=9:1) to obtain 30 mg of the title compound.

(d) (S)-5-Chloro-7-hydroxymethyl-2-(2-methylpiperazin-1-yl)benzoxazole (S)-1-tert-Butoxycarbonyl-4-(5-chloro-7-(hydroxymethyl)benzoxazol-2-yl)-3-methylpiperazine obtained in Example 15(c) (29 mg) was dissolved in dichloromethane (0.8 mL), then trifluoroacetic acid (0.4 mL) was added thereto, and the resulting mixture was stirred at room temperature for 1 hour. A 5% aqueous solution of sodium hydrogencarbonate was added to the reaction mixture, the product was extracted with ethyl acetate, then the organic layer was washed with a saturated saline solution and dried over anhydrous sodium sulfate, then the solvent was distilled off under reduced pressure, and the residue was purified by silica gel column chromatography (developing solvent, chloroform:methanol=9:1) to obtain 12 mg of the title compound.

$^1$H-NMR (400 MHz, CDCl$_3$) δ: 1.40 (3H, d, J=6.8 Hz), 2.83-2.92 (2H, m), 3.06-3.11 (2H, m), 3.34-3.41 (1H, m), 3.95-3.99 (1H, m), 4.37-4.24 (1H, m), 4.84 (2H, s), 7.04 (1H, d, J=2.0 Hz), 7.24 (1H, d, J=2.2 Hz)

MS(ESI) m/z: 282 (M+H)$^+$

Example 16

(S)-5-Chloro-2-(2-methylpiperazin-1-yl)-7-(thiophen-3-yl)benzoxazole

(a) (S)-1-tert-Butoxycarbonyl-4-(7-bromo-5-chlorobenzoxazol-2-yl)-3-methylpiperazine 7-Bromo-5-chloro-2-mercaptobenzoxazole obtained in Reference Example 9 (500 mg) and (S)-1-tert-butoxycarbonyl-3-methylpiperazine (757 mg, 2.0 equivalents) were dissolved in xylene (5 mL), and the resulting mixture was stirred in an oil bath at 140° C. overnight. TLC (developing solvent, hexane:ethyl acetate=2:1) was carried out to verify the product, then 1 N hydrochloric acid was added thereto to weakly acidify the reaction mixture, and the resulting mixture was extracted with ethyl acetate. The organic layer was washed with a saturated saline solution and dried over anhydrous magnesium sulfate, then the solvent was distilled off under reduced pressure, and the residue was purified by silica gel column chromatography (developing solvent, hexane:ethyl acetate=5:1) to obtain 613 mg of the title compound.

$^1$H-NMR (400 MHz, CDCl$_3$) δ: 1.32 (3H, d, J=6.8 Hz), 1.50 (9H, s), 2.27-2.30 (1H, m), 3.18-3.21 (1H, m), 3.42 (1H, dt, J=3.6, 12.8 Hz), 3.80-3.82 (1H, m), 4.01-4.05 (1H, m), 4.22-4.25 (1H, m), 4.45-4.48 (1H, m), 7.15 (1H, d, J=1.6 Hz), 7.23 (1H, d, J=1.6 Hz)

MS(ESI) m/z: 430 (M+H)$^+$

(b) (S)-1-tert-Butoxycarbonyl-4-(5-chloro-7-(thiophen-3-yl)benzoxazol-2-yl)-3-methylpiperazine (S)-1-tert-Butoxycarbonyl-4-(7-bromo-5-chlorobenzoxazol-2-yl)-3-methylpiperazine obtained in Example 16(a)

(120 mg), potassium carbonate (85 mg, 2.2 equivalents), and 3-thiophene boronic acid (43 mg, 1.2 equivalents) were dissolved in toluene (1.6 mL) and ethanol (0.4 mL), the resulting mixture was stirred in an argon atmosphere for 15 minutes, then tetrakis(triphenylphosphine)palladium(0) (16 mg, 0.05 equivalents) was added thereto, and the resulting mixture was heated under reflux for 2 hours. Water was added to the reaction mixture, and the product was extracted with ethyl acetate. The organic layer was dried over anhydrous magnesium sulfate, then the solvent was distilled off under reduced pressure, and the residue was purified by silica gel column chromatography (developing solvent, hexane:ethyl acetate=4:1) to obtain 74 mg of the title compound.

$^1$H-NMR (400 MHz, CDCl$_3$) δ: 1.33 (3H, d, J=6.8 Hz), 1.45 (9H, s), 2.94-3.10 (1H, br s), 3.19-3.28 (1H, br s), 3.42-3.47 (1H, m), 4.01-4.05 (2H, m), 4.23-4.25 (1H, br s), 4.48-4.50 (1H, br s), 7.24-7.27 (2H, m), 7.44-7.46 (1H, m), 7.53-7.55 (1H, m), 7.75-7.76 (1H, m)

MS(ESI) m/z: 434 (M+H)$^+$ (c) (S)-5-Chloro-2-(2-methylpiperazin-1-yl)-7-(thiophen-3-yl)benzoxazole (S)-1-tert-Butoxycarbonyl-4-(5-chloro-7-(thiophen-3-yl)benzoxazol-2-yl)-3-methylpiperazine obtained in Example 16(b) (74 mg) was dissolved in dichloromethane (1.4 mL) and trifluoroacetic acid (0.7 mL), and the resulting mixture was stirred at room temperature for 1 hour. The reaction solvent was distilled off under reduced pressure, then ethyl acetate was added thereto, and the resulting mixture was washed with an aqueous solution of sodium hydrogencarbonate. The organic layer was dried over anhydrous magnesium sulfate, then the solvent was distilled off under reduced pressure to obtain 45 mg of the title compound.

$^1$H-NMR (400 MHz, CDCl$_3$) δ: 1.43 (3H, d, J=6.8 Hz), 2.88-2.97 (2H, m), 3.10-3.16 (2H, m), 3.44 (1H, dt, J=3.6, 12.8 Hz), 4.00-4.03 (1H, m), 4.43-4.45 (1H, m), 7.23-7.27 (2H, m), 7.43-7.45 (1H, m), 7.54 (1H, d, J=5.2 Hz), 7.76 (1H, d, J=3.2 Hz)

MS(ESI) m/z: 334 (M+H)$^+$

Example 17

(S)-5-Chloro-7-(furan-3-yl)-2-(2-methylpiperazin-1-yl)benzoxazole (a) (S)-1-tert-Butoxycarbonyl-4-(5-chloro-7-(furan-3-yl)benzoxazol-2-yl)-3-methylpiperazine The title compound was obtained in a similar manner as in Example 16(b) except that 3-furylboronic acid was used instead of 3-thiophene boronic acid.

(b) (S)-5-Chloro-7-(furan-3-yl)-2-(2-methylpiperazin-1-yl)benzoxazole

The title compound was obtained in a similar manner as in Example 16(c) except that (S)-1-tert-butoxycarbonyl-(5-chloro-7-(furan-3-yl)benzoxazol-2-yl)-3-methyl piperazine obtained in Example 17(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.44 (3H, d, J=6.8 Hz), 2.87-2.97 (2H, m), 3.09-3.16 (2H, m), 3.40-3.47 (1H, m), 3.98-4.02 (1H, m), 4.41-4.44 (1H, m), 6.83 (1H, dd, J=0.7, 1.7 Hz), 7.14 (1H, d, J=2.0 Hz), 7.21 (1H, d, J=2.0 Hz), 7.54 (1H, d, J=2.0 Hz), 7.97-7.98 (m, 1H)

MS(ESI) m/z: 318 (M+H)$^+$

Example 18

(S)-5-Chloro-2-(2-methylpiperazin-1-yl)-7-(thiophen-2-yl)benzoxazole (a) (S)-1-tert-Butoxycarbonyl-4-(5-chloro-7-(thiophen-2-yl)benzoxazol-2-yl)-3-methylpiperazine The title compound was obtained in a similar manner as in Example 16(b) except that 2-thiophene boronic acid was used instead of 3-thiophene boronic acid.

(b) (S)-5-Chloro-2-(2-methylpiperazin-1-yl)-7-(thiophen-2-yl)benzoxazole

The title compound was obtained in a similar manner as in Example 16(c) except that (S)-1-tert-butoxycarbonyl-(5-chloro-7-(thiophen-2-yl)benzoxazol-2-yl)-3-methylpiperazine obtained in Example 18(a) was used instead of (S)-1-tert-butoxycarbonyl-4-(5-chloro-7-(thiophen-3-yl)benzoxazol-2-yl)-3-methylpiperazine.

$^1$H-NMR (400 MHz, DMSO-d$_6$) δ: 1.31 (3H, d, J=6.8 Hz), 2.65-2.66 (1H, m), 2.77-2.85 (2H, m), 2.95-2.98 (1H, m), 3.26-3.37 (1H, m), 3.83-3.87 (1H, m), 4.26 (1H, m), 7.22 (1H, dd, J=3.7, 5.1 Hz), 7.25 (1H, d, J=2.0 Hz), 7.37 (1H, d, J=2.0 Hz), 7.73 (1H, dd, J=1.0, 5.1 Hz), 7.79 (1H, dd, J=1.2, 3.9 Hz)

MS(ESI) m/z: 334 (M+H)$^+$

Example 19

(S)-5-Chloro-2-(2-methylpiperazin-1-yl)-7-phenyl-benzoxazole (a) (S)-1-tert-Butoxycarbonyl-4-(5-chloro-7-phenyl-benzoxazol-2-yl)-3-methylpiperazine The title compound was obtained in a similar manner as in Example 16(b) except that phenylboronic acid was used instead of 3-thiophene boronic acid.

(b) (S)-5-Chloro-2-(2-methylpiperazin-1-yl)-7-phenylbenzoxazole

The title compound was obtained in a similar manner as in Example 16(c) except that (S)-1-tert-butoxycarbonyl-(5-chloro-7-phenylbenzoxazol-2-yl)-3-methylpiperazine obtained in Example 19(a) was used instead of (S)-1-tert-butoxycarbonyl-4-(5-chloro-7-(thiophen-3-yl)benzoxazol-2-yl)-3-m ethylpiperazine.

$^1$H-NMR (400 MHz, CDCl$_3$) δ: 1.41 (3H, d, J=6.8 Hz), 2.83-2.92 (2H, m), 3.06-3.10 (2H, m), 3.34-3.42 (1H, m), 3.94-3.98 (1H, m), 4.36-4.42 (1H, m), 7.18 (1H, d, J=2.0 Hz), 7.28 (1H, d, J=2.2 Hz), 7.43-7.38 (1H, m), 7.51-7.47 (2H, m), 7.73-7.75 (2H, m)

MS(ESI) m/z: 328 (M+H)$^+$

Example 20

(S)-5-Chloro-2-(2-methylpiperazin-1-yl)-7-(pyrrolidin-1-yl)benzoxazole (a) (S)-1-tert-Butoxycarbonyl-4-(5-chloro-7-(pyrrolidin-1-yl)benzoxazol-2-yl)-3-methylpiperazine (S)-1-tert-Butoxycarbonyl-4-(7-bromo-5-chlorobenzoxazol-2-yl)-3-methylpiperazine obtained in Example 16(a) (60 mg), cesium carbonate (64 mg, 1.4 equivalents), (S)-Tol BINAP (7 mg, 0.075 equivalents), and pyrrolidine (18 μL, 1.5 equivalents) were dissolved in toluene (1.0 mL), the resulting mixture was stirred in an argon atmosphere for 15 minutes, then tris(dibenzylideneacetone)dipalladium(0) (6.5 mg, 0.05 equivalents) was added thereto, and the resulting mixture was stirred in an oil bath at 80° C. for 21 hours. Water was added to the reaction mixture, and the product was extracted with ethyl acetate. The organic layer was dried over anhydrous sodium sulfate, then the solvent was distilled off under reduced pressure, and the residue was purified by silica gel column chromatography (developing solvent, hexane:ethyl acetate=3:1) to obtain 40 mg of the title compound.
MS(ESI) m/z: 421 (M+H)+

(b) (S)-5-Chloro-2-(2-methylpiperazin-1-yl)-7-(pyrrolidin-1-yl)benzoxazole

The title compound was obtained in a similar manner as in Example 16(c) except that (S)-1-tert-butoxycarbonyl-4-(5-chloro-7-(pyrrolidin-1-yl)benzoxazol-2-yl)-3-methylpiperazine obtained in Example 20(a) was used instead of (S)-1-tert-butoxycarbonyl-(5-chloro-7-(thiophen-3-yl)benzoxazol-2-yl)-3-methylpiperazine.
$^1$H-NMR (400 MHz, CDCl$_3$) δ: 1.37 (3H, d, J=6.8 Hz), 1.98-2.01 (4H, m), 2.83-2.91 (2H, m), 3.06-3.10 (2H, m), 3.30-3.37 (1H, m), 3.49-3.52 (4H, m), 3.87-3.91 (1H, m), 4.29-4.34 (1H, m), 6.21 (1H, d, J=2.0 Hz), 6.70 (1H, d, J=2.0 Hz)
MS(ESI) m/z: 321 (M+H)+

Example 21

(S)-5-Chloro-2-(2-methylpiperazin-1-yl)-7-(morpholin-1-yl)benzoxazole (a) (S)-1-tert-Butoxycarbonyl-4-(5-chloro-7-(morpholin-1-yl)benzoxazol-2-yl)-3-methylpiperazine The title compound was obtained in a similar manner as in Example 20(a) except that morpholine was used instead of pyrrolidine.

(b) (S)-5-Chloro-2-(2-methylpiperazin-1-yl)-7-(morpholin-1-yl)benzoxazole

The title compound was obtained in a similar manner as in Example 16(c) except that (S)-1-tert-butoxycarbonyl-(5-chloro-7-(morpholin-1-yl)benzoxazol-2-yl)-3-m ethylpiperazine obtained in Example 21(a) was used instead of (S)-1-tert-butoxycarbonyl-4-(5-chloro-7-(thiophen-3-yl)benzoxazol-2-yl)-3-m ethylpiperazine.
$^1$H-NMR (400 MHz, CDCl$_3$) δ: 1.39 (3H, d, J=6.8 Hz), 2.83-2.92 (2H, m), 3.06-3.10 (2H, m), 3.26 (4H, t, J=4.9 Hz), 3.33-3.40 (1H, m), 3.87-3.88 (1H, m), 3.90 (4H, t, J=4.9 Hz), 4.32-4.35 (1H, m), 6.51 (1H, d, J=1.7 Hz), 6.96 (1H, d, J=1.7 Hz)
MS(ESI) m/z: 337 (M+H)+

Example 22

(S)-5-Chloro-2-(2-methylpiperazin-1-yl)-7-(piperidin-1-yl)benzoxazole (a) (S)-1-tert-Butoxycarbonyl-4-(5-chloro-7-(piperidin-1-yl)benzoxazol-2-yl)-3-methylpiperazine The title compound was obtained in a similar manner as in Example 20(a) except that piperidine was used instead of pyrrolidine.

(b) (S)-5-Chloro-2-(2-methylpiperazin-1-yl)-7-(piperidin-1-yl)benzoxazole

The title compound was obtained in a similar manner as in Example 16(c) except that (S)-1-tert-butoxycarbonyl-(5-chloro-7-(piperidin-1-yl)benzoxazol-2-yl)-3-methylpiperazine obtained in Example 22(a) was used instead of (S)-1-tert-butoxycarbonyl-4-(5-chloro-7-(thiophen-3-yl)benzoxazol-2-yl)-3-methylpiperazine.
$^1$H-NMR (400 MHz, CDCl$_3$) δ: 1.38 (3H, d, J=6.8 Hz), 1.61-1.65 (2H, m), 1.73-1.78 (4H, m), 2.83-2.91 (2H, m), 3.06-3.10 (2H, m), 3.22 (4H, t, J=5.6 Hz), 3.32-3.39 (1H, m), 3.89-3.93 (1H, m), 4.32-4.38 (1H, m), 6.52 (1H, d, J=1.7 Hz), 6.91 (1H, d, J=1.7 Hz)
MS(ESI) m/z: 335 (M+H)+

Example 23

(S)-5-Chloro-7-(furan-2-yl)-2-(2-methylpiperazin-1-yl)benzoxazole (a) (S)-1-tert-Butoxycarbonyl-4-(5-chloro-7-(furan-2-yl)benzoxazol-2-yl)-3-methylpiperazine (S)-1-tert-Butoxycarbonyl-(7-bromo-5-chlorobenzoxazol-2-yl)-3-methylpiperazine obtained in Example 16(a) (60 mg), potassium carbonate (43 mg, 2.2 equivalents), tetrakis(triphenylphosphine)palladium(0) (8.1 mg, 0.05 equivalents), and 2-furyl boronic acid MIDA ester (47 mg, 1.5 equivalents) were dissolved in toluene (1.6 mL) and ethanol (0.4 mL), water (50 μL) was added thereto, and the resulting mixture was stirred in an oil bath at 80° C. for 2 hours. Water was added to the reaction mixture, and the product was extracted with ethyl acetate. The organic layer was dried over anhydrous sodium sulfate, then the solvent was distilled off under reduced pressure, and the residue was purified by silica gel column chromatography (developing solvent, hexane:ethyl acetate=17:3) to obtain 33 mg of the title compound.

(b) (S)-5-Chloro-7-(furan-2-yl)-2-(2-methylpiperazin-1-yl)benzoxazole

The title compound was obtained in a similar manner as in Example 16(c) except that (S)-1-tert-butoxycarbonyl-(5-chloro-7-(furan-2-yl)benzoxazol-2-yl)-3-methyl piperazine obtained in Example 23(a) was used instead of (S)-1-tert-butoxycarbonyl-4-(5-chloro-7-(thiophen-3-yl)benzoxazol-2-yl)-3-m ethylpiperazine.

¹H-NMR (400 MHz, CDCl₃) δ: 1.43 (3H, d, J=6.8 Hz), 2.87-2.95 (2H, m), 3.09-3.13 (2H, m), 3.39-3.46 (1H, m), 3.99-4.03 (1H, m), 4.40-4.46 (1H, m), 6.55 (1H, dd, J=1.7, 3.4 Hz), 6.88 (1H, d, J=3.4 Hz), 7.21 (1H, d, J=2.0 Hz), 7.41 (1H, d, J=2.0 Hz), 7.54 (1H, dd, J=0.7, 1.7 Hz)
MS(ESI) m/z: 318 (M+H)⁺

Example 24

(S)-5-Chloro-7-(cyclopentylamino)-2-(2-methylpiperazin-1-yl)benzoxazole (a) (S)-1-tert-Butoxycarbonyl-4-(5-chloro-7-(cyclopentylamino)benzoxazol-2-yl)-3-methylpiperazine The title compound was obtained in a similar manner as in Example 20(a) except that cyclopentylamine was used instead of pyrrolidine.
MS(ESI) m/z: 435 (M+H)⁺

(b) (S)-5-Chloro-7-(cyclopentylamino)-2-(2-methylpiperazin-1-yl)benzoxazole

The title compound was obtained in a similar manner as in Example 16(c) except that (S)-1-tert-butoxycarbonyl-(5-chloro-7-(cyclopentylamino)benzoxazol-2-yl)-3-methylpiperazine obtained in Example 24(a) was used instead of (S)-1-tert-butoxycarbonyl-4-(5-chloro-7-(thiophen-3-yl)benzoxazol-2-yl)-3-methylpiperazine.
¹H-NMR (400 MHz, CDCl₃) δ: 1.38 (3H, d, J=6.8 Hz), 1.51-1.53 (2H, m), 1.64-1.70 (2H, m), 1.75-1.77 (2H, m), 2.05-2.09 (2H, m), 2.82-2.90 (2H, m), 3.05-3.09 (2H, m), 3.31-3.38 (1H, m), 3.91-3.95 (2H, m), 4.35-4.37 (1H, m), 6.36 (1H, d, J=1.7 Hz), 6.73 (1H, d, J=2.0 Hz)
MS(ESI) m/z: 335 (M+H)⁺

Example 25

(S)-5-Chloro-7-diethylamino-2-(2-methylpiperazin-1-yl)benzoxazole (a) (S)-1-tert-Butoxycarbonyl-4-(5-chloro-7-(diethylamino)benzoxazol-2-yl)-3-methylpiperazine The title compound was obtained in a similar manner as in Example 20(a) except that diethylamine was used instead of pyrrolidine.

(b) (S)-5-Chloro-7-diethylamino-2-(2-methylpiperazin-1-yl)benzoxazole

The title compound was obtained in a similar manner as in Example 16(c) except that (S)-1-tert-butoxycarbonyl-(5-chloro-7-(diethylamino)benzoxazol-2-yl)-3-methylpiperazine obtained in Example 25(a) was used instead of (S)-1-tert-butoxycarbonyl-4-(5-chloro-7-(thiophen-3-yl)benzoxazol-2-yl)-3-m ethylpiperazine.
¹H-NMR (400 MHz, CDCl₃) δ: 1.19 (6H, t, J=7.1 Hz), 1.49 (3H, d, J=6.8 Hz), 3.02-3.09 (1H, m), 3.14-3.17 (1H, m), 3.24-3.28 (1H, m), 3.42-3.47 (5H, m), 3.55-3.63 (1H, m), 4.06-4.10 (1H, m), 4.52-4.58 (1H, m), 6.40 (1H, d, J=1.7 Hz), 6.78 (1H, d, J=2.0 Hz)
MS(ESI) m/z: 323 (M+H)⁺

Example 26

(S)-5-Chloro-7-dimethylamino-2-(2-methylpiperazin-1-yl)benzoxazole (a) (S)-1-tert-Butoxycarbonyl-4-(5-chloro-7-(dimethylamino)benzoxazol-2-yl)-3-methylpiperazine The title compound was obtained in a similar manner as in Example 20(a) except that dimethylamine was used instead of pyrrolidine.
MS(ESI) m/z: 395 (M+H)⁺

(b) (S)-5-Chloro-7-dimethylamino-2-(2-methylpiperazin-1-yl)benzoxazole

The title compound was obtained in a similar manner as in Example 16(c) except that (S)-1-tert-butoxycarbonyl-4-(5-chloro-7-(dimethylamino)benzoxazol-2-yl)-3-methylpiperazine obtained in Example 26(a) was used instead of (S)-1-tert-butoxycarbonyl-4-(5-chloro-7-(thiophen-3-yl)benzoxazol-2-yl)-3-m ethylpiperazine.
¹H-NMR (400 MHz, CDCl₃) δ: 1.38 (3H, d, J=6.6 Hz), 2.83-2.91 (2H, m), 3.00 (6H, s), 3.06-3.10 (2H, m), 3.32-3.39 (1H, m), 3.90-3.94 (1H, m), 4.33-4.36 (1H, m), 6.39 (1H, d, J=2.0 Hz), 6.85 (1H, d, J=2.0 Hz)
MS(ESI) m/z: 295 (M+H)⁺

Example 27

(S)-5-Chloro-7-cyclopropyl-2-(2-methylpiperazin-1-yl)benzoxazole (a) (S)-1-tert-Butoxycarbonyl-4-(5-chloro-7-cyclopropylbenzoxazol-2-yl)-3-methylpiperazine (S)-1-tert-Butoxycarbonyl-(7-bromo-5-chlorobenzoxazol-2-yl)-3-methylpiperazine obtained in Example 16(a) (60 mg), tripotassium phosphate (103 mg, 3.5 equivalents), tricyclohexylphosphine (3.9 mg, 0.1 equivalents), palladium acetate (II) (1.6 mg, 0.05 equivalents), and cyclopropyl boronic acid (16 mg, 1.3 equivalents) were dissolved in toluene (1.0 mL), water was added thereto (50 μL), and the resulting mixture was stirred in an oil bath at 80° C. for 15 hours. Water was added to the reaction mixture, and the product was extracted with ethyl acetate. The organic layer was dried over anhydrous sodium sulfate, then the solvent was distilled off under reduced pressure, and the residue was purified by silica gel column chromatography (developing solvent, hexane:ethyl acetate=4:1) to obtain 34 mg of the title compound.

(b) (S)-5-Chloro-7-cyclopropyl-2-(2-methylpiperazin-1-yl)benzoxazole

The title compound was obtained in a similar manner as in Example 16(c) except that (S)-1-tert-butoxycarbonyl-4-(5-chloro-7-cyclopropylbenzoxazol-2-yl)-3-meth ylpiperazine obtained in Example 27(a) was used instead of (S)-1-tert-butoxycarbonyl-4-(5-chloro-7-(thiophen-3-yl)benzoxazol-2-yl)-3-m ethylpiperazine.
¹H-NMR (400 MHz, CDCl₃) δ: 0.86-0.91 (2H, m), 1.00-1.05 (2H, m), 1.39 (3H, d, J=6.8 Hz), 2.02-2.09 (1H, m), 2.84-2.92 (2H, m), 3.06-3.11 (2H, m), 3.33-3.40 (1H, m), 3.94-3.98 (1H, m), 4.35-4.41 (1H, m), 6.57 (1H, d, J=2.0 Hz), 7.10 (1H, d, J=2.0 Hz)
MS(ESI) m/z: 292 (M+H)$^+$ Example 28

(S)-5-Chloro-7-(cyclopentyloxy)-2-(2-methylpiperazin-1-yl)benzoxazole (a) (S)-1-tert-Butoxycarbonyl-4-(5-chloro-7-(cyclopentyloxy)benzoxazol-2-yl)-3-methylpiperazine (S)-1-tert-Butoxycarbonyl-(7-bromo-5-chlorobenzoxazol-2-yl)-3-methylpiperazine obtained in Example 16(a) (60 mg), cesium carbonate (68 mg, 1.5 equivalents), RockPhos (3.9 mg, 0.06 equivalents), allylpalladium(II)chloride (dimer) (2.6 mg, 0.05 equivalents), and cyclopentyl alcohol (25 µL, 2.0 equivalents) were dissolved in triethylamine (1.0 mL), and the resulting mixture was stirred in an oil bath at 60 to 90° C. for 18 hours. Water was added to the reaction mixture, and the product was extracted with ethyl acetate. The organic layer was dried over anhydrous sodium sulfate, then the solvent was distilled off under reduced pressure, and the residue was roughly purified by silica gel column chromatography (developing solvent, hexane:ethyl acetate=3:2) to obtain 10.4 mg of the title compound.

(b) (S)-5-Chloro-7-(cyclopentyloxy)-2-(2-methylpiperazin-1-yl)benzoxazole 2.2 mg of the title compound was obtained in a similar manner as in Example 16(c) except that (S)-1-tert-butoxycarbonyl-4-(5-chloro-7-(cyclopentyloxy)benzoxazol-2-yl)-3-methylpiperazine obtained in Example 28(a) (10.4 mg) was used instead of (S)-1-tert-butoxycarbonyl-4-(5-chloro-7-(thiophen-3-yl)benzoxazol-2-yl)-3-m ethylpiperazine.
$^1$H-NMR (400 MHz, CDCl$_3$) δ: 1.39 (3H, d, J=6.8 Hz), 1.64-1.92 (8H, m), 2.85-2.94 (2H, m), 3.07-3.13 (2H, m), 3.34-3.40 (1H, m), 3.97-4.00 (1H, m), 4.41 (1H, m), 4.89-4.91 (1H, m), 6.58 (1H, d, J=1.7 Hz), 6.94 (1H, d, J=2.0 Hz)
MS(ESI) m/z: 336 (M+H)$^+$ Example 29

(S)-5-Chloro-7-ethoxy-2-(2-methylpiperazin-1-yl)benzoxazole (a) (S)-1-tert-Butoxycarbonyl-4-(5-chloro-7-ethoxybenzoxazol-2-yl)-3-methylpiperazine The title compound was obtained in a similar manner as in Example 28(a) except that ethanol was used instead of cyclopentyl alcohol.

(b) (S)-5-Chloro-7-ethoxy-2-(2-methylpiperazin-1-yl)benzoxazole

The title compound was obtained in a similar manner as in Example 16(c) except that (S)-1-tert-butoxycarbonyl-4-(5-chloro-7-ethoxybenzoxazol-2-yl)-3-methylpiperazine obtained in Example 29(a) was used instead of (S)-1-tert-butoxycarbonyl-4-(5-chloro-7-(thiophen-3-yl)benzoxazol-2-yl)-3-m ethylpiperazine.
$^1$H-NMR (400 MHz, CDCl$_3$) δ: 1.39 (3H, d, J=6.8 Hz), 1.47 (3H, t, J=7.1 Hz), 2.82-2.90 (2H, m), 3.05-3.09 (2H, m), 3.32-3.39 (1H, m), 3.96-4.00 (1H, m), 4.19 (2H, q, J=7.1 Hz), 4.37-4.43 (1H, m), 6.59 (1H, d, J=2.0 Hz), 6.95 (1H, d, J=1.7 Hz)
MS(ESI) m/z: 296 (M+H)$^+$ Example 30

(S)-5-Chloro-2-(2-methylpiperazin-1-yl)-7-n-propoxybenzoxazole (a) (S)-1-tert-Butoxycarbonyl-4-(5-chloro-7-n-propoxybenzoxazol-2-yl)-3-methylpiperazine The title compound was obtained in a similar manner as in Example 28(a) except that 1-propanol was used instead of cyclopentyl alcohol.

(b) (S)-5-Chloro-2-(2-methylpiperazin-1-yl)-7-n-propoxybenzoxazole

The title compound was obtained in a similar manner as in Example 16(c) except that (S)-1-tert-butoxycarbonyl-4-(5-chloro-7-n-propoxybenzoxazol-2-yl)-3-methylpiperazine obtained in Example 30(a) was used instead of (S)-1-tert-butoxycarbonyl-4-(5-chloro-7-(thiophen-3-yl)benzoxazol-2-yl)-3-methylpiperazine.
$^1$H-NMR (400 MHz, CDCl$_3$) δ: 1.06 (3H, t, J=7.6 Hz), 1.39 (3H, d, J=6.8 Hz), 1.81-1.90 (2H, m), 2.83-2.91 (2H, m), 3.05-3.09 (2H, m), 3.32-3.39 (1H, m), 3.94-4.02 (1H, m), 4.08 (2H, t, J=6.6 Hz), 4.37-4.43 (1H, m), 6.60 (1H, d, J=1.7 Hz), 6.95 (1H, d, J=1.7 Hz)
MS(ESI) m/z: 310 (M+H)$^+$ Example 31

(S)-5-Chloro-7-cyclopentyl-2-(2-methylpiperazin-1-yl)benzoxazole (a) (S)-1-tert-Butoxycarbonyl-4-(5-chloro-7-cyclopentylbenzoxazol-2-yl)-3-methylpiperazine (S)-1-tert-Butoxycarbonyl-(7-bromo-5-chlorobenzoxazol-2-yl)-3-methylpiperazine obtained in Example 16(a) (60 mg), tris-tert-butylphosphine (a 1 M solution in toluene, 14 µL, 0.1 equivalents), tris(dibenzylideneacetone)dipalladium(0) (6.4 mg, 0.05 equivalents), and cyclopentyl zinc bromide (a 0.5 M solution in toluene, 560 µL, 2.0 equivalents) were dissolved in toluene (0.5 mL), and the resulting mixture was stirred in an oil bath at 50° C. for 17.5 hours. Water was added to the reaction mixture, and the product was extracted with ethyl acetate. The organic layer was dried over anhydrous sodium sulfate, then the solvent was distilled off under reduced pressure, and the residue was purified by silica gel column chromatography (developing solvent, hexane:ethyl acetate=17:3) to obtain 28 mg of the title compound.

(b) (S)-5-Chloro-7-cyclopentyl-2-(2-methylpiperazin-1-yl)benzoxazole

The title compound was obtained in a similar manner as in Example 16(c) except that (S)-1-tert-butoxycarbonyl-4-(5-chloro-7-cyclopentylbenzoxazol-2-yl)-3-methylpiperazine obtained in Example 31(a) was used instead of (S)-1-tert-butoxycarbonyl-4-(5-chloro-7-(thiophen-3-yl)benzoxazol-2-yl)-3-methylpiperazine.

¹H-NMR (400 MHz, CDCl₃) δ: 1.39 (3H, d, J=6.6 Hz), 1.67-1.85 (6H, m), 2.07-2.13 (2H, m), 2.84-2.92 (2H, m), 3.07-3.11 (2H, m), 3.18-3.23 (1H, m), 3.32-3.39 (1H, m), 3.93-3.96 (1H, m), 4.35-4.38 (1H, m), 6.85 (1H, d, J=2.0 Hz), 7.14 (1H, d, J=2.2 Hz)
MS(ESI) m/z: 320 (M+H)⁺

Example 32

(S)-7-n-Butyl-5-chloro-2-(2-methylpiperazin-1-yl)benzoxazole (a) (S)-1-tert-Butoxycarbonyl-4-(7-n-butyl-5-chlorobenzoxazol-2-yl)-3-methylpiperazine The title compound was obtained in a similar manner as in Example 31(a) except that n-butyl zinc bromide (a 0.5 M solution in THF) was used instead of cyclopentyl zinc bromide (a 0.5 M solution in toluene).

(b) (S)-7-n-Butyl-5-chloro-2-(2-methylpiperazin-1-yl)benzoxazole

The title compound was obtained in a similar manner as in Example 16(c) except that
(S)-1-tert-butoxycarbonyl-4-(7-n-butyl-5-chlorobenzoxazol-2-yl)-3-methylpiperazine obtained in Example 32(a) was used instead of (S)-1-tert-butoxycarbonyl-4-(5-chloro-7-(thiophen-3-yl)benzoxazol-2-yl)-3-methylpiperazine.
¹H-NMR (400 MHz, CDCl₃) δ: 0.95 (3H, t, J=7.3 Hz), 1.34-1.38 (2H, m), 1.41 (3H, d, J=6.8 Hz), 1.63-1.70 (2H, m), 2.72 (2H, t, J=7.6 Hz), 2.87-2.96 (2H, m), 3.10-3.15 (2H, m), 3.36-3.43 (1H, m), 3.97-4.00 (1H, m), 4.38-4.44 (1H, m), 6.82 (1H, d, J=2.2 Hz), 7.15 (1H, d, J=2.2 Hz)
MS(ESI) m/z: 308 (M+H)⁺

Example 33

(S)-5-Chloro-2-(2-methylpiperazin-1-yl)-'7-(1H-pyrazol-1-yl)benzoxazole (a) (S)-1-tert-Butoxycarbonyl-4-(5-chloro-7-(1H-pyrazol-1-yl)benzoxazol-2-yl)-3-methylpiperazine (S)-1-tert-Butoxycarbonyl-(7-bromo-5-chlorobenzoxazol-2-yl)-3-methylpiperazine obtained in Example 16(a) (60 mg), pyrazole (19 mg, 2.0 equivalents), copper(I) iodide (27 mg, 1.0 equivalent), and cesium carbonate (137 mg, 3.0 equivalents) were dissolved in DMF (1.0 mL), and the reaction was performed by using a microwave reactor at 150° C. for 2 hours. Water was added to the reaction mixture, and the product was extracted with ethyl acetate. The organic layer was dried over anhydrous sodium sulfate, then the solvent was distilled off under reduced pressure, and the residue was purified by silica gel column chromatography (developing solvent, hexane:ethyl acetate=10:3) to obtain 38 mg of the title compound.

(b) (S)-5-Chloro-2-(2-methylpiperazin-1-yl)-7-(1H-pyrazol-1-yl)benzoxazole

The title compound was obtained in a similar manner as in Example 16(c) except that (S)-1-tert-butoxycarbonyl-4-(5-chloro-7-(1H-pyrazol-2-yl)benzoxazol-2-yl)-3-methylpiperazine obtained in Example 33(a) was used instead of (S)-1-tert-butoxycarbonyl-4-(5-chloro-7-(thiophen-3-yl)benzoxazol-2-yl)-3-m ethylpiperazine.

¹H-NMR (400 MHz, CDCl₃) δ: 1.43 (3H, d, J=6.8 Hz), 2.86-2.95 (2H, m), 3.08-3.14 (2H, m), 3.40-3.47 (1H, m), 3.97-4.01 (1H, m), 4.38-4.44 (1H, m), 6.53 (1H, dd, J=0.7, 1.7 Hz), 7.21 (1H, d, J=2.2 Hz), 7.62 (1H, d, J=2.0 Hz), 7.77 (1H, d, J=2.0 Hz), 8.18 (1H, dd, J=0.5, 2.0 Hz)
MS(ESI) m/z: 318 (M+H)⁺

Example 34

(S)-5-Chloro-2-(2-methylpiperazin-1-yl)-7-(oxazol-2-yl)benzoxazole (a) (S)-1-tert-Butoxycarbonyl-4-(5-chloro-7-(oxazol-2-yl)benzoxazol-2-yl)-3-methylpiperazine (S)-1-tert-Butoxycarbonyl-4-(7-bromo-5-chlorobenzoxazol-2-yl)-3-m ethylpiperazine obtained in Example 16(a) (60 mg), tetrakis(triphenylphosphine)palladium(0) (8.1 mg, 0.05 equivalents), and 2-(tributylstannyl)oxazole (44 μL 1.5 equivalents) were dissolved in DMF (1.0 mL), and the resulting mixture was stirred in an argon atmosphere in an oil bath at 90° C. for 3 hours. Water was added to the reaction mixture, and the product was extracted with ethyl acetate. The organic layer was dried over anhydrous magnesium sulfate, then the solvent was distilled off under reduced pressure, and the residue was purified by silica gel column chromatography (developing solvent, hexane:ethyl acetate=7:3) to obtain 30.1 mg of the title compound.

(b) (S)-5-Chloro-2-(2-methylpiperazin-1-yl)-7-(oxazol-2-yl)benzoxazole

The title compound was obtained in a similar manner as in Example 16(c) except that (S)-1-tert-butoxycarbonyl-4-(5-chloro-7-(oxazol-2-yl)benzoxazol-2-yl)-3-methylpiperazine obtained in Example 34(a) was used instead of (S)-1-tert-butoxycarbonyl-4-(5-chloro-7-(thiophen-3-yl)benzoxazol-2-yl)-3-m ethylpiperazine.
¹H-NMR (400 MHz, CDCl₃) δ: 1.43 (3H, d, J=6.8 Hz), 2.86-2.95 (2H, in), 3.09-3.13 (2H, m), 3.40-3.47 (1H, m), 4.06-4.09 (1H, m), 4.46-4.52 (1H, m), 7.33 (1H, d, J=0.7 Hz), 7.36 (1H, d, J=2.0 Hz), 7.65 (1H, d, J=2.0 Hz), 7.80 (1H, d, J=0.7 Hz)
MS(ESI) m/z: 319 (M+H)⁺

Example 35

(S)-5-Chloro-2-(2-methylpiperazin-1-yl)-7-(thiazol-2-yl)benzoxazole (a) (S)-1-tert-Butoxycarbonyl-4-(5-chloro-7-(thiazol-2-yl)benzoxazol-2-yl)-3-methylpiperazine The title compound was obtained in a similar manner as in Example 34(a) except that 2-(tributylstannyl)thiazole was used instead of 2-(tributylstannyl)oxazole.

(b) (S)-5-Chloro-2-(2-methylpiperazin-1-yl)-7-(oxazol-2-yl)benzoxazole

The title compound was obtained in a similar manner as in Example 16(c) except that
(S)-1-tert-butoxycarbonyl-4-(5-chloro-7-(thiazol-2-yl)benzoxazol-2-yl)-3-methylpiperazine obtained in Example 35(a) was used instead of (S)-1-tert-butoxycarbonyl-4-(5-chloro-7-(thiophen-3-yl)benzoxazol-2-yl)-3-m ethylpiperazine.

¹H-NMR (400 MHz, CDCl₃) δ: 1.45 (3H, d, J=6.8 Hz), 2.88-2.97 (2H, m), 3.11-3.15 (2H, m), 3.42-3.49 (1H, m), 4.05-4.08 (1H, m), 4.45-4.50 (1H, m), 7.34 (1H, d, J=2.2 Hz), 7.49 (1H, d, J=3.2 Hz), 7.84 (1H, d, J=2.0 Hz), 7.97 (1H, d, J=3.2 Hz)

MS(ESI) m/z: 335 (M+H)⁺

Example 36

(S)-5-Chloro-7-(1H-imidazol-1-yl)-2-(2-methylpiperazin-1-yl)benzoxazole (a) (S)-1-tert-Butoxycarbonyl-4-(5-chloro-7-(1H-imidazol-1-yl)benzoxazol-2-yl)-3-methylpiperazine The title compound was obtained in a similar manner as in Example 33(a) except that imidazole was used instead of pyrazole.

(b) (S)-5-Chloro-7-(1H-imidazol-1-yl)-2-(2-methylpiperazin-1-yl)benzoxazole

The title compound was obtained in a similar manner as in Example 16(c) except that (S)-1-tert-butoxycarbonyl-4-(5-chloro-7-(1H-imidazol-1-yl)benzoxazol-2-yl)-3-methylpiperazine obtained in Example 36(a) was used instead of (S)-1-tert-butoxycarbonyl-4-(5-chloro-7-(thiophen-3-yl)benzoxazol-2-yl)-3-m ethylpiperazine.

¹H-NMR (400 MHz, DMSO-d₆) δ: 1.31 (3H, d, J=6.8 Hz), 2.77-2.97 (3H, m), 3.24-3.27 (2H, m), 3.79-3.86 (1H, m), 4.26 (1H, m), 7.17 (1H, s), 7.30-7.34 (1H, m), 7.44-7.47 (1H, m), 7.87-7.88 (1H, m), 8.36 (1H, s)

MS(ESI) m/z: 318 (M+H)⁺

Example 37

(S)-5-Chloro-2-(2-methylpiperazin-1-yl)-7-(thiazol-4-yl)benzoxazole (a) (S)-1-tert-Butoxycarbonyl-4-(5-chloro-7-(thiazol-4-yl)benzoxazol-2-yl)-3-methylpiperazine The title compound was obtained in a similar manner as in Example 34(a) except that 4-(tributylstannyl)thiazole was used instead of 2-(tributylstannyl)oxazole.

(b) (S)-5-Chloro-2-(2-methylpiperazin-1-yl)-7-(thiazol-4-yl)benzoxazole

The title compound was obtained in a similar manner as in Example 16(c) except that (S)-1-tert-butoxycarbonyl-4-(5-chloro-7-(thiazol-4-yl)benzoxazol-2-yl)-3-methylpiperazine obtained in Example 37(a) was used instead of (S)-1-tert-butoxycarbonyl-4-(5-chloro-7-(thiophen-3-yl)benzoxazol-2-yl)-3-m ethylpiperazine.

¹H-NMR (400 MHz, CDCl₃) δ: 1.44 (3H, d, J=6.8 Hz), 2.88-2.96 (2H, m), 3.10-3.14 (2H, m), 3.41-3.48 (1H, m), 4.00-4.04 (1H, m), 4.41-4.48 (1H, m), 7.30 (1H, d, J=2.0 Hz), 7.86 (1H, d, J=2.0 Hz), 7.88 (1H, d, J=2.0 Hz), 8.92 (1H, d, J=2.0 Hz)

MS(ESI) m/z: 335 (M+H)⁺

Example 38

(S)-5-Chloro-2-(2-methylpiperazin-1-yl)-7-(thiazol-5-yl)benzoxazole (a) (S)-1-tert-Butoxycarbonyl-4-(5-chloro-7-(thiazol-5-yl)benzoxazol-2-yl)-3-methylpiperazine The title compound was obtained in a similar manner as in Example 34(a) except that 5-(tributylstannyl)thiazole was used instead of 2-(tributylstannyl)oxazole.

(b) (S)-5-Chloro-2-(2-methylpiperazin-1-yl)-7-(thiazol-5-yl)benzoxazole

The title compound was obtained in a similar manner as in Example 16(c) except that (S)-1-tert-butoxycarbonyl-4-(5-chloro-7-(thiazol-5-yl)benzoxazol-2-yl)-3-methylpiperazine obtained in Example 38(a) was used instead of (S)-1-tert-butoxycarbonyl-4-(5-chloro-7-(thiophen-3-yl)benzoxazol-2-yl)-3-m ethylpiperazine.

¹H-NMR (400 MHz, CDCl₃) δ: 1.44 (3H, d, J=6.8 Hz), 2.86-2.96 (2H, m), 3.09-3.14 (2H, m), 3.40-3.47 (1H, m), 4.00-4.04 (1H, m), 4.41-4.47 (1H, m), 7.21 (1H, d, J=2.0 Hz), 7.27 (1H, d, J=2.0 Hz), 8.37 (1H, s), 8.86 (1H, s)

MS(ESI) m/z: 335 (M+H)⁺

Example 39

(S)-5-Chloro-7-(5-methylfuran-2-yl)-2-(2-methylpiperazin-1-yl)benzoxazole (a) (S)-1-tert-Butoxycarbonyl-4-(5-chloro-7-(5-methylfuran-2-yl)benzoxazol-2-yl)-3-methylpiperazine (S)-1-tert-Butoxycarbonyl-4-(7-bromo-5-chlorobenzoxazol-2-yl)-3-m ethylpiperazine obtained in Example 16(a) (60 mg), tetrakis(triphenylphosphine)palladium(0) (16.2 mg, 0.1 equivalents), and 5-methyl-2-furyl boronic acid pinacol ester (65 μL, 2.25 equivalents) were dissolved in DMF (1.0 mL), and the resulting mixture was stirred in an argon atmosphere in an oil bath at 90° C. for 4.5 hours. Water was added to the reaction mixture, and the product was extracted with ethyl acetate. The organic layer was dried over anhydrous magnesium sulfate, then the solvent was distilled off under reduced pressure, and the residue was purified by silica gel column chromatography (developing solvent, hexane:ethyl acetate=4:1) to obtain 51.0 mg of the title compound.

(b) (S)-5-Chloro-7-(5-methylfuran-2-yl)-2-(2-methylpiperazin-1-yl)benzoxazole

The title compound was obtained in a similar manner as in Example 16(c) except that (S)-1-tert-butoxycarbonyl-4-(5-chloro-7-(5-methylfuran-2-yl)benzoxazol-2-yl)-3-methylpiperazine obtained in Example 39(a) was used instead of (S)-1-tert-butoxycarbonyl-4-(5-chloro-7-(thiophen-3-yl)benzoxazol-2-yl)-3-m ethylpiperazine.

¹H-NMR (400 MHz, CDCl₃) δ: 1.43 (3H, d, J=6.8 Hz), 2.41 (3H, s), 2.86-2.95 (2H, m), 3.09-3.13 (2H, m), 3.38-3.45 (1H, m), 3.98-4.01 (1H, m), 4.39-4.45 (1H, m), 6.13-6.14 (1H, m), 6.77 (1H, d, J=3.2 Hz), 7.17 (1H, d, J=2.0 Hz), 7.38 (1H, d, J=2.0 Hz)

MS(ESI) m/z: 332 (M+H)⁺

Example 40

(S)-5-Chloro-7-(4-methyl-1H-pyrazol-1-yl)-2-(2-methylpiperazin-1-yl)benzoxazole

(a) (S)-1-tert-Butoxycarbonyl-4-(5-chloro-7-(4-methyl-1H-pyrazol-1-yl)benzoxazol-2-yl)-3-methyl-piperazine The title compound was obtained in a similar manner as in Example 33(a) except that 4-methylpyrazole was used instead of pyrazole.

(b) (S)-5-Chloro-7-(4-methyl-1H-imidazol-1-yl)-2-(2-methylpiperazin-1-yl)benzoxazole The title compound was obtained in a similar manner as in Example 16(c) except that (S)-1-tert-butoxycarbonyl-4-(5-chloro-7-(4-methyl-1H-pyrazol-1-yl)benzoxazol-2-yl)-3-methylpiperazine obtained in Example 40(a) was used instead of (S)-1-tert-butoxycarbonyl-4-(5-chloro-7-(thiophen-3-yl)benzoxazol-2-yl)-3-m ethylpiperazine.
$^1$H-NMR (400 MHz, CDCl$_3$) δ: 1.43 (3H, d, J=6.8 Hz), 2.20 (3H, s), 2.87-2.96 (2H, m), 3.09-3.15 (2H, m), 3.40-3.47 (1H, m), 3.97-4.01 (1H, m), 4.39-4.45 (1H, m), 7.18 (1H, d, J=2.0 Hz), 7.56 (1H, d, J=2.0 Hz), 7.57 (1H, s), 7.90 (1H, s)
MS(ESI) m/z: 332 (M+H)$^+$

Example 41

(S)-5-Chloro-2-(2-methylpiperazin-1-yl)-7-(pyridin-2-yl)benzoxazole

(a) (S)-1-tert-Butoxycarbonyl-4-(5-chloro-7-(pyridin-2-yl)benzoxazol-2-yl)-3-methylpiperazine The title compound was obtained in a similar manner as in Example 34(a) except that 2-(tributylstannyl)pyridine was used instead of 2-(tributylstannyl)oxazole.

(b) (S)-5-Chloro-2-(2-methylpiperazin-1-yl)-7-(pyridin-2-yl)benzoxazole

The title compound was obtained in a similar manner as in Example 16(c) except that (S)-1-tert-butoxycarbonyl-4-(5-chloro-7-(pyridin-2-yl)benzoxazol-2-yl)-3-methylpiperazine obtained in Example 41(a) was used instead of (S)-1-tert-butoxycarbonyl-4-(5-chloro-7-(thiophen-3-yl)benzoxazol-2-yl)-3-m ethylpiperazine.
$^1$H-NMR (400 MHz, CDCl$_3$) δ: 1.43 (3H, d, J=6.6 Hz), 2.86-2.95 (2H, m), 3.09-3.13 (2H, m), 3.39-3.46 (1H, m), 3.98-4.02 (1H, m), 4.40-4.46 (1H, m), 7.27-7.31 (1H, m), 7.35 (1H, d, J=2.0 Hz), 7.80-7.84 (2H, m), 7.97-7.99 (1H, m), 7.74-8.76 (1H, m)
MS(ESI) m/z: 329 (M+H)$^+$

Example 42

(S)-5-Chloro-2-(2-methylpiperazin-1-yl)-7-(pyridin-3-yl)benzoxazole

(a) (S)-1-tert-Butoxycarbonyl-4-(5-chloro-7-(pyridin-3-yl)benzoxazol-2-yl)-3-methylpiperazine (S)-1-tert-Butoxycarbonyl-(7-bromo-5-chlorobenzoxazol-2-yl)-3-methylpiperazine obtained in Example 16(a) (60 mg), 3-pyridyl boronic acid MIDA ester (49 mg, 1.5 equivalents), copper(I) iodide (13.3 mg, 0.5 equivalents), potassium carbonate (39 mg, 2.0 equivalents), tetrakis(triphenylphosphine)palladium(0) (16 mg, 0.1 equivalents), and isopropyl alcohol (300 µL) were dissolved in DMF (1.2 mL), and the resulting mixture was stirred in an argon atmosphere in an oil bath at 100° C. for 22 hours. Water was added to the reaction mixture, and the product was extracted with ethyl acetate. The organic layer was dried over anhydrous sodium sulfate, then the solvent was distilled off under reduced pressure, and the residue was purified by silica gel column chromatography (developing solvent, hexane:ethyl acetate=1:1) to obtain 29.5 mg of the title compound.

(b) (S)-5-Chloro-2-(2-methylpiperazin-1-yl)-7-(pyridin-3-yl)benzoxazole

The title compound was obtained in a similar manner as in Example 16(c) except that (S)-1-tert-butoxycarbonyl-4-(5-chloro-7-(pyridin-3-yl)benzoxazol-2-yl)-3-methylpiperazine obtained in Example 42(a) was used instead of (S)-1-tert-butoxycarbonyl-4-(5-chloro-7-(thiophen-3-yl)benzoxazol-2-yl)-3-m ethylpiperazine.
$^1$H-NMR (400 MHz, CDCl$_3$) δ: 1.47 (3H, d, J=6.8 Hz), 2.92-3.06 (2H, m), 3.15-3.25 (2H, m), 3.47-3.55 (1H, m), 4.05-4.08 (1H, m), 4.49-4.55 (1H, m), 7.20 (1H, d, J=2.0 Hz), 7.34 (1H, d, J=2.2 Hz), 7.44 (1H, dd, J=4.9, 8.1 Hz), 8.00 (1H, dt, J=2.4, 7.8 Hz), 8.65 (1H, dd, J=1.7, 4.9 Hz), 9.04 (1H, d, J=2.2 Hz)
MS(ESI) m/z: 329 (M+H)$^+$

Example 43

(S)-5-Chloro-2-(2-methylpiperazin-1-yl)-7-(pyridin-4-yl)benzoxazole

(a) (S)-1-tert-Butoxycarbonyl-4-(5-chloro-7-(pyridin-4-yl)benzoxazol-2-yl)-3-methylpiperazine The title compound was obtained in a similar manner as in Example 42(a) except that 4-pyridyl boronic acid MIDA ester was used instead of 3-pyridyl boronic acid MIDA ester.

(b) (S)-5-Chloro-2-(2-methylpiperazin-1-yl)-7-(pyridin-4-yl)benzoxazole

The title compound was obtained in a similar manner as in Example 16(c) except that (S)-1-tert-butoxycarbonyl-4-(5-chloro-7-(pyridin-4-yl)benzoxazol-2-yl)-3-methylpiperazine obtained in Example 43(a) was used instead of (S)-1-tert-butoxycarbonyl-4-(5-chloro-7-(thiophen-3-yl)benzoxazol-2-yl)-3-m ethylpiperazine.
$^1$H-NMR (400 MHz, CDCl$_3$) δ: 1.44 (3H, d, J=6.8 Hz); 2.88-2.99 (2H, m), 3.10-3.18 (2H, m), 3.42-3.49 (1H, m), 3.98-4.02 (1H, m), 4.41-4.47 (1H, m), 7.24 (1H, d, J=2.2 Hz), 7.36 (1H, d, J=2.0 Hz), 7.66 (2H, d, J=6.1 Hz), 8.73 (2H, d, J=6.1 Hz)
MS(ESI) m/z: 329 (M+H)$^+$

Example 44

(S)-5-Chloro-7-cyclohexyl-2-(2-methylpiperazin-1-yl)benzoxazole

(a) (S)-1-tert-Butoxycarbonyl-4-(5-chloro-7-cyclohexylbenzoxazol-2-yl)-3-methylpiperazine 58.9 mg of the title compound was obtained in a similar manner as in Example 31(a) except that cyclohexyl zinc bromide (a 0.5 M solution in THF) was used instead of cyclopentyl zinc bromide (a 0.5 M solution in toluene).

(b) (S)-5-Chloro-7-cyclohexyl-2-(2-methylpiperazin-1-yl)benzoxazole 4.0 mg of the title compound was obtained in a similar manner as in Example 16(c) except that (S)-1-tert-butoxycarbonyl-4-(5-chloro-7-cyclohexylbenzoxazol-2-yl)-3-methylpiperazine obtained in Example 44(a) (58.9 mg) was used instead of (S)-1-tert-butoxycarbonyl-4-(5-chloro-7-(thiophen-3-yl)benzoxazol-2-yl)-3-m ethylpiperazine.

$^1$H-NMR (400 MHz, CDCl$_3$) δ: 1.40 (3H, d, J=6.8 Hz), 1.23-1.92 (10H, m), 2.75-2.82 (1H, m), 2.85-2.93 (2H, m), 3.07-3.12 (2H, m), 3.33-3.40 (1H, m), 3.94-3.97 (1H, m), 4.37-4.39 (1H, m), 6.83 (1H, d, J=2.0 Hz), 7.14 (1H, d, J=2.0 Hz)

MS(ESI) in/z: 334 (M+H)$^+$

Example 45

(S)-5-Chloro-2-(2-methylpiperazin-1-yl)-7-(2H-1,2,3-triazol-2-yl)benzoxazole

(a) (S)-1-tert-Butoxycarbonyl-4-(5-chloro-7-(2H-1,2,3-triazol-2-yl)benzoxazol-2-yl)-3-methylpiperazine (S)-1-tert-Butoxycarbonyl-(7-bromo-5-chlorobenzoxazol-2-yl)-3-methylpiperazine obtained in Example 16(a) (60 mg), tripotassium phosphate (59 mg, 2.0 equivalents), Me4t-butylXPhos (8.1 mg, 0.12 equivalents), tris(dibenzylideneacetone)dipalladium(0) (6.4 mg, 0.05 equivalents), and 1,2,3-triazole (12 μL 1.5 equivalents) were dissolved in toluene (1.0 mL), and the resulting mixture was stirred in an oil bath at 120° C. for 5.5 hours. Water was added to the reaction mixture, and the product was extracted with ethyl acetate. The organic layer was dried over anhydrous sodium sulfate, then the solvent was distilled off under reduced pressure, and the residue was purified by silica gel column chromatography (developing solvent, hexane:ethyl acetate=7:3) to obtain 33 mg of the title compound.

(b) (S)-5-Chloro-7-(2H-1,2,3-triazol-2-yl)-2-(2-methylpiperazin-1-yl)benzoxazole The title compound was obtained in a similar manner as in Example 16(c) except that (S)-1-tert-butoxycarbonyl-4-(5-chloro-7-(2H-1,2,3-triazol-2-yl)benzoxazol-2-yl)-3-methylpiperazine obtained in Example 45(a) was used instead of (S)-1-tert-butoxycarbonyl-4-(5-chloro-7-(thiophen-3-yl)benzoxazol-2-yl)-3-m ethylpiperazine.

$^1$H-NMR (400 MHz, CDCl$_3$) δ: 1.43 (3H, d, J=6.8 Hz), 2.86-2.95 (2H, m), 3.09-3.13 (2H, m), 3.40-3.48 (1H, m), 4.04-4.08 (1H, m), 4.45-4.51 (1H, m), 7.29 (1H, d, J=2.0 Hz), 7.68 (1H, d, J=2.0 Hz), 7.89 (2H, s)

MS(ESI) m/z: 319 (M+H)$^+$

Example 46

(S)-5-Chloro-2-(2-methylpiperazin-1-yl)-7-(1H-1,2,4-triazol-1-yl)benzoxazole

(a) (S)-1-tert-Butoxycarbonyl-4-(5-chloro-7-(1H-1,2,4-triazol-1-yl)benzoxazol-2-yl)-3-methylpiperazine The title compound was obtained in a similar manner as in Example 45(a) except that 1,2,4-triazole was used instead of 1,2,3-triazole.

(b) (S)-5-Chloro-7-(1H-1,2,4-triazol-1-yl)-2-(2-methylpiperazin-1-yl)benzoxazole The title compound was obtained in a similar manner as in Example 16(c) except that (S)-1-tert-butoxycarbonyl-4-(5-chloro-7-(1H-1,2,4-triazol-1-yl)benzoxazol-2-yl)-3-methylpiperazine obtained in Example 46(a) was used instead of (S)-1-tert-butoxycarbonyl-4-(5-chloro-7-(thiophen-3-yl)benzoxazol-2-yl)-3-m ethylpiperazine.

$^1$H-NMR (400 MHz, CDCl$_3$) δ: 1.44 (3H, d, J=6.6 Hz), 2.86-2.96 (2H, m), 3.08-3.15 (2H, m), 3.41-3.48 (1H, m), 3.97-4.00 (1H, m), 4.38-4.44 (1H, m), 7.29 (1H, d, J=2.0 Hz), 7.58 (1H, d, J=2.0 Hz), 8.15 (1H, s), 8.83 (1H, s)

MS(ESI) m/z: 319 (M+H)$^+$

Example 47

(S)-5-Chloro-7-isobutyl-2-(2-methylpiperazin-1-yl)benzoxazole

(a) (S)-1-tert-Butoxycarbonyl-4-(5-chloro-7-isobutylbenzoxazole-2-yl)-3-methylpiperazine The title compound was obtained in a similar manner as in Example 31(a) except that isobutyl zinc bromide (a 0.5 M solution in THF) was used instead of cyclopentyl zinc bromide (a 0.5 M solution in toluene).

(b) (S)-5-Chloro-7-isobutyl-2-(2-methylpiperazin-1-yl)benzoxazole

The title compound was obtained in a similar manner as in Example 16(c) except that (S)-1-tert-butoxycarbonyl-4-(5-chloro-7-isobutylbenzoxazole-2-yl)-3-methylpiperazine obtained in Example 47(a) was used instead of (S)-1-tert-butoxycarbonyl-4-(5-chloro-7-(thiophen-3-yl)benzoxazol-2-yl)-3-m ethylpiperazine.

$^1$H-NMR (400 MHz, CDCl$_3$) δ: 0.94 (6H, dd, J=3.7, 6.6 Hz), 1.38 (3H, d, J 6.8 Hz), 1.95-2.06 (1H, m), 2.59 (2H, d, J=7.1 Hz), 2.84-2.92 (2H, m), 3.07-3.11 (2H, m), 3.32-3.39 (1H, m), 3.93-3.96 (1H, m), 4.34-4.39 (1H, m), 6.78 (1H, d, J=2.0 Hz), 7.15 (1H, d, J=2.0 Hz)

MS(ESI) m/z: 308 (M+H)$^+$

Example 48

(S)-5-Chloro-2-(2-methylpiperazin-1-yl)-7-(2-hydroxymethylphenyl)benzoxazole

(a) (S)-1-tert-Butoxycarbonyl-4-(5-chloro-7-(2-hydroxymethylphenyl)benzoxazol-2-yl)-3-methylpiperazine The title compound was obtained in a similar manner as in Example 16(b) except that o-hydroxymethylphenyl boronic acid was used instead of 3-thiophene boronic acid.

(b) (S)-5-Chloro-2-(2-methylpiperazin-1-yl)-7-(2-hydroxymethylphenyl)benzoxazole The title compound was obtained in a similar manner as in Example 16(c) except that (S)-1-tert-butoxycarbonyl-4-(5-chloro-7-(2-hydroxymethylphenyl)benzoxazol-2-yl)-3-methylpiperazine obtained in Example 48(a) was used instead of (S)-1-tert-butoxycarbonyl-4-(5-chloro-7-(thiophen-3-yl)benzoxazol-2-yl)-3-m ethylpiperazine.

$^1$H-NMR (400 MHz, CDCl$_3$) δ: 1.42 (3H, d, J=6.8 Hz), 2.88-3.01 (2H, m), 3.11-3.20 (2H, m), 3.41-3.48 (1H, m), 3.96-3.99 (1H, m), 4.42-4.45 (1H, m), 4.60 (2H, s), 6.99 (1H, d, J=2.2 Hz), 7.32-7.35 (2H, m), 7.40 (1H, t, J=7.6 Hz), 7.46-7.50 (1H, m), 7.66 (1H, d, J=7.6 Hz)

MS(ESI) m/z: 358 (M+H)$^+$

Example 49

(S)-5-Chloro-7-(1-methyl-1H-imidazol-2-yl)-2-(2-methylpiperazin-1-yl)-benzoxazole (a) (S)-1-tert-Butoxycarbonyl-4-(5-chloro-7-(1-methyl-1H-imidazol-2-yl)benzoxazol-2-yl)-3-methylpiperazine N-Methylimidazole (44 µL, 1.0 mmol) was dissolved in diethyl ether (1.0 mL), then resulting mixture was cooled to −78° C., and n-butyllithium (a 2.77 M solution in hexane, 542 µL, 1.5 mmol) was added thereto, and the resulting mixture was stirred for 1 hour in this state. Tributylstannyl chloride (405 µL, 1.5 mmol) was added to the reaction mixture, the temperature of the reaction mixture was gradually raised, and the mixture was further stirred at room temperature for 1 hour. The precipitate was removed from the reaction system, then the solvent was distilled off from the reaction mixture under reduced pressure, the residue was dissolved in DMF (1.0 mL), (S)-1-tert-butoxycarbonyl-4-(7-bromo-5-chlorobenzoxazol-2-yl)-3-methylpiperazine obtained in Example 16(a) (60 mg, 0.14 mmol) and tetrakis (triphenylphosphine)palladium(0) (16.2 mg, 0.014 mmol) were added thereto, and the resulting mixture was stirred in an argon atmosphere in an oil bath at 120° C. for 14 hours. Water was added to the reaction mixture, and the product was extracted with ethyl acetate. The organic layer was dried over anhydrous magnesium sulfate, then the solvent was distilled off under reduced pressure, and the residue was purified by silica gel column chromatography (developing solvent, hexane:ethyl acetate=1:1) to obtain 54.3 mg of the title compound.

(b) (S)-5-Chloro-7-(1-methyl-1H-imidazol-2-yl)-2-(2-methylpiperazin-1-yl)-benzoxazole The title compound was obtained in a similar manner as in Example 16(c) except that (S)-1-tert-butoxycarbonyl-4-(5-chloro-7-(1-methyl-1H-imidazol-2-yl)benzoxazol-2-yl)-3-methylpiperazine obtained in Example 49(a) was used instead of (S)-1-tert-butoxycarbonyl-4-(5-chloro-7-(thiophen-3-yl)benzoxazol-2-yl)-3-m ethylpiperazine.

$^1$H-NMR (400 MHz, DMSO-d$_6$) δ: 1.40 (3H, d, J=6.8 Hz), 2.83-2.94 (2H, m), 3.06-3.13 (2H, m), 3.36-3.43 (1H, m), 3.71 (3H, s), 3.94-3.98 (1H, m), 4.37-4.43 (1H, m), 7.05 (1H, d, J=1.2 Hz), 7.20 (1H, d, J=2.0 Hz), 7.20 (1H, d, J=1.2 Hz), 7.36 (1H, d, J=2.0 Hz)

MS(ESI) m/z: 332 (M+H)$^+$

Example 50

(S)-5-Chloro-7-(1H-imidazol-2-yl)-2-(2-methylpiperazin-1-yl)benzoxazole (a) (S)-1-tert-Butoxycarbonyl-4-(5-chloro-7-(4,4,5,5-tetramethyl-1,3,2-dioxaboran-2-yl)benzoxazol-2-yl)-3-methylpiperazine (S)-1-tert-Butoxycarbonyl-4-(7-bromo-5-chlorobenzoxazol-2-yl)-3-m ethylpiperazine obtained in Example 16(a) (860 mg, 2.0 mmol), bis(pinacolato)diboron (762 mg, 1.5 equivalents), potassium acetate (589 mg, 3.0 equivalents), and [1,1'-bis(diphenylphosphino)ferrocene]palladium(II) dichloride dichloromethane adduct (163 mg, 0.01 equivalents) were dissolved in 1,4-dioxane (10 mL), and the resulting mixture was stirred in an oil bath at 90° C. for 2 hours. The solvent was distilled off from the reaction mixture under reduced pressure, a small amount of ethyl acetate was added to the residue, insoluble matter was removed, and then the resultant was purified by silica gel column chromatography (developing solvent, hexane:ethyl acetate=17:3) to obtain 927 mg of the title compound.

MS(ESI) m/z: 478 (M+H)$^+$ (b) (S)-1-tert-Butoxycarbonyl-4-(5-chloro-7-(1H-imidazol-2-yl)benzoxazol-2-yl)-3-methylpiperazine (S)-1-tert-Butoxycarbonyl-4-(5-chloro-7-(4,4,5,5-tetramethyl-1,3,2-dioxaboran-2-yl)benzoxazol-2-yl)-3-methylpiperazine obtained in Example 50(a) (48 mg, 0.1 mmol), 2-bromo-1H-imidazole (29 mg, 2.0 equivalents), tetrakis (triphenylphosphine)palladium(0) (11.6 mg, 0.1 equivalents), and potassium carbonate (55 mg, 4.0 equivalents) were dissolved in 1,4-dioxane (800 µL) and water (200 µL), and the resulting mixture was stirred in an argon atmosphere in an oil bath at 110° C. for 4 hours. Water was added to the reaction mixture, the product was extracted with ethyl acetate, and the organic layer was washed with a saturated saline solution. The organic layer was dried over anhydrous sodium sulfate, then the solvent was distilled off under reduced pressure, and the residue was purified by preparative TLC (developing solvent, methanol:chloroform=1:19) to obtain 21.3 mg of the title compound.

(c) (S)-5-Chloro-7-(1H-imidazol-2-yl)-2-(2-methylpiperazin-1-yl)benzoxazole

The title compound was obtained in a similar manner as in Example 16(c) except that (S)-1-tert-butoxycarbonyl-4-(5-chloro-7-(1H-imidazol-2-yl)benzoxazol-2-yl)-3-methylpiperazine obtained in Example 50(b) was used instead of (S)-1-tert-butoxycarbonyl-4-(5-chloro-7-(thiophen-3-yl)benzoxazol-2-yl)-3-methylpiperazine.

$^1$H-NMR (400 MHz, DMSO-d$_6$) δ: 1.31 (3H, d, J=7.1 Hz), 2.64-2.70 (1H, m), 2.79-2.90 (2H, m), 2.97-3.00 (1H, m), 3.24-3.28 (1H, m), 3.99-4.02 (1H, m), 4.39 (1H, m), 7.15 (1H, s), 7.29 (1H, d, J=2.0 Hz), 7.35 (1H, s), 7.52 (1H, d, J=2.0 Hz), 12.28 (1H, s)

MS(ESI) m/z: 318 (M+H)$^+$

Example 51

(S)-5-Chloro-7-(cyclohexylmethyl)-2-(2-methylpiperazin-1-yl)-benzoxazole (a) (S)-1-tert-Butoxycarbonyl-4-(5-chloro-7-(cyclohexylmethyl)benzoxazol-2-yl)-3-methylpiperazine Methylenecyclohexane (60 µL, 0.5 mmol) was added to 9-BBN (a 0.5 M solution in THF, 2.0 mL, 1.0 mmol), and the resulting mixture was stirred at 80° C. by using a microwave device for 1 hour. A 5 N aqueous solution of sodium hydroxide (0.2 mL, 1.0 mmol) was added to the reaction mixture, then (S)-1-tert-butoxycarbonyl-4-(7-bromo-5-chlorobenzoxazol-2-yl)-3-methylpiperazine obtained in Example 16(a) (60 mg, 0.14 mmol), [1,1'-bis (diphenylphosphino)ferrocene]palladium(II) dichloride dichloromethane adduct (11.4 mg, 0.01 equivalents), and potassium carbonate (58 mg, 0.42 mmol) were added thereto, and the resulting mixture was stirred at room temperature for 3 hours. The solvent was distilled off from the reaction mixture under reduced pressure, and the residue was purified by preparative TLC (developing solvent, hexane:ethyl acetate=4:1).

(b) (S)-5-Chloro-7-(cyclohexylmethyl)-2-(2-methyl-piperazin-1-yl)-benzoxazole (S)-1-tert-Butoxycarbonyl-4-(5-chloro-7-(cyclohexylmethyl)benzoxazol-2-yl)-3-methylpiperazine obtained in Example 51(a) (the whole amount) was dissolved in chloroform (0.6 mL) and trifluoroacetic acid (0.3 mL), and the resulting mixture was stirred at room temperature for 1.5 hours. The reaction solvent was distilled off under reduced pressure, then ethyl acetate was added thereto, and the resulting mixture was sequentially washed with an aqueous solution of sodium hydrogencarbonate and a saturated saline solution. The organic layer was dried over anhydrous sodium sulfate, then the solvent was distilled off under reduced pressure, and the residue was purified by silica gel column chromatography (developing solvent, methanol:chloroform=2:98) to obtain 2.7 mg of the title compound.
$^1$H-NMR (400 MHz, CDCl$_3$) δ: 0.95-1.02 (2H, m), 1.09-1.23 (2H, m), 1.50 (3H, d, J=7.1 Hz), 1.61-1.69 (4H, m), 1.87-2.00 (3H, m), 2.60 (2H, d, J=6.8 Hz), 3.02-3.09 (1H, m), 3.14-3.28 (2H, m), 3.34-3.38 (1H, m), 3.55-3.63 (1H, m), 4.11-4.16 (1H, m), 4.58-4.61 (1H, m), 6.83 (1H, d, J=2.0 Hz), 7.17 (1H, d, J=2.0 Hz)
MS(ESI) m/z: 348 (M+H)$^+$ Example 52

(S)-5-Chloro-7-(cyclohexyloxy)-2-(2-methylpiperazin-1-yl)benzoxazole (a) (S)-1-tert-Butoxycarbonyl-4-(5-chloro-7-hydroxybenzoxazol-2-yl)-3-methylpiperazine The title compound was obtained in a similar manner as in Example 28(a) except that water was used instead of cyclopentyl alcohol.

(b) (S)-1-tert-Butoxycarbonyl-4-(5-chloro-7-(cyclohexyloxy)benzoxazol-2-yl)-3-methylpiperazine (S)-1-tert-Butoxycarbonyl-4-(5-chloro-7-hydroxybenzoxazol-2-yl)-3-methylpiperazine obtained in Example 52(a) (49 mg, 0.14 mmol), cethyltrimethyl ammonium bromide (5.1 mg, 0.1 equivalents), bromocyclohexane (34 μL 2.0 equivalents), and potassium hydroxide (24 mg, 3.0 equivalents) were dissolved in 1,4-dioxane (0.5 mL), the resulting mixture was stirred in an oil bath at 100° C. for 14 hours, then acetyltrimethyl ammonium bromide (20 mg, 0.4 equivalents), bromocyclohexane (51 μL, 3.0 equivalents), and potassium hydroxide (24 mg, 3.0 equivalents) were further added, and the resulting mixture was continuously stirred for 2 hours. A saturated saline solution was added to the reaction mixture, and the product was extracted with ethyl acetate. The organic layer was washed with a saturated saline solution and dried over anhydrous sodium sulfate, and then the solvent was distilled off under reduced pressure, and the residue was purified by silica gel column chromatography (developing solvent, hexane:ethyl acetate=17:3) to obtain 17.7 mg of the title compound.

(c) (S)-5-Chloro-7-(cyclohexyloxy)-2-(2-methylpiperazin-1-yl)benzoxazole

The title compound was obtained in a similar manner as in Example 16(c) except that (S)-1-tert-butoxycarbonyl-4-(5-chloro-7-(cyclohexyloxy)benzoxazol-2-yl)-3-methylpiperazine obtained in Example 52(b) was used instead of (S)-1-tert-butoxycarbonyl-4-(5-chloro-7-(thiophen-3-yl)benzoxazol-2-yl)-3-m ethylpiperazine.
$^1$H-NMR (400 MHz, CDCl$_3$) δ: 1.33-1.35 (4H, m), 1.39 (3H, d, J=6.8 Hz), 1.54-1.59 (2H, m), 1.82-1.84 (2H, m), 2.01-2.05 (2H, m), 2.83-2.91 (2H, m), 3.06-3.10 (2H, m), 3.32-3.39 (1H, m), 3.94-3.98 (1H, m), 4.40-4.34 (2H, m), 6.61 (1H, d, J=2.0 Hz), 6.95 (1H, d, J=2.0 Hz)
MS(ESI) m/z: 350 (M+H)$^+$ Example 53

(S)-5-Chloro-7-(cyclopropylmethoxy)-2-(2-methylpiperazin-1-yl)benzoxazole (a) (S)-1-tert-Butoxycarbonyl-4-(5-chloro-7-(cyclopropylmethoxy)benzoxazol-2-yl)-3-methylpiperazine The title compound was obtained in a similar manner as in Example 52(b) except that bromomethylcyclopropane was used instead of bromocyclohexane.

(b) (S)-5-Chloro-7-(cyclopropylmethoxy)-2-(2-methylpiperazin-1-yl)benzoxazole

The title compound was obtained in a similar manner as in Example 16(c) except that (S)-1-tert-butoxycarbonyl-4-(5-chloro-7-(cyclopropylmethoxy)benzoxazol-2-yl)-3-methylpiperazine obtained in Example 53(a) was used instead of (S)-1-tert-butoxycarbonyl-4-(5-chloro-7-(thiophen-3-yl)benzoxazol-2-yl)-3-m ethylpiperazine.
$^1$H-NMR (400 MHz, CDCl$_3$) δ: 0.40-0.36 (2H, m), 0.65-0.69 (2H, m), 1.26-1.36 (1H, m), 1.39 (3H, d, J=6.8 Hz), 2.82-2.90 (2H, m), 3.05-3.09 (2H, m), 3.32-3.40 (1H, m), 3.95 (2H, d, J=7.1 Hz), 3.96-4.00 (1H, m), 4.39-4.42 (1H, m), 6.58 (1H, d, J=1.7 Hz), 6.95 (1H, d, J=2.0 Hz)
MS(ESI) m/z: 322 (M+H)$^+$ Example 54

(S)-5-Chloro-7-(isothiazole-3-yl)-2-(2-methylpiperazin-1-yl)benzoxazole (a) (S)-1-tert-Butoxycarbonyl-4-(5-chloro-7-(isothiazole-3-yl)benzoxazol-2-yl)-3-methylpiperazine The title compound was obtained in a similar manner as in Example 50(b) except that 3-bromoisothiazole was used instead of 2-bromo-1H-imidazole.

(b) (S)-5-Chloro-7-(isothiazole-3-yl)-2-(2-methylpiperazin-1-yl)benzoxazole

The title compound was obtained in a similar manner as in Example 16(c) except that (S)-1-tert-butoxycarbonyl-4-

(5-chloro-7-(isothiazole-3-yl)benzoxazol-2-yl)-3-methylpiperazine obtained in Example 54(a) was used instead of (S)-1-tert-butoxycarbonyl-4-(5-chloro-7-(thiophen-3-yl)benzoxazol-2-yl)-3-m ethylpiperazine.

$^1$H-NMR (400 MHz, CDCl$_3$) δ: 1.44 (3H, d, J=6.8 Hz), 2.88-2.96 (2H, m), 3.10-3.15 (2H, m), 3.41-3.48 (1H, m), 4.01-4.04 (1H, m), 4.42-4.48 (1H, m), 7.34 (1H, d, J=2.0 Hz), 7.78 (1H, d, J=2.0 Hz), 7.84 (1H, d, J=4.9 Hz), 8.80 (1H, d, J=4.9 Hz)

MS(ESI) m/z: 335 (M+H)$^+$

Example 55

(S)-5-Chloro-7-(5-hydroxymethylthiazol-2-yl)-2-(2-methylpiperazin-1-yl)benzoxazole (a) (S)-1-tert-Butoxycarbonyl-4-(5-chloro-7-(5-hydroxymethylthiazol-2-yl)benzoxazol-2-yl)-3-methylpiperazine The title compound was obtained in a similar manner as in Example 50(b) except that 2-bromothiazole-5-methanol was used instead of 2-bromo-1H-imidazole.

(b) (S)-5-Chloro-7-(5-hydroxymethylthiazol-2-yl)-2-(2-methylpiperazin-1-yl)benzoxazole The title compound was obtained in a similar manner as in Example 16(c) except that (S)-1-tert-butoxycarbonyl-4-(5-chloro-7-(5-hydroxymethylthiazol-2-yl)benzoxazol-2-yl)-3-methylpiperazine obtained in Example 55(a) was used instead of (S)-1-tert-butoxycarbonyl-4-(5-chloro-7-(thiophen-3-yl)benzoxazol-2-yl)-3-m ethylpiperazine.

$^1$H-NMR (400 MHz, DMSO-d$_6$) δ: 1.36 (3H, d, J=6.6 Hz), 2.66-2.73 (1H, m), 2.82-2.92 (2H, m), 3.00-3.03 (1H, m), 3.38 (1H, m), 3.87-3.90 (1H, m), 4.29-4.31 (1H, m), 4.78 (2H, d, J=5.4 Hz), 5.71 (1H, t, J=5.6 Hz), 7.41 (1H, d, J=2.0 Hz), 7.66 (1H, d, J=2.2 Hz), 7.87 (1H, s)

MS(ESI) m/z: 365 (M+H)$^+$

Example 56

(S)-5-Chloro-2-(2-methylpiperazin-1-yl)-7-(pyrimidin-2-yl)benzoxazole (a) (S)-1-tert-Butoxycarbonyl-4-(5-chloro-7-(pyrimidin-2-yl)benzoxazol-2-yl)-3-methylpiperazine The title compound was obtained in a similar manner as in Example 34(a) except that 2-(tributylstannyl)pyrimidine was used instead of 2-(tributylstannyl)oxazole.

(b) (S)-5-Chloro-2-(2-methylpiperazin-1-yl)-7-(pyrimidin-2-yl)benzoxazole

The title compound was obtained in a similar manner as in Example 16(c) except that (S)-1-tert-butoxycarbonyl-4-(5-chloro-7-(pyrimidin-2-yl)benzoxazol-2-yl)-3-methylpiperazine obtained in Example 56(a) was used instead of (S)-1-tert-butoxycarbonyl-4-(5-chloro-7-(thiophen-3-yl)benzoxazol-2-yl)-3-m ethylpiperazine.

$^1$H-NMR (400 MHz, CDCl$_3$) δ: 1.41 (3H, d, J=6.8 Hz), 2.86-2.93 (2H, m), 3.09-3.13 (2H, m), 3.40-3.47 (1H, m), 4.05-4.08 (1H, m), 4.45-4.51 (1H, m), 7.26 (1H, t, J=4.9 Hz), 7.41 (1H, d, J=2.2 Hz), 7.95 (1H, d, J=2.2 Hz), 8.88 (2H, d, J=4.9 Hz)

MS(ESI) m/z: 330 (M+H)$^+$

Example 57

(S)-5-Chloro-7-(5-chlorothiophen-2-yl)-2-(2-methylpiperazin-1-yl)benzoxazole (a) (S)-1-tert-Butoxycarbonyl-4-(5-chloro-7-(5-chlorothiophen-2-yl)benzoxazol-2-yl)-3-methylpiperazine The title compound was obtained in a similar manner as in Example 16(b) except that 5-chloro-2-thiophene boronic acid was used instead of 3-thiophene boronic acid.

(b) (S)-5-Chloro-7-(5-chlorothiophen-2-yl)-2-(2-methylpiperazin-1-yl)benzoxazole The title compound was obtained in a similar manner as in Example 16(c) except that (S)-1-tert-butoxycarbonyl-4-(5-chloro-7-(5-chlorothiophen-2-yl)benzoxazol-2-yl)-3-methylpiperazine obtained in Example 57(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.46 (3H, d, J=6.8 Hz), 2.91-3.02 (2H, m), 3.13-3.22 (2H, m), 3.44-3.52 (1H, m), 4.04-4.07 (1H, m), 4.45-4.51 (1H, m), 6.97 (1H, d, J=3.9 Hz), 7.17 (1H, d, J=2.0 Hz), 7.22 (1H, d, J=2.0 Hz), 7.32 (1H, d, J=3.9 Hz)

MS(ESI) m/z: 368 (M+H)$^+$

Example 58

(S)-5-Chloro-7-(5-chloropyridin-2-yl)-2-(2-methylpiperazin-1-yl)benzoxazole (a) (S)-1-tert-Butoxycarbonyl-4-(5-chloro-7-(5-chloropyridin-2-yl)benzoxazol-2-yl)-3-methylpiperazine The title compound was obtained in a similar manner as in Example 34(a) except that 5-chloro-2-(tributylstannyl)pyridine was used instead of 2-(tributylstannyl)oxazole.

(b) (S)-5-Chloro-7-(5-chloropyridin-2-yl)-2-(2-methylpiperazin-1-yl)benzoxazole

The title compound was obtained in a similar manner as in Example 16(c) except that (S)-1-tert-butoxycarbonyl-4-(5-chloro-7-(5-chloropyridin-2-yl)benzoxazol-2-yl)-3-methylpiperazine obtained in Example 58(a) was used instead of (S)-1-tert-butoxycarbonyl-4-(5-chloro-7-(thiophen-3-yl)benzoxazol-2-yl)-3-m ethylpiperazine.

$^1$H-NMR (400 MHz, CDCl$_3$) δ: 1.43 (3H, d, J=6.8 Hz), 2.87-2.95 (2H, m), 3.09-3.13 (2H, m), 3.39-3.47 (1H, m), 3.98-4.00 (1H, m), 4.39-4.45 (1H, m), 7.35 (1H, d, J=2.2 Hz), 7.78-7.81 (2H, m), 7.94 (1H, d, J=8.3 Hz), 8.69 (1H, d, J=2.4 Hz)

MS(ESI) m/z: 363 (M+H)$^+$

Example 59

(S)-5-Chloro-7-(4-chloropyridin-2-yl)-2-(2-methyl-piperazin-1-yl)benzoxazole (a) (S)-1-tert-Butoxycarbonyl-4-(5-chloro-7-(4-chloropyridin-2-yl)benzoxazol-2-yl)-3-methylpiperazine The title compound was obtained in a similar manner as in Example 34(a) except that 4-chloro-2-(tributylstannyl) pyridine was used instead of 2-(tributylstannyl)oxazole.

(b) (S)-5-Chloro-7-(4-chloropyridin-2-yl)-2-(2-methylpiperazin-1-yl)benzoxazole

The title compound was obtained in a similar manner as in Example 16(c) except that (S)-1-tert-butoxycarbonyl-4-(5-chloro-7-(4-chloropyridin-2-yl)benzoxazol-2-yl)-3-methylpiperazine obtained in Example 59(a) was used instead of (S)-1-tert-butoxycarbonyl-4-(5-chloro-7-(thiophen-3-yl)benzoxazol-2-yl)-3-methylpiperazine.
$^1$H-NMR (500 MHz, CDCl$_3$) δ: 1.44 (3H, d, J=6.5 Hz), 2.88-2.96 (2H, m), 3.10-3.15 (2H, m), 3.42-3.47 (1H, m), 3.97-4.00 (1H, m), 4.40-4.45 (1H, m), 7.30 (1H, dd, J=2.0, 5.5 Hz), 7.36 (1H, d, J=2.0 Hz), 7.82 (1H, d, J=2.0 Hz), 8.01 (1H, d, J=2.0 Hz), 8.64 (1H, d, J=5.0 Hz)
MS(ESI) m/z: 363 (M+H)$^+$ Example 60

(S)-5-Chloro-7-(6-fluoropyridin-2-yl)-2-(2-methyl-piperazin-1-yl)benzoxazole (a) (S)-1-tert-Butoxycarbonyl-4-(5-chloro-7-(6-fluoropyridin-2-yl)benzoxazol-2-yl)-3-methylpiperazine The title compound was obtained in a similar manner as in Example 34(a) except that 6-fluoro-2-(tributylstannyl) pyridine was used instead of 2-(tributylstannyl)oxazole.

(b) (S)-5-Chloro-7-(6-fluoropyridin-2-yl)-2-(2-methylpiperazin-1-yl)benzoxazole

The title compound was obtained in a similar manner as in Example 16(c) except that (S)-1-tert-butoxycarbonyl-4-(5-chloro-7-(6-fluoropyridin-2-yl)benzoxazol-2-yl)-3-methylpiperazine obtained in Example 60(a) was used instead of (S)-1-tert-butoxycarbonyl-4-(5-chloro-7-(thiophen-3-yl)benzoxazol-2-yl)-3-m ethylpiperazine.
$^1$H-NMR (400 MHz, CDCl$_3$) δ: 1.44 (3H, d, J=6.8 Hz), 2.87-2.96 (2H, m), 3.10-3.14 (2H, m), 3.41-3.48 (1H, m), 3.99-4.02 (1H, m), 4.41-4.47 (1H, m), 6.92-6.95 (1H, m), 7.36 (1H, d, J=2.2 Hz), 7.84 (1H, d, J=2.0 Hz), 7.89-7.95 (2H, m)
MS(ESI) m/z: 347 (M+H)$^+$ Example 61

(S)-5-Chloro-7-(3-fluoropyridin-2-yl)-2-(2-methyl-piperazin-1-yl)benzoxazole (a) (S)-1-tert-Butoxycarbonyl-4-(5-chloro-7-(3-fluoropyridin-2-yl)benzoxazol-2-yl)-3-methylpiperazine The title compound was obtained in a similar manner as in Example 34(a) except that 3-fluoro-2-(tributylstannyl) pyridine was used instead of 2-(tributylstannyl)oxazole.

(b) (S)-5-Chloro-7-(3-fluoropyridin-2-yl)-2-(2-methylpiperazin-1-yl)benzoxazole

The title compound was obtained in a similar manner as in Example 16(c) except that (S)-1-tert-butoxycarbonyl-4-(5-chloro-7-(3-fluoropyridin-2-yl)benzoxazol-2-yl)-3-methylpiperazine obtained in Example 61(a) was used instead of (S)-1-tert-butoxycarbonyl-4-(5-chloro-7-(thiophen-3-yl)benzoxazol-2-yl)-3-methylpiperazine.
$^1$H-NMR (400 MHz, CDCl$_3$) δ: 1.39 (3H, d, J=6.8 Hz), 2.83-2.91 (2H, m), 3.06-3.10 (2H, m), 3.33-3.40 (1H, m), 3.93-3.96 (1H, m), 4.34-4.40 (1H, m), 7.36-7.40 (3H, m), 7.53-7.58 (1H, m), 8.57-8.59 (1H, m)
MS(ESI) m/z: 347 (M+H)$^+$ Example 62

(S)-5-Chloro-7-(5-cyanothiazol-2-yl)-2-(2-methyl-piperazin-1-yl)benzoxazole (a) (S)-1-tert-Butoxycarbonyl-4-(5-chloro-7-(5-cyanothiazol-2-yl)benzoxazol-2-yl)-3-methylpiperazine The title compound was obtained in a similar manner as in Example 50(b) except that 2-bromo-5-cyanothiazole was used instead of 2-bromo-1H-imidazole.

(b) (S)-5-Chloro-7-(5-cyanothiazol-2-yl)-2-(2-methylpiperazin-1-yl)benzoxazole

The title compound was obtained in a similar manner as in Example 16(c) except that (S)-1-tert-butoxycarbonyl-4-(5-chloro-7-(5-cyanothiazol-2-yl)benzoxazol-2-yl)-3-methylpiperazine obtained in Example 62(a) was used instead of (S)-1-tert-butoxycarbonyl-4-(5-chloro-7-(thiophen-3-yl)benzoxazol-2-yl)-3-m ethylpiperazine.
$^1$H-NMR (400 MHz, DMSO-d$_6$) δ: 1.36 (3H, d, J=6.8 Hz), 2.67-2.72 (1H, m), 2.88-2.92 (2H, m), 3.02-3.05 (1H, m), 3.37-3.40 (1H, m), 3.94-3.97 (1H, m), 4.37 (1H, m), 7.56 (1H, d, J=2.2 Hz), 7.74 (1H, d, J=2.2 Hz), 8.88 (1H, s)
MS(ESI) m/z: 360 (M+H)$^+$ Example 63

(S)-5-Chloro-2-(2-methylpiperazin-1-yl)-7-(5-methylthiazol-2-yl)benzoxazole (a) (S)-1-tert-Butoxycarbonyl-4-(5-chloro-7-(5-methylthiazol-2-yl)benzoxazol-2-yl)-3-methylpiperazine The title compound was obtained in a similar manner as in Example 50(b) except that 2-bromo-5-methylthiazol was used instead of 2-bromo-1H-imidazole.

(b) (S)-5-Chloro-2-(2-methylpiperazin-1-yl)-7-(5-methylthiazol-2-yl)benzoxazole

The title compound was obtained in a similar manner as in Example 16(c) except that (S)-1-tert-butoxycarbonyl-4-(5-chloro-7-(5-methylthiazol-2-yl)benzoxazol-2-yl)-3-methylpiperazine obtained in Example 63(a) was used instead of (S)-1-tert-butoxycarbonyl-4-(5-chloro-7-(thiophen-3-yl)benzoxazol-2-yl)-3-methylpiperazine.
$^1$H-NMR (400 MHz, CDCl$_3$) δ: 1.46 (3H, d, J=6.8 Hz), 2.58 (3H, s), 2.89-2.99 (2H, m), 3.12-3.18 (2H, m), 3.43-

3.50 (1H, m), 4.05-4.08 (1H, m), 4.45-4.52 (1H, m), 7.31 (1H, d, J=2.2 Hz), 7.60 (1H, s), 7.77 (1H, d, J=2.0 Hz)

MS(ESI) m/z: 349 (M+H)$^+$

Example 64

(S)-5-Chloro-7-(2-chlorothiophen-3-yl)-2-(2-methylpiperazin-1-yl)benzoxazole (a) (S)-1-tert-Butoxycarbonyl-4-(5-chloro-7-(2-chlorothiophen-3-yl)benzoxazol-2-yl)-3-methylpiperazine The title compound was obtained in a similar manner as in Example 16(b) except that 2-chloro-3-thiophene boronic acid was used instead of 3-thiophene boronic acid.

(b) (S)-5-Chloro-7-(2-chlorothiophen-3-yl)-2-(2-methylpiperazin-1-yl)benzoxazole The title compound was obtained in a similar manner as in Example 16(c) except that (S)-1-tert-butoxycarbonyl-4-(5-chloro-7-(2-chlorothiophen-3-yl)benzoxazol-2-yl)-3-methylpiperazine obtained in Example 64(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.39 (3H, d, J=6.8 Hz), 2.82-2.91 (2H, m), 3.05-3.09 (2H, m), 3.32-3.40 (1H, m), 3.93-3.96 (1H, m), 4.34-4.40 (1H, m), 7.14 (1H, d, J=5.6 Hz), 7.17 (1H, d, J=2.0 Hz), 7.21 (1H, d, J=5.9 Hz), 7.30 (1H, d, J=2.0 Hz)

MS(ESI) m/z: 368 (M+H)$^+$

Example 65

(S)-5-Chloro-7-(5-carbamoylthiazol-2-yl)-2-(2-methylpiperazin-1-yl)benzoxazole (a) (S)-1-tert-Butoxycarbonyl-4-(5-chloro-7-(5-carbamoylthiazol-2-yl)benzoxazol-2-yl)-3-methylpiperazine The title compound was obtained in a similar manner as in Example 50(b) except that 2-bromo-5-carbamoylthiazole was used instead of 2-bromo-1H-imidazole.

(b) (S)-5-Chloro-7-(5-carbamoylthiazol-2-yl)-2-(2-methylpiperazin-1-yl)benzoxazole The title compound was obtained in a similar manner as in Example 16(c) except that (S)-1-tert-butoxycarbonyl-4-(5-chloro-7-(5-carbamoylthiazol-2-yl)benzoxazol-2-yl)-3-methylpiperazine obtained in Example 65(a) was used instead of (S)-1-tert-butoxycarbonyl-4-(5-chloro-7-(thiophen-3-yl)benzoxazol-2-yl)-3-methylpiperazine.

$^1$H-NMR (400 MHz, DMSO-d$_6$) δ: 1.36 (3H, d, J=6.8 Hz), 2.68-2.74 (1H, m), 2.84-2.94 (2H, m), 3.03-3.05 (1H, m), 3.37-3.40 (1H, m), 3.88-3.94 (1H, m), 4.29-4.35 (1H, m), 7.48 (1H, s), 7.71 (1H, s), 7.79 (1H, br s), 8.29 (1H, br s), 8.55 (1H, s)

MS(ESI) m/z: 378 (M+H)$^+$

Example 66

(S)-5-Chloro-7-(3-cyanopyridin-2-yl)-2-(2-methylpiperazin-1-yl)benzoxazole (a) (S)-1-tert-Butoxycarbonyl-4-(5-chloro-7-(3-cyanopyridin-2-yl)benzoxazol-2-yl)-3-methylpiperazine The title compound was obtained in a similar manner as in Example 50(b) except that 2-bromo-3-cyanopyridine was used instead of 2-bromo-1H-imidazole.

(b) (S)-5-Chloro-7-(3-cyanopyridin-2-yl)-2-(2-methylpiperazin-1-yl)benzoxazole

The title compound was obtained in a similar manner as in Example 16(c) except that (S)-1-tert-butoxycarbonyl-4-(5-chloro-7-(3-cyanopyridin-2-yl)benzoxazol-2-yl)-3-methylpiperazine obtained in Example 66(a) was used instead of (S)-1-tert-butoxycarbonyl-4-(5-chloro-7-(thiophen-3-yl)benzoxazol-2-yl)-3-m ethylpiperazine.

$^1$H-NMR (400 MHz, CDCl$_3$) δ: 1.42 (3H, d, J=6.8 Hz), 2.84-2.90 (2H, m), 3.06-3.10(2H, in), 3.35-3.43 (1H, m), 3.95-3.99 (1H, m), 4.37-4.43 (1H, m), 7.35 (1H, d, J=2.2 Hz), 7.43 (1H, d, J=2.2 Hz), 7.48 (1H, dd, J=4.9, 8.1 Hz), 8.14 (1H, d, J=7.8 Hz), 8.95 (1H, d, J=4.9 Hz)

MS(ESI) m/z: 354 (M+H)$^+$

Example 67

(S)-5-Chloro-7-(5-fluorothiophen-2-yl)-2-(2-methylpiperazin-1-yl)benzoxazole (a) (S)-1-tert-Butoxycarbonyl-4-(5-chloro-7-(5-fluorothiophen-2-yl)benzoxazol-2-yl)-3-methylpiperazine (S)-1-tert-Butoxycarbonyl-4-(7-bromo-5-chlorobenzoxazol-2-yl)-3-m ethylpiperazine obtained in Example 16(a) (48 mg), potassium carbonate (69 mg, 5.0 equivalents), tetrakis(triphenylphosphine)palladium(0) (12 mg, 0.1 equivalents), and 2-fluoro-5-(4,4,5,5-tetramethyl-1,3,2-dioxaboran-2-yl)thiophene (46 mg, 2.0 equivalents) were dissolved in 1,4-dioxane (0.8 mL) and water (0.2 mL), and the resulting mixture was stirred in an argon atmosphere in an oil bath at 100° C. for 4 hours. Water was added to the reaction mixture, and the product was extracted with ethyl acetate. The organic layer was dried over anhydrous magnesium sulfate, then the solvent was distilled off under reduced pressure, and the residue was purified by silica gel column chromatography (developing solvent, hexane:ethyl acetate=17:3) to obtain 21.8 mg of the title compound.

(b) (S)-5-Chloro-7-(5-fluorothiophen-2-yl)-2-(2-methylpiperazin-1-yl)benzoxazol

The title compound was obtained in a similar manner as in Example 16(c) except that (S)-1-tert-butoxycarbonyl-4-(5-chloro-7-(5-fluorothiophen-2-yl)benzoxazol-2-yl)-3-methylpiperazine obtained in Example 67(a) was used instead of (S)-1-tert-butoxycarbonyl-4-(5-chloro-7-(thiophen-3-yl)benzoxazol-2-yl)-3-m ethylpiperazine.

$^1$H-NMR (400 MHz, CDCl$_3$) δ: 1.43 (3H, d, J=6.8 Hz), 2.86-2.96 (2H, m), 3.09-3.14 (2H, m), 3.38-3.46 (1H, m), 3.98-4.02 (1H, m), 4.39-4.45 (1H, m), 6.53 (1H, dd, J=2.0, 4.2 Hz), 7.12 (1H, d, J=2.0 Hz), 7.17 (1H, t, J=3.9 Hz), 7.20 (1H, d, J=2.0 Hz)

MS(ESI) m/z: 352 (M+H)$^+$

Example 68

(S)-5-Chloro-2-(2-methylpiperazin-1-yl)-7-(3-methylpyridin-2-yl)benzoxazole (a) (S)-1-tert-Butoxycarbonyl-4-(5-chloro-7-(3-methylpyridin-2-yl)benzoxazol-2-yl)-3-methylpiperazine The title compound was obtained in a similar manner as in Example 34(a) except that 3-methyl-2-pyridyl zinc bromide was used instead of 2-(tributylstannyl)oxazole.

(b) (S)-5-Chloro-2-(2-methylpiperazin-1-yl)-7-(3-methylpyridin-2-yl)benzoxazol

The title compound was obtained in a similar manner as in Example 16(c) except that (S)-1-tert-butoxycarbonyl-4-(5-chloro-7-(3-methylpyridin-2-yl)benzoxazol-2-yl)-3-methylpiperazine obtained in Example 68(a) was used instead of (S)-1-tert-butoxycarbonyl-4-(5-chloro-7-(thiophen-3-yl)benzoxazol-2-yl)-3-m ethylpiperazine.

$^1$H-NMR (400 MHz, CDCl$_3$) δ: 1.36 (3H, d, J=6.8 Hz), 2.30 (3H, s), 2.79-2.88 (2H, m), 3.02-3.06 (2H, m), 3.29-3.36 (1H, m), 3.86-3.89 (1H, m), 4.29-4.35 (1H, m), 7.11 (1H, d, J=2.0 Hz), 7.26-7.28 (1H, m), 7.35 (1H, d, J=2.0 Hz), 7.64 (1H, d, J=7.8 Hz), 8.57 (1H, d, J=4.9 Hz)

MS(ESI) m/z: 343 (M+H)$^+$

Example 69

(S)-5-Chloro-2-(2-methylpiperazin-1-yl)-7-(2-methylthiazol-4-yl)benzoxazole (a) (S)-1-tert-Butoxycarbonyl-4-(5-chloro-7-(2-methylthiazol-4-yl)benzoxazol-2-yl)-3-methylpiperazine The title compound was obtained in a similar manner as in Example 50(b) except that 4-bromo-2-methylthiazol was used instead of 2-bromo-1H-imidazole.

(b) (S)-5-Chloro-2-(2-methylpiperazin-1-yl)-7-(2-methylthiazol-4-yl)benzoxazole

The title compound was obtained in a similar manner as in Example 16(c) except that (S)-1-tert-butoxycarbonyl-4-(5-chloro-7-(2-methylthiazol-4-yl)benzoxazol-2-yl)-3-methylpiperazine obtained in Example 69(a) was used instead of (S)-1-tert-butoxycarbonyl-4-(5-chloro-7-(thiophen-3-yl)benzoxazol-2-yl)-3-m ethylpiperazine.

$^1$H-NMR (400 MHz, CDCl$_3$) δ: 1.44 (3H, d, J=6.8 Hz), 2.80 (3H, s), 2.88-2.96 (2H, m), 3.10-3.14 (2H, m), 3.40-3.47 (1H, m), 3.99-4.02 (1H, m), 4.41-4.47 (1H, m), 7.27 (1H, s), 7.66 (1H, s), 7.81 (1H, s)

MS(ESI) m/z: 349 (M+H)$^+$

Example 70

(S)-5-Chloro-2-(2-methylpiperazin-1-yl)-7-phenoxybenzoxazole (a) (S)-1-tert-Butoxycarbonyl-4-(5-chloro-7-phenoxybenzoxazol-2-yl)-3-methylpiperazine (S)-1-tert-Butoxycarbonyl-(7-bromo-5-chlorobenzoxazol-2-yl)-3-methylpiperazine obtained in Example 16(a) (60 mg), tripotassium phosphate (59 mg, 2.0 equivalents), Me4t-butyl XPhos (4.8 mg, 0.01 equivalents), palladium(II) acetate (3.1 mg, 0.1 equivalents), and phenol (20 mg, 1.5 equivalents) were dissolved in toluene (1.0 mL), and the resulting mixture was stirred in an oil bath at 110° C. for 2 hours. Water was added to the reaction mixture, and the product was extracted with ethyl acetate. The organic layer was dried over anhydrous sodium sulfate, then the solvent was distilled off under reduced pressure, and the residue was purified by silica gel column chromatography (developing solvent, hexane:ethyl acetate=17:3) to obtain 19 mg of the title compound.

(b) (S)-5-Chloro-2-(2-methylpiperazin-1-yl)-7-phenoxybenzoxazole 7.9 mg of the title compound was obtained in a similar manner as in Example 16(c) except that (S)-1-tert-butoxycarbonyl-4-(5-chloro-7-phenoxybenzoxazol-2-yl)-3-methylpiperazine obtained in Example 70(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.35 (3H, d, J=6.8 Hz), 2.79-2.88 (2H, m), 3.02-3.06 (2H, m), 3.29-3.36 (2H, m), 3.88-3.92 (1H, m), 4.27-4.33 (1H, m), 6.60 (1H, d, J=1.7 Hz), 7.06-7.09 (3H, m), 7.14-7.18 (1H, m), 7.35-7.39 (2H, m)

MS(ESI) m/z: 344 (M+H)$^+$

Example 71

(S)-5-Chloro-2-(2-methylpiperazin-1-yl)-7-(2-oxopyrrolidin-1-yl)benzoxazole (a) (S)-1-tert-Butoxycarbonyl-4-(5-chloro-7-(2-oxopyrrolidin-1-yl)benzoxazol-2-yl)-3-methylpiperazine (S)-1-tert-Butoxycarbonyl-4-(7-bromo-5-chlorobenzoxazol-2-yl)-3-m ethylpiperazine obtained in Example 16(a) (60 mg), cesium carbonate (91 mg, 2.0 equivalents), XantPhos (12.1 mg, 0.15 equivalents), tris(dibenzylideneacetone)dipalladium(0) (12.8 mg, 0.1 equivalents), and 2-pyrrolidone (54 μL, 5.0 equivalents) were dissolved in DMF (1.0 mL), and the resulting mixture was stirred in an argon atmosphere in an oil bath at 120° C. for 16.5 hours. Water was added to the reaction mixture, and the product was extracted with ethyl acetate. The organic layer was dried over anhydrous sodium sulfate, then the solvent was distilled off under reduced pressure, and the residue was purified by silica gel column chromatography (developing solvent, hexane:ethyl acetate=1:1) to obtain 48.7 mg of the title compound.

(b) (S)-5-Chloro-2-(2-methylpiperazin-1-yl)-7-(pyrrolidin-1-yl)benzoxazole

The title compound was obtained in a similar manner as in Example 16(c) except that (S)-1-tert-butoxycarbonyl-4-(5-chloro-7-(2-oxo-pyrrolidin-1-yl)benzoxazol-2-yl)-3-methylpiperazine obtained in Example 71(a) was used instead of (S)-1-tert-butoxycarbonyl-(5-chloro-7-(thiophen-3-yl)benzoxazol-2-yl)-3-methylpiperazine.

$^1$H-NMR (400 MHz, CDCl$_3$) δ: 1.40 (3H, d, J=6.8 Hz), 2.21-2.28 (2H, m), 2.61 (2H, t, J=8.3 Hz), 2.83-2.91 (2H, m), 3.06-3.10 (2H, m), 3.33-3.40 (1H, m), 3.90-3.98 (3H, m), 4.32-4.38 (1H, m), 7.16 (1H, d, J=2.0 Hz), 7.21 (1H, d, J=2.0 Hz)

MS(ESI) m/z: 335 (M+H)$^+$

Example 72

(S)-5-Chloro-2-(2-methylpiperazin-1-yl)-7-(2-oxo-oxazolidin-3-yl)benzoxazole (a) (S)-1-tert-Butoxycarbonyl-4-(5-chloro-7-(2-oxo-oxazolidin-3-yl)benzoxazol-2-yl)-3-methylpiperazine The title compound was obtained in a similar manner as in Example 71(a) except that 2-oxazolidinone was used instead of 2-pyrrolidone.

(b) (S)-5-Chloro-2-(2-methylpiperazin-1-yl)-7-(2-oxo-oxazolidin-3-yl)benzoxazole The title compound was obtained in a similar manner as in Example 16(c) except that (S)-1-tert-butoxycarbonyl-4-(5-chloro-7-(2-oxo-oxazolidin-3-yl)benzoxazol-2-yl)-3-methylpiperazine obtained in Example 72(a) was used instead of (S)-1-tert-butoxycarbonyl-(5-chloro-7-(thiophen-3-yl)benzoxazol-2-yl)-3-methylpiperazine.

$^1$H-NMR (400 MHz, CDCl$_3$) δ: 1.40 (3H, d, J=6.8 Hz), 2.83-2.92 (2H, m), 3.06-3.10 (2H, m), 3.34-3.41 (1H, m), 3.91-3.94 (1H, m), 4.19-4.23 (2H, m), 4.32-4.38 (1H, m), 4.55 (2H, t, J=8.1 Hz), 7.16 (1H, d, J=2.0 Hz), 7.28 (1H, d, J=2.0 Hz)

MS(ESI) m/z: 337 (M+H)$^+$

Example 73

(S)-5-Chloro-7-(5-fluoropyridin-2-yl)-2-(2-methylpiperazin-1-yl)benzoxazole (a) (S)-1-tert-Butoxycarbonyl-4-(5-chloro-7-(5-fluoropyridin-2-yl)benzoxazol-2-yl)-3-methylpiperazine The title compound was obtained in a similar manner as in Example 50(b) except that 2-bromo-5-fluoropyridine was used instead of 2-bromo-1H-imidazole.

(b) (S)-5-Chloro-7-(5-fluoropyridin-2-yl)-2-(2-methylpiperazin-1-yl)benzoxazole

The title compound was obtained in a similar manner as in Example 16(c) except that (S)-1-tert-butoxycarbonyl-4-(5-chloro-7-(5-fluoropyridin-2-yl)benzoxazol-2-yl)-3-methylpiperazine obtained in Example 73(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.43 (3H, d, J=6.8 Hz), 2.86-2.95 (2H, m), 3.09-3.13 (2H, m), 3.39-3.46 (1H, m), 3.97-4.01 (1H, m), 4.39-4.45 (1H, m), 7.34 (1H, d, J=2.0 Hz), 7.53 (1H, dt, J=2.9, 8.8 Hz), 7.77 (1H, d, J=2.2 Hz), 7.99 (1H, dd, J=4.4, 8.8 Hz), 8.60 (1H, d, J=2.9 Hz)

MS(ESI) m/z: 347 (M+H)$^+$

Example 74

(S)-5-Chloro-7-(5-chlorothiazol-2-yl)-2-(2-methylpiperazin-1-yl)benzoxazole (a) (S)-1-tert-Butoxycarbonyl-4-(5-chloro-7-(5-chlorothiazol-2-yl)benzoxazol-2-yl)-3-methylpiperazine The title compound was obtained in a similar manner as in Example 50(b) except that 2-bromo-5-chlorothiazole was used instead of 2-bromo-1H-imidazole.

(b) (S)-5-Chloro-7-(5-chlorothiazol-2-yl)-2-(2-methylpiperazin-1-yl)benzoxazole

The title compound was obtained in a similar manner as in Example 16(c) except that (S)-1-tert-butoxycarbonyl-4-(5-chloro-7-(5-chlorothiazol-2-yl)benzoxazol-2-yl)-3-methylpiperazine obtained in Example 74(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.46 (3H, d, J=6.8 Hz), 2.88-2.98 (2H, m), 3.10-3.17 (2H, m), 3.42-3.49 (1H, m), 4.02-4.06 (1H, m), 4.43-4.49 (1H, m), 7.34 (1H, d, J=2.0 Hz), 7.73 (1H, s), 7.75 (1H, d, J=2.0 Hz)

MS(ESI) m/z: 369 (M+H)$^+$

Example 75

(S)-7-Benzyl-5-chloro-2-(2-methylpiperazin-1-yl)benzoxazole (a) (S)-1-tert-Butoxycarbonyl-4-(7-benzyl-5-chloro-benzoxazol-2-yl)-3-methylpiperazine (S)-1-tert-Butoxycarbonyl-4-(7-bromo-5-chlorobenzoxazol-2-yl)-3-m ethylpiperazine obtained in Example 16(a) (60 mg), sodium carbonate (30 mg, 2.0 equivalents), RuPhos (6.5 mg, 0.1 equivalents), palladium(II) acetate (11.6 mg, 0.05 equivalents), and benzyl trifluoro boronic acid potassium (5.6 mg, 2.0 equivalents) were dissolved in ethanol (1.0 mL), and the resulting mixture was stirred in an argon atmosphere in an oil bath at 85° C. for 4.5 hours. Water was added to the reaction mixture, and the product was extracted with ethyl acetate. The organic layer was dried over anhydrous sodium sulfate, then the solvent was distilled off under reduced pressure, and the residue was purified by silica gel column chromatography (developing solvent, hexane:ethyl acetate=17:3) to obtain 41.4 mg of the title compound.

(b) (S)-7-Benzyl-5-chloro-2-(2-methylpiperazin-1-yl)benzoxazole 5.5 mg of the title compound was obtained in a similar manner as in Example 16(c) except that (S)-1-tert-butoxycarbonyl-4-(7-benzyl-5-chloro-benzoxazol-2-yl)-3-methylpiperazine obtained in Example 75(a) was used instead of (S)-1-tert-butoxycarbonyl-(5-chloro-7-(thiophen-3-yl)benzoxazol-2-yl)-3-methylpiperazine.

$^1$H-NMR (400 MHz, CDCl$_3$) δ: 1.35 (3H, d, J=6.8 Hz), 2.81-2.91 (2H, m), 3.04-3.08 (2H, m), 3.29-3.36 (1H, m), 3.89-3.93 (1H, m), 4.06 (2H, s), 4.29-4.35 (1H, m), 6.78 (1H, d, J=2.0 Hz), 7.16 (1H, d, J=2.2 Hz), 7.20-7.31 (5H, m)

MS(ESI) m/z: 342 (M+H)$^+$

Example 76

(S)-5-Chloro-7-(5-(hydroxymethyl)thiazol-4-yl)-2-(2-methylpiperazin-1-yl)benzoxazole

(a) (S)-1-tert-Butoxycarbonyl-4-(5-chloro-7-(5-(hydroxymethyl)thiazol-4-yl)benzoxazol-2-yl)-3-methylpiperazine The title compound was obtained in a similar manner as in Example 50(b) except that 4-bromo-5-hydroxymethylthiazole was used instead of 2-bromo-1H-imidazole.

(b) (S)-5-Chloro-7-(5-(hydroxymethyl)thiazol-4-yl)-2-(2-methylpiperazin-1-yl)benzoxazole The title compound was obtained in a similar manner as in Example 16(c) except that the whole amount of (S)-1-tert-butoxycarbonyl-4-(5-chloro-7-(5-(hydroxymethyl)thiazol-4-yl)benz oxazol-2-yl)-3-methylpiperazine obtained in Example 76(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.39 (3H, d, J=6.6 Hz), 2.81-2.90 (2H, m), 3.04-3.08 (2H, m), 3.32-3.40 (1H, m), 3.91-3.93 (1H, m), 4.32-4.39 (1H, m), 4.93 (2H, s), 7.22 (1H, d, J=2.0 Hz), 7.33 (1H, d, J=2.0 Hz), 8.87 (1H, s)

MS(ESI) m/z: 365 (M+H)$^+$

Example 77

(S)-5-Chloro-2-(2-methylpiperazin-1-yl)-7-(thiazol-2-yloxy)benzoxazole

(a) (S)-1-tert-Butoxycarbonyl-4-(5-chloro-7-(thiazol-2-yloxy)benzoxazol-2-yl)-3-methylpiperazine The title compound was obtained in a similar manner as in Example 70(a) except that (S)-1-tert-butoxycarbonyl-4-(5-chloro-7-hydroxybenzoxazol-2-yl)-3-methylpiperazine obtained in Example 28(a) was used instead of (S)-1-tert-butoxycarbonyl-(7-bromo-5-chlorobenzoxazol-2-yl)-3-methylpiperazine and that 2-bromothiazole was used instead of phenol.

(b) (S)-5-Chloro-2-(2-methylpiperazin-1-yl)-7-(thiazol-2-yloxy)benzoxazole

The title compound was obtained in a similar manner as in Example 16(c) except that (S)-1-tert-butoxycarbonyl-4-(5-chloro-7-(thiazol-2-yloxy)benzoxazol-2-yl)-3-methylpiperazine obtained in Example 77(a) was used instead of (S)-1-tert-butoxycarbonyl-4-(5-chloro-7-(thiophen-3-yl)benzoxazol-2-yl)-3-m ethylpiperazine.

$^1$H-NMR (400 MHz, CDCl$_3$) δ: 1.36 (3H, d, J=6.8 Hz), 2.80-2.89 (2H, m), 3.03-3.08 (2H, m), 3.30-3.37 (1H, m), 3.89-3.92 (1H, m), 4.29-4.35 (1H, m), 6.88 (1H, d, J=3.9 Hz), 7.01 (1H, d, J=1.7 Hz), 7.19 (1H, d, J=2.0 Hz), 7.25 (1H, d, J=3.9 Hz)

MS(ESI) 351 (M+H)$^+$

Example 78

(S)-5-Chloro-2-(2-methylpiperazin-1-yl)-7-(5-nitrothiazol-2-yl)benzoxazole

(a) (S)-1-tert-Butoxycarbonyl-4-(5-chloro-7-(5-nitrothiazol-2-yl)benzoxazol-2-yl)-3-methylpiperazine The title compound was obtained in a similar manner as in Example 50(b) except that 2-bromo-5-nitrothiazole was used instead of 2-bromo-1H-imidazole.

(b) (S)-5-Chloro-2-(2-methylpiperazin-1-yl)-7-(5-nitrothiazol-2-yl)benzoxazole The title compound was obtained in a similar manner as in Example 16(c) except that the whole amount of (S)-1-tert-butoxycarbonyl-4-(5-chloro-7-(5-nitrothiazol-2-yl)benzoxazol-2-yl)-3-methylpiperazine obtained in Example 78(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.48 (3H, d, J=6.8 Hz), 2.90-3.01 (2H, m), 3.12-3.21 (2H, m), 3.46-3.53 (1H, m), 4.05-4.07 (1H, m), 4.46-4.51 (1H, m), 7.44 (1H, d, J=2.0 Hz), 7.88 (1H, d, J=2.0 Hz), 8.66 (1H, s)

MS(ESI) m/z: 380 (M+H)$^+$

Example 79

(S)-5-Chloro-7-(3-methoxypyridin-2-yl)-2-(2-methylpiperazin-1-yl)benzoxazole

(a) (S)-1-tert-Butoxycarbonyl-4-(5-chloro-7-(3-methoxypyridin-2-yl)benzoxazol-2-yl)-3-methylpiperazine The title compound was obtained in a similar manner as in Example 34(a) except that 2-(tributylstannyl)-3-methoxypyridine was used instead of 2-(tributylstannyl)oxazole.

(b) (S)-5-Chloro-2-(2-methylpiperazin-1-yl)-7-(oxazol-2-yl)benzoxazole

The title compound was obtained in a similar manner as in Example 16(c) except that (S)-1-tert-butoxycarbonyl-4-(5-chloro-7-(3-methoxypyridin-2-yl)benzoxazol-2-yl)-3-methylpiperazine obtained in Example 79(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.41 (3H, d, J=6.8 Hz), 2.86-2.97 (2H, m), 3.08-3.15 (2H, m), 3.38-3.44 (1H, m), 3.87 (3H, s), 3.96-3.99 (1H, m), 4.39-4.45 (1H, m), 7.30-7.31 (1H, m), 7.33-7.35 (3H, m), 8.33-8.35 (1H, m)

MS(ESI) m/z: 359 (M+H)$^+$

Example 80

5-Chloro-2-((S)-2-methylpiperazin-1-yl)-7-(tetrahydrofuran-2-yl)benzoxazole

(a) (3 S)-1-tert-Butoxycarbonyl-4-(5-chloro-7-(tetrahydrofuran-2-yl)benzoxazol-2-yl)-3-methylpiperazine (S)-1-tert-Butoxycarbonyl-4-(7-bromo-5-chlorobenzoxazol-2-yl)-3-m ethylpiperazine obtained in Example 16(a)

(430 mg) and magnesium (26.7 mg, 1.1 equivalents) were dissolved in THF (2.0 mL), and the resulting mixture was stirred in an argon atmosphere in an oil bath at 40° C. for 1 hour. The temperature of the resulting mixture was raised to 60° C., a small amount of iodine and zinc bromide (157 mg, 0.6 equivalents) were added thereto, the resulting mixture was stirred, then 2-(phenylsulfonyl)tetrahydrofuran was added, and the resulting mixture was further stirred at room temperature for 16 hours. Water was added to the reaction mixture, and the product was extracted with ethyl acetate. The organic layer was dried over anhydrous magnesium sulfate, then the solvent was distilled off under reduced pressure, and the residue was purified by silica gel column chromatography (developing solvent, hexane:ethyl acetate=4:1) to obtain 19.1 mg of the title compound.

(b) 5-Chloro-24(S)-2-methylpiperazin-1-yl)-7-(tetrahydrofuran-2-yl)benzoxazole

The title compound was obtained in a similar manner as in Example 16(c) except that (3 S)-1-tert-butoxycarbonyl-4-(5-chloro-7-(tetrahydrofuran-2-yl)benzoxazol-2-yl)-3-methylpiperazine obtained in Example 80(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.39 (3H, d, J=6.6 Hz), 1.90-2.09 (3H, m), 2.36-2.43 (1H, m), 2.84-2.92 (2H, m), 3.06-3.10 (2H, m), 3.33-3.40 (1H, m), 3.93-4.00 (2H, m), 4.09-4.15 (1H, m), 4.34-4.40 (1H, m), 5.11-5.15 (1H, m), 7.02-7.03 (1H, m), 7.20(1H, d, J=2.2 Hz)

MS(ESI) m/z: 322 (M+H)$^+$

Example 81

(S)-5-Chloro-7-(4-fluorophenyl)-2-(2-methylpiperazin-1-yl)benzoxazole (a) (S)-1-tert-Butoxycarbonyl-4-(5-chloro-7-(4-fluorophenyl)benzoxazol-2-yl)-3-methylpiperazine (S)-1-tert-Butoxycarbonyl-4-(7-bromo-5-chlorobenzoxazol-2-yl)-3-m ethylpiperazine obtained in Example 16(a) (86 mg), potassium carbonate (55.3 mg, 2.0 equivalents), and 2,4,6-tris(4-fluorophenyl)boroxine (73 mg, 1.0 equivalent) were dissolved in THF (1.6 mL) and ethanol (0.4 mL), the resulting mixture was stirred in an argon atmosphere for 15 minutes, then tetrakis(triphenylphosphine)palladium(0) (23 mg, 0.1 equivalents) was added thereto, and the resulting mixture was stirred in an oil bath at 90° C. for 14.5 hours. Water was added to the reaction mixture, and the product was extracted with ethyl acetate. The organic layer was dried over anhydrous magnesium sulfate, then the solvent was distilled off under reduced pressure, and the residue was purified by silica gel column chromatography (developing solvent, hexane:ethyl acetate=17:3) to obtain 94.6 mg of the title compound.

(b) (S)-5-Chloro-7-(4-fluorophenyl)-2-(2-methylpiperazin-1-yl)benzoxazole 63.4 mg of the title compound was obtained in a similar manner as in Example 16(c) except that the whole amount of the (S)-1-tert-butoxycarbonyl-4-(5-chloro-7-(4-fluorophenyl)benzoxazol-2-yl)-3-methylpiperazine obtained in Example 81(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.41 (3H, d, J=6.6 Hz), 2.83-2.93 (2H, m), 3.06-3.10 (2H, m), 3.35-3.42 (1H, m), 3.93-3.97 (1H, m), 4.35-4.41 (1H, m), 7.12 (1H, d, J=2.0 Hz), 7.18 (2H, t, J=8.8 Hz), 7.27 (1H, d, J=2.0 Hz), 7.70 (2H, dd, J=5.4, 9.0 Hz)

MS(ESI) m/z: 346 (M+H)$^+$

Example 82

(S)-5-Chloro-2-(2-methylpiperazin-1-yl)-7-(pyridin-2-yl)-4-(trifluoromethyl)benzoxazole (a) (S)-1-tert-Butoxycarbonyl-4-(7-bromo-5-chloro-4-(trifluoromethyl)benzoxazol-2-yl)-3-methylpiperazine The title compound was obtained in a similar manner as in Example 16(a) except that 7-bromo-5-chloro-2-mercapto-4-(trifluoromethyl)benzoxazole obtained in Reference Example 10 was used instead of 7-bromo-5-chloro-2-mercaptobenzoxazole.

(b) (S)-1-tert-Butoxycarbonyl-4-(5-chloro-7-(pyridin-2-yl)-4-(trifluoromethyl)benzoxazol-2-yl)-3-methylpiperazine The title compound was obtained in a similar manner as in Example 41(a) except that (S)-1-tert-butoxycarbonyl-4-(7-bromo-5-chloro-4-(trifluoromethyl)benzoxazol-2-yl)-3-methylpiperazine obtained in Example 82(a) was used instead of (S)-1-tert-butoxycarbonyl-4-(7-bromo-5-chlorobenzoxazol-2-yl)-3-methylpiperazine.

(c) (S)-5-Chloro-2-(2-methylpiperazin-1-yl)-7-(pyridin-2-yl)-4-(trifluoromethyl)benzoxazole The title compound was obtained in a similar manner as in Example 16(c) except that (S)-1-tert-butoxycarbonyl-4-(5-chloro-7-(pyridin-2-yl)-4-(trifluoromethyl)benzoxazol-2-yl)-3-methylpiperazine obtained in Example 82(b) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.44 (3H, d, J=6.6 Hz), 2.86-2.96 (2H, m), 3.09-3.14 (2H, m), 3.42-3.50 (1H, m), 4.06-4.10 (1H, m), 4.46-4.52 (1H, m), 7.32-7.36 (1H, m), 7.83-7.87 (1H, m), 7.94 (1H, s), 7.99-8.01 (1H, m), 8.77-8.79 (1H, m)

MS(ESI) m/z: 397 (M+H)$^+$

Example 83

(S)-5-Chloro-2-(2-methylpiperazin-1-yl)-7-(1H-pyrazol-1-yl)-4-(trifluoromethyl)benzoxazole (a) (S)-1-tert-Butoxycarbonyl-4-(5-chloro-7-(1H-pyrazol-1-yl)-4-(trifluoromethyl)benzoxazol-2-yl)-3-methylpiperazine The title compound was obtained in a similar manner as in Example 45(a) except that (S)-1-tert-butoxycarbonyl-4-(7-bromo-5-chloro-4-(trifluoromethyl)benzoxazol-2-yl)-3-methylpiperazine obtained in Example 82(a) was used instead of (S)-1-tert-butoxycarbonyl-4-(7-bromo-5-chlorobenzoxazol-2-yl)-3-methylpiperazine and that pyrazole was used instead of 1,2,3-triazole.

(b) (S)-5-Chloro-2-(2-methylpiperazin-1-yl)-7-(1H-pyrazol-1-yl)-4-(trifluoromethyl)benzoxazole The title compound was obtained in a similar manner as in Example 16(c) except that (S)-1-tert-butoxycarbonyl-4-(5-chloro-7-(1H-pyrazol-1-yl)-4-(trifluoromethyl)benzoxazol-2-yl)-3-methylpiperazine obtained in Example 83(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.45 (3H, d, J=6.6 Hz), 2.86-2.96 (2H, m), 3.09-3.15 (2H, m), 3.43-3.51 (1H, m), 4.05-4.09 (1H, m), 4.46-4.49 (1H, m), 6.57 (1H, t, J=2.4 Hz), 7.79 (1H, s), 7.80 (1H, d, J=2.0 Hz), 8.23 (1H, d, J=2.7 Hz)

MS(ESI) m/z: 386 (M+H)$^+$

Example 84

(S)-5-Chloro-2-(2-methylpiperazin-1-yl)-7-(thiazol-2-yl)-4-(trifluoromethyl)benzoxazole (a) (S)-1-tert-Butoxycarbonyl-4-(5-chloro-7-(thiazol-2-yl)-4-(trifluoromethyl)benzoxazol-2-yl)-3-methylpiperazine The title compound was obtained in a similar manner as in Example 35(a) except that (S)-1-tert-butoxycarbonyl-4-(7-bromo-5-chloro-4-trifluoromethyl)benzoxazol-2-yl)-3-methylpiperazine was used instead of (S)-1-tert-butoxycarbonyl-4-(7-bromo-5-chlorobenzoxazol-2-yl)-3-methylpiperazine.

(b) (S)-5-Chloro-2-(2-methylpiperazin-1-yl)-7-(thiazol-2-yl)-4-(trifluoromethyl)benzoxazole The title compound was obtained in a similar manner as in Example 16(c) except that (S)-1-tert-butoxycarbonyl-4-(5-chloro-7-(thiazol-2-yl)-4-(trifluoromethyl)benzoxazol-2-yl)-3-methylpiperazine obtained in Example 84(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.47 (3H, d, J=6.6 Hz), 2.88-2.97 (2H, m), 3.11-3.16 (2H, m), 3.45-3.52 (1H, m), 4.13-4.16 (1H, m), 4.51-4.57 (1H, m), 7.56 (1H, d, J=3.2 Hz), 7.96 (1H, s), 8.01 (1H, d, J=3.2 Hz)

MS(ESI) m/z: 403 (M+H)$^+$

Example 85

(S)-5-Chloro-2-(2-methylpiperazin-1-yl)-7-(pyridin-2-yl)-6-(trifluoromethyl)benzoxazole (a) (S)-1-tert-Butoxycarbonyl-4-(7-bromo-5-chloro-6-(trifluoromethyl)benzoxazol-2-yl)-3-methylpiperazine The title compound was obtained in a similar manner as in Example 16(a) except that 7-bromo-5-chloro-2-mercapto-6-(trifluoromethyl)benzoxazole obtained in Reference Example 11 was used instead of 7-bromo-5-chloro-2-mercaptobenzoxazole.

(b) (S)-1-tert-Butoxycarbonyl-4-(5-chloro-7-(pyridin-2-yl)-6-(trifluoromethyl)benzoxazol-2-yl)-3-methylpiperazine The title compound was obtained in a similar manner as in Example 41(a) except that (S)-1-tert-butoxycarbonyl-4-(7-bromo-5-chloro-6-(trifluoromethyl)benzoxazol-2-yl)-3-methylpiperazine obtained in Example 85(a) was used instead of (S)-1-tert-butoxycarbonyl-4-(7-bromo-5-chlorobenzoxazol-2-yl)-3-methylpiperazine.

(c) (S)-5-Chloro-2-(2-methylpiperazin-1-yl)-7-(pyridin-2-yl)-6-(trifluoromethyl)benzoxazole The title compound was obtained in a similar manner as in Example 16(c) except that the whole amount of (S)-1-tert-butoxycarbonyl-4-(5-chloro-7-(pyridin-2-yl)-6-(trifluoromethyl)benzoxazol-2-yl)-3-methylpiperazine obtained in Example 85(b) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.33 (3H, d, J=6.8 Hz), 2.74-2.86 (2H, m), 2.98-3.02 (2H, m), 3.25-3.32 (1H, m), 3.75-3.78 (1H, m), 4.22-4.30 (1H, m), 7.34-7.40 (2H, m), 7.45 (1H, s), 7.78-7.82 (1H, m), 8.71-8.72 (1H, m)

MS(ESI) m/z: 397 (M+H)$^+$

Example 86

(S)-5-Chloro-2-(2-methylpiperazin-1-yl)-7-(pyridin-2-yl)-4-(trifluoromethoxy)benzoxazole (a) (S)-1-tert-Butoxycarbonyl-4-(7-bromo-5-chloro-4-(trifluoromethoxy)benzoxazol-2-yl)-3-methylpiperazine The title compound was obtained in a similar manner as in Example 16(a) except that 7-bromo-5-chloro-2-mercapto-4-(trifluoromethoxy)benzoxazole obtained in Reference Example 12 was used instead of 7-bromo-5-chloro-2-mercaptobenzoxazole.

(b) (S)-1-tert-Butoxycarbonyl-4-(5-chloro-7-(pyridin-2-yl)-4-(trifluoromethoxy)benzoxazol-2-yl)-3-methylpiperazine The title compound was obtained in a similar manner as in Example 41(a) except that (S)-1-tert-butoxycarbonyl-4-(7-bromo-5-chloro-4-(trifluoromethoxy)benzoxazol-2-yl)-3-methylpiperazine obtained in Example 86(a) was used instead of (S)-1-tert-butoxycarbonyl-4-(7-bromo-5-chlorobenzoxazol-2-yl)-3-methylpiperazine.

(c) (S)-5-Chloro-2-(2-methylpiperazin-1-yl)-7-(pyridin-2-yl)-4-(trifluoromethoxy)benzoxazole The title compound was obtained in a similar manner as in Example 16(c) except that (S)-1-tert-butoxycarbonyl-4-(5-chloro-7-(pyridin-2-yl)-4-(trifluoromethoxy)benzoxazol-2-yl)-3-methylpiperazine obtained in Example 86(b) was used instead of (S)-1-tert-butoxycarbonyl-4-(5-chloro-7-(thiophen-3-yl)benzoxazol-2-yl)-3-m ethylpiperazine.

$^1$H-NMR (400 MHz, CDCl$_3$) δ: 1.44 (3H, d, J=6.8 Hz), 2.87-2.95 (2H, m), 3.09-3.13 (2H, m), 3.40-3.48 (1H, m), 4.03-4.07 (1H, m), 4.44-4.50 (1H, m), 7.29-7.32 (1H, m), 7.81-7.85 (1H, m), 7.93 (1H, s), 7.95-7.97 (1H, m), 8.74-8.76 (1H, m)

MS(ESI) m/z: 413 (M+H)$^+$

Example 87

(S)-5-Chloro-2-(2-methylpiperazin-1-yl)-7-(thiazol-2-yl)-4-(trifluoromethoxy)benzoxazole (a) (S)-1-tert-Butoxycarbonyl-4-(5-chloro-7-(thiazol-2-yl)-4-(trifluoromethoxy)benzoxazol-2-yl)-3-methylpiperazine The title compound was obtained in a similar manner as in Example 35(a) except that (S)-1-tert-butoxycarbonyl-4-(7-bromo-5-chloro-4-(trifluoromethoxy)benzoxazol-2-yl)-3-methylpiperazine obtained in Example 86(a) was used instead of (S)-1-tert-butoxycarbonyl-4-(7-bromo-5-chlorobenzoxazol-2-yl)-3-methylpiperazine.

(b) (S)-5-Chloro-2-(2-methylpiperazin-1-yl)-7-(thiazol-2-yl)-4-(trifluoromethoxy)benzoxazole The title compound was obtained in a similar manner as in Example 16(c) except that (S)-1-tert-butoxycarbonyl-4-(5-chloro-7-(thiazol-2-yl)-4-(trifluoromethoxy)benzoxazol-2-yl)-3-methylpiperazine obtained in Example 87(a) was used instead of (S)-1-tert-butoxycarbonyl-4-(5-chloro-7-(thiophen-3-yl)benzoxazol-2-yl)-3-methylpiperazine.
$^1$H-NMR (400 MHz, CDCl$_3$) δ: 1.46 (3H, d, J=6.8 Hz), 2.86-2.97 (2H, m), 3.10-3.15 (2H, m), 3.43-3.50 (1H, m), 4.09-4.12 (1H, m), 4.49-4.55 (1H, m), 7.51 (1H, d, J=3.2 Hz), 7.94 (1H, s), 7.97 (1H, d, J=3.4 Hz)
MS(ESI) m/z: 419 (M+H)$^+$

Example 88

(S)-5-Chloro-2-(2-methylpiperazin-1-yl)-7-(1H-pyrazol-1-yl)-4-(trifluoromethoxy)benzoxazole (a) (S)-1-tert-Butoxycarbonyl-4-(5-chloro-7-(1H-pyrazol-1-yl)-4-(trifluoromethoxy)benzoxazol-2-yl)-3-methylpiperazine The title compound was obtained in a similar manner as in Example 83(a) except that (S)-1-tert-butoxycathonyl-4-(7-bromo-5-chloro-4-(trifluoromethoxy)benzoxazol-2-yl)-3-methylpiperazine obtained in Example 86(a) was used instead of (S)-1-tert-butoxycarbonyl-4-(7-bromo-5-chloro-4-(trifluoromethyl)benzoxazol-2-yl)-3-methylpiperazine (b) (S)-5-Chloro-2-(2-methylpiperazin-1-yl)-7-(1H-pyrazol-1-yl)-4-(trifluoromethoxy)benzoxazole The title compound was obtained in a similar manner as in Example 16(c) except that (S)-1-tert-butoxycarbonyl-4-(5-chloro-7-(1H-pyrazol-1-yl)-4-(trifluoromethoxy)benzoxazol-2-yl)-3-methylpiperazine obtained in Example 88(a) was used instead of (S)-1-tert-butoxycarbonyl-4-(5-chloro-7-(thiophen-3-yl)benzoxazol-2-yl)-3-methylpiperazine.
$^1$H-NMR (400 MHz, CDCl$_3$) δ: 1.44(3H, d, J=6.8 Hz), 2.87-2.96 (2H, m), 3.08-3.14 (2H, m), 3.41-3.49 (1H, m), 4.02-4.05 (1H, m), 4.43-4.49 (1H, m), 6.54 (1H, t, J=2.4 Hz), 7.71 (1H, s), 7.77 (1H, d, J=1.7 Hz), 8.16 (1H, d, J=2.7 Hz)
MS(ESI) m/z: 402 (M+H)$^+$

Example 89

(S)-4,5-Difluoro-2-(2-methylpiperazin-1-yl)-7-(pyridin-2-yl)benzoxazole (a) (S)-1-tert-Butoxycarbonyl-4-(7-bromo-4,5-difluorobenzoxazol-2-yl)-3-methylpiperazine The title compound was obtained in a similar manner as in Example 16(a) except that 7-bromo-4,5-difluoro-2-mercaptobenzoxazole obtained in Reference Example 13 was used instead of 7-bromo-5-chloro-2-mercaptobenzoxazole.

(b) (S)-1-tert-Butoxycarbonyl-4-(4,5-difluoro-7-(pyridin-2-yl)benzoxazol-2-yl)-3-methylpiperazine The title compound was obtained in a similar manner as in Example 41(a) except that (S)-1-tert-butoxycarbonyl-4-(7-bromo-4,5-difluorobenzoxazol-2-yl)-3-methyl piperazine obtained in Example 89(a) was used instead of (S)-1-tert-butoxycarbonyl-4-(7-bromo-5-chlorobenzoxazol-2-yl)-3-methylpiperazine.

(c) (S)-4,5-Difluoro-2-(2-methylpiperazin-1-yl)-7-(pyridin-2-yl)benzoxazole

The title compound was obtained in a similar manner as in Example 16(c) except that (S)-1-tert-butoxycarbonyl-4-(4,5-difluoro-7-(pyridin-2-yl)benzoxazol-2-yl)-3-methylpiperazine obtained in Example 89(b) was used instead of (S)-1-tert-butoxycarbonyl-4-(5-chloro-7-(thiophen-3-yl)benzoxazol-2-yl)-3-methylpiperazine.
$^1$H-NMR (500 MHz, CDCl$_3$) δ: 1.44 (3H, d, J=6.8 Hz), 2.87-2.95 (2H, m), 3.09-3.14 (2H, m), 3.41-3.47 (1H, m), 4.02-4.06 (1H, m), 4.47-4.49 (1H, m), 7.26-7.30 (1H, m), 7.70 (1H, dd, J=7.4, 12.6 Hz), 7.79-7.83 (1H, m), 7.94-7.96 (1H, m), 8.72-8.74(1H, m)
MS(ESI) m/z: 331 (M+H)$^+$

Example 90

(S)-4,5-Difluoro-2-(2-methylpiperazin-1-yl)-7-(thiazol-2-yl)benzoxazole (a) (S)-1-tert-Butoxycarbonyl-4-(4,5-difluoro-7-(thiazol-2-yl)benzoxazol-2-yl)-3-methylpiperazine The title compound was obtained in a similar manner as in Example 35(a) except that (S)-1-tert-butoxycarbonyl-4-(7-bromo-4,5-difluorobenzoxazol-2-yl)-3-methyl piperazine obtained in Example 89(a) was used instead of (S)-1-tert-butoxycarbonyl-4-(7-bromo-5-chlorobenzoxazol-2-yl)-3-methylpiperazine.

(b) (S)-4,5-Difluoro-2-(2-methylpiperazin-1-yl)-7-(thiazol-2-yl)benzoxazole

The title compound was obtained in a similar manner as in Example 16(c) except that (S)-1-tert-butoxycarbonyl-4-(4,5-difluoro-7-(thiazol-2-yl)benzoxazol-2-yl)-3-methylpiperazine obtained in Example 90(a) was used instead of (S)-1-tert-butoxycarbonyl-4-(5-chloro-7-(thiophen-3-yl)benzoxazol-2-yl)-3-methylpiperazine.
$^1$H-NMR (500 MHz, CDCl$_3$) δ: 1.46 (3H, d, J=6.8 Hz), 2.89-2.96 (2H, m), 3.10-3.15 (2H, m), 3.44-3.49 (1H, m), 4.08-4.11 (1H, m), 4.51-4.53 (1H, m), 7.47 (1H, dd, J=3.2 Hz), 7.67 (1H, dd, J=7.2, 12.0 Hz), 7.94 (1H, d, J=3.2 Hz)
MS(ESI) m/z: 337 (M+H)$^+$ Example 91

(S)-4,5-Difluoro-2-(2-methylpiperazin-1-yl)-7-(1H-pyrazol-1-yl)benzoxazole (a) (S)-1-tert-Butoxycarbonyl-4-(4,5-difluoro-7-(1H-pyrazol-1-yl)benzoxazol-2-yl)-3-methylpiperazine The title compound was obtained in a similar manner as in Example 83(a) except that (S)-1-tert-butoxycarbonyl-4-(7-bromo-4,5-difluorobenzoxazol-2-yl)-3-methyl piperazine obtained in Example 89(a) was used instead of (S)-1-tert-butoxycarbonyl-4-(7-bromo-5-chloro-4-(trifluoromethyl) benzoxazol-2-yl)-3-methylpiperazine.

(b) (S)-4,5-Difluoro-2-(2-methylpiperazin-1-yl)-7-(1H-pyrazol-1-yl)benzoxazole

The title compound was obtained in a similar manner as in Example 16(c) except that (S)-1-tert-butoxycarbonyl-4-(4,5-difluoro-7-(1H-pyrazol-1-yl)benzoxazol-2-yl)-3-methylpiperazine obtained in Example 91(a) was used instead of (S)-1-tert-butoxycarbonyl-4-(5-chloro-7-(thiophen-3-yl)benzoxazol-2-yl)-3-methylpiperazine.
$^1$H-NMR (500 MHz, CDCl$_3$) δ: 1.44 (3H, d, J=6.9 Hz), 2.86-2.95 (2H, m), 3.08-3.14 (2H, m), 3.41-3.47 (1H, m), 4.00-4.03 (1H, m), 4.45-4.47 (1H, m), 6.52 (1H, t, J=2.1 Hz), 7.43 (1H, dd, J=6.6, 12.1 Hz), 7.75 (1H, d, J=1.6 Hz), 8.12 (1H, d, J=2.4 Hz)
MS(ESI) m/z: 320 (M+H)$^+$ Example 92

(S)-5-Chloro-6-fluoro-2-(2-methylpiperazin-1-yl)-7-(pyridin-2-yl)benzoxazole (a) (S)-1-tert-Butoxycarbonyl-4-(7-bromo-5-chloro-6-fluorobenzoxazol-2-yl)-3-methylpiperazine The title compound was obtained in a similar manner as in Example 16(a) except that 7-bromo-5-chloro-6-fluoro-2-mercaptobenzoxazole obtained in Reference Example 14 was used instead of 7-bromo-5-chloro-2-mercaptobenzoxazole.

(b) (S)-1-tert-Butoxycarbonyl-4-(5-chloro-6-fluoro-7-(pyridin-2-yl)benzoxazol-2-yl)-3-methylpiperazine The title compound was obtained in a similar manner as in Example 41(a) except that (S)-1-tert-butoxycarbonyl-4-(7-bromo-5-chloro-6-fluorobenzoxazol-2-yl)-3-m ethylpiperazine obtained in Example 92(a) was used instead of (S)-1-tert-butoxycarbonyl-4-(7-bromo-5-chlorobenzoxazol-2-yl)-3-methylpiperazine.

(c) (S)-5-Chloro-6-fluoro-2-(2-methylpiperazin-1-yl)-7-(pyridin-2-yl)benzoxazole The title compound was obtained in a similar manner as in Example 16(c) except that (S)-1-tert-butoxycarbonyl-4-(5-chloro-6-fluoro-7-(pyridin-2-yl)benzoxazol-2-yl)-3-methylpiperazine obtained in Example 92(b) was used instead of (S)-1-tert-butoxycarbonyl-4-(5-chloro-7-(thiophen-3-yl)benzoxazol-2-yl)-3-methylpiperazine.
$^1$H-NMR (400 MHz, CDCl$_3$) δ: 1.36 (3H, d, J=6.8 Hz), 2.80-2.89 (2H, m), 3.04-3.08 (2H, m), 3.31-3.38 (1H, m), 3.87-3.90 (1H, m), 4.31-4.37 (1H, m), 7.33-7.37 (2H, m), 7.66-7.69 (1H, m), 7.84 (1H, dt, J=2.0, 7.8 Hz), 8.78-8.80 (1H, m)
MS(ESI) m/z: 347 (M+H)$^+$ Example 93

(S)-5-Chloro-6-fluoro-2-(2-methylpiperazin-1-yl)-7-(thiazol-2-yl)benzoxazole (a) (S)-1-tert-Butoxycarbonyl-4-(5-chloro-6-fluoro-7-(thiazol-2-yl)benzoxazol-2-yl)-3-methylpiperazine The title compound was obtained in a similar manner as in Example 35(a) except that (S)-1-tert-butoxycarbonyl-4-(7-bromo-5-chloro-6-fluorobenzoxazol-2-yl)-3-m ethylpiperazine obtained in Example 92(a) was used instead of (S)-1-tert-butoxycarbonyl-4-(7-bromo-5-chlorobenzoxazol-2-yl)-3-methylpiperazine.

(b) (S)-5-Chloro-6-fluoro-2-(2-methylpiperazin-1-yl)-7-(thiazol-2-yl)benzoxazole The title compound was obtained in a similar manner as in Example 16(c) except that (S)-1-tert-butoxycarbonyl-4-(5-chloro-6-fluoro-7-(thiazol-2-yl)benzoxazol-2-yl)-3-methylpiperazine obtained in Example 93(a) was used instead of (S)-1-tert-butoxycarbonyl-4-(5-chloro-7-(thiophen-3-yl)benzoxazol-2-yl)-3-methylpiperazine.
$^1$H-NMR (400 MHz, CDCl$_3$) δ: 1.42 (3H, d, J=6.8 Hz), 2.86-2.94 (2H, m), 3.09-3.13 (2H, m), 3.40-3.47 (1H, m), 4.01-4.05 (1H, m), 4.41-4.47 (1H, m), 7.38 (1H, d, J=6.3 Hz), 7.57 (1H, d, J=3.4 Hz), 8.06 (1H, dd, J=2.0, 3.4 Hz)
MS(ESI) m/z: 353 (M+H)$^+$ Example 94

(S)-5-Chloro-6-fluoro-2-(2-methylpiperazin-1-yl)-7-(1H-pyrazol-1-yl)benzoxazole (a) (S)-1-tert-Butoxycarbonyl-4-(5-chloro-6-fluoro-7-(1H-pyrazol-1-yl)benzoxazol-2-yl)-3-methylpiperazine The title compound was obtained in a similar manner as in Example 83(a) except that (S)-1-tert-butoxycarbonyl-4-(7-bromo-5-chloro-6-fluorobenzoxazol-2-yl)-3-m ethylpiperazine obtained in Example 92(a) was used instead of (S)-1-tert-butoxycarbonyl-4-(7-bromo-5-chloro-4-(trifluoromethyl)benzoxazol-2-yl)-3-methylpiperazine.

(b) (S)-5-Chloro-6-fluoro-2-(2-methylpiperazin-1-yl)-7-(1H-pyrazol-1-yl)benzoxazole The title compound was obtained in a similar manner as in Example 16(c) except that (S)-1-tert-butoxycarbonyl-4-(5-chloro-6-fluoro-7-(1H-pyrazol-1-yl)benzoxazol-2-yl)-3-methylpiperazine obtained in Example 94(a) was used instead of (S)-1-tert-butoxycarbonyl-4-(5-chloro-7-(thiophen-3-yl)benzoxazol-2-yl)-3-methylpiperazine.
$^1$H-NMR (400 MHz, CDCl$_3$) δ: 1.38 (3H, d, J=6.8 Hz), 2.81-2.90 (2H, m), 3.04-3.08 (2H, m), 3.33-3.40 (1H, m), 3.90-3.94 (1H, m), 4.33-4.39 (1H, m), 6.54 (1H, t, J=2.7 Hz), 7.31 (1H, d, J=6.1 Hz), 7.84 (1H, d, J=2.0 Hz), 7.89 (1H, d, J=2.7 Hz)

MS(ESI) m/z: 336 (M+H)$^+$

Example 95

(S)-5-Chloro-2-(2-methylpiperazin-1-yl)-7-n-propyl-benzoxazole

The title compound was obtained in a similar manner as in Example 2 except that 5-chloro-2-mercapto-7-propylbenzoxazole obtained in Reference Example 15 was used instead of 5-chloro-7-methoxy-2-mercaptobenzoxazole.

$^1$H-NMR (400 MHz, CDCl$_3$) δ: 0.97 (3H, t, J=7.4 Hz), 1.40 (3H, d, J=6.8 Hz), 1.67-1.76 (2H, m), 2.70 (2H, m), 2.84-2.92 (2H, m), 3.07-3.11 (2H, m), 3.33-3.40 (1H, m), 3.97 (1H, m), 4.39 (1H, m), 6.80 (1H, d, J=2.0 Hz), 7.15 (1H, d, J=2.0 Hz)

MS(ESI) m/z: 294 (M+H)$^+$

Example 96

(S)-5-Chloro-7-dimethylaminocarbonyl-2-(2-methylpiperazin-1-yl)benzoxazole (a) (S)-1-tert-Butoxycarbonyl-4-(5-chloro-7-dimethylaminocarbonylbenzoxazol-2-yl)-3-methylpiperazine (S)-1-tert-Butoxycarbonyl-4-(5-chloro-7-carboxybenzoxazol-2-yl)-3-methylpiperazine obtained in Example 15(b) (59 mg) was dissolved in DMF (1.5 mL), WSCI (43 mg) and HOBT (30 mg) were added thereto, the resulting mixture was stirred at room temperature for 10 minutes, then dimethylamine (a 2 M solution in THF, 0.275 mL) was added, and the resulting mixture was stirred for 1.5 hours in this state. Water was added, the product was extracted with ethyl acetate, the organic layer was washed with a saturated saline solution and then dried over anhydrous sodium sulfate, then the solvent was distilled off under reduced pressure, and the residue was purified by preparative TLC (developing solvent, chloroform:methanol=9:1) to obtain 66 mg of the title compound.

(b) (S)-5-Chloro-7-dimethylaminocarbonyl-2-(2-methylpiperazin-1-yl)benzoxazole (S)-1-tert-Butoxycarbonyl-4-(5-chloro-7-dimethylaminocarbonylbenzoxazol-2-yl)-3-methylpiperazine obtained in Example 96(a) (65 mg) was dissolved in dichloromethane (1.5 mL), then trifluoroacetic acid (0.75 mL) was added thereto, and the resulting mixture was stirred at room temperature for 1 hour. A 5% aqueous solution of sodium hydrogencarbonate was added to the reaction mixture, the product was extracted with ethyl acetate, then the organic layer was washed with a saturated saline solution and dried over anhydrous sodium sulfate, then the solvent was distilled off under reduced pressure, and the residue was purified by silica gel column chromatography (developing solvent, chloroform:methanol=9:1) to obtain 36 mg of the title compound.

$^1$H-NMR (400 MHz, CDCl$_3$) δ: 1.39 (3H, d, J=6.8 Hz), 2.82-2.91 (2H, m), 3.00 (3H, s), 3.04-3.10 (2H, m), 3.16 (3H, s), 3.33-3.40 (1H, m), 3.94-3.97 (1H, m), 4.35-4.41 (1H, m), 7.02 (1H, d, J=2.0 Hz), 7.31 (1H, d, J=2.0 Hz)

MS(ESI) m/z: 323 (M+H)$^+$

Example 97

(S)-5-Chloro-7-diethylaminocarbonyl-2-(2-methylpiperazin-1-yl)benzoxazole

The title compound was obtained in a similar manner as in Example 96 except that diethylamine was used instead of dimethylamine $^1$H-NMR (400 MHz, CDCl$_3$) δ: 1.11 (3H, t, J=7.1 Hz), 1.28 (3H, t, J=7.3 Hz), 1.38 (3H, d, J=6.8 Hz), 2.81-2.91 (2H, m), 3.04-3.09 (2H, m), 3.27 (2H, q, J=7.1 Hz), 3.30-3.39 (1H, m), 3.60 (2H, q, J=6.8 Hz), 3.92-3.95 (1H, m), 4.33-4.39 (1H, m), 6.95 (1H, d, J=2.0 Hz), 7.29 (1H, d, J=2.0 Hz)

MS(ESI) m/z: 351 (M+H)$^+$

Example 98

(S)-5-Chloro-7-hydroxyaminocarbonyl-2-(2-methylpiperazin-1-yl)benzoxazole

The title compound was obtained in a similar manner as in Example 96 except that triethylamine and hydroxyamine hydrochloride were used instead of dimethylamine.

$^1$H-NMR (400 MHz, DMSO-d$_6$) δ: 1.31 (3H, d, J=6.8 Hz), 2.66-2.73 (1H, m), 2.84-2.93 (2H, m), 3.01-3.03 (1H, m), 3.25-3.39 (1H, m), 3.88-3.92 (1H, m), 4.32 (1H, m), 7.21 (1H, d, J=2.2 Hz), 7.44 (1H, d, J=2.0 Hz), 9.32 (1H, br s), 11.08 (1H, br s)

MS(ESI) m/z: 311 (M+H)$^+$

Example 99

(S)-5-Chloro-7-carboxy-2-(2-methylpiperazin-1-yl)benzoxazole (S)-1-tert-Butoxycarbonyl-4-(5-chloro-7-carboxybenzoxazol-2-yl)-3-methylpiperazine obtained in Example 15(b) (40 mg) was dissolved in dichloromethane (1.0 mL), then trifluoroacetic acid (0.5 mL) was added, and the resulting mixture was stirred at room temperature for 1 hour. Acetone was added to the reaction mixture, the solvent was distilled off under reduced pressure, and the residue was washed with hexane to obtain the title compound as a trifluoroacetate salt.

$^1$H-NMR (400 MHz, DMSO-d$_6$) δ: 1.39 (3H, d, J=7.1 Hz), 2.51 (1H, m), 3.19-3.12 (1H, m), 3.38-3.40 (2H, m), 3.52-3.59 (1H, m), 4.11-4.14 (1H, m), 4.58-4.60 (1H, m), 7.47 (1H, d, J=2.2 Hz), 7.65 (1H, d, J=2.2 Hz)

MS(ESI) m/z: 296 (M+11)$^+$

Example 100

(S)-5-Chloro-7-methylaminocarbonyl-2-(2-methylpiperazin-1-yl)benzoxazole

The title compound was obtained in a similar manner as in Example 96 except that methylamine was used instead of dimethylamine $^1$H-NMR (400 MHz, CDCl$_3$) δ: 1.43 (3H, d, J=6.8 Hz), 2.86-2.95 (2H, m), 3.09 (3H, d, J=4.9 Hz), 3.11-3.15 (2H, m), 3.40-3.47 (1H, m), 3.91-3.95 (1H, m), 4.35-4.41 (1H, m), 6.61(1H, bs), 7.39 (1H, d, J=2.0 Hz), 7.63 (1H, d, J 2.2 Hz)

MS(ESI) m/z: 309 (M+H)$^+$

Example 101

(S)-5-Chloro-7-ethylaminocarbonyl-2-(2-methylpiperazin-1-yl)benzoxazole

The title compound was obtained in a similar manner as in Example 96 except that ethylamine was used instead of dimethylamine.

$^1$H-NMR (400 MHz, CDCl$_3$) δ: 1.29 (3H, t, J=7.3 Hz), 1.43 (3H, d, J=6.8 Hz), 2.87-2.96 (2H, m), 3.09-3.15 (2H, m), 3.41-3.48 (1H, m), 3.53-3.60 (2H, m), 3.90-3.94 (1H, m), 4.33-4.39 (1H, m), 6.59 (1H, br s), 7.39 (1H, d, J=2.0 Hz), 7.62 (1H, d, J=2.0 Hz)

MS(ESI) m/z: 323 (M+H)$^+$

Example 102

(S)-5-Fluoro-2-(2-methylpiperazin-1-yl)-7-(pyridin-2-yl)benzoxazole (a) (S)-1-tert-Butoxycarbonyl-4-(7-bromo-5-fluorobenzoxazol-2-yl)-3-methylpiperazine The title compound was obtained in a similar manner as in Example 16(a) except that 7-bromo-5-fluoro-2-mercaptobenzoxazole obtained in Reference Example 16 was used instead of 7-bromo-5-chloro-2-mercaptobenzoxazole.

(b) (S)-1-tert-Butoxycarbonyl-4-(5-fluoro-7-(pyridin-2-yl)benzoxazol-2-yl)-3-methylpiperazine The title compound was obtained in a similar manner as in Example 34(a) except that (S)-1-tert-butoxycarbonyl-4-(7-bromo-5-fluorobenzoxazol-2-yl)-3-methylpiperazine obtained in Example 102(a) was used instead of (S)-1-tert-butoxycarbonyl-4-(7-bromo-5-chlorobenzoxazol-2-yl)-3-methylpiperazine and that 2-(tributylstannyl)pyridine was used instead of 2-(tributylstannyl)oxazole.

(c) (S)-5-Fluoro-2-(2-methylpiperazin-1-yl)-7-(pyridin-2-yl)benzoxazole

The title compound was obtained in a similar manner as in Example 16(c) except that (S)-1-tert-butoxycarbonyl-4-(5-fluoro-7-(pyridin-2-yl)benzoxazol-2-yl)-3-methylpiperazine obtained in Example 102(b) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.43 (3H, d, J=6.7 Hz), 2.87-2.96 (2H, m), 3.09-3.15 (2H, m), 3.38-3.49 (1H, m), 3.98-4.04 (1H, m), 4.40-4.50 (1H, m), 7.07-7.11 (1H, m), 7.25-7.28 (1H, m), 7.56 (1H, dd, J=2.6, 11.0 Hz), 7.82 (1H, t, J=7.7 Hz), 7.98-8.02 (1H, m), 8.73-8.76 (1H, m)

MS(ESI) m/z: 313 (M+H)$^+$

Example 103

(S)-5-Fluoro-2-(2-methylpiperazin-1-yl)-7-(thiazol-2-yl)benzoxazole

The title compound was obtained in a similar manner as in Example 102 except that 2-(tributylstannyl)thiazole was used instead of 2-(tributylstannyl)pyridine.

$^1$H-NMR (400 MHz, CDCl$_3$) δ: 1.45 (3H, d, J=6.9 Hz), 2.88-2.98 (2H, m), 3.10-3.17 (2H, m), 3.41-3.49 (1H, m), 4.04-4.10 (1H, m), 4.45-4.51 (1H, m), 7.09 (1H, dd, J=2.5, 8.4 Hz), 7.49 (1H, d, J=3.2 Hz), 7.54-7.58 (1H, m), 7.96 (1H, d, J=3.2 Hz)

MS(ESI) m/z: 319 (M+H)$^+$

Example 104

(S)-5-Fluoro-2-(2-methylpiperazin-1-yl)-7-(oxazol-2-yl)benzoxazole

The title compound was obtained in a similar manner as in Example 102 except that 2-(tributylstannyl)oxazole was used instead of 2-(tributylstannyl)pyridine.

MS(ESI) m/z: 303 (M+H)$^+$

Example 105

(S)-5-Chloro-2-(2-methylpiperazin-1-yl)-7-(1,2,4-oxadiazol-3-yl)benzoxazole (a) (S)-1-tert-Butoxycarbonyl-4-(5-chloro-7-cyanobenzoxazol-2-yl)-3-methylpiperazine The title compound was obtained in a similar manner as in Example 15(a) except that 5-chloro-7-cyano-2-mercaptobenzoxazole obtained in Reference Example 8 was used instead of 5-chloro-7-ethoxycarbonyl-2-mercaptobenzoxazole.

(b) (S)-1-tert-Butoxycarbonyl-4-(5-chloro-7-hydroxycarbamidoyl)benzoxazol-2-yl)-3-methylpiperazine (S)-1-tert-Butoxycarbonyl-4-(5-chloro-7-cyanobenzoxazol-2-yl)-3-methylpiperazine obtained in Example 105(a) (363 mg) was dissolved in ethanol (7.3 mL), hydroxyamine hydrochloride (80 mg) and diisopropylethylamine (0.26 mL) were added thereto, and the resulting mixture was stirred in an oil bath at 85° C. for 3.5 hours. Water was added, the product was extracted with ethyl acetate, the organic layer was washed with a saturated saline solution and then dried over magnesium sulfate, then the solvent was distilled off under reduced pressure, and the residue was purified by silica gel column chromatography (developing solvent, hexane:ethyl acetate=2:1) to obtain 372 mg of the title compound.

(c) (S)-5-Chloro-2-(2-methylpiperazin-1-yl)-7-(1,2,4-oxadiazol-3-yl)benzoxazole (S)-1-tert-Butoxycarbonyl-4-(5-chloro-7-hydroxycarbamidoyl)-3-methylpiperazine obtained in Example 105(b) (370 mg) was dissolved in trimethyl orthoformate (3.7 mL), boron trifluoride-ethyl ether complex (catalytic amount) was added, and the resulting mixture was stirred in an oil bath at 55° C. for 1 hour. The reaction solvent was distilled off under reduced pressure, then chloroform (6 mL) and trifluoroacetic acid (2 mL) were added, and the resulting mixture was stirred at room temperature for 1.5 hours. A 1 N aqueous solution of sodium hydroxide was added to the reaction mixture, the product was extracted with chloroform, then the organic layer was washed with a saturated saline solution and dried over magnesium sulfate, then the solvent was distilled off under reduced pressure, and the residue was purified by silica gel column chromatography (developing solvent, chloroform:methanol=10:1) to obtain 117 mg of the title compound.

MS(ESI) m/z: 320 (M+H)$^+$

Example 106

(S)-5-Chloro-7-(4,5-dihydro-oxazol-2-yl)-2-(2-methylpiperazin-1-yl)benzoxazole

(a) (S)-1-tert-Butoxycarbonyl-4-(5-chloro-7-(2-hydroxyethyl)aminocarbonyl)benzoxazol-2-yl)-3-methylpiperazine The title compound was obtained in a similar manner as in Example 96(a) except that 2-hydroxyethylamine was used instead of dimethylamine.

(b) (S)-1-tert-Butoxycarbonyl-4-(5-chloro-7-(4,5-dihydro-oxazol-2-yl)benzoxazol-2-yl)-3-methylpiperazine (S)-1-tert-Butoxycarbonyl-4-(5-chloro-7-(2-hydroxyethyl)aminocarbonyl)benzoxazol-2-yl)-3-methylpiperazine obtained in Example 106(a) (0.5 mmol) was dissolved in 1,4-dioxane (2.5 mL), the resulting mixture was added to a solution of triphenylphosphine (203 mg) and DDQ (175 mg) dissolved in 1,4-dioxane (2.5 mL), and the resulting mixture was stirred at room temperature for 1 hour. A 1 N aqueous solution of sodium hydroxide was added to the reaction mixture, the product was extracted with ethyl acetate, and then the organic layer was washed with a saturated saline solution and dried over anhydrous magnesium sulfate, then the solvent was distilled off under reduced pressure, and the residue was purified by silica gel column chromatography (developing solvent, chloroform:methanol=200:1) to obtain 76 mg of the title compound.

(c) (S)-5-Chloro-7-(4,5-dihydro-oxazol-2-yl)-2-(2-methylpiperazin-1-yl)benzoxazole The title compound was obtained in a similar manner as in Example 16(c) except that (S)-1-tert-butoxycarbonyl-4-(5-chloro-7-(4,5-dihydro-oxazol-2-yl)benzoxazol-2-yl)-3-methylpiperazine obtained in Example 106(b) was used instead of (S)-1-tert-butoxycarbonyl-4-(5-chloro-7-(thiophen-3-yl)benzoxazol-2-yl)-3-methylpiperazine
MS(ESI) m/z: 321 (M+H)$^+$

Example 107

(S)-5-Chloro-7-(methoxymethyl)-2-(2-methylpiperazin-1-yl)benzoxazole

(a) (S)-1-tert-Butoxycarbonyl-4-(5-chloro-7-methoxy methylbenzoxazol-2-yl)-3-methylpiperazine (S)-5-Chloro-7-hydroxymethyl-2-(2-methylpiperazin-1-yl)benzoxazole obtained in Example 15(c) (166 mg) was dissolved in THF (2.2 mL), sodium hydride (content 60%, 21 mg) was added thereto, the resulting mixture was stirred at room temperature for 30 minutes, then methyl iodide (270 µL) was added thereto, and the resulting mixture was stirred at room temperature for 1.5 hours in this state. Water was added to the reaction mixture, the product was extracted with ethyl acetate, the organic layer was washed with a saturated saline solution and then dried over anhydrous sodium sulfate, then the solvent was distilled off under reduced pressure, and the residue was purified by silica gel column chromatography (developing solvent, hexane:ethyl acetate=7:3) to obtain 91.5 mg of the title compound.

(b) (S)-5-Chloro-7-methoxymethyl-2-(2-methylpiperazin-1-yl)benzoxazole

The title compound was obtained in a similar manner as in Example 16(c) except that (S)-1-tert-butoxycarbonyl-4-(5-chloro-7-methoxy methylbenzoxazol-2-yl)-3-methylpiperazine obtained in Example 107(a) was used instead of (S)-1-tert-butoxycarbonyl-4-(5-chloro-7-(thiophen-3-yl)benzoxazol-2-yl)-3-methylpiperazine.
$^1$H-NMR (400 MHz, CDCl$_3$) δ: 1.39 (3H, d, J=6.6 Hz), 2.83-2.92 (2H, m), 3.06-3.11 (2H, m), 3.33-3.40 (1H, m), 3.42 (3H, s), 3.95-3.99 (1H, m), 4.36-4.42 (1H, m), 4.56-4.63 (2H, m), 7.01 (1H, d, J=2.2 Hz), 7.25 (1H, d, J=2.2 Hz)
MS(ESI) m/z: 296 (M+H)$^+$

Example 108

(S)-5-Chloro-7-(isoxazol-3-yl)-2-(2-methylpiperazin-1-yl)benzoxazole

(a) (S)-1-tert-Butoxycarbonyl-4-(7-acetyl-5-chlorobenzoxazol-2-yl)-3-methylpiperazine The title compound was obtained in a similar manner as in Example 15(a) except that 7-acetyl-5-chloro-2-mercaptobenzoxazole obtained in Reference Example 3 was used instead of 5-chloro-7-ethoxycarbonyl-2-mercaptobenzoxazole.

(b) (S)-1-tert-Butoxycarbonyl-4-(5-chloro-7-(3-(dimethylamino)acryloyl)benzoxazol-2-yl)-3-methylpiperazine (S)-1-tert-Butoxycarbonyl-4-(7-acetyl-5-chlorobenzoxazol-2-yl)-3-m ethylpiperazine obtained in Example 108(a) (394 mg) was dissolved in 1,4-dioxane (5 mL), a Bredereck's reagent (250 µL) was added thereto, and the resulting mixture was stirred in an oil bath at 120° C. for 2.5 hours. The reaction mixture was concentrated under reduced pressure, and the obtained residue was purified by silica gel column chromatography (developing solvent, chloroform:methanol=96:4) to obtain 388 mg of the title compound.

(c) (S)-5-Chloro-7-(isoxazol-3-yl)-2-(2-methylpiperazin-1-yl)benzoxazole (S)-1-tert-Butoxycarbonyl-4-(5-chloro-7-(3-(dimethylamino)acryloyl)benzoxazol-2-yl)-3-methylpiperazine obtained in Example 108(b) (314 mg), hydroxyamine-hydrochloride (97 mg), and pyridine (113 µL) were dissolved in ethanol (10 mL), and the resulting mixture was stirred in an oil bath at 80° C. for 20 hours. The reaction mixture was concentrated under reduced pressure, the obtained residue was dissolved in ethyl acetate and washed sequentially with water and a saturated saline solution, then dried over anhydrous sodium sulfate, the solvent was distilled off under reduced pressure, and the residue was purified by silica gel column chromatography (developing solvent, chloroform:methanol=96:4) to obtain 73 mg of a crude product. The obtained product was dissolved in chloroform (1.8 mL), trifluoroacetic acid (0.9 mL) was added thereto, and the resulting mixture was stirred at room temperature for 1.5 hours. The reaction mixture was concentrated under reduced pressure, the obtained residue was dissolved in ethyl acetate, sequentially washed with water and a saturated saline solution, then dried over anhydrous sodium sulfate, the solvent was distilled off under reduced pressure, and the residue was purified by silica gel column chromatography (developing solvent, chloroform:methanol=96:4) to obtain 29.6 mg of the title compound.

$^1$H-NMR (400 MHz, CDCl$_3$) δ: 1.43 (3H, d, J=6.6 Hz), 2.86-2.95 (2H, m), 3.08-3.14 (2H, m), 3.39-3.47 (1H, m), 4.00-4.03 (1H, m), 4.41-4.46 (1H, m), 6.84 (1H, d, J=1.7 Hz), 7.37 (1H, d, J=2.0 Hz), 7.54 (1H, d, J=2.0 Hz), 8.54 (1H, d, J=1.7 Hz)

MS(ESI) m/z: 319 (M+H)$^+$

Example 109

(S)-5-Chloro-7-(isoxazol-5-yl)-2-(2-methylpiperazin-1-yl)benzoxazole (S)-1-tert-Butoxycarbonyl-4-(5-chloro-7-(3-(dimethylamino)acryloyl)benzoxazol-2-yl)-3-methylpiperazine obtained in Example 108(b) (74 mg) and hydroxyamine hydrochloride (23 mg) were dissolved in ethanol (3.0 mL), and the resulting mixture was stirred in an oil bath at 80° C. for 20 hours. The reaction mixture was concentrated under reduced pressure, the obtained residue was dissolved in ethyl acetate, sequentially washed with water and a saturated saline solution, then dried over anhydrous sodium sulfate, the solvent was distilled off under reduced pressure, and the residue was purified by silica gel column chromatography (developing solvent, chloroform:methanol=96:4) to obtain 53.9 mg of a crude product. The obtained product was dissolved in chloroform (1.3 mL), trifluoroacetic acid (0.65 mL) was added, and the resulting mixture was stirred at room temperature for 2 hours. The reaction mixture was concentrated under reduced pressure, the obtained residue was dissolved in ethyl acetate, sequentially washed with water and a saturated saline solution, then dried over anhydrous sodium sulfate, the solvent was distilled off under reduced pressure, and the residue was purified by silica gel column chromatography (developing solvent, chloroform:methanol=96:4) to obtain 31.4 mg of the title compound.

$^1$H-NMR (400 MHz, CDCl$_3$) δ: 1.44 (3H, d, J=6.6 Hz), 2.87-2.96 (2H, m), 3.09-3.15 (2H, m), 3.41-3.48 (1H, m), 4.00-4.04 (1H, m), 4.41-4.47 (1H, m), 6.73 (1H, d, J=2.0 Hz), 7.36 (1H, d, J=2.0 Hz), 7.51 (1H, d, J=2.0 Hz), 8.37 (1H, d, J=1.7 Hz)

MS(ESI) m/z: 319 (M+H)$^+$

Example 110

(S)-7-Bromo-5-chloro-2-(2-methylpiperazin-1-yl)benzoxazole

The title compound was obtained in a similar manner as in Example 2 except that 7-bromo-5-chloro-2-mercaptobenzoxazole obtained in Reference Example 9 was used instead of 5-chloro-7-methoxy-2-mercaptobenzoxazole.

$^1$H-NMR (400 MHz, CD$_3$OD) δ: 1.40 (3H, d, J=7.2 Hz), 2.85 (1H, dt, J=3.6, 12.8 Hz), 2.94 (1H, d, J=12.8 Hz), 3.06 (1H, dd, J=4.0, 12.8 Hz), 3.10-3.12 (1H, m), 3.41 (1H, dt, J=3.6, 12.8 Hz), 3.94-3.97 (1H, m), 4.35-4.37 (1H, m), 7.19-7.20 (2H, m)

MS(ESI) m/z: 330 (M+H)$^+$

Example 111

(S)-5-Cyano-2-(2-methylpiperazin-1-yl)-7-(pyridin-2-yl)benzoxazole (a) (S)-1-tert-Butoxycarbonyl-4-(7-bromo-5-cyanobenzoxazol-2-yl)-3-methylpiperazine The title compound was obtained in a similar manner as in Example 16(a) except that 7-bromo-5-cyano-2-mercaptobenzoxazole obtained in Reference Example 17 was used instead of 7-bromo-5-chloro-2-mercaptobenzoxazole.

(b) (S)-1-tert-Butoxycarbonyl-4-(5-cyano-7-(pyridin-2-yl)benzoxazol-2-yl)-3-methylpiperazine The title compound was obtained in a similar manner as in Example 102(b) except that (S)-1-tert-butoxycarbonyl-4-(7-bromo-5-cyanobenzoxazol-2-yl)-3-methylpiperazine obtained in Example 111(a) was used instead of (S)-1-tert-butoxycarbonyl-4-(7-bromo-5-fluorobenzoxazol-2-yl)-3-methylpiperazine.

(c) (S)-5-Cyano-2-(2-methylpiperazin-1-yl)-7-(pyridin-2-yl)benzoxazole

The title compound was obtained in a similar manner as in Example 16(c) except that (S)-1-tert-butoxycarbonyl-4-(5-cyano-7-(pyridin-2-yl)benzoxazol-2-yl)-3-methylpiperazine obtained in Example 111(b) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.45 (3H, d, J=6.8 Hz), 2.88-2.96 (2H, m), 3.10-3.18 (2H, m), 3.42-3.52 (1H, m), 4.01-4.06 (1H, m), 4.43-4.49 (1H, m), 7.32-7.36 (1H, m), 7.61 (1H, d, J=1.6 Hz), 7.83-7.87 (1H, m), 7.95-8.00 (1H, m), 8.19 (1H, d, J=1.6 Hz), 8.76-8.78 (1H, m)

MS(APCI) m/z: 320 (M+H)$^+$

Example 112

(S)-5-Cyano-2-(2-methylpiperazin-1-yl)-7-(thiazol-2-yl)benzoxazole

The title compound was obtained in a similar manner as in Example 111 except that 2-(tributylstannyl)thiazole was used instead of 2-(tributylstannyl)pyridine.

MS(ESI) m/z: 326 (M+H)$^+$

Example 113

(S)-5-Cyano-2-(2-methylpiperazin-1-yl)-7-(oxazol-2-yl)benzoxazole

The title compound was obtained in a similar manner as in Example 111 except that 2-(tributylstannyl)oxazole was used instead of 2-(tributylstannyl)pyridine.

$^1$H-NMR (400 MHz, CDCl$_3$) δ: 1.47 (3H, d, J=6.8 Hz), 2.87-3.00 (2H, m), 3.08-3.19 (2H, m), 3.44-3.53 (1H, m), 4.08-4.17 (1H, m), 4.48-4.55 (1H, m), 7.36 (1H, d, J=0.73 Hz), 7.61 (1H, d, J=1.6 Hz), 7.83 (1H, d, J=0.73 Hz), 7.99 (1H, d, J=1.6 Hz)

MS(ESI) m/z: 310 (M+H)$^+$

Example 114

(S)-5-methyl-2-(2-methylpiperazin-1-yl)-7-(pyridin-2-yl)benzoxazole

(a) (S)-1-tert-Butoxycarbonyl-4-(7-bromo-5-methyl-benzoxazol-2-yl)-3-methylpiperazine The title compound was obtained in a similar manner as in Example 16(a) except that 7-bromo-5-methyl-2-mercaptobenzoxazole obtained in Reference Example 18 was used instead of 7-bromo-5-chloro-2-mercaptobenzoxazole.

(b) (S)-1-tert-Butoxycarbonyl-4-(5-methyl-7-(pyridin-2-yl)benzoxazol-2-yl)-3-methylpiperazine The title compound was obtained in a similar manner as in Example 102(b) except that (S)-1-tert-butoxycarbonyl-4-(7-bromo-5-methylbenzoxazol-2-yl)-3-methylpiperazine obtained in Example 114(a) was used instead of (S)-1-tert-butoxycarbonyl-4-(7-bromo-5-fluorobenzoxazol-2-yl)-3-methylpiperazine.

(c) (S)-5-methyl-2-(2-methylpiperazin-1-yl)-7-(pyridin-2-yl)benzoxazole

The title compound was obtained in a similar manner as in Example 16(c) except that (S)-1-tert-butoxycarbonyl-4-(5-methyl-7-(pyridin-2-yl)benzoxazol-2-yl)-3-methylpiperazine obtained in Example 114(b) was used instead of (S)-1-tert-butoxycarbonyl-4-(5-chloro-7-(thiophen-3-yl)benzoxazol-2-yl)-3-methylpiperazine.
MS(APCI) m/z: 309 (M+H)+

Example 115

(S)-5-methyl-2-(2-methylpiperazin-1-yl)-7-(thiazol-2-yl)benzoxazole

The title compound was obtained in a similar manner as in Example 114 except that 2-(tributylstannyl)thiazole was used instead of 2-(tributylstannyl)pyridine.
MS(APCI) m/z: 315 (M+H)+

Example 116

(S)-5-methyl-2-(2-methylpiperazin-1-yl)-7-(oxazol-2-yl)benzoxazole

The title compound was obtained in a similar manner as in Example 114 except that 2-(tributylstannyl)oxazole was used instead of 2-(tributylstannyl)pyridine.
MS(ESI) m/z: 299 (M+H)+

Example 117

(S)-5-Fluoro-2-(2-methylpiperazin-1-yl)-7-(pyridin-2-yl)-4-(trifluoromethyl)benzoxazole

(a) (S)-1-tert-Butoxycarbonyl-4-(7-bromo-5-fluoro-4-(trifluoromethyl)benzoxazol-2-yl)-3-methylpiperazine The title compound was obtained in a similar manner as in Example 16(a) except that a mixture of 7-bromo-5-fluoro-2-mercapto-4-(trifluoromethyl)benzoxazole, and 7-bromo-5-fluoro-2-mercapto-6-(trifluoromethyl)benzoxazole obtained in Reference Example 19 was used instead of 7-bromo-5-chloro-2-mercaptobenzoxazole.

(b) (S)-1-tert-Butoxycarbonyl-4-(5-fluoro-7-(pyridin-2-yl)-4-(trifluoromethyl)benzoxazol-2-yl)-3-methylpiperazine The title compound was obtained in a similar manner as in Example 102(b) except that (S)-1-tert-butoxycarbonyl-4-(7-bromo-5-fluoro-4-(trifluoromethyl)benzoxazol-2-yl)-3-methylpiperazine obtained in Example 117(a) was used instead of (S)-1-tert-butoxycarbonyl-4-(7-bromo-5-fluorobenzoxazol-2-yl)-3-methylpiperazine.

(c) (S)-5-Fluoro-2-(2-methylpiperazin-1-yl)-7-(pyridin-2-yl)-4-(trifluoromethyl)benzoxazole The title compound was obtained in a similar manner as in Example 16(c) except that (S)-1-tert-butoxycarbonyl-4-(5-fluoro-7-(pyridin-2-yl)-4-(trifluoromethyl)benzoxazol-2-yl)-3-methylpiperazine obtained in Example 117(b) was used instead of (S)-1-tert-butoxycarbonyl-4-(5-chloro-7-(thiophen-3-yl)benzoxazol-2-yl)-3-methylpiperazine.
$^1$H-NMR (400 MHz, CDCl$_3$) δ: 1.44 (3H, d, J=6.8 Hz), 2.86-2.96 (2H, m), 3.09-3.15 (2H, m), 3.42-3.49 (1H, m), 4.07-4.11 (1H, m), 4.47-4.52 (1H, m), 7.34 (1H, ddd, J=1.0, 4.9, 7.6 Hz), 7.64 (1H, d, J=12.7 Hz), 7.85 (1H, dt, J=2.0, 7.8 Hz), 8.02 (1H, dd, J=1.0, 8.1 Hz), 8.76-8.78 (1H, m)
MS (ESI) m/z: 381 (M+H)+

Example 118

(S)-5-Fluoro-2-(2-methylpiperazin-1-yl)-7-(thiazol-2-yl)-4-(trifluoromethyl)benzoxazole The title compound was obtained in a similar manner as in Example 114 except that 2-(tributylstannyl)thiazole was used instead of 2-(tributylstannyl)pyridine.
$^1$H-NMR (400 MHz, CDCl$_3$) δ: 1.47 (3H, d, J=6.8 Hz), 2.88-2.98 (2H, m), 3.11-3.16 (2H, m), 3.45-3.53 (1H, m), 4.13-4.17 (1H, m), 4.52-4.58 (1H, m), 7.56 (1H, d, J=3.2 Hz), 7.63 (1H, d, J 12.5 Hz), 8.01 (d, 1H, J=3.2 Hz)
MS(ESI) m/z: 387 (M+H)+

Example 119

(S)-5-Fluoro-2-(2-methylpiperazin-1-yl)-7-(1H-pyrazol-1-yl)-4-(trifluoromethyl)benzoxazole The title compound was obtained in a similar manner as in Examples 83(a) and 83 (b) except that (S)-1-tert-butoxycarbonyl-4-(7-bromo-5-fluoro-4-(trifluoromethyl)benzoxazol-2-yl)-3-methylpiperazine obtained in Example 117(a) was used instead of (S)-1-tert-butoxycarbonyl-4-(7-bromo-5-chloro-4-(trifluoromethyl)benzoxazol-2-yl)-3-methylpiperazine.
$^1$H-NMR (400 MHz, CDCl$_3$) δ: 1.45 (3H, d, J=6.8 Hz), 2.86-2.96 (2H, m), 3.09-3.15 (2H, m), 3.43-3.50 (1H, m), 4.06-4.10 (1H, m), 4.45-4.51 (1H, m), 6.57 (1H, dd, J=2.0, 2.7 Hz), 7.47 (1H, d, J=12.7 Hz), 7.80 (1H, d, J=1.7 Hz), 8.25 (dd, 1H, J=0.5, 2.7 Hz)
MS(ESI) m/z: 370 (M+H)+

Example 120

(S)-5-Chloro-4,6-difluoro-2-(2-methylpiperazin-1-yl)-7-(pyridin-2-yl)benzoxazole

(a) (S)-1-tert-Butoxycarbonyl-4-(7-bromo-5-chloro-4,6-difluorobenzoxazol-2-yl)-3-methylpiperazine The title compound was obtained in a similar manner as in Example 16(a) except that 7-bromo-5-chloro-4,6-difluoro-2-mercaptobenzoxazole obtained in Reference Example 20 was used instead of 7-bromo-5-chloro-2-mercaptobenzoxazole.

(b) (S)-1-tert-Butoxycarbonyl-4-(5-chloro-4,6-difluoro-7-(pyridin-2-yl)benzoxazol-2-yl)-3-methylpiperazine The title compound was obtained in a similar manner as in Example 102(b) except that (S)-1-tert-butoxycarbonyl-4-(7-bromo-5-chloro-4,6-difluorobenzoxazol-2-yl)-3-methylpiperazine obtained in Example 120(a) was used instead of (S)-1-tert-butoxycarbonyl-4-(7-bromo-5-fluorobenzoxazol-2-yl)-3-methylpiperazine.

(c) (S)-5-Chloro-4,6-difluoro-2-(2-methylpiperazin-1-yl)-7-(pyridin-2-yl)benzoxazole The title compound was obtained in a similar manner as in Example 16(c) except that (S)-1-tert-butoxycarbonyl-4-(5-chloro-4,6-difluoro-7-(pyridin-2-yl)benzoxazol-2-yl)-3-methylpiperazine obtained in Example 120(b) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.44 (3H, d, J=6.6 Hz), 2.86-2.94 (2H, m), 3.09-3.13 (2H, m), 3.39-3.46 (1H, m), 4.02-4.06 (1H, m), 4.43-4.49 (1H, m), 7.33-7.36 (1H, m), 7.48 (1H, d, J=7.8 Hz), 7.81 (1H, dt, J=2.0, 7.8 Hz), 8.76-8.78 (1H, m)

MS(ESI) m/z: 365 (M+H)$^+$

Example 121

(S)-5-Chloro-4,6-difluoro-2-(2-methylpiperazin-1-yl)-7-(thiazol-2-yl)benzoxazole The title compound was obtained in a similar manner as in Example 120 except that 2-(tributylstannyl)thiazole was used instead of 2-(tributylstannyl)pyridine.

$^1$H-NMR (400 MHz, CDCl$_3$) δ: 1.44 (3H, d, J=6.8 Hz), 2.86-2.95 (2H, m), 3.08-3.14 (2H, m), 3.40-3.47 (1H, m), 4.02-4.06 (1H, m), 4.43-4.49 (1H, m), 7.57 (1H, d, J=3.4 Hz), 8.04 (d, 1H, J=3.4 Hz)

MS(ESI) m/z: 371 (M+H)$^+$

Example 122

(S)-4,5,6-Trifluoro-2-(2-methylpiperazin-1-yl)-7-(pyridin-2-yl)benzoxazole

(a) (S)-1-tert-Butoxycarbonyl-4-(7-bromo-4,5,6-trifluorobenzoxazol-2-yl)-3-methylpiperazine The title compound was obtained in a similar manner as in Example 16(a) except that 7-bromo-4,5,6-trifluoro-2-mercaptobenzoxazole obtained in Reference Example 21 was used instead of 7-bromo-5-chloro-2-mercaptobenzoxazole.

(b) (S)-1-tert-Butoxycarbonyl-4-(4,5,6-trifluoro-7-(pyridin-2-yl)benzoxazol-2-yl)-3-methylpiperazine The title compound was obtained in a similar manner as in Example 102(b) except that (S)-1-tert-butoxycarbonyl-4-(7-bromo-4,5,6-trifluorobenzoxazol-2-yl)-3-methylpiperazine obtained in Example 122(a) was used instead of (S)-1-tert-butoxycarbonyl-4-(7-bromo-5-fluorobenzoxazol-2-yl)-3-methylpiperazine.

(c) (S)-4,5,6-Trifluoro-2-(2-methylpiperazin-1-yl)-7-(pyridin-2-yl)benzoxazole The title compound was obtained in a similar manner as in Example 16(c) except that (S)-1-tert-butoxycarbonyl-4-(4,5,6-trifluoro-7-(pyridin-2-yl)benzoxazol-2-yl)-3-methylpiperazine obtained in Example 122(b) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.38 (3H, d, J=6.8 Hz), 2.79-2.94 (2H, m), 3.01-3.12 (2H, m), 3.31-3.45 (1H, m), 3.89-3.99 (1H, m), 4.35-4.45 (1H, m), 7.35 (1H, ddd, J=7.6, 4.9, 1.1 Hz), 7.61-7.70 (1H, m), 7.80-7.88 (1H, m), 8.75-8.81 (1H, m)

MS(ESI) m/z: 349 (M+H)$^+$

Example 123

(S)-4,5,6-Trifluoro-2-(2-methylpiperazin-1-yl)-7-(thiazol-2-yl)benzoxazole

The title compound was obtained in a similar manner as in Example 122 except that 2-(tributylstannyl)thiazole was used instead of 2-(tributylstannyl)pyridine.

$^1$H-NMR (400 MHz, CDCl$_3$) δ: 1.43 (3H, d, J=6.8 Hz), 2.84-2.99 (2H, m), 3.04-3.16 (2H, m), 3.38-3.53 (1H, m), 4.01-4.10 (1H, m), 4.40-4.54 (1H, m), 7.53-7.59 (1H, m), 8.02-8.08 (1H, m)

MS(ESI) m/z: 355 (M+H)$^+$

Example 124

(S)-4,5,6-Trifluoro-2-(2-methylpiperazin-1-yl)-7-(1H-pyrazol-1-yl)benzoxazole The title compound was obtained in a similar manner as in Examples 83(a) and 83(b) except that (S)-1-tert-butoxycarbonyl-4-(7-bromo-4,5,6-trifluorobenzoxazol-2-yl)-3-methylpiperazine obtained in Example 122(a) was used instead of (S)-1-tert-butoxycarbonyl-4-(7-bromo-5-chloro-4-(trifluoromethyl)benzoxazol-2-yl)-3-methylpiperazine.

$^1$H-NMR (400 MHz, CDCl$_3$) δ: 1.39 (3H, d, J=6.8 Hz), 2.79-2.94 (2H, m), 3.01-3.15 (2H, m), 3.32-3.44 (1H, m), 3.89-4.00 (1H, m), 4.34-4.46 (1H, m), 6.51-6.57 (1H, m), 7.80-7.87 (2H, m)

MS(ESI) m/z: 338 (M+H)$^+$

Example 125

(S)-2-(2-Methylpiperazin-1-yl)-7-(pyridin-2-yl)-5-(trifluoromethyl)benzoxazole

(a) (S)-1-tert-Butoxycarbonyl-4-(7-bromo-5-(trifluoromethyl)benzoxazol-2-yl)-3-methylpiperazine The title compound was obtained in a similar manner as in Example 16(a) except that 7-bromo-2-mercapto-5-trifluoromethylbenzoxazole obtained in Reference Example 22 was used instead of 7-bromo-5-chloro-2-mercaptobenzoxazole.

(b) (S)-1-tert-Butoxycarbonyl-4-(7-(pyridin-2-yl)-5-(trifluoromethyl)benzoxazol-2-yl)-3-methylpiperazine The title compound was obtained in a similar manner as in Example 102(b) except that (S)-1-tert-butoxycarbonyl-4-(7-bromo-5-(trifluoromethyl)benzoxazol-2-yl)-3-methylpiperazine obtained in Example 125(a) was used instead of (S)-1-tert-butoxycarbonyl-4-(7-bromo-5-fluorobenzoxazol-2-yl)-3-methylpiperazine.

(c) (S)-2-(2-Methylpiperazin-1-yl)-7-(pyridin-2-yl)-5-(trifluoromethyl)benzoxazole The title compound was obtained in a similar manner as in Example 16(c) except that (S)-1-tert-butoxycarbonyl-4-(7-(pyridin-2-yl)-5-(trifluoromethyl)benzoxazol-2-yl)-3-methylpiperazine obtained in Example 125(b) was used instead of (S)-1-tert-butoxycarbonyl-4-(5-chloro-7-(thiophen-3-yl)benzoxazol-2-yl)-3-methylpiperazine.
MS(ESI) m/z: 363 (M+H)$^+$

Example 126

(S)-2-(2-Methylpiperazin-1-yl)-7-(thiazol-2-yl)-5-(trifluoromethyl)benzoxazole The title compound was obtained in a similar manner as in Example 125 except that 2-(tributylstannyl)thiazole was used instead of 2-(tributylstannyl)pyridine.
MS(ESI) m/z: 369 (M+H)$^+$

Example 127

(S)-2-(2-Methylpiperazin-1-yl)-7-(oxazol-2-yl)-5-(trifluoromethyl)benzoxazole The title compound was obtained in a similar manner as in Example 114 except that 2-(tributylstannyl)oxazole was used instead of 2-(tributylstannyl)pyridine.
MS(ESI) m/z: 353 (M+H)$^+$

Example 128

(S)-5-Chloro-4-fluoro-2-(2-methylpiperazin-1-yl)-7-(pyridin-2-yl)benzoxazole

(a) (S)-1-tert-Butoxycarbonyl-4-(7-bromo-5-chloro-4-fluorobenzoxazol-2-yl)-3-methylpiperazine The title compound was obtained in a similar manner as in Example 16(a) except that 7-bromo-5-chloro-4-fluoro-2-mercaptobenzoxazole obtained in Reference Example 23 was used instead of 7-bromo-5-chloro-2-mercaptobenzoxazole.

(b) (S)-1-tert-Butoxycarbonyl-4-(5-chloro-4-fluoro-7-(pyridin-2-yl)benzoxazol-2-yl)-3-methylpiperazine The title compound was obtained in a similar manner as in Example 102(b) except that (S)-1-tert-butoxycarbonyl-4-(7-bromo-5-chloro-4-fluorobenzoxazol-2-yl)-3-m ethylpiperazine obtained in Example 128(a) was used instead of (S)-1-tert-butoxycarbonyl-4-(7-bromo-5-fluorobenzoxazol-2-yl)-3-methylpiperazine.

(c) (S)-5-Chloro-4-fluoro-2-(2-methylpiperazin-1-yl)-7-(pyridin-2-yl)benzoxazole The title compound was obtained in a similar manner as in Example 16(c) except that (S)-1-tert-butoxycarbonyl-4-(5-chloro-4-fluoro-7-(pyridin-2-yl)benzoxazol-2-yl)-3-methylpiperazine obtained in Example 128(b) was used instead of (S)-1-tert-butoxycarbonyl-4-(5-chloro-7-(thiophen-3-yl)benzoxazol-2-yl)-3-methylpiperazine.
$^1$H-NMR (500 MHz, CDCl$_3$) δ: 1.44 (3H, d, J=6.9 Hz), 2.87-2.95 (2H, m), 3.09-3.14 (2H, m), 3.41-3.47 (1H, m), 4.02-4.05 (1H, m), 4.45-4.50 (1H, m), 7.27-7.29 (1H, m), 7.81 (1H, dt, J=1.9, 7.9 Hz), 7.89 (1H, d, J=6.9 Hz), 7.92-7.96 (1H, m), 8.72-8.74 (1H, m)
MS(ESI) m/z: 347 (M+H)$^+$

Example 129

(S)-5-Chloro-4-fluoro-2-(2-methylpiperazin-1-yl)-7-(thiazol-2-yl)benzoxazole The title compound was obtained in a similar manner as in Example 128 except that 2-(tributylstannyl)thiazole was used instead of 2-(tributylstannyl)pyridine.
$^1$H-NMR (500 MHz, CDCl$_3$) δ: 1.46 (3H, d, J=6.8 Hz), 2.89-2.96 (2H, m), 3.11-3.15 (2H, m), 3.44-3.50 (1H, m), 4.08-4.11 (1H, m), 4.51-4.52 (1H, m), 7.47 (1H, d, J=3.3 Hz), 7.89 (1H, d, J=6.5 Hz), 7.94 (d, 1H, J=3.3 Hz)
MS(ESI) m/z: 353 (M+H)$^+$

Example 130

(S)-5-Chloro-4-fluoro-2-(2-methylpiperazin-1-yl)-7-(1H-pyrazol-1-yl)benzoxazole The title compound was obtained in a similar manner as in Examples 83(a) and 83(b) except that (S)-1-tert-butoxycarbonyl-4-(7-bromo-5-chloro-4-fluorobenzoxazol-2-yl)-3-m ethylpiperazine obtained in Example 128(a) was used instead of (S)-1-tert-butoxycarbonyl-4-(7-bromo-5-chloro-4-(trifluoromethyl)benzoxazol-2-yl)-3-methylpiperazine.
$^1$H-NMR (500 MHz, CDCl$_3$) δ: 1.44 (3H, d, J=6.8 Hz), 2.86-2.95 (2H, m), 3.08-3.14 (2H, m), 3.42-3.48 (1H, m), 4.00-4.03 (1H, m), 4.43-4.48 (1H, m), 6.52-6.53 (1H, m), 7.62 (1H, d, J=6.0 Hz), 7.76 (1H, d, J=1.7 Hz), 8.10 (1H, d, J=2.5 Hz)
MS(ESI) m/z: 336 (M+H)$^+$

Example 131

(S)-5-Chloro-4-methyl-2-(2-methylpiperazin-1-yl)-7-(pyridin-2-yl)benzoxazole (a) (S)-1-tert-Butoxycarbonyl-4-(7-bromo-5-chloro-4-methylbenzoxazol-2-yl)-3-methylpiperazine The title compound was obtained in a similar manner as in Example 16(a) except that 7-bromo-5-chloro-2-mercapto-4-methylbenzoxazole obtained in Reference Example 24 was used instead of 7-bromo-5-chloro-2-mercaptobenzoxazole.

(b) (S)-1-tert-Butoxycarbonyl-4-(5-chloro-4-methyl-7-(pyridin-2-yl)benzoxazol-2-yl)-3-methylpiperazine The title compound was obtained in a similar manner as in Example 102(b) except that (S)-1-tert-butoxycarbonyl-4-(7-bromo-5-chloro-4-methylbenzoxazol-2-yl)-3-methylpiperazine obtained in Example 131(a) was used instead of (S)-1-tert-butoxycarbonyl-4-(7-bromo-5-fluorobenzoxazol-2-yl)-3-methylpiperazine.

(c) (S)-5-Chloro-4-methyl-2-(2-methylpiperazin-1-yl)-7-(pyridin-2-yl)benzoxazole The title compound was obtained in a similar manner as in Example 16(c) except that (S)-1-tert-butoxycarbonyl-4-(5-chloro-4-methyl-7-(pyridin-2-yl)benzoxazol-2-yl)-3-methylpiperazine obtained in Example 131(b) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.42 (3H, d, J=6.7 Hz), 2.54 (3H, s), 2.84-2.98 (2H, m), 3.06-3.18 (2H, m), 3.42 (1H, m), 3.96-4.07 (1H, m), 4.39-4.51 (1H, m), 7.21-7.30 (1H, m), 7.79(1H, td, J=1.9, 7.8 Hz), 7.87 (1H, s), 7.96 (1H, dt, J=1.0, 8.0 Hz), 8.69-8.76 (1H, m)

MS(ESI) m/z: 343 (M+H)$^+$

Example 132

(S)-5-Chloro-4-methyl-2-(2-methylpiperazin-1-yl)-7-(thiazol-2-yl)benzoxazole

The title compound was obtained in a similar manner as in Example 131 except that 2-(tributylstannyl)thiazole was used instead of 2-(tributylstannyl)pyridine.

$^1$H-NMR (400 MHz, CDCl$_3$) δ: 1.44 (3H, d, J=6.8 Hz), 2.53 (3H, s), 2.85-3.01 (2H, m), 3.11-3.15 (2H, m), 3.44 (1H, m), 4.02-4.13 (1H, m), 4.43-4.57 (1H, m), 7.44 (1H, d, J=3.3 Hz), 7.87 (1H, s), 7.93 (d, 1H, J=3.3 Hz)

MS(ESI) m/z: 349 (M+H)$^+$

Example 133

(S)-5-Chloro-4-methyl-2-(2-methylpiperazin-1-yl)-7-(1H-pyrazol-1-yl)benzoxazole

The title compound was obtained in a similar manner as in Examples 83(a) and 83(b) except that (S)-1-tert-butoxycarbonyl-4-(7-bromo-5-chloro-4-methylbenzoxazol-2-yl)-3-methylpiperazine obtained in Example 131(a) was used instead of (S)-1-tert-butoxycarbonyl-4-(7-bromo-5-chloro-4-(trifluoromethyl)benzoxazol-2-yl)-3-methylpiperazine.

$^1$H-NMR (400 MHz, CDCl$_3$) δ: 1.42 (3H, d, J=6.7 Hz), 2.50 (3H, s), 2.83-2.98 (2H, m), 3.06-3.17 (2H, m), 3.42 (1H, m), 3.94-4.06 (1H, m), 4.37-4.49 (1H, m), 6.46-6.54 (1H, m), 7.63 (1H, s), 7.75 (1H, d, J=1.4 Hz), 8.14 (1H, d, J=2.4 Hz)

MS(ESI) m/z: 332 (M+H)$^+$

Example 134

(S)-5-Fluoro-2-(2-methylpiperazin-1-yl)-7-(pyridin-2-yl)-4-(trifluoromethoxy)benzoxazole (a) (S)-1-tert-Butoxycarbonyl-4-(7-bromo-5-fluoro-4-(trifluoromethoxy)benzoxazol-2-yl)-3-methylpiperazine The title compound was obtained in a similar manner as in Example 16(a) except that 7-bromo-5-fluoro-2-mercapto-4-(trifluoromethoxy)benzoxazole obtained in Reference Example 25 was used instead of 7-bromo-5-chloro-2-mercaptobenzoxazole.

(b) (S)-1-tert-Butoxycarbonyl-4-(5-fluoro-7-(pyridin-2-yl)-4-(trifluoromethoxy)benzoxazol-2-yl)-3-methylpiperazine The title compound was obtained in a similar manner as in Example 102(b) except that (S)-1-tert-butoxycarbonyl-4-(7-bromo-5-fluoro-4-(trifluoromethoxy)benzoxazol-2-yl)-3-methylpiperazine obtained in Example 134(a) was used instead of (S)-1-tert-butoxycarbonyl-4-(7-bromo-5-fluorobenzoxazol-2-yl)-3-methylpiperazine.

(c) (S)-5-Fluoro-2-(2-methylpiperazin-1-yl)-7-(pyridin-2-yl)-4-(trifluoromethoxy)benzoxazole The title compound was obtained in a similar manner as in Example 16(c) except that (S)-1-tert-butoxycarbonyl-4-(5-fluoro-7-(pyridin-2-yl)-4-(trifluoromethoxy)benzoxazol-2-yl)-3-methylpiperazine obtained in Example 134(b) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.44 (3H, d, J=6.8 Hz), 2.84-2.98 (2H, m), 3.05-3.17 (2H, m), 3.44 (1H, dt, J=3.5, 12.6 Hz), 4.05 (1H, dd, J=2.0, 13.0 Hz), 4.40-4.54 (1H, m), 7.30 (1H, ddd, J=1.1, 4.8, 7.5 Hz), 7.68 (1H, d, J=12.2 Hz), 7.82 (1H, dt, J=1.9, 7.8 Hz), 7.98(1H, td, J=1.0, 8.0 Hz), 8.70-8.79 (1H, m)

MS(ESI) m/z: 397 (M+H)$^+$

Example 135

(S)-5-Fluoro-2-(2-methylpiperazin-1-yl)-7-(thiazol-2-yl)-4-(trifluoromethoxy)benzoxazole The title compound was obtained in a similar manner as in Example 134 except that 2-(tributylstannyl)thiazole was used instead of 2-(tributylstannyl)pyridine.

$^1$H-NMR (400 MHz, CDCl$_3$) δ: 1.46 (3H, d, J=6.8 Hz), 2.85-3.00 (2H, m), 3.06-3.20 (2H, m), 3.46 (1H, dt, J=3.6, 12.6 Hz), 4.11(1H, td, J=1.8, 11.4 Hz), 4.44-4.59 (1H, m), 7.50 (1H, d, J=3.3 Hz), 7.66 (1H, d, J=11.6 Hz), 7.97 (1H, d, J=3.3 Hz)

MS(ESI) m/z: 403 (M+H)$^+$

Example 136

(S)-5-Fluoro-2-(2-methylpiperazin-1-yl)-7-(1H-pyrazol-1-yl)-4-(trifluoromethoxy)benzoxazole The title compound was obtained in a similar manner as in Examples 83(a) and 83 (b) except that (S)-1-tert-butoxycarbonyl-4-(7-bromo-5-fluoro-4-(trifluoromethoxy)benzoxazol-2-yl)-3-methylpiperazine obtained in Example 134(a) was used instead of (S)-1-tert-butoxycarbonyl-4-(7-bromo-5-chloro-4-(trifluoromethyl)benzoxazol-2-yl)-3-methylpiperazine.

¹H-NMR (400 MHz, CDCl₃) δ: 1.44 (3H, d, J=6.8 Hz), 2.82-3.00 (2H, m), 3.05-3.17 (2H, m), 3.44 (1H, dt, J=3.5, 12.7 Hz), 4.04 (1H, dd, J=2.0, 13.0 Hz), 4.38-4.54 (1H, m), 6.54 (1H, dd, J=1.8, 2.5 Hz), 7.47 (1H, d, J=11.9 Hz), 7.77 (1H, d, J=1.7 Hz), 8.17 (1H, d, J=2.6 Hz)

MS(ESI) m/z: 386 (M+H)⁺

Example 137

(S)-5-Chloro-6-methyl-2-(2-methylpiperazin-1-yl)-7-(pyridin-2-yl)benzoxazole (a) (S)-1-tert-Butoxycarbonyl-4-(7-bromo-5-chloro-6-methylbenzoxazol-2-yl)-3-methylpiperazine The title compound was obtained in a similar manner as in Example 16(a) except that 7-bromo-5-chloro-2-mercapto-6-methylbenzoxazole obtained in Reference Example 26 was used instead of 7-bromo-5-chloro-2-mercaptobenzoxazole.

(b) (S)-1-tert-Butoxycarbonyl-4-(5-chloro-6-methyl-7-(pyridin-2-yl)benzoxazol-2-yl)-3-methylpiperazine The title compound was obtained in a similar manner as in Example 102(b) except that (S)-1-tert-butoxycarbonyl-4-(7-bromo-5-chloro-6-methylbenzoxazol-2-yl)-3-methylpiperazine obtained in Example 137(a) was used instead of (S)-1-tert-butoxycarbonyl-4-(7-bromo-5-fluorobenzoxazol-2-yl)-3-methylpiperazine.

(c) (S)-5-Chloro-6-methyl-2-(2-methylpiperazin-1-yl)-7-(pyridin-2-yl)benzoxazole The title compound was obtained in a similar manner as in Example 16(c) except that (S)-1-tert-butoxycarbonyl-4-(5-chloro-6-methyl-7-(pyridin-2-yl)benzoxazol-2-yl)-3-methylpiperazine obtained in Example 137(b) was used instead of (S)-1-tert-butoxycarbonyl-4-(5-chloro-7-(thiophen-3-yl)benzoxazol-2-yl)-3-methylpiperazine.

¹H-NMR (400 MHz, CDCl₃) δ: 1.33 (3H, d, J=6.8 Hz), 2.30 (3H, s), 2.77-2.86 (2H, m), 3.01-3.05 (2H, m), 3.25-3.32 (1H, m), 3.79-3.82 (1H, m), 4.24-4.30 (1H, m), 7.32-7.46 (3H, m), 7.82 (1H, dt, J=1.7, 7.8 Hz), 8.77 (1H, d, J=4.9 Hz)

MS(ESI) 343 (M+H)⁺

Example 138

(S)-5-Chloro-6-methyl-2-(2-methylpiperazin-1-yl)-7-(thiazol-2-yl)benzoxazole

The title compound was obtained in a similar manner as in Example 137 except that 2-(tributylstannyl)thiazole was used instead of 2-(tributylstannyl)pyridine.

¹H-NMR (400 MHz, CDCl₃) δ: 1.38 (3H, d, J=6.8 Hz), 2.54 (s, 3H), 2.81-2.90 (2H, m), 3.04-3.08 (2H, m), 3.31-3.38 (1H, m), 3.88-3.92 (1H, m), 4.30-4.36 (1H, m), 7.42 (1H, s), 7.55 (1H, d, J=3.4 Hz), 8.01 (d, 1H, J=3.4 Hz)

MS(ESI) m/z: 349 (M+H)⁺

Example 139

(S)-5-Chloro-6-methyl-2-(2-methylpiperazin-1-yl)-7-(1H-pyrazol-1-yl)benzoxazole

The title compound was obtained in a similar manner as in Examples 83(a) and 83(b) except that (S)-1-tert-butoxycarbonyl-4-(7-bromo-5-chloro-6-methylbenzoxazol-2-yl)-3-methylpiperazine obtained in Example 137(a) was used instead of (S)-1-tert-butoxycarbonyl-4-(7-bromo-5-chloro-4-(trifluoromethyl)benzoxazol-2-yl)-3-methylpiperazine.

¹H-NMR (400 MHz, CDCl₃) δ: 1.35 (3H, d, J=6.8 Hz), 2.19 (3H, s), 2.77-2.87 (2H, m), 3.01-3.05 (2H, m), 3.27-3.34 (1H, m), 3.81-3.85 (1H, m), 4.26-4.32 (1H, m), 6.52 (1H, t, J=2.4 Hz), 7.41 (1H, s), 7.64 (1H, d, J=2.4 Hz), 7.80 (1H, d, J=1.7 Hz)

MS(ESI) m/z: 332 (M+H)⁺

Example 140

(S)-5-Chloro-6-methoxy-2-(2-methylpiperazin-1-yl)-7-(pyridin-2-yl)benzoxazole (a) (S)-1-tert-Butoxycarbonyl-4-(7-bromo-5-chloro-6-methoxybenzoxazol-2-yl)-3-methylpiperazine The title compound was obtained in a similar manner as in Example 16(a) except that 7-bromo-5-chloro-2-mercapto-6-methoxybenzoxazole obtained in Reference Example 27 was used instead of 7-bromo-5-chloro-2-mercaptobenzoxazole.

(b) (S)-1-tert-Butoxycarbonyl-4-(5-chloro-6-methoxy-7-(pyridin-2-yl)benzoxazol-2-yl)-3-methylpiperazine The title compound was obtained in a similar manner as in Example 102(b) except that (S)-1-tert-butoxycarbonyl-4-(7-bromo-5-chloro-6-methoxybenzoxazol-2-yl)-3-methylpiperazine obtained in Example 140(a) was used instead of (S)-1-tert-butoxycarbonyl-4-(7-bromo-5-fluorobenzoxazol-2-yl)-3-methylpiperazine.

(c) (S)-5-Chloro-6-methoxy-2-(2-methylpiperazin-1-yl)-7-(pyridin-2-yl)benzoxazole The title compound was obtained in a similar manner as in Example 16(c) except that (S)-1-tert-butoxycarbonyl-4-(5-chloro-6-methoxy-7-(pyridin-2-yl)benzoxazol-2-yl)-3-methylpiperazine obtained in Example 140(b) was used instead of (S)-1-tert-butoxycarbonyl-4-(5-chloro-7-(thiophen-3-yl)benzoxazol-2-yl)-3-methylpiperazine.

¹H-NMR (400 MHz, CDCl₃) δ: 1.34 (3H, d, J=6.9 Hz), 2.78-2.87 (2H, m), 2.96-3.06 (2H, m), 3.28-3.35 (1H, m), 3.58 (3H, s), 3.84-3.88 (1H, m), 4.39-4.23 (1H, m), 7.33 (1H, ddd, J=1.2, 4.9, 7.5 Hz), 7.37 (1H, s), 7.71 (1H, dt, J=1.0, 7.9 Hz), 7.82 (1H, m), 8.77 (1H, m)

MS(ESI) m/z: 359 (M+H)⁺

Example 141

(S)-5-Chloro-6-methoxy-2-(2-methylpiperazin-1-yl)-7-(thiazol-2-yl)benzoxazole

The title compound was obtained in a similar manner as in Example 140 except that 2-(tributylstannyl)thiazole was used instead of 2-(tributylstannyl)pyridine.

¹H-NMR (400 MHz, CDCl₃) δ: 1.40 (3H, d, J=6.8 Hz), 2.85-2.92 (2H, m), 3.08-3.12 (2H, m), 3.38-3.45 (1H, m), 3.89 (3H, s), 4.02-4.06 (1H, m), 4.42-4.47 (1H, m), 7.38 (1H, s), 7.52 (1H, d, J=3.3 Hz), 8.03 (d, 1H, J=3.3 Hz)
MS(ESI) m/z: 365 (M+H)⁺

Example 142

(S)-5-Chloro-6-cyano-2-(2-methylpiperazin-1-yl)-7-(thiazol-2-yl)benzoxazole (a) (S)-1-tert-Butoxycarbonyl-4-(7-bromo-5-chloro-6-cyanobenzoxazol-2-yl)-3-methylpiperazine The title compound was obtained in a similar manner as in Example 16(a) except that a mixture of 7-bromo-5-chloro-6-cyano-2-mercaptobenzoxazole and 7-bromo-5-chloro-4-cyano-2-mercaptobenzoxazole obtained in Reference Example 28 was used instead of 7-bromo-5-chloro-2-mercaptobenzoxazole.

(b) (S)-1-tert-Butoxycarbonyl-4-(5-chloro-6-cyano-7-(thiazol-2-yl)benzoxazol-2-yl)-3-methylpiperazine The title compound was obtained in a similar manner as in Example 35(a) except that (S)-1-tert-butoxycarbonyl-4-(7-bromo-5-chloro-6-cyano benzoxazol-2-yl)-3-methylpiperazine obtained in Example 142(a) was used instead of (S)-1-tert-butoxycarbonyl-4-(7-bromo-5-chlorobenzoxazol-2-yl)-3-methylpiperazine.

(c) (S)-5-Chloro-6-cyano-2-(2-methylpiperazin-1-yl)-7-(thiazol-2-yl)benzoxazole

The title compound was obtained in a similar manner as in Example 16(c) except that (S)-1-tert-butoxycathonyl-4-(5-chloro-6-cyano-7-(thiazol-2-yl)benzoxazol-2-yl)-3-methylpiperazine obtained in Example 142(b) was used instead of (S)-1-tert-butoxycarbonyl-4-(5-chloro-7-(thiophen-3-yl)benzoxazol-2-yl)-3-methylpiperazine.
¹H-NMR (400 MHz, CDCl₃) δ: 1.46 (3H, d, J=6.8 Hz), 2.86-2.97 (2H, m), 3.08-3.15 (2H, m), 3.43-3.50 (1H, m), 4.04-4.06 (1H, m), 4.44-4.49 (1H, m), 7.42 (1H, s), 7.63 (1H, d, J=3.2 Hz), 8.12 (1H, d, J=3.2 Hz)
MS(ESI) m/z: 360 (M+H)⁺

Example 143

(S)-5-Chloro-4-cyano-2-(2-methylpiperazin-1-yl)-7-(thiazol-2-yl)benzoxazole (a) (S)-1-tert-Butoxycarbonyl-4-(7-bromo-5-chloro-4-cyanobenzoxazol-2-yl)-3-methylpiperazine The title compound was obtained in a similar manner as in Example 16(a) except that a mixture of 7-bromo-5-chloro-6-cyano-2-mercaptobenzoxazole and 7-bromo-5-chloro-4-cyano-2-mercaptobenzoxazole obtained in Reference Example 28 was used instead of 7-bromo-5-chloro-2-mercaptobenzoxazole.

(b) (S)-1-tert-Butoxycarbonyl-4-(5-chloro-4-cyano-7-(thiazol-2-yl)benzoxazol-2-yl)-3-methylpiperazine The title compound was obtained in a similar manner as in Example 35(a) except that (S)-1-tert-butoxycarbonyl-4-(7-bromo-5-chloro-4-cyanobenzoxazol-2-yl)-3-methylpiperazine obtained in Example 143(a) was used instead of (S)-1-tert-butoxycarbonyl-4-(7-bromo-5-chlorobenzoxazol-2-yl)-3-methylpiperazine.

(c) (S)-5-Chloro-4-cyano-2-(2-methylpiperazin-1-yl)-7-(thiazol-2-yl)benzoxazole

The title compound was obtained in a similar manner as in Example 16(c) except that (S)-1-tert-butoxycarbonyl-4-(5-chloro-4-cyano-7-(thiazol-2-yl)benzoxazol-2-yl)-3-methylpiperazine obtained in Example 143(b) was used instead of (S)-1-tert-butoxycarbonyl-4-(5-chloro-7-(thiophen-3-yl)benzoxazol-2-yl)-3-methylpiperazine.
¹H-NMR (400 MHz, CDCl₃) δ: 1.48 (3H, d, J=6.8 Hz), 2.88-2.99 (2H, m), 3.10-3.18 (2H, m), 3.47-3.55 (1H, m), 4.14-4.18 (1H, m), 4.55-4.61 (1H, m), 7.59 (1H, d, J=3.2 Hz), 7.91 (1H, s), 8.03 (1H, d, J=3.2 Hz)
MS(ESI) m/z: 360 (M+H)⁺

Example 144

(S)-5-Fluoro-2-(2-methylpiperazin-1-yl)-7-(thiazol-2-yl)-6-(trifluoromethyl)benzoxazole (a) (S)-1-tert-Butoxycarbonyl-4-(7-bromo-5-fluoro-6-(trifluoromethyl)benzoxazol-2-yl)-3-methylpiperazine The title compound was obtained in a similar manner as in Example 16(a) except that a mixture of 7-bromo-5-fluoro-6-trifluoromethyl-2-mercaptobenzoxazole and 7-bromo-5-fluoro-4-trifluoromethyl-2-mercaptobenzoxazole obtained in Reference Example 19 was used instead of 7-bromo-5-chloro-2-mercaptobenzoxazole.

(b) (S)-1-tert-Butoxycarbonyl-4-(5-fluoro-6-trifluoromethyl-7-(thiazol-2-yl)benzoxazol-2-yl)-3-methylpiperazine The title compound was obtained in a similar manner as in Example 35(a) except that (S)-1-tert-butoxycarbonyl-4-(7-bromo-5-chloro-6-(trifluoromethyl)benzoxazol-2-yl)-3-methylpiperazine obtained in Example 144(a) was used instead of (S)-1-tert-butoxycarbonyl-4-(7-bromo-5-chlorobenzoxazol-2-yl)-3-methylpiperazine.

(c) (S)-5-Fluoro-2-(2-methylpiperazin-1-yl)-7-(thiazol-2-yl)-6-(trifluoromethyl)benzoxazole The title compound was obtained in a similar manner as in Example 16(c) except that (S)-1-tert-butoxycarbonyl-4-(5-fluoro-6-trifluoromethyl-7-(thiazol-2-yl)benzoxazol-2-yl)-3-methylpiperazine obtained in Example 144(b) was used instead of (S)-1-tert-butoxycarbonyl-4-(5-chloro-7-(thiophen-3-yl)benzoxazol-2-yl)-3-m ethylpiperazine.
¹H-NMR (400 MHz, CDCl₃) δ: 1.37 (3H, d, J=6.8 Hz), 2.77-2.89 (2H, m), 3.00-3.06 (2H, m), 3.29-3.37 (1H, m), 3.83-3.86 (1H, m), 4.28-4.34 (1H, m), 7.17 (1H, d, J=11.0 Hz), 7.59 (1H, d, J=3.4 Hz), 8.00 (d, 1H, J=3.4 Hz)
MS(ESI) m/z: 387 (M+H)⁺

Example 145

(S)-5-Chloro-2-(2-methylpiperazin-1-yl)-7-(methylsulfonyl)benzoxazole

(a) (S)-1-tert-Butoxycarbonyl-4-(5-chloro-7-(methylsulfonyl)benzoxazol-2-yl)-3-methylpiperazine Copper(I) iodide (38 mg), L-proline (46 mg), and sodium hydroxide (16 mg) were dissolved in DMSO (1.0 mL), and the resulting mixture was stirred in an oil bath at 100° C. for 5 minutes. (S)-1-tert-Butoxycarbonyl-4-(7-bromo-5-chlorobenzoxazol-2-yl)-3-methylpiperazine obtained in Example 16(a) (86 mg) and sodium methanesulfinate (41 mg) were added to the reaction mixture, and the reaction was performed by using a microwave reactor at 140° C. for 2 hours. Water was added to the reaction mixture, and the product was extracted with ethyl acetate. The organic layer was washed with a saturated saline solution and dried over anhydrous sodium sulfate, and then the solvent was distilled off under reduced pressure, and the residue was purified by silica gel column chromatography (developing solvent, hexane:ethyl acetate=2:3) to obtain 50 mg of the title compound.

(b) (S)-5-Chloro-2-(2-methylpiperazin-1-yl)-7-(methylsulfonyl)benzoxazole

The title compound was obtained in a similar manner as in Example 16(c) except that (S)-1-tert-butoxycarbonyl-4-(5-chloro-7-(methylsulfonyl)benzoxazol-2-yl)-3-methylpiperazine obtained in Example 145(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.43 (3H, d, J=6.8 Hz), 2.82-2.97 (2H, m), 3.06-3.13 (2H, m), 3.21 (3H, s), 3.36-3.49 (1H, m), 3.95-4.06 (1H, m), 4.36-4.48 (1H, m), 7.47 (1H, d, J=2.0 Hz), 7.50 (1H, d, J=2.0 Hz)

MS(ESI) in/z: 330 (M+H)$^+$

Example 146

(S)-5-Chloro-4-iodo-2-(2-methylpiperazin-1-yl)-7-(pyridin-2-yl)benzoxazole (S)-1-tert-Butoxycarbonyl-4-(5-chloro-7-(pyridin-2-yl)benzoxazol-2-yl)-3-methylpiperazine obtained in Example 41(a) (108 mg), N-iodosuccinimide (56 mg), and acetonitrile (2.0 mL) were dissolved in trifluoroacetic acid (11 mL), and the resulting mixture was stirred in an oil bath at 70° C. for 7 hours. Water was added to the reaction mixture, the product was extracted with ethyl acetate and then dried over anhydrous sodium sulfate, and the solvent was distilled off under reduced pressure. The obtained residue was dissolved in chloroform (2 mL), trifluoroacetic acid (1 mL) was added thereto, and the resulting mixture was stirred at room temperature for 1 hour. An aqueous solution of saturated sodium hydrogencarbonate was added to the reaction mixture, the product was extracted with a mixed solution of chloroform and methanol and then dried over anhydrous sodium sulfate, the solvent was distilled off under reduced pressure, and the residue was purified by fractional HPLC (for acetonitrile:water=from 1:3 to 3:1) to obtain 11 mg of the title compound.

$^1$H-NMR (500 MHz, CDCl$_3$) δ: 1.44 (3H, d, J=7.0 Hz), 2.87-2.95 (2H, m), 3.10-3.13 (2H, m), 3.42-3.48 (1H, m), 4.06-4.09 (1H, m), 4.47-4.49 (1H, m), 7.28-7.31 (1H, m), 7.79-7.83 (1H, m), 7.96 (1H, d, J=8.0 Hz), 8.00 (1H, s), 8.74 (1H, d, J=4.0 Hz)

MS(ESI) m/z: 455 (M+H)$^+$

Example 147

(S)-5-Chloro-6-iodo-2-(2-methylpiperazin-1-yl)-7-(pyridin-2-yl)benz oxazole

In a similar manner as in Example 146, all the reagents and the solvents were reacted in an amount of 3 times, and as a result, 104 mg of the title compound, i.e., a positional isomer of the compound obtained in Example 146 was obtained.

$^1$H-NMR (400 MHz, CDCl$_3$) δ: 1.32 (3H, d, J=6.8 Hz), 2.71-2.88 (2H, m), 2.95-3.06 (2H, m), 3.21-3.34 (1H, m), 3.78 (1H, dd, J=1.9 Hz, 13.0 Hz), 4.20-4.32 (1H, m), 7.38 (1H, ddd, J=7.6, 4.9, 1.2 Hz), 7.42-7.46 (1H, m), 7.50 (1H, s), 7.80-7.89 (1H, m), 8.74-8.79 (1H, m)

MS(ESI) m/z: 455 (M+H)$^+$

Example 148

(S)-5-Chloro-2-(2-methylpiperazin-1-yl)-4-phenyl-7-(pyridin-2-yl)benzoxazole

(a) (S)-1-tert-Butoxycarbonyl-4-(5-chloro-4-iodo-7-(pyridin-2-yl)benzoxazol-2-yl)-3-methylpiperazine (S)-5-Chloro-4-iodo-2-(2-methylpiperazin-1-yl)-7-(pyridin-2-yl)benz oxazole obtained in Example 146 (103 mg), di-tert-butyl dicarbonate (42.6 mg), and sodium hydrogencarbonate (21.8 mg) were dissolved in water (2 mL) and 1,4-dioxane (2 mL), and the resulting mixture was stirred at room temperature for 14 hours. Water was added to the reaction mixture, the product was extracted with ethyl acetate, then the organic layer was washed with a saturated saline solution and dried over anhydrous sodium sulfate, and then the solvent was distilled off under reduced pressure to obtain 51 mg of the title compound as a crude product.

(b) (S)-1-tert-Butoxycarbonyl-4-(5-chloro-4-phenyl-7-(pyridin-2-yl)benzoxazol-2-yl)-3-methylpiperazine The title compound was obtained in a similar manner as in Example 27(b) except that (S)-1-tert-butoxycarbonyl-4-(5-chloro-4-iodo-7-(pyridin-2-yl)benzoxazol-2-yl)-3-methylpiperazine obtained in Example 148(a) was used instead of (S)-1-tert-butoxycarbonyl-(7-bromo-5-chlorobenzoxazol-2-yl)-3-methylpiperazine and that phenylboronic acid was used instead of cyclopropyl boronic acid.

(c) (S)-5-Chloro-2-(2-methylpiperazin-1-yl)-4-phenyl-7-(pyridin-2-yl)benzoxazole The title compound was obtained in a similar manner as in Example 16(c) except that (S)-1-tert-butoxycarbonyl-4-(5-chloro-4-phenyl-7-(pyridin-2-yl)benzoxazol-2-yl)-3-methylpiperazine obtained in Example 148(b) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.39 (3H, d, J=6.8 Hz), 2.81-2.97 (2H, m), 3.04-3.15 (2H, m), 3.32-3.47 (1H, m), 3.95-4.07 (1H, m), 4.36-4.48 (1H, m), 7.29 (1H, ddd, J=7.5, 4.8, 1.1 Hz), 7.36-7.43 (1H, m), 7.44-7.52 (2H, m), 7.59-7.66 (2H, m), 7.79-7.87 (1H, m), 8.00 (1H, s), 8.02 (1H, m), 8.72-8.80 (1H, m)
MS(ESI) m/z: 405 (M+H)+

Example 149

(S)-5-Chloro-4-cyclopropyl-2-(2-methylpiperazin-1-yl)-7-(pyridin-2-yl)benzoxazole (a) (S)-1-tert-Butoxycarbonyl-4-(5-chloro-4-cyclopropyl-7-(pyridin-2-yl)benzoxazol-2-yl)-3-methylpiperazine The title compound was obtained in a similar manner as in Example 27(b) except that (S)-1-tert-butoxycarbonyl-4-(5-chloro-4-iodo-7-(pyridin-2-yl)benzoxazol-2-yl)-3-methylpiperazine obtained in Example 148(a) was used instead of (S)-1-tert-butoxycarbonyl-(7-bromo-5-chlorobenzoxazol-2-yl)-3-methylpiperazine.

(b) (S)-5-Chloro-2-(2-methylpiperazin-1-yl)-4-cyclopropyl-7-(pyridin-2-yl)benzoxazole The title compound was obtained in a similar manner as in Example 16(c) except that (S)-1-tert-butoxycarbonyl-4-(5-chloro-4-cyclopropyl-7-(pyridin-2-yl)benzoxazol-2-yl)-3-methylpiperazine obtained in Example 149(a) was used instead of (S)-1-tert-butoxycarbonyl-4-(5-chloro-7-(thiophen-3-yl)benzoxazol-2-yl)-3-methylpiperazine
$^1$H-NMR (400 MHz, CDCl$_3$) δ: 1.00-1.11 (2H, m), 1.47-1.60 (5H, m), 2.23-2.38 (1H, m), 3.04-3.18 (1H, m), 3.20-3.38 (2H, m), 3.40-3.52 (1H, m), 3.62-3.77(114, m), 4.15-4.27 (1H, m), 4.60-4.74(114, m), 7.23-7.31 (1H, m), 7.75-7.83 (1H, m), 7.84-7.91 (2H, m), 8.70-8.78 (1H, m)
MS(ESI) m/z: 369 (M+H)+

Example 150

(S)-5-Chloro-2-(2-methylpiperazin-1-yl)-4-(methylthio)-7-(pyridin-2-yl)benzoxazole (a) (S)-1-tert-Butoxycarbonyl-4-(7-bromo-5-chloro-4-(methylthio)benzoxazol-2-yl)-3-methylpiperazine (S)-1-tert-Butoxycarbonyl-(7-bromo-5-chlorobenzoxazol-2-yl)-3-methylpiperazine obtained in Example 16(a) (430 mg) was dissolved in THF (1.0 mL), a solution of 2,2,6,6-tetramethylpiperidinyl-magnesium chloride-lithium chloride complex (1.0 M, THY/toluene solution, 1.2 mL) was added thereto, the resulting mixture was stirred at −55° C. for 2 hours, then S-methyl methanethiosulfonate (113 μL) was added thereto, and the resulting mixture was further stirred at −20° C. for 2 hours. A saturated aqueous solution of ammonium chloride was added to the reaction mixture, the product was extracted with ethyl acetate and then dried over anhydrous sodium sulfate, and the solvent was distilled off under reduced pressure. The obtained residue was purified by silica gel column chromatography (developing solvent, hexane:ethyl acetate=4:1) to obtain 371 mg of the title compound as a crude product.

(b) (S)-5-Chloro-2-(2-methylpiperazin-1-yl)-4-(methylthio)-7-(pyridin-2-yl)benzoxazole The title compound was obtained in a similar manner as in Examples 41(a) and 41(b) except that (S)-1-tert-butoxycarbonyl-4-(7-bromo-5-chloro-4-(methylthio)benzoxazol-2-yl)-3-methylpiperazine obtained in Example 150(a) was used instead of (S)-1-tert-butoxycarbonyl-4-(7-bromo-5-chlorobenzoxazol-2-yl)-3-methylpiperazine.
$^1$H-NMR (400 MHz, CDCl$_3$) δ: 1.43 (3H, d, J=6.9 Hz), 2.72 (3H, s), 2.83-2.99 (2H, m), 3.03-3.19 (2H, m), 3.43 (1H, m), 4.06 (1H, dd, J=13.0, 2.0 Hz), 4.42-4.54 (1H, m), 7.26-7.28 (1H, m), 7.80 (1H, m), 7.92 (1H, s), 7.96 (1H, m), 8.71-8.77 (1H, m)
MS(ESI) m/z: 375 (M+H)+

Example 151

(S)-5-Chloro-2-(2-methylpiperazin-1-yl)-4-(methylsulfonyl)-7-(pyridin-2-yl)benzoxazole (a) (S)-1-tert-Butoxycarbonyl-4-(7-bromo-5-chloro-4-(methylsulfonyl)benzoxazol-2-yl)-3-methylpiperazine (S)-1-tert-Butoxycarbonyl-(7-bromo-5-chlorobenzoxazol-2-yl)-3-methylpiperazine obtained in Example 16(a) (430 mg) was dissolved in THF (1.0 mL), a solution of 2,2,6,6-tetramethylpiperidinyl-magnesium chloride-lithium chloride complex (1.0 M, THF/toluene solution, 1.2 mL) was added thereto, and the resulting mixture was stirred at −55° C. for 2 hours, then S-methyl methanethiosulfate (113 μL) was added thereto, and the resulting mixture was further stirred at −20° C. for 2 hours. A saturated aqueous solution of ammonium chloride was added to the reaction mixture, the product was extracted with ethyl acetate and then dried over anhydrous sodium sulfate, and the solvent was distilled off under reduced pressure. The obtained residue and m-chloroperbenzoic acid (155 mg) were dissolved in chloroform (1.0 mL), and the resulting mixture was stirred at room temperature for 2 hours. Water was added to the reaction mixture, the product was extracted with chloroform and then dried over anhydrous sodium sulfate, and the solvent was distilled off under reduced pressure. The obtained residue was purified by silica gel column chromatography (developing solvent, hexane:ethyl acetate=2:1) to obtain 97.4 mg of the title compound as a crude product.

(b) (S)-5-Chloro-2-(2-methylpiperazin-1-yl)-4-(methylsulfonyl)-7-(pyridin-2-yl)benzoxazole The title compound was obtained in a similar manner as in Examples 41(a) and 41(b) except that (S)-1-tert-butoxycarbonyl-4-(7-bromo-5-chloro-4-(methylsulfonyl)benzoxazol-2-yl)-3-methylpiperazine obtained in Example 151(a) was used instead of (S)-1-tert-butoxycarbonyl-4-(7-bromo-5-chlorobenzoxazol-2-yl)-3-methylpiperazine.
$^1$H-NMR (500 MHz, CDCl$_3$) δ: 1.53 (3H, t, J=6.9 Hz), 3.08(1H, td, J=3.8, 12.5 Hz), 3.18 (1H, d, J=12.9 Hz), 3.24-3.33 (1H, m), 3.37(1H, J=11.0H), 3.49 (3H, s), 3.63-3.74 (1H, m), 4.25 (1H, dd, J=2.1, 13.7 Hz), 4.64-4.74 (1H, m), 7.36 (1H, ddd, J=1.1, 4.9, 7.6 Hz), 7.87 (1H, dt, J=1.9, 7.7 Hz), 7.93 (1H, s), 7.95-7.99 (1H, m), 8.75-8.77 (1H, m)
MS(ESI) in/z: 407 (M+H)+

Example 152

(S)-6-Bromo-5-chloro-2-(2-methylpiperazin-1-yl)-7-(pyridin-2-yl)benzoxazole (a) (S)-1-tert-Butoxycarbonyl-4-(6-bromo-5-chloro-7-(pyridin-2-yl)benzoxazol-2-yl)-3-methylpiperazine (S)-1-tert-Butoxycarbonyl-4-(5-chloro-7-(pyridin-2-yl)benzoxazol-2-yl)-3-methylpiperazine obtained in Example 41(a) (53.5 mg) and N-bromosuccimide (22 mg) were dissolved in acetonitrile (1.0 mL), and the resulting mixture was stirred at room temperature for 3 hours. Water was added to the reaction mixture, the product was extracted with ethyl acetate and then dried over anhydrous sodium sulfate, and the solvent was distilled off under reduced pressure to obtain 65.7 mg of the title compound as a crude product.

(b) (S)-6-Bromo-5-chloro-2-(2-methylpiperazin-1-yl)-7-(pyridin-2-yl)benzoxazol

The title compound was obtained in a similar manner as in Example 16(c) except that (S)-1-tert-butoxycarbonyl-4-(6-bromo-5-chloro-7-(pyridin-2-yl)benzoxazol-2-yl)-3-methylpiperazine obtained in Example 152(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.33 (3H, d, J=6.8 Hz), 2.76-2.86 (2H, m), 3.00-3.04 (2H, m), 3.25-3.33 (1H, m), 3.78-3.82 (1H, m), 4.28-4.29 (1H, m), 7.36-7.39 (1H, m), 7.47 (1H, s), 7.51 (1H, d, J=7.6 Hz), 7.8-7.86 (1H, m), 8.77 (1H, d, J=4.4 Hz)

MS(ESI) m/z: 407 (M+H)$^+$

Example 153

(S)-5-Chloro-4-methoxy-2-(2-methylpiperazin-1-yl)-7-(pyridin-2-yl)benzoxazole (a) (S)-1-tert-Butoxycarbonyl-4-(7-bromo-5-chloro-4-hydroxybenzoxazol-2-yl)-3-methylpiperazine (S)-1-tert-Butoxycarbonyl-4-(7-bromo-5-chlorobenzoxazol-2-yl)-3-m ethylpiperazine obtained in Example 16(a) (430 mg) was dissolved in THF (1.0 mL), a solution of 2,2,6,6-tetramethylpiperidinyl-magnesium chloride-lithium chloride complex (1.0 M, THF/toluene solution, 12 mL) was added thereto, and the resulting mixture was stirred at −55° C. for 2 hours and then was further stirred in an air atmosphere at −20° C. for 2 hours. A saturated aqueous solution of ammonium chloride was added to the reaction mixture, the product was extracted with ethyl acetate and then dried over anhydrous sodium sulfate, and the solvent was distilled off under reduced pressure. The obtained residue and m-chloroperbenzoic acid (155 mg) were dissolved in chloroform (1.0 mL), and the resulting mixture was stirred at room temperature for 2 hours. Water was added to the reaction mixture, the product was extracted with chloroform and then dried over anhydrous sodium sulfate, and the solvent was distilled off under reduced pressure. The obtained residue was purified by silica gel column chromatography (developing solvent, hexane:ethyl acetate=2:1) to obtain 57 mg of the title compound as a crude product.

(b) (S)-1-tert-Butoxycarbonyl-4-(7-bromo-5-chloro-4-methoxybenzoxazol-2-yl)-3-methylpiperazine The title compound was obtained in a similar manner as in Example 107(a) except that (S)-1-tert-butoxycarbonyl-4-(7-bromo-5-chloro-4-hydroxybenzoxazol-2-yl)-3-methylpiperazine obtained in Example 153(a) was used instead of (S)-5-chloro-7-hydroxymethyl-2-(2-methylpiperazin-1-yl) benzoxazole.

(c) (S)-5-Chloro-4-methoxy-2-(2-methylpiperazin-1-yl)-7-(pyridin-2-yl)benzoxazole The title compound was obtained in a similar manner as in Examples 41(a) and 41(b) except that (S)-1-tert-butoxycarbonyl-4-(7-bromo-5-chloro-4-methoxybenzoxazol-2-yl)-3-methylpiperazine obtained in Example 153(b) was used instead of (S)-1-tert-butoxycarbonyl-4-(7-bromo-5-chlorobenzoxazol-2-yl)-3-methylpiperazine.

$^1$H-NMR (400 MHz, CDCl$_3$) δ: 1.42 (3H, d, J=6.9 Hz), 2.93-2.96 (2H, m), 3.12-3.15 (2H, m), 3.38-3.45 (1H, m), 4.02 (1H, m), 4.31 (3H, s), 4.45 (1H, m), 7.21-7.25 (1H, m), 7.78 (1H, m), 7.88 (1H, s), 7.92 (1H, m), 8.68-8.75 (1H, m)

MS(ESI) m/z: 359 (M+H)$^+$

Example 154

(S)-5-Chloro-7-methyl-2-(2-methylpiperazin-1-yl)benzoxazole

The title compound was obtained in a similar manner as in Example 2 except that 5-chloro-7-methyl-2-mercaptobenzoxazole was used instead of 5-chloro-7-methoxy-2-mercaptobenzoxazole.

MS(ESI) m/z: 266 (M+H)$^+$

Example 155

(S)-5-Chloro-4-methoxy-2-(2-methylpiperazin-1-yl)-7-(thiazol-2-yl)benzoxazole (a) (S)-1-tert-Butoxycarbonyl-4-(5-chloro-4-methoxy-7-(thiazol-2-yl)benzoxazol-2-yl)-3-methylpiperazine The title compound was obtained in a similar manner as in Example 35(a) except that (S)-1-tert-butoxycarbonyl-4-(7-bromo-5-chloro-4-methoxybenzoxazol-2-yl)-3-methylpiperazine obtained in Example 153(b) was used instead of (S)-1-tert-butoxycarbonyl-4-(7-bromo-5-chlorobenzoxazol-2-yl)-3-methylpiperazine obtained in Example 16(a).

(b) (S)-5-Chloro-4-methoxy-2-(2-methylpiperazin-1-yl)-7-(thiazol-2-yl)benzoxazole The title compound was obtained in a similar manner as in Example 16(c) except that (S)-1-tert-butoxycarbonyl-4-(5-chloro-4-methoxy-7-(thiazol-2-yl)benzoxazol-2-yl)-3-methylpiperazine obtained in Example 155(a) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.44 (3H, d, J=6.7 Hz), 2.86-2.99 (2H, m), 3.10-3.18 (2H, m), 3.47-3.55 (1H, m), 4.00-4.12 (1H, m), 4.34 (3H, s), 4.40-4.55 (1H, m), 7.41 (1H, d, J=3.3 Hz), 7.89 (1H, s), 7.91 (d, 1H, J=3.3 Hz)

MS(ESI) m/z: 365 (M+H)$^+$

Example 156

(S)-5-Chloro-4-methoxy-2-(2-methylpiperazin-1-yl)-7-(1H-pyrazol-1-yl)benzoxazole The title compound was obtained in a similar manner as in Examples 83(a) and 83(b) except that (S)-1-tert-butoxycarbonyl-4-(7-bromo-5-chloro-4-methoxybenzoxazol-2-yl)-3-methylpiperazine obtained in Example 153(b) was used instead of (S)-1-tert-butoxycarbonyl-4-(7-bromo-5-chloro-4-(trifluoromethyl)benzoxazol-2-yl)-3-methylpiperazine.

¹H-NMR (400 MHz, CDCl₃) δ: 1.43(3H, d, J=6.2 Hz), 2.86-2.99 (2H, m), 3.08-3.17 (2H, m), 3.38-3.47 (1H, m), 3.97-4.04 (1H, m), 4.24 (3H, s), 4.39-4.48 (1H, m), 6.50 (t, 1H, J=2.1 Hz), 7.59 (1H, s), 7.74 (d, 1H, J=1.4 Hz), 8.07 (d, 1H, J=2.2 Hz)

MS(ESI) m/z: 348 (M+H)⁺

Example 157

(R)-5-Chloro-2-(2-methylpiperazin-1-yl)-7-(pyridin-2-yl)-4-(trifluoromethoxy)benzoxazole (a) (R)-1-tert-Butoxycarbonyl-4-(7-bromo-5-chloro-4-(trifluoromethoxy)benzoxazol-2-yl)-3-methylpiperazine The title compound was obtained in a similar manner as in Example 16(a) except that 7-bromo-5-chloro-2-mercapto-4-(trifluoromethoxy)benzoxazole obtained in Reference Example 12 was used instead of 7-bromo-5-chloro-2-mercaptobenzoxazole obtained in Reference Example 9 and that (R)-1-tert-butoxycarbonyl-3-methylpiperazine was used instead of (S)-1-tert-butoxycarbonyl-3-methylpiperazine.

(b) (R)-1-tert-Butoxycarbonyl-4-(5-chloro-7-(pyridin-2-yl)-4-(trifluoromethoxy)benzoxazol-2-yl)-3-methylpiperazine The title compound was obtained in a similar manner as in Example 41(a) except that (R)-1-tert-butoxycarbonyl-4-(7-bromo-5-chloro-4-(trifluoromethoxy)benzoxazol-2-yl)-3-methylpiperazine obtained in Example 157(a) was used instead of (S)-1-tert-butoxycarbonyl-4-(7-bromo-5-chlorobenzoxazol-2-yl)-3-methylpiperazine.

(c) (R)-5-Chloro-2-(2-methylpiperazin-1-yl)-7-(pyridin-2-yl)-4-(trifluoromethoxy)benzoxazole The title compound was obtained in a similar manner as in Example 16(c) except that (R)-1-tert-butoxycarbonyl-4-(5-chloro-7-(pyridin-2-yl)-4-(trifluoromethoxy)benzoxazol-2-yl)-3-methylpiperazine obtained in Example 157(b) was used instead of (S)-1-tert-butoxycarbonyl-4-(5-chloro-7-(thiophen-3-yl)benzoxazol-2-yl)-3-methylpiperazine.

¹H-NMR (400 MHz, CDCl₃) δ: 1.43 (3H, d, J=6.8 Hz), 2.86-2.95 (2H, m), 3.09-3.14 (2H, m), 3.40-3.48 (1H, m), 4.03-4.06 (1H, m), 4.44-4.50 (1H, m), 7.29-7.32 (1H, m), 7.81-7.85 (1H, m), 7.93 (1H, s), 7.95-7.97 (1H, m), 8.74-8.76 (1H, m)

MS(ESI) m/z: 413 (M+H)⁺

Example 158

(R)-5-Chloro-2-(2-methylpiperazin-1-yl)-7-(thiazol-2-yl)-4-(trifluoromethoxy)benzoxazole (a) (R)-1-tert-Butoxycarbonyl-4-(5-chloro-7-(thiazol-2-yl)-4-(trifluoromethoxy)benzoxazol-2-yl)-3-methylpiperazine The title compound was obtained in a similar manner as in Example 35(a) except that (R)-1-tert-butoxycarbonyl-4-(7-bromo-5-chloro-4-(trifluoromethoxy)benzoxazol-2-yl)-3-methylpiperazine obtained in Example 157(a) was used instead of (S)-1-tert-butoxycarbonyl-4-(7-bromo-5-chlorobenzoxazol-2-yl)-3-methylpiperazine obtained in Example 16(a).

(b) (R)-5-Chloro-2-(2-methylpiperazin-1-yl)-7-(thiazol-2-yl)-4-(trifluoromethoxy)benzoxazole The title compound was obtained in a similar manner as in Example 16(c) except that (R)-1-tert-butoxycarbonyl-4-(5-chloro-7-(thiazol-2-yl)-4-(trifluoromethoxy)benzoxazol-2-yl)-3-methylpiperazine obtained in Example 158(a) was used instead of (S)-1-tert-butoxycarbonyl-4-(5-chloro-7-(thiophen-3-yl)benzoxazol-2-yl)-3-methylpiperazine.

¹H-NMR (400 MHz, CDCl₃) δ: 1.46 (3H, d, J=6.8 Hz), 2.85-3.02 (2H, m), 3.07-3.19 (2H, m), 3.43-3.50 (1H, m), 4.09-4.12 (1H, m), 4.45-4.60 (1H, m), 7.51 (1H, d, J=3.3 Hz), 7.94 (1H, s), 7.97 (1H, d, J=3.2 Hz)

MS(ESI) m/z: 419 (M+H)⁺

Example 159

(R)-5-Chloro-2-(2-methylpiperazin-1-yl)-7-(1H-pyrazol-1-yl)-4-(trifluoromethoxy)benzoxazole (a) (R)-1-tert-Butoxycarbonyl-4-(5-chloro-7-(1H-pyrazol-1-yl)-4-(trifluoromethoxy)benzoxazol-2-yl)-3-methylpiperazine The title compound was obtained in a similar manner as in Example 83(a) except that (R)-1-tert-butoxycarbonyl-4-(7-bromo-5-chloro-4-(trifluoromethoxy)benzoxazol-2-yl)-3-methylpiperazine obtained in Example 157(a) was used instead of (S)-1-tert-butoxycarbonyl-4-(7-bromo-5-chloro-4-(trifluoromethyl)benzoxazol-2-yl)-3-methylpiperazine.

(b) (R)-5-Chloro-2-(2-methylpiperazin-1-yl)-7-(1H-pyrazol-1-yl)-4-(trifluoromethoxy)benzoxazole The title compound was obtained in a similar manner as in Example 16(c) except that (R)-1-tert-butoxycarbonyl-4-(5-chloro-7-(1H-pyrazol-1-yl)-4-(trifluoromethoxy)benzoxazol-2-yl)-3-methylpiperazine obtained in Example 159(a) was used instead of (S)-1-tert-butoxycarbonyl-4-(5-chloro-7-(thiophen-3-yl)benzoxazol-2-yl)-3-methylpiperazine.

¹H-NMR (400 MHz, CDCl₃) δ: 1.44 (3H, d, J=6.8 Hz), 2.86-2.95 (2H, m), 3.08-3.14 (2H, m), 3.41-3.49 (1H, m), 4.01-4.05 (1H, m), 4.42-4.48 (1H, m), 6.54 (1H, dd, J=1.9, 2.5 Hz), 7.71 (1H, s), 7.77 (1H, d, J=1.4 Hz), 8.15 (1H, d, J=2.6 Hz)

MS(ESI) m/z: 402 (M+H)⁺

Example 160

(S)-5-Chloro-2-(2-methylpiperazin-1-yl)-7-(thiazol-2-yl)-6-(trifluoromethoxy)benzoxazole (a) (S)-1-tert-Butoxycarbonyl-4-(7-bromo-5-chloro-6-(trifluoromethoxy)benzoxazol-2-yl)-3-methylpiperazine The title compound was obtained in a similar manner as in Example 16(a) except that 7-bromo-5-chloro-2-mercapto-6-(trifluoromethoxy)benzoxazole obtained in Reference Example 29 was used instead of 7-bromo-5-chloro-2-mercaptobenzoxazole obtained in Reference Example 9.

(b) (S)-1-tert-Butoxycarbonyl-4-(5-chloro-7-(thiazol-2-yl)-6-(trifluoromethoxy)benzoxazol-2-yl)-3-methylpiperazine The title compound was obtained in a similar manner as in Example 35(a) except that (S)-1-tert-butoxycarbonyl-4-(7-bromo-5-chloro-6-(trifluoromethoxy)benzoxazol-2-yl)-3-methylpiperazine obtained in Example 160(a) was used instead of (S)-1-tert-butoxycarbonyl-4-(7-bromo-5-chlorobenzoxazol-2-yl)-3-methylpiperazine obtained in Example 16(a).

(c) (S)-5-Chloro-2-(2-methylpiperazin-1-yl)-7-(thiazol-2-yl)-6-(trifluoromethoxy)benzoxazole The title compound was obtained in a similar manner as in Example 16(c) except that (S)-1-tert-butoxycarbonyl-4-(5-chloro-7-(thiazol-2-yl)-6-(trifluoromethoxy)benzoxazol-2-yl)-3-methylpiperazine obtained in Example 160(b) was used instead of (S)-1-tert-butoxycarbonyl-4-(5-chloro-7-(thiophen-3-yl)benzoxazol-2-yl)-3-methylpiperazine.

$^1$H-NMR (400 MHz, CDCl$_3$) δ: 1.41 (3H, d, J=6.4 Hz), 2.82-2.92 (2H, m), 3.05-3.11 (2H, m), 3.36-3.43 (1H, m), 3.95-3.96 (1H, m), 4.38-4.41 (1H, m), 7.43 (1H, s), 7.59 (1H, d, J=3.2 Hz), 8.04 (1H, d, J=3.2 Hz)

MS(ESI) m/z: 419 (M+H)$^+$

Example 161

(S)-5-Chloro-6-methoxy-7-methyl-2-(2-methylpiperazin-1-yl)benzoxazole

The title compound was obtained in a similar manner as in Example 2 from 5-chloro-6-methoxy-7-methyl-2-mercaptobenzoxazole obtained in Reference Example 30 and (S)-1-tert-butoxycarbonyl-3-methylpiperazine.

$^1$H-NMR (400 MHz, CDCl$_3$) δ: 1.42 (3H, d, J=6.8 Hz), 2.37 (3H, s), 2.91 (1H, dt, J=3.6, 12.4 Hz), 3.00 (1H, d, J=12.4 Hz), 3.12 (1H, dd, J=4.4, 12.4 Hz), 3.20 (1H, d, J=12 Hz), 3.43 (1H, dt, J=3.6, 12.8 Hz), 3.71 (3H, s), 3.99-4.03 (1H, m), 4.43-4.46 (1H, m), 7.19 (1H, s)

MS(ESI) m/z: 296 (M+H)$^+$

Example 162

(S)-5-Chloro-6-hydroxy-7-methyl-2-(2-methylpiperazin-1-yl)benzoxazole (S)-5-Chloro-6-methoxy-7-methyl-2-(2-methylpiperazin-1-yl)benzoxazole obtained in Example 161 (216 mg) was dissolved in dichloromethane (8 mL), boron tribromide (a 1 M solution in dichloromethane, 2.9 mL) was added thereto at room temperature, and then the resulting mixture was stirred for 3 hours in this state. An aqueous solution of sodium hydrogencarbonate was added to the reaction mixture, and the product was extracted with ethyl acetate. The solvent was distilled off under reduced pressure to obtain 130 mg of the title compound.

$^1$H-NMR (400 MHz, CD$_3$OD) δ: 1.36 (3H, d, J=6.8 Hz), 2.31 (3H, s), 2.81 (1H, dd, J=4, 12.4 Hz), 2.90 (1H, d, J=12.4 Hz), 3.03 (1H, dd, J=4, 13.2 Hz), 3.06 (1H, d, J=7.6 Hz), 3.38-3.40 (1H, m), 3.85-3.88 (1H, m), 4.26-4.30 (1H, m), 7.03 (1H, s)

MS(ESI) m/z: 282 (M+H)$^+$

Example 163

(S)-4-Bromo-6-chloro-2-(2-methylpiperazin-1-yl)benzoxazole

The title compound was obtained in a similar manner as in Example 2 from 4-bromo-6-chloro-2-mercaptobenzoxazole obtained in Reference Example 31 and (S)-1-tert-butoxycarbonyl-3-methylpiperazine.

MS(ESI) m/z: 330 (M+H)$^+$

Example 164

(S)-6-Chloro-4-(furan-2-yl)-2-(2-methylpiperazin-1-yl)benzoxazole (a) (S)-1-tert-Butoxycarbonyl-4-(4-bromo-6-chlorobenzoxazol-2-yl)-3-methylpiperazine The title compound was obtained in a similar manner as in Example 16(a) except that 4-bromo-6-chloro-2-mercaptobenzoxazole obtained in Reference Example 31 was used instead of 7-bromo-5-chloro-2-mercaptobenzoxazole.

(b) (S)-6-Chloro-4-(furan-2-yl)-2-(2-methylpiperazin-1-yl)benzoxazole

The title compound was obtained in a similar manner as in Examples 23(a) and 23(b) except that (S)-1-tert-butoxycarbonyl-4-(4-bromo-6-chlorobenzoxazol-2-yl)-3-methylpiperazine obtained in Example 164(a) was used instead of (S)-1-tert-butoxycarbonyl-(7-bromo-5-chlorobenzoxazol-2-yl)-3-methylpiperazine obtained in Example 16(a).

$^1$H-NMR (400 MHz, CDCl$_3$) δ: 1.41 (3H, d, J=6.5 Hz), 2.85-2.93 (2H, m), 3.08-3.13 (2H, m), 3.36-3.43 (1H, m), 4.03-4.07 (1H, m), 4.41-4.47 (1H, m), 6.54 (1H, dd, J=2.0, 3.4 Hz), 7.13 (1H, d, J=2.0 Hz), 7.36 (1H, d, J=3.4 Hz), 7.49 (1H, d, J=1.7 Hz), 7.60 (1H, d, J=2.0 Hz)

MS(ESI) m/z: 318 (M+H)$^+$

Example 165

(R)-6-Chloro-4-(furan-2-yl)-2-(2-methylpiperazin-1-yl)benzoxazole (a) (R)-1-tert-Butoxycarbonyl-4-(4-bromo-6-chlorobenzoxazol-2-yl)-3-methylpiperazine The title compound was obtained in a similar manner as in Example 16(a) except that 4-bromo-6-chloro-2-mercaptobenzoxazole obtained in Reference Example 31 was used instead of 7-bromo-5-chloro-2-mercaptobenzoxazole obtained in Reference Example 9 and that (R)-1-tert-butoxycarbonyl-3-methylpiperazine was used instead of (S)-1-tert-butoxycarbonyl-3-methylpiperazine.

(b) (R)-6-Chloro-4-(furan-2-yl)-2-(2-methylpiperazin-1-yl)benzoxazole

The title compound was obtained in a similar manner as in Examples 23(a) and 23(b) except that (R)-1-tert-butoxycarbonyl-4-(4-bromo-6-chlorobenzoxazol-2-yl)-3-methylpiperazine obtained in Example 165(a) was used instead of (S)-1-tert-butoxycarbonyl-(7-bromo-5-chlorobenzoxazol-2-yl)-3-methylpiperazine obtained in Example 16(a).

Example 166

(S)-6-Chloro-2-(2-methylpiperazin-1-yl)-4-(1H-pyrazol-1-yl)benzoxazole

The title compound was obtained in a similar manner as in Examples 33(a) and 33(b) except that (S)-1-tert-butoxycarbonyl-4-(4-bromo-6-chlorobenzoxazol-2-yl)-3-methylpiperazine obtained in Example 164(a) was used instead of (S)-1-tert-butoxycarbonyl-(7-bromo-5-chlorobenzoxazol-2-yl)-3-methylpiperazine obtained in Example 16(a).

$^1$H-NMR (400 MHz, CDCl$_3$) δ: 1.46 (3H, d, J=6.8 Hz), 2.91-3.03 (2H, m), 3.14-3.22 (2H, m), 3.44-3.51 (1H, m), 4.08-4.11 (1H, m), 4.48-4.54 (1H, m), 6.47 (1H, dd, J=1.7, 2.4 Hz), 7.16 (1H, d, J=2.0 Hz), 7.72 (1H, d, J=1.7 Hz), 7.95 (1H, d, J=1.7 Hz), 8.99 (1H, d, J=2.4 Hz)
MS(ESI) m/z: 318 (M+H)$^+$

Example 167

(S)-5-Bromo-2-(2-methylpiperazin-1-yl)benzoxazole

The title compound was obtained in a similar manner as in Example 2 from 4-bromo-2-mercaptobenzoxazole obtained in Reference Example 32 and (S)-1-tert-butoxycarbonyl-3-methylpiperazine $^1$H-NMR (400 MHz, CDCl$_3$) δ: 1.39 (3H, d, J=6.8 Hz), 2.83-2.93 (2H, m), 3.06-3.11 (2H, m), 3.36 (1H, dt, J=3.6, 12.4 Hz), 3.95-3.98 (1H, m), 4.47-4.40 (1H, m), 7.08-7.11 (2H, m), 7.45 (1H, s)
MS(ESI) m/z: 296 (M+H)$^+$

Example 168

(S)-5-Cyano-7-methoxy-2-(2-methylpiperazin-1-yl)benzoxazole

The title compound was obtained in a similar manner as in Example 2 from 5-cyano-6-methoxy-2-mercaptobenzoxazole obtained in Reference Example 33 and (S)-1-tert-butoxycarbonyl-3-methylpiperazine.

$^1$H-NMR (400 MHz, CDCl$_3$) δ: 1.40 (3H, d, J=6.8 Hz), 2.83-2.93 (2H, m), 3.06-3.12 (2H, m), 3.39 (1H, dt, J=3.6, 12.4 Hz), 3.98 (3H, s), 4.00-4.02 (1H, m), 4.39-4.45 (1H, m), 6.88 (1H, s), 7.28 (1H, s)
MS(ESI) m/z: 273 (M+H)$^+$

Example 169

(S)-5-Chloro-6,7-dimethoxy-2-(2-methylpiperazin-1-yl)benzoxazole

The title compound was obtained in a similar manner as in Example 2 from 5-chloro-6,7-dimethoxy-2-mercaptobenzoxazole obtained in Reference Example 34 and (S)-1-tert-butoxycarbonyl-3-methylpiperazine.

$^1$H-NMR (400 MHz, CDCl$_3$) δ: 1.42 (3H, d, J=6.8 Hz), 2.92 (1H, dt, J=4, 12.8 Hz), 3.03 (1H, d, J=12.8 Hz), 3.13 (1H, dd, J=4.4, 12.8 Hz), 3.22 (1H, d, J=12.4 Hz), 3.45 (1H, dt, J=4, 12.8 Hz), 3.86 (3H, s), 3.98-4.02 (1H, m), 4.15 (3H, s), 4.42-4.45 (1H, m), 7.04 (1H, s)
MS(ESI) m/z: 312 (M+H)$^+$

Example 170

(S)-5-Chloro-6-methyl-2-(2-methylpiperazin-1-yl)benzoxazole

The title compound was obtained in a similar manner as in Example 2 from 5-chloro-6-methyl-2-mercaptobenzoxazole obtained in Reference Example 35 and (S)-1-tert-butoxycarbonyl-3-methylpiperazine.
MS(ESI) m/z: 266 (M+H)$^+$

Example 171

(S)-5-Chloro-6-methoxy-2-(2-methylpiperazin-1-yl)benzoxazole

The title compound was obtained in a similar manner as in Example 2 from 5-chloro-6-methoxy-2-mercaptobenzoxazole obtained in Reference Example 36 and (S)-1-tert-butoxycarbonyl-3-methylpiperazine.
MS(ESI) m/z: 282 (M+H)$^+$

Example 172

(S)-7-Methyl-5-(pyrrolidin-1-yl)-2-(2-methylpiperazin-1-yl)benzoxazole (a) (S)-1-tert-Butoxycarbonyl-4-(5-bromo-7-methylbenzoxazol-2-yl)-3-methylpiperazine The title compound was obtained in a similar manner as in Example 16(a) except that 5-bromo-7-methyl-2-mercaptobenzoxazole obtained in Reference Example 5 was used instead of 7-bromo-5-chloro-2-mercaptobenzoxazole.

(b) (S)-7-Methyl-5-(pyrrolidin-1-yl)-2-(2-methylpiperazin-1-yl)benzoxazole

The title compound was obtained in a similar manner as in Examples 20(a) and 20(b) except that (S)-1-tert-butoxycarbonyl-4-(5-bromo-7-methylbenzoxazol-2-yl)-3-methylpiperazine obtained in Example 172(a) was used instead of (S)-1-tert-Butoxycarbonyl-(7-bromo-5-chlorobenzoxazol-2-yl)-3-methylpiperazine obtained in Example 16(a).
MS(ESI) m/z: 301 (M+H)$^+$

Example 173

(S)-7-Methyl-5-(thiophen-3-yl)-2-(2-methylpiperazin-1-yl)benzoxazole

The title compound was obtained in a similar manner as in Examples 16(b) and 16(c) except that (S)-1-tert-butoxycarbonyl-4-(5-bromo-7-methylbenzoxazol-2-yl)-3-methylpiperazine obtained in Example 172(a) was used instead of (S)-1-tert-Butoxycarbonyl-(7-bromo-5-chlorobenzoxazol-2-yl)-3-methylpiperazine obtained in Example 16(a).
MS(ESI) m/z: 314 (M+H)$^+$

Example 174

(R)-5-Chloro-7-ethyl-2-(2-methylpiperazin-1-yl)benzoxazole

The title compound was obtained in a similar manner as in Example 2 from 5-chloro-7-ethyl-2-mercaptobenzoxazole obtained in Reference Example 7 and (R)-1-tert-butoxycarbonyl-3-methylpiperazine.

¹H-NMR (400 MHz, CDCl₃) δ: 1.30 (3H, t, J=7.7 Hz), 1.57 (3H, d, J=7.1 Hz), 2.77 (2H, q, J=7.7 Hz), 3.02-3.11 (1H, m), 3.20-3.30 (2H, m), 3.39-3.47 (1H, m), 3.62-3.71 (1H, m), 4.15-4.22 (1H, m), 4.62-4.70 (1H, m), 6.89 (1H, d, J=2.0 Hz), 7.19 (1H, d, J=2.0 Hz)

MS(ESI) m/z: 280 (M+H)⁺

Example 175

5-Chloro-2-(piperazin-1-yl)-7-(thiazol-2-yl)-4-(trifluoromethoxy)benzoxazole (a) 1-tert-Butoxycarbonyl-4-(7-bromo-5-chloro-4-(trifluoromethoxy)benzoxazol-2-yl)piperazine The title compound was obtained in a similar manner as in Example 16(a) except that 7-bromo-5-chloro-2-mercapto-4-(trifluoromethoxy)benzoxazole obtained in Reference Example 12 was used instead of 7-bromo-5-chloro-2-mercaptobenzoxazole obtained in Reference Example 9 and that 1-tert-butoxycarbonylpiperazine was used instead of (S)-1-tert-butoxycarbonyl-3-methylpiperazine.

(b) 1-tert-Butoxycarbonyl-4-(5-chloro-7-(thiazol-2-yl)-4-(trifluoromethoxy)benzoxazol-2-yl)piperazine The title compound was obtained in a similar manner as in Example 35(a) except that 1-tert-butoxycarbonyl-4-(7-bromo-5-chloro-4-(trifluoromethoxy)benzoxazol-2-yl)piperazine obtained in Example 175(a) was used instead of (S)-1-tert-butoxycarbonyl-4-(7-bromo-5-chlorobenzoxazol-2-yl)-3-methylpiperazine obtained in Example 16(a).

(c) 5-Chloro-2-(piperazin-1-yl)-7-(thiazol-2-yl)-4-(trifluoromethoxy)benzoxazole The title compound was obtained in a similar manner as in Example 16(c) except that 1-tert-butoxycarbonyl-4-(5-chloro-7-(thiazol-2-yl)-4-(trifluoromethoxy)benzoxazol-2-yl)piperazine obtained in Example 175(b) was used instead of (S)-1-tert-butoxycarbonyl-4-(5-chloro-7-(thiophen-3-yl)benzoxazol-2-yl)-3-methylpiperazine.

¹H-NMR (400 MHz, CDCl₃) δ: 2.99-3.08 (4H, m), 3.76-3.85 (4H, m), 7.51 (1H, d, J=3.3 Hz), 7.94 (1H, s), 7.97 (1H, d, J=3.2 Hz)

MS(ESI) m/z: 405 (M+H)⁺

Example 176

(R)-5-Chloro-2-(3-methylpiperazin-1-yl)-7-(thiazol-2-yl)-4-(trifluoromethoxy)benzoxazole (a) (R)-1-tert-Butoxycarbonyl-4-(7-bromo-5-chloro-4-(trifluoromethoxy)benzoxazol-2-yl)-2-methylpiperazine The title compound was obtained in a similar manner as in Example 16(a) except that 7-bromo-5-chloro-2-mercapto-4-(trifluoromethoxy)benzoxazole obtained in Reference Example 12 was used instead of 7-bromo-5-chloro-2-mercaptobenzoxazole obtained in Reference Example 9 and that (R)-1-tert-butoxycarbonyl-2-methylpiperazine was used instead of (S)-1-tert-butoxycarbonyl-3-methylpiperazine.

(b) (R)-1-tert-Butoxycarbonyl-4-(5-chloro-7-(thiazol-2-yl)-4-(trifluoromethoxy)benzoxazol-2-yl)-2-methylpiperazine The title compound was obtained in a similar manner as in Example 35(a) except that (R)-1-tert-butoxycarbonyl-4-(7-bromo-5-chloro-4-(trifluoromethoxy)benzoxazol-2-yl)-2-methylpiperazine obtained in Example 176(a) was used instead of (S)-1-tert-butoxycarbonyl-4-(7-bromo-5-chlorobenzoxazol-2-yl)-3-methylpiperazine obtained in Example 16(a).

(c) (R)-5-Chloro-2-(3-methylpiperazin-1-yl)-7-(thiazol-2-yl)-4-(trifluoromethoxy)benzoxazole The title compound was obtained in a similar manner as in Example 16(c) except that (R)-1-tert-butoxycarbonyl-4-(5-chloro-7-(thiazol-2-yl)-4-(trifluoromethoxy)benzoxazol-2-yl)-2-methylpiperazine obtained in Example 176(b) was used instead of (S)-1-tert-butoxycarbonyl-4-(5-chloro-7-(thiophen-3-yl)benzoxazol-2-yl)-3-methylpiperazine.

¹H-NMR (400 MHz, CDCl₃) δ: 1.19 (3H, d, J=6.1 Hz), 2.83-2.92 (1H, m), 2.92-3.05 (2H, m), 3.12-3.20 (1H, m), 3.26 (1H, dt, J=3.3, 12.3 Hz), 4.18-4.32 (2H, m), 7.51 (1H, d, J=3.3 Hz), 7.94 (1H, s), 7.97 (1H, d, J=3.2 Hz)

MS(ESI) m/z: 419 (M+H)⁺

Example 177

(S)-5-Chloro-2-(3-methylpiperazin-1-yl)-7-(thiazol-2-yl)-4-(trifluoromethoxy)benzoxazole (a) (S)-1-tert-Butoxycarbonyl-4-(7-bromo-5-chloro-4-(trifluoromethoxy)benzoxazol-2-yl)-2-methylpiperazine The title compound was obtained in a similar manner as in Example 16(a) except that 7-bromo-5-chloro-2-mercapto-4-(trifluoromethoxy)benzoxazole obtained in Reference Example 12 was used instead of 7-bromo-5-chloro-2-mercaptobenzoxazole obtained in Reference Example 9 and that (S)-1-tert-butoxycarbonyl-2-methylpiperazine was used instead of (S)-1-tert-butoxycarbonyl-3-methylpiperazine.

(b) (S)-1-tert-Butoxycarbonyl-4-(5-chloro-7-(thiazol-2-yl)-4-(trifluoromethoxy)benzoxazol-2-yl)-2-methylpiperazine The title compound was obtained in a similar manner as in Example 35(a) except that (S)-1-tert-butoxycarbonyl-4-(7-bromo-5-chloro-4-(trifluoromethoxy)benzoxazol-2-yl)-2-methylpiperazine obtained in Example 177(a) was used instead of (S)-1-tert-butoxycarbonyl-4-(7-bromo-5-chlorobenzoxazol-2-yl)-3-methylpiperazine obtained in Example 16(a).

(c) (S)-5-Chloro-2-(3-methylpiperazin-1-yl)-7-(thiazol-2-yl)-4-(trifluoromethoxy)benzoxazole The title compound was obtained in a similar manner as in Example 16(c) except that (S)-1-tert-butoxycarbonyl-4-(5-chloro-7-(thiazol-2-yl)-4-(trifluoromethoxy)benzoxazol-2-yl)-2-methylpiperazine obtained in Example 177(b) was used instead of (S)-1-tert-butoxycarbonyl-4-(5-chloro-7-(thiophen-3-yl)benzoxazol-2-yl)-3-methylpiperazine.

¹H-NMR (400 MHz, CDCl₃) δ: 1.19 (3H, d, J=6.1 Hz), 2.83-2.92 (1H, m), 2.92-3.06 (2H, m), 3.12-3.19 (1H, m), 3.26 (1H, dt, J=3.3, 12.3 Hz), 4.18-4.33 (2H, m), 7.51 (1H, d, J=3.3 Hz), 7.94 (1H, s), 7.98 (1H, d, J=3.2 Hz)
MS(ESI) m/z: 419 (M+H)+

Example 178

(R)-5-Chloro-2-(2-methylpiperazin-1-yl)-7-(pyridin-2-yl)-4-(trifluoromethyl)benzoxazole (a) (R)-1-tert-Butoxycarbonyl-4-(7-bromo-5-chloro-4-(trifluoromethyl)benzoxazol-2-yl)-3-methylpiperazine The title compound was obtained in a similar manner as in Example 16(a) except that 7-bromo-5-chloro-2-mercapto-4-(trifluoromethyl)benzoxazole obtained in Reference Example 10 was used instead of 7-bromo-5-chloro-2-mercaptobenzoxazole and that (R)-1-tert-butoxycarbonyl-3-methylpiperazine was used instead of (S)-1-tert-butoxycarbonyl-3-methylpiperazine.

(b) (R)-1-tert-Butoxycarbonyl-4-(5-chloro-7-(pyridin-2-yl)-4-(trifluoromethyl)benzoxazol-2-yl)-3-methylpiperazine The title compound was obtained in a similar manner as in Example 41(a) except that (R)-1-tert-butoxycarbonyl-4-(7-bromo-5-chloro-4-(trifluoromethyl)benzoxazol-2-yl)-3-methylpiperazine obtained in Example 178(a) was used instead of (S)-1-tert-butoxycarbonyl-4-(7-bromo-5-chlorobenzoxazol-2-yl)-3-methylpiperazine.

(c) (S)-5-Chloro-2-(2-methylpiperazin-1-yl)-7-(pyridin-2-yl)-4-(trifluoromethyl)benzoxazole The title compound was obtained in a similar manner as in Example 16(c) except that (R)-1-tert-butoxycarbonyl-4-(5-chloro-7-(pyridin-2-yl)-4-(trifluoromethyl)benzoxazol-2-yl)-3-methylpiperazine obtained in Example 178(b) was used instead of (S)-1-tert-butoxycarbonyl-4-(5-chloro-7-(thiophen-3-yl)benzoxazol-2-yl)-3-methylpiperazine.
$^1$H-NMR (400 MHz, CDCl$_3$) δ: 1.44 (3H, d, J=6.8 Hz), 2.86-2.95 (2H, m), 3.09-3.15 (2H, m), 3.42-3.50 (1H, m), 4.06-4.10 (1H, m), 4.46-4.51 (1H, m), 7.32-7.36 (1H, m), 7.83-7.87 (1H, m), 7.94 (1H, s), 7.99-8.01 (1H, m), 8.76-8.78 (1H, m)
MS(ESI) m/z: 397 (M+H)+

Example 179

(R)-5-Chloro-2-(2-methylpiperazin-1-yl)-7-(thiazol-2-yl)-4-(trifluoromethyl)benzoxazole (a) (S)-1-tert-Butoxycarbonyl-4-(5-chloro-7-(thiazol-2-yl)-4-(trifluoromethyl)benzoxazol-2-yl)-3-methylpiperazine (R)-1-tert-Butoxycarbonyl-4-(7-bromo-5-chloro-4-(trifluoromethyl)benzoxazol-2-yl)-3-methylpiperazine obtained in Example 178(a) (100 mg, 0.2 mmol), 2-thiazolyl zinc bromide (0.8 mL, 2.0 equivalents, a 0.5 M solution in THF), [1,1'-bis(diphenylphosphino)ferrocene]palladium(II) dichloride dichloromethane adduct (16 mg, 0.1 equivalents) were dissolved in toluene (1.4 mL), and the resulting mixture was stirred in an oil bath at 85° C. for 2.5 hours. Ethyl acetate was added to the reaction mixture, and the resulting mixture was washed with an aqueous solution of ammonium chloride and a saturated saline solution. The organic layer was dried over anhydrous sodium sulfate, then the solvent was distilled off under reduced pressure, and the residue was purified by silica gel column chromatography (developing solvent, hexane:ethyl acetate=7:3) to obtain 85 mg of the title compound.
MS(ESI) m/z: 503 (M+H)+

(b) (R)-5-Chloro-2-(2-methylpiperazin-1-yl)-7-(thiazol-2-yl)-4-(trifluoromethyl)benzoxazole The title compound was obtained in a similar manner as in Example 16(c) except that (R)-1-tert-butoxycarbonyl-4-(5-chloro-7-(thiazol-2-yl)-4-(trifluoromethyl)benzoxazol-2-yl)-3-methylpiperazine obtained in Example 179(a) was used instead of (S)-1-tert-butoxycarbonyl-4-(5-chloro-7-(thiophen-3-yl)benzoxazol-2-yl)-3-methylpiperazine.
$^1$H-NMR (400 MHz, CDCl$_3$) δ: 1.47 (3H, d, J=6.8 Hz), 2.88-2.97 (2H, m), 3.10-3.16 (2H, m), 3.45-3.52 (1H, m), 4.13-4.16 (1H, m), 4.51-4.57 (1H, m), 7.56 (1H, d, J=3.3 Hz), 7.95 (1H, s), 8.01 (1H, d, J=3.2 Hz)
MS(ESI) m/z: 403 (M+H)+

Example 180

(R)-5-Chloro-2-(2-methylpiperazin-1-yl)=7-(1H-pyrazol-1-yl)-4-(trifluoromethyl)benzoxazole (a) (R)-1-tert-Butoxycarbonyl-4-(5-chloro-7-(1H-pyrazol-1-yl)-4-(trifluoromethyl)benzoxazol-2-yl)-3-methylpiperazine The title compound was obtained in a similar manner as in Example 45(a) except that (R)-1-tert-butoxycarbonyl-4-(7-bromo-5-chloro-4-(trifluoromethyl)benzoxazol-2-yl)-3-methylpiperazine obtained in Example 178(a) was used instead of (S)-1-tert-butoxycarbonyl-4-(7-bromo-5-chlorobenzoxazol-2-yl)-3-methylpiperazine and that pyrazole was used instead of 1,2,3-triazole.

(b) (R)-5-Chloro-2-(2-methylpiperazin-1-yl)-7-(1H-pyrazol-1-yl)-4-(trifluoromethyl)benzoxazole The title compound was obtained in a similar manner as in Example 16(c) except that (R)-1-tert-butoxycarbonyl-4-(5-chloro-7-(1H-pyrazol-1-yl)-4-(trifluoromethyl)benzoxazol-2-yl)-3-methylpiperazine obtained in Example 180(a) was used instead of (S)-1-tert-butoxycarbonyl-4-(5-chloro-7-(thiophen-3-yl)benzoxazol-2-yl)-3-methylpiperazine.
$^1$H-NMR (400 MHz, CDCl$_3$) δ: 1.45 (3H, d, J=6.9 Hz), 2.86-2.96 (2H, m), 3.08-3.15 (2H, m), 3.43-3.51 (1H, m), 4.05-4.09 (1H, m), 4.44-4.50 (1H, m), 6.56 (1H, dd, J=1.8, 2.4 Hz), 7.78 (1H, s), 7.79 (1H, d, J=1.5 Hz), 8.22 (1H, d, J=2.2 Hz)
MS(ESI) m/z: 386 (M+H)+

In the following description, Table 1 and Table 2 illustrate the compounds of Reference Examples, and Table 3 to Table 11 illustrate the compounds of Examples.

TABLE 1

| Reference Example | |
|---|---|
| 1 | Cl-benzoxazole-SH with isopropyl |

TABLE 1-continued
| Reference Example | |
|---|---|
| 2 | 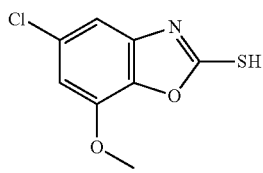 |
| 3 | 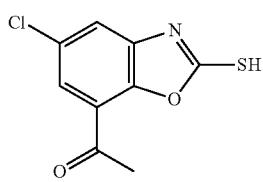 |
| 4 | 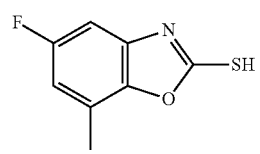 |
| 5 | 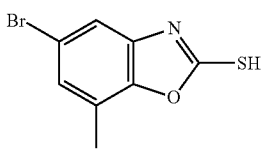 |
| 6 | 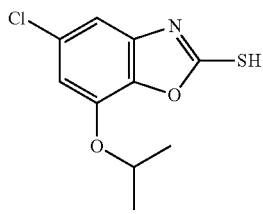 |
| 7 | 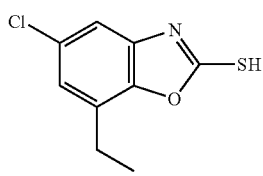 |
| 8 | 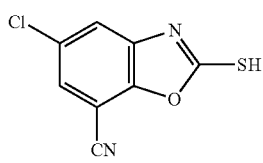 |
| 9 | 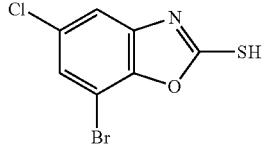 |
TABLE 1-continued
| Reference Example | |
|---|---|
| 10 | 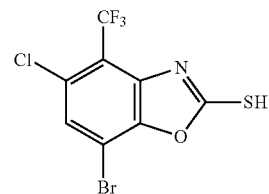 |
| 11 | 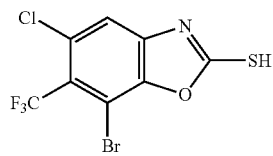 |
| 12 | 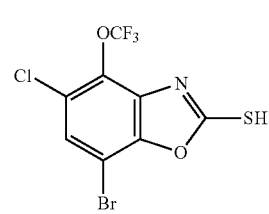 [SMILES: FC(F)(F)Oc1c(Cl)cc(Br)c2oc(S)nc12] |
| 13 | 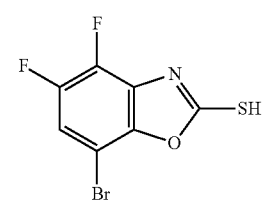 [SMILES: Fc1cc(Br)c2oc(S)nc2c1F] |
| 14 | |
| 15 | 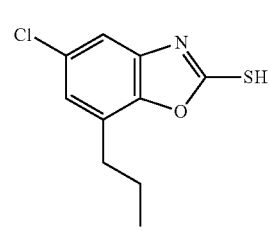 |
| 16 | 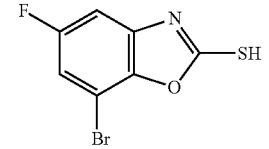 [SMILES: Fc1cc(Br)c2oc(S)nc2c1] |
| 17 |  |

TABLE 1-continued

| Reference Example | Structure |
|---|---|
| 18 | 7-bromo-5-methyl-1,3-benzoxazole-2-thiol |
| 19 | 7-bromo-5-fluoro-6-(trifluoromethyl)-1,3-benzoxazole-2-thiol |
| 20 | 7-bromo-5-chloro-4-fluoro-6-fluoro-1,3-benzoxazole-2-thiol (Cl, F, F, Br substituents) |

TABLE 2

| Reference Example | Structure |
|---|---|
| 21 | 7-bromo-4,5,6-trifluoro-1,3-benzoxazole-2-thiol |
| 22 | 7-bromo-5-(trifluoromethyl)-1,3-benzoxazole-2-thiol |
| 23 | 7-bromo-5-chloro-4-fluoro-1,3-benzoxazole-2-thiol |

TABLE 2-continued

| Reference Example | Structure |
|---|---|
| 24 | 7-bromo-5-chloro-4-methyl-1,3-benzoxazole-2-thiol |
| 25 | 7-bromo-5-fluoro-4-(trifluoromethoxy)-1,3-benzoxazole-2-thiol |
| 26 | 7-bromo-5-chloro-6-methyl-1,3-benzoxazole-2-thiol |
| 27 | 7-bromo-5-chloro-6-methoxy-1,3-benzoxazole-2-thiol |
| 28 | 7-bromo-5-chloro-6-cyano-1,3-benzoxazole-2-thiol |
| (unnumbered) | 7-bromo-5-chloro-4-cyano-1,3-benzoxazole-2-thiol |
| 29 | 7-bromo-5-chloro-6-(trifluoromethoxy)-1,3-benzoxazole-2-thiol |
| 30 | 5-chloro-6-methoxy-7-methyl-1,3-benzoxazole-2-thiol |
| 31 | 4-bromo-6-chloro-1,3-benzoxazole-2-thiol |

TABLE 2-continued

| Reference Example | Structure |
|---|---|
| 32 | 5-bromo-benzoxazole-2-thiol |
| 33 | 5-cyano-7-methoxy-benzoxazole-2-thiol |
| 34 | 5-chloro-6,7-dimethoxy-benzoxazole-2-thiol |
| 35 | 5-chloro-6-methyl-benzoxazole-2-thiol |
| 36 | 5-chloro-6-methoxy-benzoxazole-2-thiol |

TABLE 3

| Example | Structure |
|---|---|
| 1 | 5-chloro-7-isopropyl-2-((3S)-3-methylpiperazin-1-yl)benzoxazole |
| 2 | 5-chloro-7-methoxy-2-((3S)-3-methylpiperazin-1-yl)benzoxazole |
| 3 | 7-acetyl-5-chloro-2-((3S)-3-methylpiperazin-1-yl)benzoxazole |
| 4 | 5-chloro-7-methyl-2-((2S,6R)-2,6-dimethylpiperazin-1-yl)benzoxazole |
| 5 | 5-fluoro-7-methyl-2-((3S)-3-methylpiperazin-1-yl)benzoxazole |
| 6 | 5-bromo-7-methyl-2-[N-ethyl-N-(2-methylaminoethyl)amino]benzoxazole |
| 7 | 5-chloro-7-isopropoxy-2-((3S)-3-methylpiperazin-1-yl)benzoxazole |
| 8 | 5-chloro-7-ethyl-2-((3S)-3-methylpiperazin-1-yl)benzoxazole |
| 9 | 5-chloro-7-ethoxycarbonyl-2-((3S)-3-methylpiperazin-1-yl)benzoxazole |
| 10 | 5-chloro-7-cyano-2-((3S)-3-methylpiperazin-1-yl)benzoxazole |
| 11 | 5-chloro-7-ethyl-2-((3S)-3-isopropylpiperazin-1-yl)benzoxazole |
| 12 | 5-chloro-7-ethyl-2-((3S)-3-isobutylpiperazin-1-yl)benzoxazole |

TABLE 3-continued
| Example | |
|---|---|
| 13 | 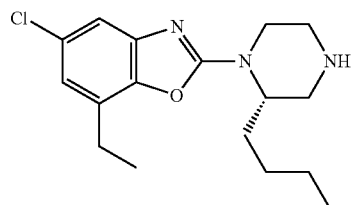 |
| 14 | 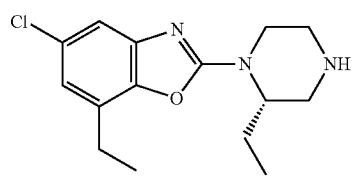 [SMILES: CCc1cc(Cl)cc2nc(N3CCNC[C@@H]3CC)oc12] |
| 15 | 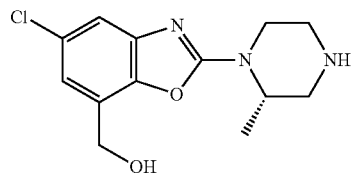 [SMILES: C[C@H]1CNCCN1c1nc2cc(Cl)cc(CO)c2o1] |
| 16 | 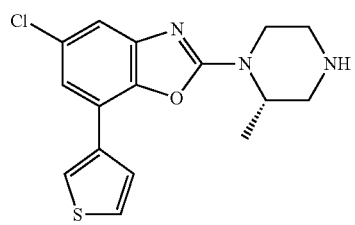 [SMILES: C[C@H]1CNCCN1c1nc2cc(Cl)cc(-c3ccsc3)c2o1] |
| 17 | 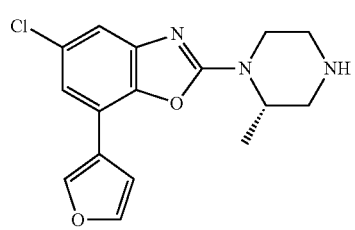 [SMILES: C[C@H]1CNCCN1c1nc2cc(Cl)cc(-c3ccoc3)c2o1] |
| 18 | 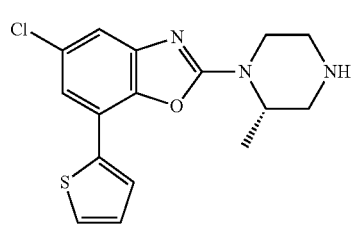 [SMILES: C[C@H]1CNCCN1c1nc2cc(Cl)cc(-c3cccs3)c2o1] |
| 19 | 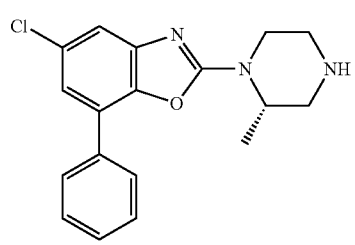 [SMILES: C[C@H]1CNCCN1c1nc2cc(Cl)cc(-c3ccccc3)c2o1] |
TABLE 3-continued
| Example | |
|---|---|
| 20 | 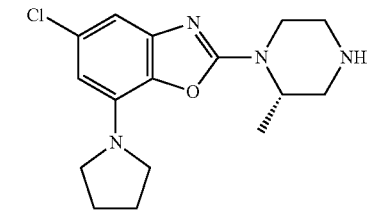 [SMILES: C[C@H]1CNCCN1c1nc2cc(Cl)cc(N3CCCC3)c2o1] |
TABLE 4
| Example | |
|---|---|
| 21 | 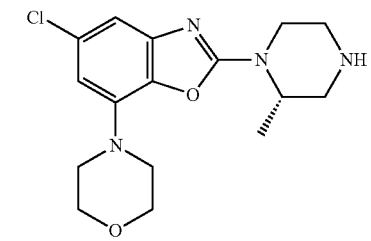 [SMILES: C[C@H]1CNCCN1c1nc2cc(Cl)cc(N3CCOCC3)c2o1] |
| 22 | 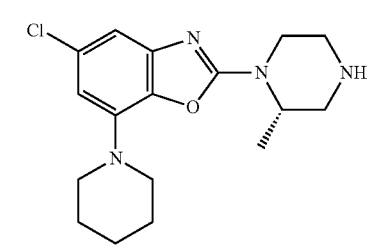 |
| 23 | 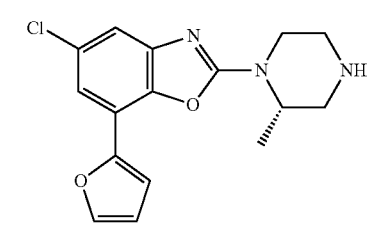 [SMILES: C[C@H]1CNCCN1c1nc2cc(Cl)cc(-c3ccco3)c2o1] |
| 24 | 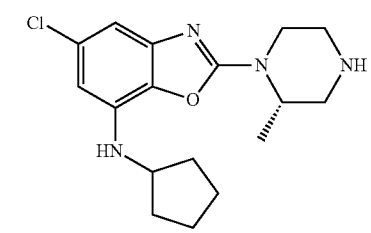 [SMILES: C[C@H]1CNCCN1c1nc2cc(Cl)cc(NC3CCCC3)c2o1] |
| 25 | 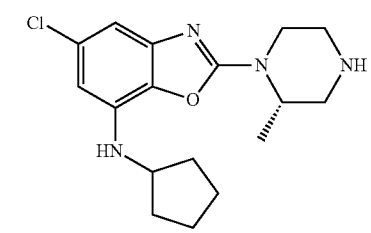 [SMILES: C[C@H]1CNCCN1c1nc2cc(Cl)cc(NC3CCCC3)c2o1] |

TABLE 4-continued

| Example | |
|---|---|
| 26 | 5-chloro-7-(dimethylamino)benzoxazole with (S)-2-methylpiperazine |
| 27 | 5-chloro-7-cyclopropylbenzoxazole with (S)-2-methylpiperazine |
| 28 | 5-chloro-7-(cyclopentyloxy)benzoxazole with (S)-2-methylpiperazine |
| 29 | 5-chloro-7-ethoxybenzoxazole with (S)-2-methylpiperazine |
| 30 | 5-chloro-7-propoxybenzoxazole with (S)-2-methylpiperazine |
| 31 | 5-chloro-7-cyclopentylbenzoxazole with (S)-2-methylpiperazine |
| 32 | 5-chloro-7-butylbenzoxazole with (S)-2-methylpiperazine |
| 33 | 5-chloro-7-(1H-pyrazol-1-yl)benzoxazole with (S)-2-methylpiperazine |
| 34 | 5-chloro-7-(oxazol-2-yl)benzoxazole with (S)-2-methylpiperazine |
| 35 | 5-chloro-7-(thiazol-2-yl)benzoxazole with (S)-2-methylpiperazine |
| 36 | 5-chloro-7-(1H-imidazol-1-yl)benzoxazole with (S)-2-methylpiperazine |
| 37 | 5-chloro-7-(thiazol-4-yl)benzoxazole with (S)-2-methylpiperazine |
| 38 | 5-chloro-7-(thiazol-5-yl)benzoxazole with (S)-2-methylpiperazine |
| 39 | 5-chloro-7-(5-methylfuran-2-yl)benzoxazole with (S)-2-methylpiperazine |

TABLE 4-continued

| Example | |
|---|---|
| 40 | (5-chloro-7-(4-methyl-1H-pyrazol-1-yl)benzo[d]oxazol-2-yl with (S)-2-methylpiperazine) |

TABLE 5

| Example | |
|---|---|
| 41 | (5-chloro-7-(pyridin-2-yl)benzo[d]oxazol-2-yl with (S)-2-methylpiperazine) |
| 42 | (5-chloro-7-(pyridin-3-yl)benzo[d]oxazol-2-yl with (S)-2-methylpiperazine) |
| 43 | (5-chloro-7-(pyridin-4-yl)benzo[d]oxazol-2-yl with (S)-2-methylpiperazine) |
| 44 | (5-chloro-7-cyclohexylbenzo[d]oxazol-2-yl with (S)-2-methylpiperazine) |
| 45 | (5-chloro-7-(2H-1,2,3-triazol-2-yl)benzo[d]oxazol-2-yl with (S)-2-methylpiperazine) |
| 46 | (5-chloro-7-(1H-1,2,4-triazol-1-yl)benzo[d]oxazol-2-yl with (S)-2-methylpiperazine) |
| 47 | (5-chloro-7-isobutylbenzo[d]oxazol-2-yl with (S)-2-methylpiperazine) |
| 48 | (5-chloro-7-(2-(hydroxymethyl)phenyl)benzo[d]oxazol-2-yl with (S)-2-methylpiperazine) |
| 49 | (5-chloro-7-(1-methyl-1H-imidazol-2-yl)benzo[d]oxazol-2-yl with (S)-2-methylpiperazine) |
| 50 | (5-chloro-7-(1H-imidazol-2-yl)benzo[d]oxazol-2-yl with (S)-2-methylpiperazine) |
| 51 | (5-chloro-7-(cyclohexylmethyl)benzo[d]oxazol-2-yl with (S)-2-methylpiperazine) |
| 52 | (5-chloro-7-(cyclohexyloxy)benzo[d]oxazol-2-yl with (S)-2-methylpiperazine) |

TABLE 5-continued
| Example | |
|---|---|
| 53 | 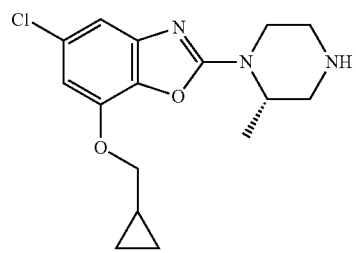 [SMILES: C[C@H]1CNCCN1c1nc2cc(Cl)cc(OCC3CC3)c2o1] |
| 54 | 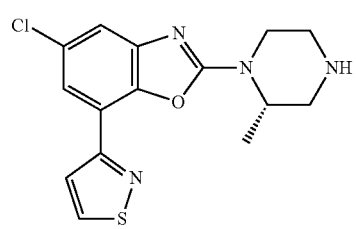 [SMILES: C[C@H]1CNCCN1c1nc2cc(Cl)cc(-c3ccsn3)c2o1] |
| 55 | 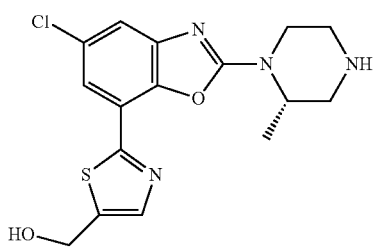 [SMILES: C[C@H]1CNCCN1c1nc2cc(Cl)cc(-c3ncc(CO)s3)c2o1] |
| 56 | 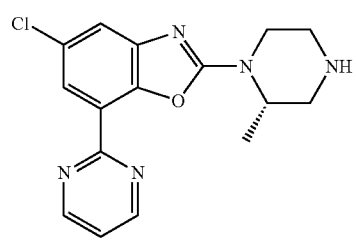 [SMILES: C[C@H]1CNCCN1c1nc2cc(Cl)cc(-c3ncccn3)c2o1] |
| 57 | 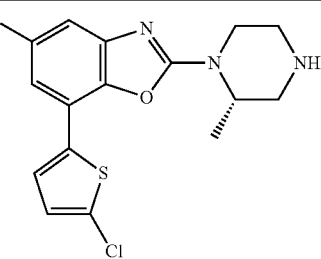 |
| 58 | 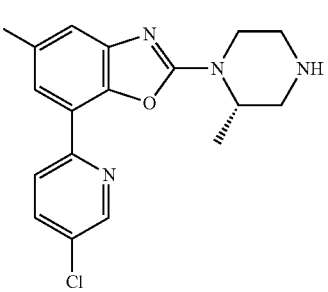 |
| 59 | 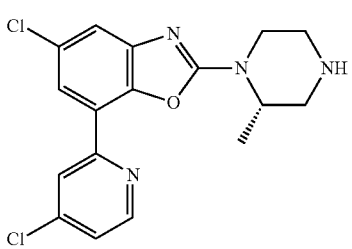 [SMILES: C[C@H]1CNCCN1c1nc2cc(Cl)cc(-c3cc(Cl)ccn3)c2o1] |
| 60 | 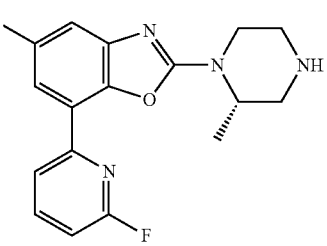 |
TABLE 6
| Example | |
|---|---|
| 61 | 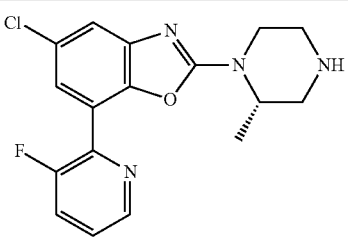 [SMILES: C[C@H]1CNCCN1c1nc2cc(Cl)cc(-c3ncccc3F)c2o1] |

TABLE 6-continued
| Example | |
|---|---|
| 62 | 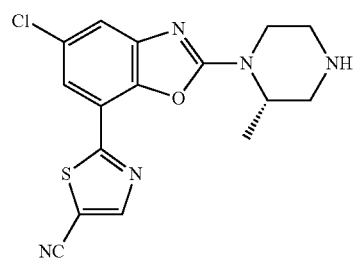 [SMILES: C[C@H]1CNCCN1c1nc2cc(Cl)cc(-c3ncc(C#N)s3)c2o1] |
| 63 | 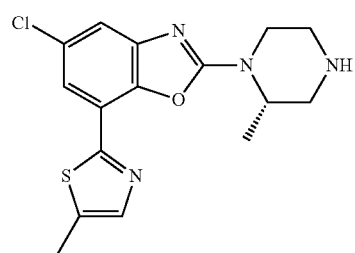 [SMILES: Cc1cnc(-c2cc(Cl)cc3nc(N4CCNC[C@@H]4C)oc23)s1] |
| 64 | 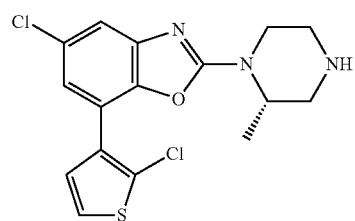 [SMILES: C[C@H]1CNCCN1c1nc2cc(Cl)cc(-c3ccsc3Cl)c2o1] |
| 65 | 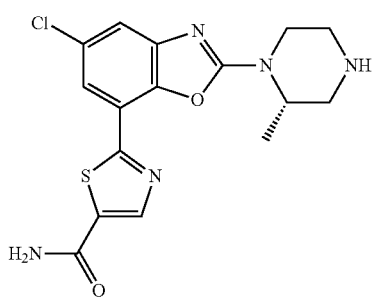 [SMILES: C[C@H]1CNCCN1c1nc2cc(Cl)cc(-c3ncc(C(N)=O)s3)c2o1] |
| 66 | 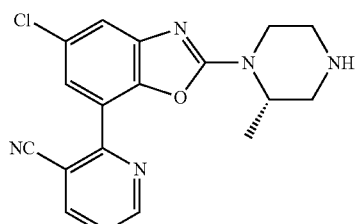 |
| 67 | 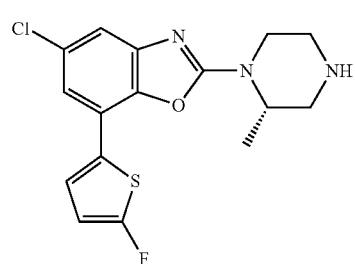 [SMILES: C[C@H]1CNCCN1c1nc2cc(Cl)cc(-c3ccc(F)s3)c2o1] |

TABLE 6-continued
| Example | |
|---|---|
| 68 | 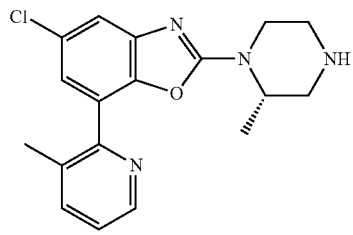 [SMILES: Cc1cccnc1-c1cc(Cl)cc2nc(N3CCNC[C@@H]3C)oc12] |
| 69 | 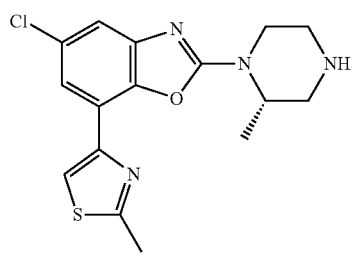 [SMILES: Cc1nc(-c2cc(Cl)cc3nc(N4CCNC[C@@H]4C)oc23)cs1] |
| 70 | 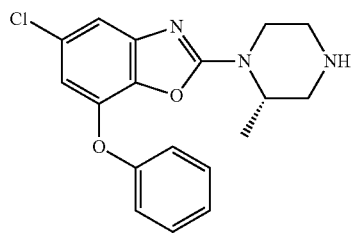 [SMILES: C[C@H]1CNCCN1c1nc2cc(Cl)cc(Oc3ccccc3)c2o1] |
| 71 | 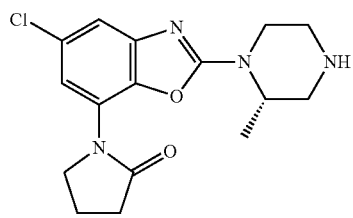 [SMILES: C[C@H]1CNCCN1c1nc2cc(Cl)cc(N3CCCC3=O)c2o1] |
| 72 | 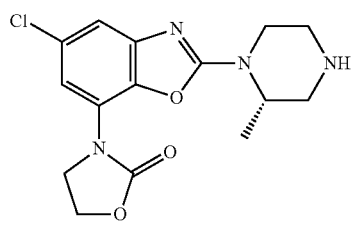 [SMILES: C[C@H]1CNCCN1c1nc2cc(Cl)cc(N3CCOC3=O)c2o1] |
| 73 | 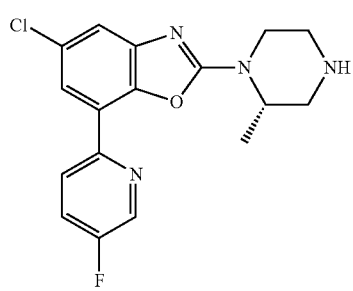 |

TABLE 6-continued
| Example | |
|---|---|
| 74 | 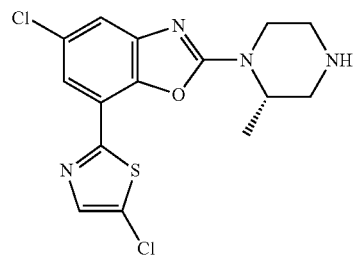 [SMILES: C[C@H]1CNCCN1c1nc2cc(Cl)cc(-c3ncc(Cl)s3)c2o1] |
| 75 | 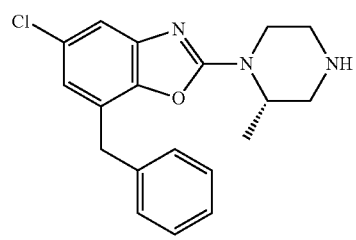 [SMILES: C[C@H]1CNCCN1c1nc2cc(Cl)cc(Cc3ccccc3)c2o1] |
| 76 | 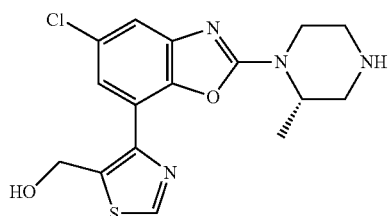 |
| 77 | 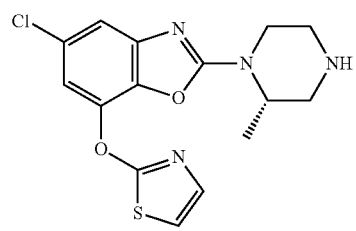 [SMILES: C[C@H]1CNCCN1c1nc2cc(Cl)cc(Oc3nccs3)c2o1] |
| 78 | 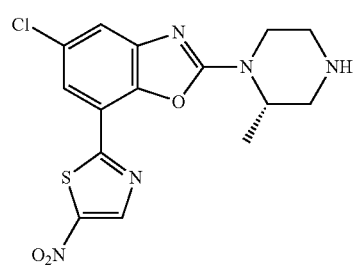 [SMILES: C[C@H]1CNCCN1c1nc2cc(Cl)cc(-c3ncc([N+](=O)[O-])s3)c2o1] |
| 79 | 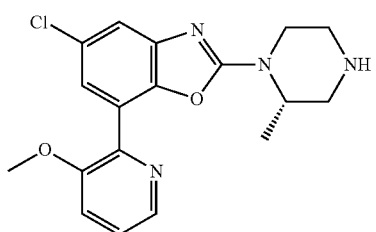 |

TABLE 6-continued
| Example | |
|---|---|
| 80 | 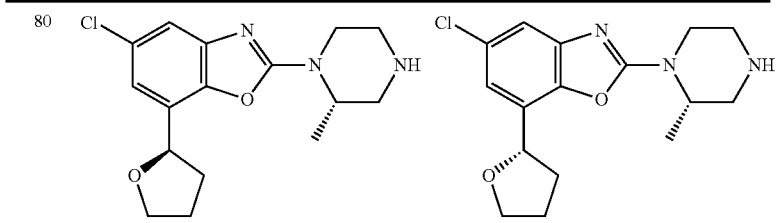 |
TABLE 7
| Example | |
|---|---|
| 81 | 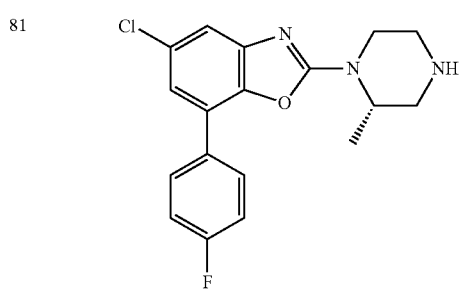 |
| 82 | 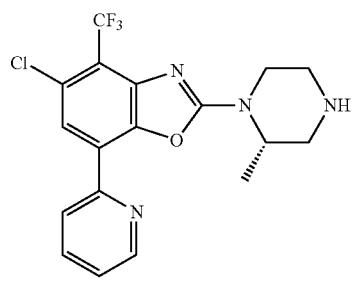 [SMILES: C[C@H]1CNCCN1c1nc2c(C(F)(F)F)c(Cl)cc(-c3ccccn3)c2o1] |
| 83 | 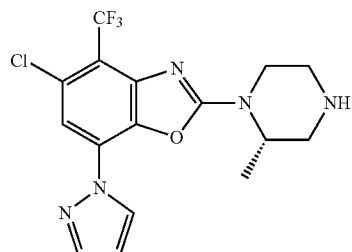 |
| 84 | 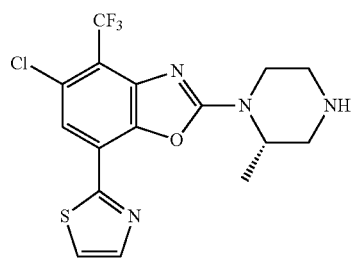 [SMILES: C[C@H]1CNCCN1c1nc2c(C(F)(F)F)c(Cl)cc(-c3nccs3)c2o1] |
TABLE 7-continued
| Example | |
|---|---|
| 85 | 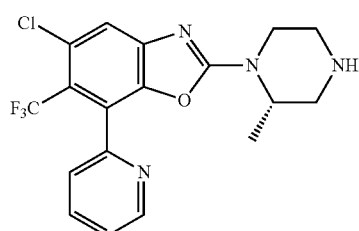 |
| 86 | 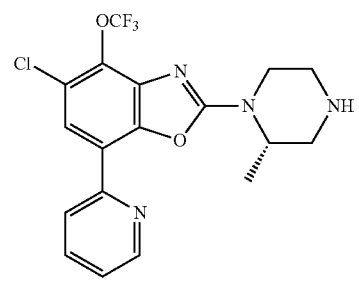 [SMILES: C[C@H]1CNCCN1c1nc2c(OC(F)(F)F)c(Cl)cc(-c3ccccn3)c2o1] |
| 87 | 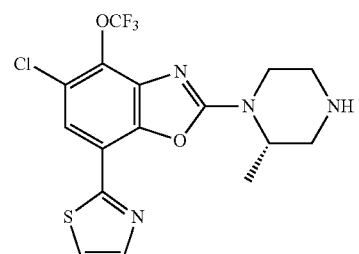 |
| 88 | 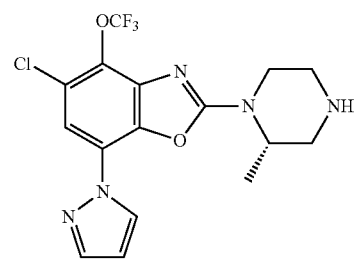 [SMILES: C[C@H]1CNCCN1c1nc2c(OC(F)(F)F)c(Cl)cc(-n3cccn3)c2o1] |

TABLE 7-continued

| Example | Structure |
|---|---|
| 89 | (4,5-difluoro-7-(pyridin-2-yl)benzoxazol-2-yl)-3-methylpiperazine |
| 90 | (4,5-difluoro-7-(thiazol-2-yl)benzoxazol-2-yl)-3-methylpiperazine |
| 91 | (4,5-difluoro-7-(1H-pyrazol-1-yl)benzoxazol-2-yl)-3-methylpiperazine |
| 92 | (5-chloro-6-fluoro-7-(pyridin-2-yl)benzoxazol-2-yl)-3-methylpiperazine |
| 93 | (5-chloro-6-fluoro-7-(thiazol-2-yl)benzoxazol-2-yl)-3-methylpiperazine |
| 94 | (5-chloro-6-fluoro-7-(1H-pyrazol-1-yl)benzoxazol-2-yl)-3-methylpiperazine |
| 95 | 5-chloro-7-propyl-benzoxazol-2-yl)-3-methylpiperazine |
| 96 | 5-chloro-N,N-dimethyl-benzoxazole-7-carboxamide piperazine |
| 97 | 5-chloro-N,N-diethyl-benzoxazole-7-carboxamide piperazine |
| 98 | 5-chloro-N-hydroxy-benzoxazole-7-carboxamide piperazine |
| 99 | 5-chloro-benzoxazole-7-carboxylic acid piperazine |
| 100 | 5-chloro-N-methyl-benzoxazole-7-carboxamide piperazine |

TABLE 8
| Example | |
|---|---|
| 101–107 | 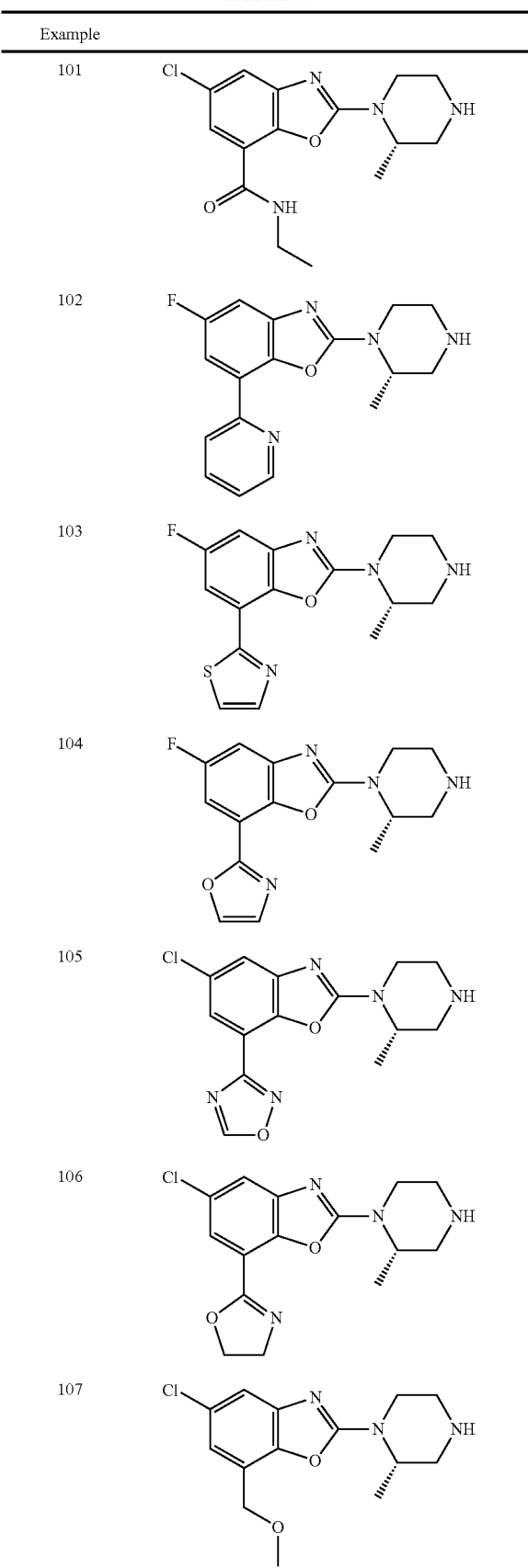 |</br>
TABLE 8-continued
| Example | |
|---|---|
| 108–114 | 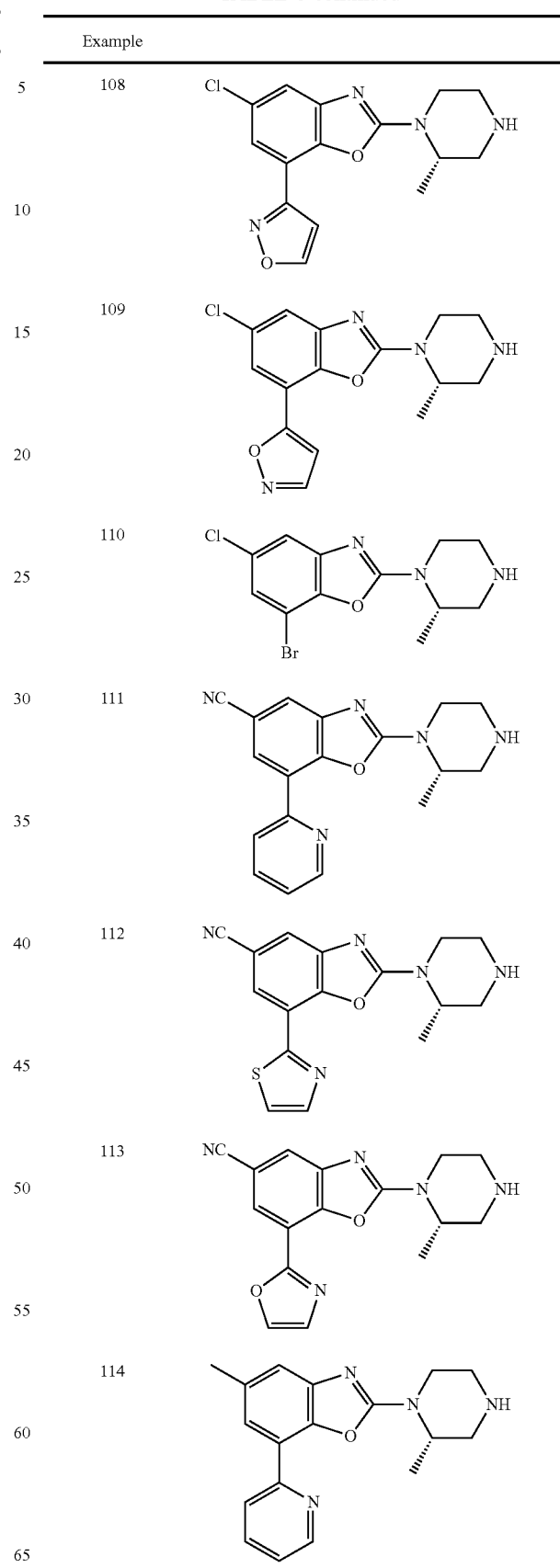 |

TABLE 8-continued
| Example | |
|---|---|
| 115 | 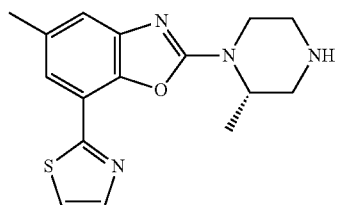 |
| 116 | 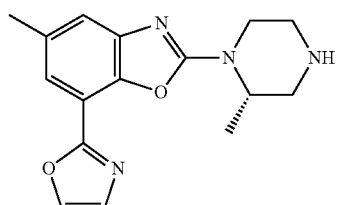 |
| 117 | 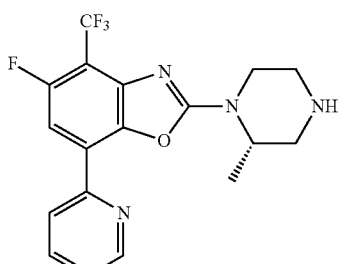 |
| 118 | 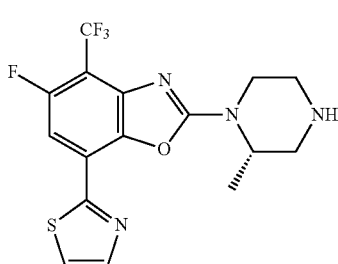 |
| 119 | 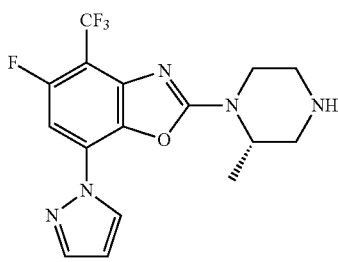 [SMILES: C[C@H]1CNCCN1c1nc2c(C(F)(F)F)c(F)cc(-n3cccn3)c2o1] |
| 120 | 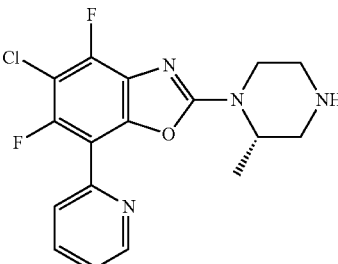 |
TABLE 9
| Example | |
|---|---|
| 121 | 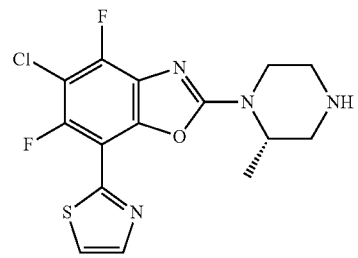 [SMILES: C[C@H]1CNCCN1c1nc2c(F)c(Cl)c(F)c(-c3nccs3)c2o1] |
| 122 | 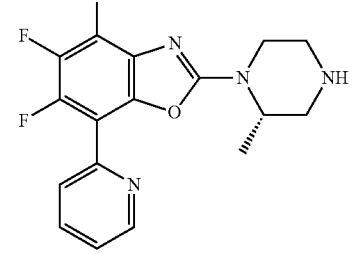 |
| 123 | 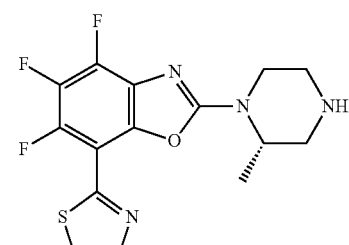 |
| 124 | 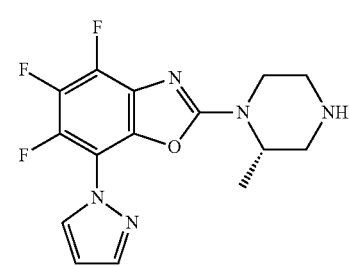 [SMILES: C[C@H]1CNCCN1c1nc2c(F)c(F)c(F)c(-n3cccn3)c2o1] |
| 125 | 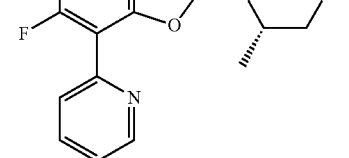 |
| 126 | 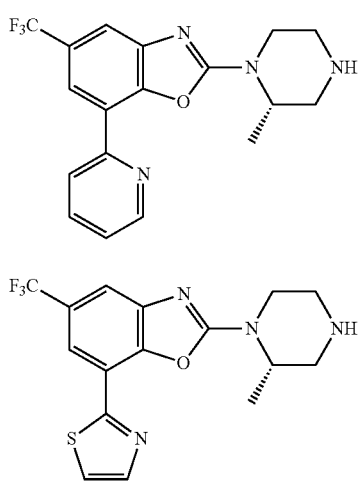 |

TABLE 9-continued

| Example | |
|---|---|
| 127 | 5-(trifluoromethyl)-benzoxazole with oxazole and (S)-methylpiperazine |
| 128 | 5-chloro-4-fluoro-benzoxazole with pyridin-2-yl and (S)-methylpiperazine |
| 129 | 5-chloro-4-fluoro-benzoxazole with thiazol-2-yl and (S)-methylpiperazine |
| 130 | 5-chloro-4-fluoro-benzoxazole with pyrazol-1-yl and (S)-methylpiperazine |
| 131 | 5-chloro-4-methyl-benzoxazole with pyridin-2-yl and (S)-methylpiperazine |
| 132 | 5-chloro-4-methyl-benzoxazole with thiazol-2-yl and (S)-methylpiperazine |
| 133 | 5-chloro-4-methyl-benzoxazole with pyrazol-1-yl and (S)-methylpiperazine |
| 134 | 4-trifluoromethoxy-5-fluoro-benzoxazole with pyridin-2-yl and (S)-methylpiperazine |
| 135 | 4-trifluoromethoxy-5-fluoro-benzoxazole with thiazol-2-yl and (S)-methylpiperazine |
| 136 | 4-trifluoromethoxy-5-fluoro-benzoxazole with pyrazol-1-yl and (S)-methylpiperazine |
| 137 | 5-chloro-6-methyl-benzoxazole with pyridazin-3-yl and (S)-methylpiperazine |
| 138 | 5-chloro-6-methyl-benzoxazole with thiazol-2-yl and (S)-methylpiperazine |

TABLE 9-continued

| Example | |
|---|---|
| 139 | (structure) |
| 140 | (structure) |

TABLE 10

| Example | |
|---|---|
| 141 | (structure) |
| 142 | (structure) |
| 143 | (structure) |
| 144 | (structure) |

TABLE 10-continued

| Example | |
|---|---|
| 145 | (structure) |
| 146 | (structure) |
| 147 | (structure) |
| 148 | (structure) |
| 149 | (structure) |

TABLE 10-continued

| Example | |
|---|---|
| 150 | (structure) |
| 151 | (structure) |
| 152 | (structure) |
| 153 | (structure) |
| 154 | (structure) |
| 155 | (structure) |
| 156 | (structure) |
| 157 | (structure) |
| 158 | (structure) |
| 159 | (structure) |
| 160 | (structure) |

TABLE 11

| Example | |
|---|---|
| 161 | (structure) |

TABLE 11-continued
| Example | |
|---|---|
| 162 | 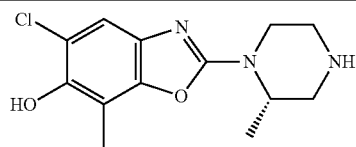 |
| 163 | 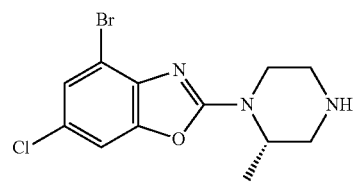 [SMILES: C[C@H]1CNCCN1c1nc2c(Br)cc(Cl)cc2o1] |
| 164 | 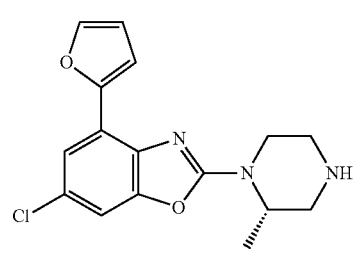 [SMILES: C[C@H]1CNCCN1c1nc2c(-c3ccco3)cc(Cl)cc2o1] |
| 165 | 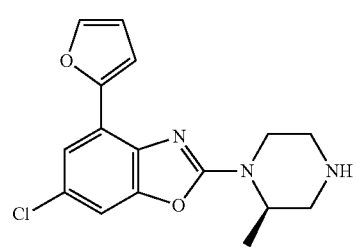 [SMILES: C[C@@H]1CNCCN1c1nc2c(-c3ccco3)cc(Cl)cc2o1] |
| 166 | 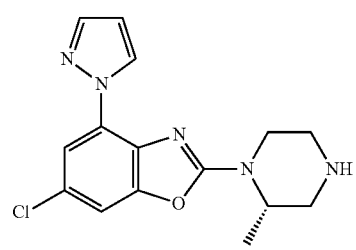 [SMILES: C[C@H]1CNCCN1c1nc2c(-n3cccn3)cc(Cl)cc2o1] |
| 167 | 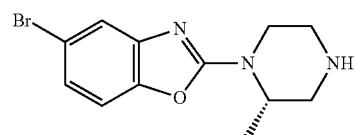 |
| 168 | 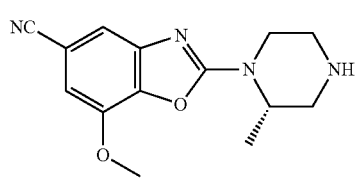 [SMILES: COc1cc(C#N)cc2nc(N3CCNC[C@@H]3C)oc12] |
| 169 | 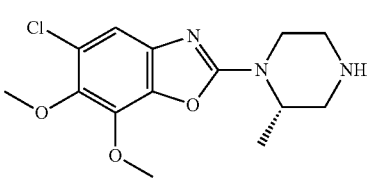 [SMILES: COc1c(Cl)cc2nc(N3CCNC[C@@H]3C)oc2c1OC] |
| 170 | 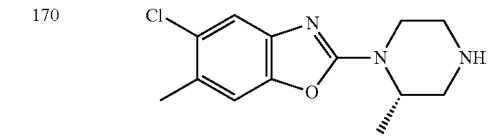 |
| 171 | 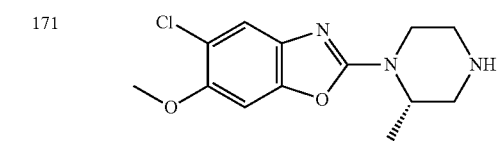 |
| 172 | 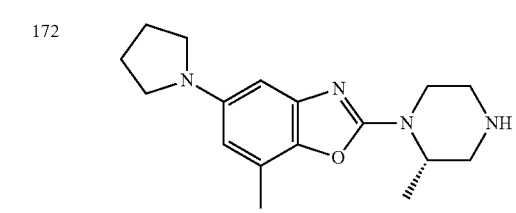 |
| 173 | 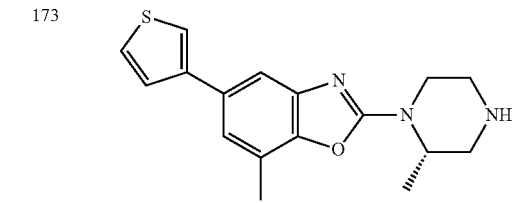 |
| 174 | 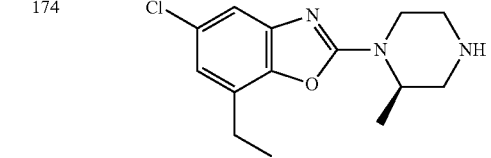 |
| 175 | 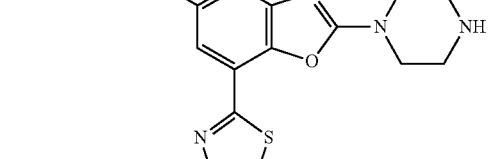 |
| 176 | 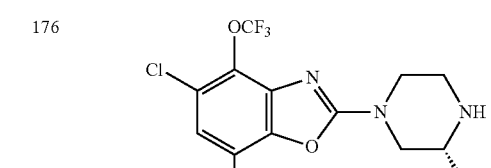 |

TABLE 11-continued

| Example | |
|---|---|
| 177 | 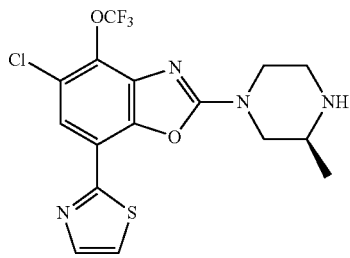 [SMILES: C[C@H]1CN(c2nc3c(OC(F)(F)F)c(Cl)cc(-c4nccs4)c3o2)CCN1] |
| 178 | 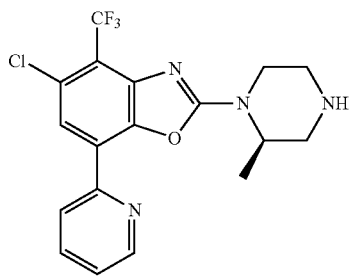 [SMILES: C[C@@H]1CNCCN1c1nc2c(C(F)(F)F)c(Cl)cc(-c3ccccn3)c2o1] |
| 179 | 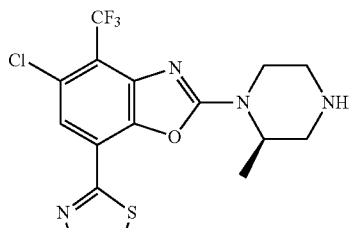 |
| 180 | 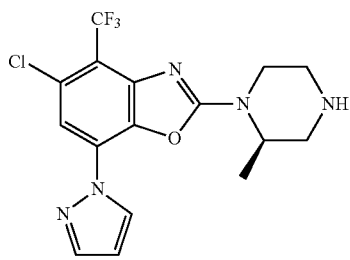 [SMILES: C[C@@H]1CNCCN1c1nc2c(C(F)(F)F)c(Cl)cc(-n3cccn3)c2o1] |

Test Example 1 Evaluation of PDE4 Inhibition

The PDE4 inhibitory activity was measured by using scintillation proximity assay (SPA) as follows: one in which a sample compound dissolved in dimethyl sulfoxide was diluted 10-fold with a buffer solution for reaction containing 50 mM Tris-HCl, pH 7.5, 8.3 mM $MgCl_2$, 1.7 mM EDTA and 0.3 mg/mL bovine serum albumin (BSA) was added at 10 μL/well to a 96-well assay plate. Further, PDE4 diluted 750-fold with a buffer solution for reaction was added at 50 μL/well, then [2,8-$^3$H]-Adenosine-3',5'-cyclic phosphate triethylammonium salt diluted 1000-fold with a buffer solution for reaction was added at 40 μL/well, and the plate was left standing at room temperature for 120 minutes. Thereafter, a suspension of RNA binding YSi-SPA Beads containing 200 mM $ZnSO_4$ was added at 50 μL/well, and the plate was left standing at room temperature for 15 minutes to adsorb the enzyme reaction product onto the Beads. Thereafter, the radioactivity was measured with a liquid scintillation counter for 96-well plates. When one supplemented with only a buffer solution for reaction without adding the enzyme preparation was used as a blank and one supplemented with the enzyme preparation but supplemented with only dimethyl sulfoxide instead of the sample solution was used as a control, the inhibition rate of the test compound relative to the control was calculated according to the following calculation expression:

Inhibition rate (%)={1−(Numeric value from the addition of each sample−Blank value)/(Control value−Blank value)}×100

The results of measuring the rate of PDE4 inhibition of the test compound at 1 μM by the method mentioned above are shown in Tables 12 to 14.

TABLE 12

| Test compound | PDE4 inhibitory activity (1 μM (%)) |
|---|---|
| Example 1 | 87 |
| Example 2 | 23 |
| Example 3 | 50 |
| Example 4 | 18 |
| Example 5 | 25 |
| Example 6 | 36 |
| Example 7 | 59 |
| Example 8 | 79 |
| Example 9 | 50 |
| Example 10 | 36 |
| Example 11 | 26 |
| Example 12 | <10 |
| Example 13 | <10 |
| Example 14 | 37 |
| Example 15 | 21 |
| Example 16 | 75 |
| Example 17 | 84 |
| Example 18 | 76 |
| Example 19 | 76 |
| Example 20 | 71 |
| Example 21 | 59 |
| Example 22 | 40 |
| Example 23 | 95 |
| Example 24 | 27 |
| Example 25 | 53 |
| Example 26 | 61 |
| Example 27 | 85 |
| Example 28 | 81 |
| Example 29 | 63 |
| Example 30 | 61 |
| Example 31 | 51 |
| Example 32 | 62 |
| Example 33 | 93 |

TABLE 12-continued

| Test compound | PDE4 inhibitory activity (1 μM (%)) |
|---|---|
| Example 34 | 89 |
| Example 35 | 96 |
| Example 36 | 39 |
| Example 37 | 98 |
| Example 38 | 68 |
| Example 39 | 42 |
| Example 40 | 68 |
| Example 41 | 93 |
| Example 42 | 66 |
| Example 43 | 61 |
| Example 44 | 64 |
| Example 45 | 87 |
| Example 46 | 29 |
| Example 47 | 35 |
| Example 48 | 53 |
| Example 49 | 17 |
| Example 50 | 62 |
| Example 51 | 12 |
| Example 52 | 57 |
| Example 53 | 50 |
| Example 54 | 92 |
| Example 55 | 80 |
| Example 56 | 87 |
| Example 57 | 54 |
| Example 58 | 77 |
| Example 59 | 71 |
| Example 60 | 63 |

TABLE 13

| Test compound | PDE4 inhibitory activity (1 μM (%)) |
|---|---|
| Example 61 | 81 |
| Example 62 | 65 |
| Example 63 | 87 |
| Example 64 | 73 |
| Example 65 | 83 |

TABLE 13-continued

| Test compound | PDE4 inhibitory activity (1 μM (%)) |
|---|---|
| Example 66 | 57 |
| Example 67 | 70 |
| Example 68 | 38 |
| Example 69 | 65 |
| Example 70 | 38 |
| Example 71 | 30 |
| Example 72 | 28 |
| Example 73 | 93 |
| Example 74 | 83 |
| Example 75 | 45 |
| Example 76 | 73 |
| Example 77 | 30 |
| Example 78 | 58 |
| Example 79 | 53 |
| Example 80 | 42 |
| Example 81 | 68 |
| Example 82 | 94 |
| Example 83 | 92 |
| Example 84 | 95 |
| Example 85 | 26 |
| Example 86 | 91 |
| Example 87 | 96 |
| Example 88 | 95 |
| Example 89 | 88 |
| Example 90 | 96 |
| Example 91 | 89 |
| Example 92 | 71 |
| Example 93 | 95 |
| Example 94 | 62 |
| Example 95 | 71 |
| Example 96 | <10 |
| Example 97 | 10 |
| Example 98 | <10 |
| Example 99 | <10 |
| Example 100 | 16 |
| Example 101 | 27 |
| Example 102 | 85 |

TABLE 13-continued

| Test compound | PDE4 inhibitory activity (1 μM (%)) |
|---|---|
| Example 103 | 96 |
| Example 104 | 88 |
| Example 105 | 61 |
| Example 106 | 42 |
| Example 107 | 66 |
| Example 108 | 66 |
| Example 109 | 61 |
| Example 110 | 57 |
| Example 111 | 83 |
| Example 112 | 94 |
| Example 113 | 71 |
| Example 114 | 77 |
| Example 115 | 91 |
| Example 116 | 80 |
| Example 117 | 88 |
| Example 118 | 99 |
| Example 119 | 91 |
| Example 120 | 41 |

TABLE 14

| Test compound | PDE4 inhibitory activity (1 μM (%)) |
|---|---|
| Example 121 | 62 |
| Example 122 | 79 |
| Example 123 | 95 |
| Example 124 | 46 |
| Example 125 | 91 |
| Example 126 | 95 |
| Example 127 | 90 |
| Example 128 | 79 |
| Example 129 | 97 |
| Example 130 | 83 |
| Example 131 | 90 |
| Example 132 | 94 |
| Example 133 | 92 |
| Example 134 | 88 |
| Example 135 | 99 |
| Example 136 | 90 |
| Example 137 | 33 |
| Example 138 | 86 |
| Example 139 | 39 |
| Example 140 | 35 |
| Example 141 | 77 |
| Example 142 | 86 |
| Example 143 | 94 |
| Example 144 | 41 |
| Example 145 | 80 |
| Example 146 | 95 |
| Example 147 | 53 |
| Example 148 | 94 |
| Example 149 | 91 |
| Example 150 | 91 |
| Example 151 | 76 |
| Example 152 | 68 |
| Example 153 | 93 |
| Example 154 | 39 |
| Example 155 | 96 |
| Example 156 | 91 |
| Example 157 | 41 |
| Example 158 | 88 |
| Example 159 | 57 |
| Example 160 | 86 |
| Example 161 | 19 |
| Example 162 | 35 |
| Example 163 | 52 |
| Example 164 | 75 |
| Example 165 | 31 |
| Example 166 | 71 |
| Example 167 | 16 |
| Example 168 | 13 |
| Example 169 | 22 |
| Example 170 | 15 |
| Example 171 | 14 |

TABLE 14-continued

| Test compound | PDE4 inhibitory activity (1 µM (%)) |
|---|---|
| Example 172 | <10 |
| Example 173 | 35 |
| Example 174 | 21 |
| Example 175 | 96 |
| Example 176 | 91 |
| Example 177 | 93 |
| Example 178 | 33 |
| Example 179 | 79 |
| Example 180 | 43 |

The invention claimed is:

1. A compound represented by formula (1a):

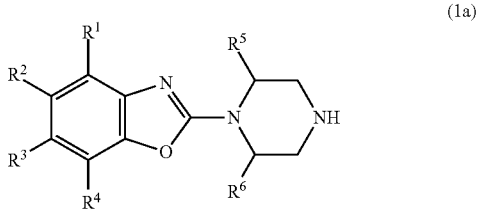

(1a)

wherein

R$^1$ is selected from the group consisting of a hydrogen atom, a halogen atom, a hydroxy group, a cyano group, an optionally substituted C$_{1-6}$ alkyl group, an optionally substituted C$_{3-7}$ cycloalkyl group, an optionally substituted C$_{6-10}$ monocyclic or polycyclic aryl group, an optionally substituted C$_{7-11}$ monocyclic or polycyclic aralkyl group, an optionally substituted 4- to 10-membered monocyclic or bicyclic heterocyclic group containing 1 to 4 heteroatoms selected from an oxygen atom, a nitrogen atom and a sulfur atom, a di-C$_{1-6}$ alkylamino group, an optionally substituted C$_{3-7}$ cycloalkylamino group, an optionally substituted C$_{1-6}$ alkyloxy group, an optionally substituted C$_{3-7}$ cycloalkyloxy group, an optionally substituted C$_{6-10}$ monocyclic or polycyclic aryloxy group, an optionally substituted C$_{7-11}$ monocyclic or polycyclic aralkyloxy group, an optionally substituted 4- to 10-membered monocyclic or bicyclic heterocyclyloxy group containing 1 to 4 heteroatoms selected from an oxygen atom, a nitrogen atom and a sulfur atom, an optionally substituted C$_{1-6}$ alkylthio group, an optionally substituted C$_{1-6}$ alkylsulfonyl group, an optionally substituted C$_{1-6}$ alkylcarbonyl group, a mono-C$_{1-6}$ alkylaminocarbonyl group, a di-C$_{1-6}$ alkylaminocarbonyl group, and an optionally substituted hydroxyaminocarbonyl group, R$^2$, R$^3$ and R$^4$ are each independently selected from the group consisting of a hydrogen atom, a halogen atom, a hydroxy group, a carboxy group, a cyano group, an optionally substituted C$_{1-6}$ alkyl group, an optionally substituted C$_{3-7}$ cycloalkyl group, an optionally substituted C$_{6-10}$ monocyclic or polycyclic aryl group, an optionally substituted C$_{7-11}$ monocyclic or polycyclic aralkyl group, an optionally substituted 4- to 10-membered monocyclic or bicyclic heterocyclic group containing 1 to 4 heteroatoms selected from an oxygen atom, a nitrogen atom and a sulfur atom, a di-C$_{1-6}$ alkylamino group, an optionally substituted C$_{3-7}$ cycloalkylamino group, an optionally substituted C$_{1-6}$ alkyloxy group, an optionally substituted C$_{3-7}$ cycloalkyloxy group, an optionally substituted C$_{6-10}$ monocyclic or polycyclic aryloxy group, an optionally substituted C$_{7-11}$ monocyclic or polycyclic aralkyloxy group, an optionally substituted 4- to 10-membered monocyclic or bicyclic heterocyclyloxy group containing 1 to 4 heteroatoms selected from an oxygen atom, a nitrogen atom and a sulfur atom, an optionally substituted C$_{1-6}$ alkylthio group, an optionally substituted C$_{1-6}$ alkylsulfonyl group, an optionally substituted C$_{1-6}$ alkylcarbonyl group, a mono-C$_{1-6}$ alkylaminocarbonyl group, a di-C$_{1-6}$ alkylaminocarbonyl group, an optionally substituted C$_{1-6}$ alkyloxycarbonyl group and an optionally substituted hydroxyaminocarbonyl group, said optionally substituted groups are optionally substituted with at least one substituent selected from the group consisting of a halogen atom, a cyano group, a hydroxy group, a C$_{1-6}$ alkyl group, a C$_{3-6}$ cycloalkyl group, a hydroxy-C$_{1-6}$ alkyl group, a C$_{1-6}$ alkyloxy group, an aminocarbonyl group, an oxo group, a nitro group, a C$_{1-6}$ alkylthio group, a C$_{1-6}$ alkylsulfonyl group and a C$_{6-10}$ aryl group, and R$^5$ and R$^6$ are each independently a hydrogen atom or a C$_{1-6}$ alkyl group, and wherein R$^4$ is not a hydrogen atom or methyl, and R$^5$ and R$^6$ are not both hydrogen atoms;

or a pharmacologically acceptable salt thereof.

2. The compound or a pharmacologically acceptable salt thereof according to claim 1, wherein R$^2$ is selected from the group consisting of a hydrogen atom, a halogen atom, a cyano group, an optionally substituted C$_{1-6}$ alkyl group and an optionally substituted 5- to 7-membered monocyclic heterocyclic group containing 1 to 4 heteroatoms selected from an oxygen atom, a nitrogen atom and a sulfur atom, wherein said optionally substituted groups are optionally substituted with at least one substituent selected from the group consisting of a halogen atom, a cyano group, a hydroxy group, a C$_{1-6}$ alkyl group, a C$_{3-6}$ cycloalkyl group, a hydroxy-C$_{1-6}$ alkyl group, a C$_{1-6}$ alkyloxy group, an aminocarbonyl group, an oxo group, a nitro group, a C$_{1-6}$ alkylthio group, a C$_{1-6}$ alkylsulfonyl group and a C$_{6-10}$ aryl group.

3. The compound or a pharmacologically acceptable salt thereof according to claim 1, wherein R$^1$ is selected from the group consisting of a hydrogen atom, a halogen atom, a cyano group, an optionally substituted C$_{1-6}$ alkyl group, an optionally substituted C$_{3-7}$ cycloalkyl group, an optionally substituted C$_{6-10}$ monocyclic or polycyclic aryl group, an optionally substituted 5- to 7-membered monocyclic heterocyclic group containing 1 to 4 heteroatoms selected from an oxygen atom, a nitrogen atom and a sulfur atom, an optionally substituted C$_{1-6}$ alkyloxy group, an optionally substituted C$_{1-6}$ alkylthio group and an optionally substituted C$_{1-6}$ alkylsulfonyl group, R² is selected from the group consisting of a hydrogen atom, a halogen atom, a cyano group, an optionally substituted $C_{1-6}$ alkyl group and an optionally substituted 5- to 7-membered monocyclic heterocyclic group containing 1 to 4 heteroatoms selected from an oxygen atom, a nitrogen atom and a sulfur atom, R³ is selected from the group consisting of a hydrogen atom, a halogen atom, a hydroxy group, a cyano group, an optionally substituted $C_{1-6}$ alkyl group and an optionally substituted $C_{1-6}$ alkyloxy group, and R⁴ is selected from the group consisting of a halogen atom, a carboxy group, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted $C_{7-11}$ monocyclic or polycyclic aralkyl group, an optionally substituted 5- to 7-membered monocyclic heterocyclic group containing 1 to 4 heteroatoms selected from an oxygen atom, a nitrogen atom and a sulfur atom, a di-$C_{1-6}$ alkylamino group, an optionally substituted $C_{3-7}$ cycloalkylamino group, an optionally substituted $C_{1-6}$ alkyloxy group, an optionally substituted $C_{3-7}$ cycloalkyloxy group, an optionally substituted $C_{6-10}$ monocyclic or polycyclic aryloxy group, an optionally substituted 5- to 7-membered monocyclic heterocyclyloxy group containing 1 to 4 heteroatoms selected from an oxygen atom, a nitrogen atom and a sulfur atom, an optionally substituted $C_{1-6}$ alkylsulfonyl group, an optionally substituted $C_{1-6}$ alkylcarbonyl group, a mono-$C_{1-6}$ alkylaminocarbonyl group, a di-$C_{1-6}$ alkylaminocarbonyl group, an optionally substituted $C_{1-6}$ alkyloxycarbonyl group and an optionally substituted hydroxyaminocarbonyl group, wherein said optionally substituted groups are optionally substituted with at least one substituent selected from the group consisting of a halogen atom, a cyano group, a hydroxy group, a $C_{1-6}$ alkyl group, a $C_{3-6}$ cycloalkyl group, a hydroxy-$C_{1-6}$ alkyl group, a $C_{1-6}$ alkyloxy group, an aminocarbonyl group, an oxo group, a nitro group, a $C_{1-6}$ alkylthio group, a $C_{1-6}$ alkylsulfonyl group and a $C_{6-10}$aryl group.

4. A compound selected from the group consisting of:
(S)-5-chloro-7-isopropyl-2-(2-methylpiperazin-1-yl)benzoxazole,
(S)-5-chloro-7-methoxy-2-(2-methylpiperazin-1-yl)benzoxazole,
(S)-5-chloro-7-acetyl-2-(2-methylpiperazin-1-yl)benzoxazole,
meso-5-chloro-2-(2,6-cis-dimethylpiperazin-1-yl)-7-methylbenzoxazole,
(S)-5-fluoro-7-methyl-2-(2-methylpiperazin-1-yl)benzoxazole,
(S)-5-bromo-7-methyl-2-(2-methylpiperazin-1-yl)benzoxazole,
(S)-5-chloro-7-isopropoxy-2-(2-methylpiperazin-1-yl)benzoxazole,
(S)-5-chloro-7-ethyl-2-(2-methylpiperazin-1-yl)benzoxazole,
(S)-5-chloro-7-ethoxycarbonyl-2-(2-methylpiperazin-1-yl)benzoxazole,
(S)-5-chloro-7-cyano-2-(2-methylpiperazin-1-yl)benzoxazole,
(S)-5-chloro-7-ethyl-2-(2-isopropylpiperazin-1-yl)benzoxazole,
(S)-5-chloro-7-ethyl-2-(2-isobutylpiperazin-1-yl)benzoxazole,
(S)-2-(2-n-butyl piperazin-1-yl)-5-chloro-7-ethylbenzoxazole,
(S)-5-chloro-7-ethyl-2-(2-ethyl piperazin-1-yl)benzoxazole,
(S)-5-chloro-7-hydroxymethyl-2-(2-methylpiperazin-1-yl)benzoxazole,
(S)-5-chloro-2-(2-methylpiperazin-1-yl)-7-(thiophen-3-yl)benzoxazole,
(S)-5-chloro-7-(furan-3-yl)-2-(2-methylpiperazin-1-yl)benzoxazole,
(S)-5-chloro-2-(2-methylpiperazin-1-yl)-7-(thiophen-2-yl)benzoxazole,
(S)-5-chloro-2-(2-methylpiperazin-1-yl)-7-phenylbenzoxazole,
(S)-5-chloro-2-(2-methylpiperazin-1-yl)-7-(pyrrolidin-1-yl)benzoxazole,
(S)-5-chloro-2-(2-methylpiperazin-1-yl)-7-(morpholin-1-yl)benzoxazole,
(S)-5-chloro-2-(2-methylpiperazin-1-yl)-7-(piperidin-1-yl)benzoxazole,
(S)-5-chloro-7-(furan-2-yl)-2-(2-methylpiperazin-1-yl)benzoxazole,
(S)-5-chloro-7-(cyclopentylamino)-2-(2-methylpiperazin-1-yl)benzoxazole,
(S)-5-chloro-7-diethylamino-2-(2-methylpiperazin-1-yl)benzoxazole,
(S)-5-chloro-7-dimethylamino-2-(2-methylpiperazin-1-yl)benzoxazole,
(S)-5-chloro-7-cyclopropyl-2-(2-methylpiperazin-1-yl)benzoxazole,
(S)-5-chloro-7-(cyclopentyloxy)-2-(2-methylpiperazin-1-yl)benzoxazole,
(S)-5-chloro-7-ethoxy-2-(2-methylpiperazin-1-yl)benzoxazole,
(S)-5-chloro-2-(2-methylpiperazin-1-yl)-7-n-propoxybenzoxazole,
(S)-5-chloro-7-cyclopentyl-2-(2-methylpiperazin-1-yl)benzoxazole,
(S)-7-n-butyl-5-chloro-2-(2-methylpiperazin-1-yl)benzoxazole,
(S)-5-chloro-2-(2-methylpiperazin-1-yl)-7-(1H-pyrazol-1-yl)benzoxazole,
(S)-5-chloro-2-(2-methylpiperazin-1-yl)-7-(oxazol-2-yl)benzoxazole,
(S)-5-chloro-2-(2-methylpiperazin-1-yl)-7-(thiazol-2-yl)benzoxazole,
(S)-5-chloro-7-(1H-imidazol-1-yl)-2-(2-methylpiperazin-1-yl)benzoxazole,
(S)-5-chloro-2-(2-methylpiperazin-1-yl)-7-(thiazol-4-yl)benzoxazole,
(S)-5-chloro-2-(2-methylpiperazin-1-yl)-7-(thiazol-5-yl)benzoxazole,
(S)-5-chloro-7-(5-methylfuran-2-yl)-2-(2-methylpiperazin-1-yl)benzoxazole,
(S)-5-chloro-7-(4-methyl-1H-pyrazol-1-yl)-2-(2-methylpiperazin-1-yl)benzoxazole,
(S)-5-chloro-2-(2-methylpiperazin-1-yl)-7-(pyridin-2-yl)benzoxazole,
(S)-5-chloro-2-(2-methylpiperazin-1-yl)-7-(pyridin-3-yl)benzoxazole,
(S)-5-chloro-2-(2-methylpiperazin-1-yl)-7-(pyridin-4-yl)benzoxazole,
(S)-5-chloro-7-cyclohexyl-2-(2-methylpiperazin-1-yl)benzoxazole,
(S)-5-chloro-2-(2-methylpiperazin-1-yl)-7-(2H-1,2,3-triazol-2-yl)benzoxazole, (S)-5-chloro-2-(2-methylpiperazin-1-yl)-7-(1H-1,2,4-triazol-1-yl)benzoxazole,
(S)-5-chloro-7-isobutyl-2-(2-methylpiperazin-1-yl)benzoxazole,
(S)-5-chloro-2-(2-methylpiperazin-1-yl)-7-(2-hydroxymethyl phenyl)benzoxazole,
(S)-5-chloro-7-(1-methyl-1H-imidazol-2-yl)-2-(2-methylpiperazin-1-yl)benzoxazole,
(S)-5-chloro-7-(1H-imidazol-2-yl)-2-(2-methylpiperazin-1-yl)benzoxazole,
(S)-5-chloro-7-(cyclohexylmethyl)-2-(2-methylpiperazin-1-yl)benzoxazole,
(S)-5-chloro-7-(cyclohexyloxy)-2-(2-methylpiperazin-1-yl)benzoxazole,
(S)-5-chloro-7-(cyclopropylmethoxy)-2-(2-methylpiperazin-1-yl)benzoxazole,
(S)-5-chloro-7-(isothiazol-3-yl)-2-(2-methylpiperazin-1-yl)benzoxazole,
(S)-5-chloro-7-(5-hydroxymethylthiazol-2-yl)-2-(2-methylpiperazin-1-yl)benzoxazole,
(S)-5-chloro-2-(2-methylpiperazin-1-yl)-7-(pyrimidin-2-yl)benzoxazole,
(S)-5-chloro-7-(5-chlorothiophen-2-yl)-2-(2-methylpiperazin-1-yl)benzoxazole,
(S)-5-chloro-7-(5-chloropyridin-2-yl)-2-(2-methylpiperazin-1-yl)benzoxazole,
(S)-5-chloro-7-(4-chloropyridin-2-yl)-2-(2-methylpiperazin-1-yl)benzoxazole,
(S)-5-chloro-7-(6-fluoropyridin-2-yl)-2-(2-methylpiperazin-1-yl)benzoxazole,
(S)-5-chloro-7-(3-fluoropyridin-2-yl)-2-(2-methylpiperazin-1-yl)benzoxazole,
(S)-5-chloro-7-(5-cyanothiazol-2-yl)-2-(2-methylpiperazin-1-yl)benzoxazole,
(S)-5-chloro-2-(2-methylpiperazin-1-yl)-7-(5-methylthiazol-2-yl)benzoxazole,
(S)-5-chloro-7-(2-chlorothiophen-3-yl)-2-(2-methylpiperazin-1-yl)benzoxazole,
(S)-5-chloro-7-(5-carbamoylthiazol-2-yl)-2-(2-methylpiperazin-1-yl)benzoxazole,
(S)-5-chloro-7-(3-cyanopyridin-2-yl)-2-(2-methylpiperazin-1-yl)benzoxazole,
(S)-5-chloro-7-(5-fluorothiophen-2-yl)-2-(2-methylpiperazin-1-yl)benzoxazole,
(S)-5-chloro-2-(2-methylpiperazin-1-yl)-7-(3-methyl pyridin-2-yl)benzoxazole,
(S)-5-chloro-2-(2-methylpiperazin-1-yl)-7-(2-methylthiazol-4-yl)benzoxazole,
(S)-5-chloro-2-(2-methylpiperazin-1-yl)-7-phenoxybenzoxazole,
(S)-5-chloro-2-(2-methylpiperazin-1-yl)-7-(2-oxopyrrolidin-1-yl)benzoxazole,
(S)-5-chloro-2-(2-methylpiperazin-1-yl)-7-(2-oxooxazolidin-3-yl)benzoxazol e,
(S)-5-chloro-7-(5-fluoropyridin-2-yl)-2-(2-methylpiperazin-1-yl)benzoxazole,
(S)-5-chloro-7-(5-chlorothiazol-2-yl)-2-(2-methylpiperazin-1-yl)benzoxazole,
(S)-7-benzyl-5-chloro-2-(2-methylpiperazin-1-yl)benzoxazole,
(S)-5-chloro-7-(5-(hydroxymethyl)thiazol-4-yl)-2-(2-methylpiperazin-1-yl)benzoxazole,
(S)-5-chloro-2-(2-methylpiperazin-1-yl)-7-(thiazol-2-yloxy)benzoxazole,
(S)-5-chloro-2-(2-methylpiperazin-1-yl)-7-(5-nitrothiazol-2-yl)benzoxazole,
(S)-5-chloro-7-(3-methoxypyridin-2-yl)-2-(2-methylpiperazin-1-yl)benzoxazole,
5-chloro-2-((S)-2-methylpiperazin-1-yl)-7-(tetrahydrofuran-2-yl)benzoxazole,
(S)-5-chloro-7-(4-fluorophenyl)-2-(2-methylpiperazin-1-yl)benzoxazole,
(S)-5-chloro-2-(2-methylpiperazin-1-yl)-7-(pyridin-2-yl)-4-(trifluoromethyl)benzoxazole,
(S)-5-chloro-2-(2-methylpiperazin-1-yl)-7-(1H-pyrazol-1-yl)-4-(trifluoromethyl)benzoxazole,
(S)-5-chloro-2-(2-methylpiperazin-1-yl)-7-(thiazol-2-yl)-4-(trifluoromethyl)benzoxazole,
(S)-5-chloro-2-(2-methylpiperazin-1-yl)-7-(pyridin-2-yl)-6-(trifluoromethyl)benzoxazole,
(S)-5-chloro-2-(2-methylpiperazin-1-yl)-7-(pyridin-2-yl)-4-(trifluoromethoxy)benzoxazole,
(S)-5-chloro-2-(2-methylpiperazin-1-yl)-7-(thiazol-2-yl)-4-(trifluoromethoxy)benzoxazole,
(S)-5-chloro-2-(2-methylpiperazin-1-yl)-7-(1H-pyrazol-1-yl)-4-(trifluoromethoxy)benzoxazole,
(S)-4,5-difluoro-2-(2-methylpiperazin-1-yl)-7-(pyridin-2-yl)benzoxazole,
(S)-4,5-difluoro-2-(2-methylpiperazin-1-yl)-7-(thiazol-2-yl)benzoxazole,
(S)-4,5-difluoro-2-(2-methylpiperazin-1-yl)-7-(1H-pyrazol-1-yl)benzoxazole,
(S)-5-chloro-6-fluoro-2-(2-methylpiperazin-1-yl)-7-(pyridin-2-yl)benzoxazole,
(S)-5-chloro-6-fluoro-2-(2-methylpiperazin-1-yl)-7-(thiazol-2-yl)benzoxazole,
(S)-5-chloro-6-fluoro-2-(2-methylpiperazin-1-yl)-7-(1H-pyrazol-1-yl)benzoxazole,
(S)-5-chloro-2-(2-methylpiperazin-1-yl)-7-n-propylbenzoxazole,
(S)-5-chloro-7-dimethyl aminocarbonyl-2-(2-methylpiperazin-1-yl)benzoxazole,
(S)-5-chloro-7-diethylaminocarbonyl-2-(2-methylpiperazin-1-yl)benzoxazole,
(S)-5-chloro-7-hydroxyaminocarbonyl-2-(2-methylpiperazin-1-yl)benzoxazole,
(S)-5-chloro-7-carboxy-2-(2-methylpiperazin-1-yl)benzoxazole,
(S)-5-chloro-7-methyl aminocarbonyl-2-(2-methylpiperazin-1-yl)benzoxazole,
(S)-5-chloro-7-ethylaminocarbonyl-2-(2-methylpiperazin-1-yl)benzoxazole,
(S)-5-fluoro-2-(2-methylpiperazin-1-yl)-7-(pyridin-2-yl)benzoxazole,
(S)-5-fluoro-2-(2-methylpiperazin-1-yl)-7-(thiazol-2-yl)benzoxazole,
(S)-5-fluoro-2-(2-methylpiperazin-1-yl)-7-(oxazol-2-yl)benzoxazole,
(S)-5-chloro-2-(2-methylpiperazin-1-yl)-7-(1,2,4-oxadiazol-3-yl)benzoxazole,
(S)-5-chloro-7-(4,5-dihydrooxazol-2-yl)-2-(2-methylpiperazin-1-yl)benzoxazole,
(S)-5-chloro-7-(methoxymethyl)-2-(2-methylpiperazin-1-yl)benzoxazole,
(S)-5-chloro-7-(isoxazol-3-yl)-2-(2-methylpiperazin-1-yl)benzoxazole,
(S)-5-chloro-7-(isoxazol-5-yl)-2-(2-methylpiperazin-1-yl)benzoxazole,
(S)-7-bromo-5-chloro-2-(2-methylpiperazin-1-yl)benzoxazole,
(S)-5-cyano-2-(2-methylpiperazin-1-yl)-7-(pyridin-2-yl)benzoxazole, (S)-5-cyano-2-(2-methylpiperazin-1-yl)-7-(thiazol-2-yl)benzoxazole,
(S)-5-cyano-2-(2-methylpiperazin-1-yl)-7-(oxazol-2-yl)benzoxazole,
(S)-5-methyl-2-(2-methylpiperazin-1-yl)-7-(pyridin-2-yl)benzoxazole,
(S)-5-methyl-2-(2-methylpiperazin-1-yl)-7-(thiazol-2-yl)benzoxazole,
(S)-5-methyl-2-(2-methylpiperazin-1-yl)-7-(oxazol-2-yl)benzoxazole,
(S)-5-fluoro-2-(2-methylpiperazin-1-yl)-7-(pyridin-2-yl)-4-(trifluoromethyl)benzoxazole,
(S)-5-fluoro-2-(2-methylpiperazin-1-yl)-7-(thiazol-2-yl)-4-(trifluoromethyl)benzoxazole,
(S)-5-fluoro-2-(2-methylpiperazin-1-yl)-7-(1H-pyrazol-1-yl)-4-(trifluoromethyl)benzoxazole,
(S)-5-chloro-4,6-difluoro-2-(2-methylpiperazin-1-yl)-7-(pyridin-2-yl)benzoxazole,
(S)-5-chloro-4,6-difluoro-2-(2-methylpiperazin-1-yl)-7-(thiazol-2-yl)benzoxazole,
(S)-4,5,6-trifluoro-2-(2-methylpiperazin-1-yl)-7-(pyridin-2-yl)benzoxazole,
(S)-4,5,6-trifluoro-2-(2-methylpiperazin-1-yl)-7-(thiazol-2-yl)benzoxazole,
(S)-4,5,6-trifluoro-2-(2-methylpiperazin-1-yl)-7-(1H-pyrazol-1-yl)benzoxazole,
(S)-2-(2-methylpiperazin-1-yl)-7-(pyridin-2-yl)-5-(trifluoromethyl)benzoxazole,
(S)-2-(2-methylpiperazin-1-yl)-7-(thiazol-2-yl)-5-(trifluoromethyl)benzoxazole,
(S)-2-(2-methylpiperazin-1-yl)-7-(oxazol-2-yl)-5-(trifluoromethyl)benzoxazole,
(S)-5-chloro-4-fluoro-2-(2-methylpiperazin-1-yl)-7-(pyridin-2-yl)benzoxazole,
(S)-5-chloro-4-fluoro-2-(2-methylpiperazin-1-yl)-7-(thiazol-2-yl)benzoxazole,
(S)-5-chloro-4-fluoro-2-(2-methylpiperazin-1-yl)-7-(1H-pyrazol-1-yl)benzoxazole,
(S)-5-chloro-4-methyl-2-(2-methylpiperazin-1-yl)-7-(pyridin-2-yl)benzoxazole,
(S)-5-chloro-4-methyl-2-(2-methylpiperazin-1-yl)-7-(thiazol-2-yl)benzoxazole,
(S)-5-chloro-4-methyl-2-(2-methylpiperazin-1-yl)-7-(1H-pyrazol-1-yl)benzoxazole,
(S)-5-fluoro-2-(2-methylpiperazin-1-yl)-7-(pyridin-2-yl)-4-(trifluoromethoxy)benzoxazole,
(S)-5-fluoro-2-(2-methylpiperazin-1-yl)-7-(thiazol-2-yl)-4-(trifluoromethoxy)benzoxazole,
(S)-5-fluoro-2-(2-methylpiperazin-1-yl)-7-(1H-pyrazol-1-yl)-4-(trifluoromethoxy)benzoxazole,
(S)-5-chloro-6-methyl-2-(2-methylpiperazin-1-yl)-7-(pyridin-2-yl)benzoxazole,
(S)-5-chloro-6-methyl-2-(2-methylpiperazin-1-yl)-7-(thiazol-2-yl)benzoxazole,
(S)-5-chloro-6-methyl-2-(2-methylpiperazin-1-yl)-7-(1H-pyrazol-1-yl)benzoxazole,
(S)-5-chloro-6-methoxy-2-(2-methylpiperazin-1-yl)-7-(pyridin-2-yl)benzoxazole,
(S)-5-chloro-6-methoxy-2-(2-methylpiperazin-1-yl)-7-(thiazol-2-yl)benzoxazole,
(S)-5-chloro-6-cyano-2-(2-methylpiperazin-1-yl)-7-(thiazol-2-yl)benzoxazole,
(S)-5-chloro-4-cyano-2-(2-methylpiperazin-1-yl)-7-(thiazol-2-yl)benzoxazole,
(S)-5-fluoro-2-(2-methylpiperazin-1-yl)-7-(thiazol-2-yl)-6-(trifluoromethyl)benzoxazole,
(S)-5-chloro-2-(2-methylpiperazin-1-yl)-7-(methyl sulfonyl)benzoxazole,
(S)-5-chloro-4-iodo-2-(2-methylpiperazin-1-yl)-7-(pyridin-2-yl)benzoxazole,
(S)-5-chloro-6-iodo-2-(2-methylpiperazin-1-yl)-7-(pyridin-2-yl)benzoxazole,
(S)-5-chloro-2-(2-methylpiperazin-1-yl)-4-phenyl-7-(pyridin-2-yl)benzoxazole,
(S)-5-chloro-4-cyclopropyl-2-(2-methylpiperazin-1-yl)-7-(pyridin-2-yl)benzoxazole,
(S)-5-chloro-2-(2-methylpiperazin-1-yl)-4-(methylthio)-7-(pyridin-2-yl)benzoxazole,
(S)-5-chloro-2-(2-methylpiperazin-1-yl)-4-(methylsulfonyl)-7-(pyridin-2-yl)benzoxazole,
(S)-6-bromo-5-chloro-2-(2-methylpiperazin-1-yl)-7-(pyridin-2-yl)benzoxazole,
(S)-5-chloro-4-methoxy-2-(2-methylpiperazin-1-yl)-7-(pyridin-2-yl)benzoxazole,
(S)-5-chloro-4-methoxy-2-(2-methylpiperazin-1-yl)-7-(thiazol-2-yl)benzoxazole,
(S)-5-chloro-4-methoxy-2-(2-methylpiperazin-1-yl)-7-(1H-pyrazol-1-yl)benzoxazole,
(R)-5-chloro-2-(2-methylpiperazin-1-yl)-7-(pyridin-2-yl)-4-(trifluoromethoxy)benzoxazole,
(R)-5-chloro-2-(2-methylpiperazin-1-yl)-7-(thiazol-2-yl)-4-(trifluoromethoxy)benzoxazole,
(R)-5-chloro-2-(2-methylpiperazin-1-yl)-7-(1H-pyrazol-1-yl)-4-(trifluoromethoxy)benzoxazole,
(S)-5-chloro-2-(2-methylpiperazin-1-yl)-7-(thiazol-2-yl)-6-(trifluoromethoxy)benzoxazole,
(S)-5-chloro-6-methoxy-7-methyl-2-(2-methylpiperazin-1-yl)benzoxazole,
(S)-5-chloro-6-hydroxy-7-methyl-2-(2-methylpiperazin-1-yl)benzoxazole,
(S)-4-bromo-6-chloro-2-(2-methylpiperazin-1-yl)benzoxazole,
(S)-6-chloro-4-(furan-2-yl)-2-(2-methylpiperazin-1-yl)benzoxazole,
(R)-6-chloro-4-(furan-2-yl)-2-(2-methylpiperazin-1-yl)benzoxazole,
(S)-6-chloro-2-(2-methylpiperazin-1-yl)-4-(1H-pyrazol-1-yl)benzoxazole,
(S)-5-bromo-2-(2-methylpiperazin-1-yl)benzoxazole,
(S)-5-cyano-7-methoxy-2-(2-methylpiperazin-1-yl)benzoxazole,
(S)-5-chloro-6,7-dimethoxy-2-(2-methylpiperazin-1-yl)benzoxazole,
(S)-5-chloro-6-methyl-2-(2-methylpiperazin-1-yl)benzoxazole,
(S)-5-chloro-6-methoxy-2-(2-methylpiperazin-1-yl)benzoxazole,
(S)-7-methyl-5-(pyrrolidin-1-yl)-2-(2-methylpiperazin-1-yl)benzoxazole,
(S)-7-methyl-5-(thiophen-3-yl)-2-(2-methylpiperazin-1-yl)benzoxazole,
(R)-5-chloro-7-ethyl-2-(2-methylpiperazin-1-yl)benzoxazole,
5-chloro-2-(piperazin-1-yl)-7-(thiazol-2-yl)-4-(trifluoromethoxy)benzoxazole,
(R)-5-chloro-2-(3-methylpiperazin-1-yl)-7-(thiazol-2-yl)-4-(trifluoromethoxy)benzoxazole,
(S)-5-chloro-2-(3-methylpiperazin-1-yl)-7-(thiazol-2-yl)-4-(trifluoromethoxy)benzoxazole,
(R)-5-chloro-2-(2-methylpiperazin-1-yl)-7-(pyridin-2-yl)-4-(trifluoromethyl)benzoxazole,
(R)-5-chloro-2-(2-methylpiperazin-1-yl)-7-(thiazol-2-yl)-4-(trifluoromethyl)benzoxazole, and (R)-5-chloro-2-(2-methylpiperazin-1-yl)-7-(1H-pyrazol-1-yl)-4-(trifluoromethyl)benzoxazole,
or a pharmacologically acceptable salt thereof.

5. A pharmaceutical composition comprising (i) the compound or the pharmacologically acceptable salt thereof according to claim 1 as an active ingredient, and (ii) an excipient, a disintegrant, a binder, a lubricant or a colorant.

6. A pharmaceutical composition comprising
(i) a phosphodiesterase 4 (PDE4) inhibitor compound represented by formula (1a) or a pharmacologically acceptable salt thereof as an active ingredient:

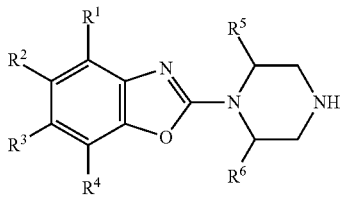

(1a)

wherein
$R^1$, $R^2$, $R^3$ and $R^4$ are each independently selected from the group consisting of a hydrogen atom, a halogen atom, a hydroxy group, a carboxy group, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted $C_{7-11}$ monocyclic or polycyclic aralkyl group, an optionally substituted 4- to 10-membered monocyclic or bicyclic heterocyclic group containing 1 to 4 heteroatoms selected from an oxygen atom, a nitrogen atom and a sulfur atom, a di-$C_{1-6}$ alkylamino group, an optionally substituted $C_{3-7}$ cycloalkylamino group, an optionally substituted $C_{1-6}$ alkyloxy group, an optionally substituted $C_{3-7}$ cycloalkyloxy group, an optionally substituted $C_{6-10}$ monocyclic or polycyclic aryloxy group, an optionally substituted $C_{7-11}$ monocyclic or polycyclic aralkyloxy group, an optionally substituted 4- to 10-membered monocyclic or bicyclic heterocyclyloxy group containing 1 to 4 heteroatoms selected from an oxygen atom, a nitrogen atom and a sulfur atom, an optionally substituted $C_{1-6}$ alkylthio group, an optionally substituted $C_{1-6}$ alkylsulfonyl group, an optionally substituted $C_{1-6}$ alkylcarbonyl group, a mono-$C_{1-6}$ alkylaminocarbonyl group, a di-$C_{1-6}$ alkylaminocarbonyl group, an optionally substituted $C_{1-6}$ alkyloxycarbonyl group and an optionally substituted hydroxyaminocarbonyl group,
said optionally substituted groups are optionally substituted with at least one substituent selected from the group consisting of a halogen atom, a cyano group, a hydroxy group, a $C_{1-6}$ alkyl group, a $C_{3-6}$cycloalkyl group, a hydroxy-$C_{1-6}$ alkyl group, a $C_{1-6}$alkyloxy group, an aminocarbonyl group, an oxo group, a nitro group, a $C_{1-6}$ alkylthio group, a $C_{1-6}$ alkylsulfonyl group and a $C_{6-10}$aryl group,
$R^5$ and $R^6$ are each independently a hydrogen atom or a $C_{1-6}$ alkyl group, and
wherein
$R^4$ is not a hydrogen atom or methyl, and
$R^5$ and $R^6$ are not both hydrogen atoms, and
(ii) an excipient, a disintegrant, a binder, a lubricant or a colorant.

7. A pharmaceutical composition comprising (i) the compound or the pharmacologically acceptable salt thereof according to claim 4 as an active ingredient, and (ii) an excipient, a disintegrant, a binder, a lubricant or a colorant.

8. A pharmaceutical composition comprising
(i) a phosphodiesterase 4 (PDE4) inhibitor compound represented by formula (1) or a pharmacologically acceptable salt thereof as an active ingredient:

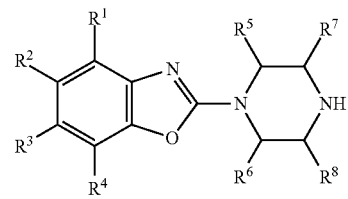

(1)

wherein
$R^1$ is selected from the group consisting of a hydrogen atom, a halogen atom, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted 5- to 7-membered monocyclic heterocyclic group containing 1 to 4 heteroatoms selected from an oxygen atom, a nitrogen atom and a sulfur atom, an optionally substituted $C_{1-6}$ alkyloxy group, an optionally substituted $C_{1-6}$ alkylthio group and an optionally substituted $C_{1-6}$ alkylsulfonyl group,
$R^2$ is selected from the group consisting of a hydrogen atom, a halogen atom, a cyano group, an optionally substituted $C_{1-6}$ alkyl group and an optionally substituted 5- to 7-membered monocyclic heterocyclic group containing 1 to 4 heteroatoms selected from an oxygen atom, a nitrogen atom and a sulfur atom,
$R^3$ is selected from the group consisting of a hydrogen atom, a halogen atom, a hydroxy group, a cyano group, an optionally substituted $C_{1-6}$ alkyl group and an optionally substituted $C_{1-6}$ alkyloxy group, and
$R^4$ is selected from the group consisting of a halogen atom, a carboxy group, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted $C_{7-11}$ monocyclic or polycyclic aralkyl group, an optionally substituted 5- to 7-membered monocyclic heterocyclic group containing 1 to 4 heteroatoms selected from an oxygen atom, a nitrogen atom and a sulfur atom, a di-$C_{1-6}$ alkylamino group, an optionally substituted $C_{3-7}$ cycloalkylamino group, an optionally substituted $C_{1-6}$ alkyloxy group, an optionally substituted $C_{3-7}$ cycloalkyloxy group, an optionally substituted $C_{6-10}$ monocyclic or polycyclic aryloxy group, an optionally substituted 5- to 7-membered monocyclic heterocyclyloxy group containing 1 to 4 heteroatoms selected from an oxygen atom, a nitrogen atom and a sulfur atom, an optionally substituted $C_{1-6}$ alkylsulfonyl group, an optionally substituted $C_{1-6}$ alkylcarbonyl group, a mono-$C_{1-6}$ alkylaminocarbonyl group, a di-$C_{1-6}$ alkylaminocarbonyl group, an optionally substituted $C_{1-6}$ alkyloxycarbonyl group and an optionally substituted hydroxyaminocarbonyl group,
said optionally substituted groups are optionally substituted with at least one substituent selected from the group consisting of a halogen atom, a cyano group, a hydroxy group, a $C_{1-6}$ alkyl group, a $C_{3-6}$cycloalkyl group, a hydroxy-$C_{1-6}$ alkyl group, a $C_{1-6}$alkyloxy group, an aminocarbonyl group, an oxo group, a nitro group, a $C_{1-6}$ alkylthio group, a $C_{1-6}$ alkylsulfonyl group and a $C_{6-10}$aryl group, and $R^5$ to $R^8$ are each independently a hydrogen atom or a $C_{1-6}$alkyl group, and wherein $R^4$ is not methyl, and $R^5$ and $R^6$ are not both hydrogen atoms, and (ii) an excipient, a disintegrant, a binder, a lubricant or a colorant.

9. A method of treating a disease caused by PDE4 in a subject, comprising administering the compound or the pharmacologically acceptable salt thereof according to claim 1 to the subject having the disease caused by PDE4, wherein the disease is selected from the group consisting of asthma, chronic obstructive pulmonary disease (COPD), atopic dermatitis, psoriatic arthritis, and psoriasis vulgaris.

10. A method of treating a disease caused by PDE4 in a subject, comprising administering the compound or the pharmacologically acceptable salt thereof according to claim 4 to the subject having the disease caused by PDE4, wherein the disease is selected from the group consisting of asthma, chronic obstructive pulmonary disease (COPD), atopic dermatitis, psoriatic arthritis, and psoriasis vulgaris.

11. The pharmaceutical composition according to claim 6, wherein $R^2$ is selected from the group consisting of a hydrogen atom, a halogen atom, a cyano group, an optionally substituted $C_{1-6}$ alkyl group and an optionally substituted 5- to 7-membered monocyclic heterocyclic group containing 1 to 4 heteroatoms selected from an oxygen atom, a nitrogen atom and a sulfur atom.

12. The pharmaceutical composition according to claim 6, wherein $R^1$ is selected from the group consisting of a hydrogen atom, a halogen atom, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted 5- to 7-membered monocyclic heterocyclic group containing 1 to 4 heteroatoms selected from an oxygen atom, a nitrogen atom and a sulfur atom, an optionally substituted $C_{1-6}$ alkyloxy group, an optionally substituted $C_{1-6}$ alkylthio group and an optionally substituted $C_{1-6}$ alkylsulfonyl group, $R^2$ is selected from the group consisting of a hydrogen atom, a halogen atom, a cyano group, an optionally substituted $C_{1-6}$ alkyl group and an optionally substituted 5- to 7-membered monocyclic heterocyclic group containing 1 to 4 heteroatoms selected from an oxygen atom, a nitrogen atom and a sulfur atom, $R^3$ is selected from the group consisting of a hydrogen atom, a halogen atom, a hydroxy group, a cyano group, an optionally substituted $C_{1-6}$ alkyl group and an optionally substituted $C_{1-6}$ alkyloxy group, and $R^4$ is selected from the group consisting of a halogen atom, a carboxy group, a cyano group, an optionally substituted $C_{1-6}$ alkyl group, an optionally substituted $C_{3-7}$ cycloalkyl group, an optionally substituted $C_{6-10}$ monocyclic or polycyclic aryl group, an optionally substituted $C_{7-11}$ monocyclic or polycyclic aralkyl group, an optionally substituted 5- to 7-membered monocyclic heterocyclic group containing 1 to 4 heteroatoms selected from an oxygen atom, a nitrogen atom and a sulfur atom, a di-$C_{1-6}$ alkylamino group, an optionally substituted $C_{3-7}$cycloalkylamino group, an optionally substituted $C_{1-6}$ alkyloxy group, an optionally substituted $C_{3-7}$cycloalkyloxy group, an optionally substituted $C_{6-10}$ monocyclic or polycyclic aryloxy group, an optionally substituted 5- to 7-membered monocyclic heterocyclyloxy group containing 1 to 4 heteroatoms selected from an oxygen atom, a nitrogen atom and a sulfur atom, an optionally substituted $C_{1-6}$ alkylsulfonyl group, an optionally substituted $C_{1-6}$ alkylcarbonyl group, a mono-$C_{1-6}$alkylaminocarbonyl group, a di-$C_{1-6}$alkylaminocarbonyl group, an optionally substituted $C_{1-6}$ alkyloxycarbonyl group and an optionally substituted hydroxyaminocarbonyl group.

13. A method of treating a disease caused by PDE4 in a subject, comprising administering the compound or the pharmacologically acceptable salt thereof according to claim 1 to the subject having the disease caused by PDE4, wherein the disease is selected from the group consisting of asthma, chronic obstructive pulmonary disease (COPD), psoriatic arthritis, and psoriasis vulgaris.

\* \* \* \* \*